(12) United States Patent
Heffernan et al.

(10) Patent No.: US 7,884,124 B2
(45) Date of Patent: Feb. 8, 2011

(54) FLUORO-SUBSTITUTED INHIBITORS OF D-AMINO ACID OXIDASE

(75) Inventors: Michele L. R. Heffernan, Worcester, MA (US); Robert J. Foglesong, Durham, NC (US); Seth C. Hopkins, Clinton, MA (US); Mustapha Soukri, Raleigh, NC (US); Steven W. Jones, Milford, MA (US); Kerry L. Spear, Concord, MA (US); Mark A. Varney, Laguna Niguel, CA (US)

(73) Assignee: Sepracor Inc., Marlborough, MA (US)

( * ) Notice: Subject to any disclaimer, the term of this patent is extended or adjusted under 35 U.S.C. 154(b) by 627 days.

(21) Appl. No.: 11/772,798

(22) Filed: Jul. 2, 2007

(65) Prior Publication Data

US 2008/0004327 A1   Jan. 3, 2008

Related U.S. Application Data

(60) Provisional application No. 60/806,391, filed on Jun. 30, 2006, provisional application No. 60/842,465, filed on Sep. 5, 2006, provisional application No. 60/914,293, filed on Apr. 26, 2007.

(51) Int. Cl.
*A61K 31/40* (2006.01)
*C07D 487/02* (2006.01)
*C07D 491/02* (2006.01)
*C07D 495/02* (2006.01)
*C07D 497/02* (2006.01)

(52) U.S. Cl. ........................ 514/412; 548/453
(58) Field of Classification Search ............... 548/453; 514/412
See application file for complete search history.

(56) References Cited

U.S. PATENT DOCUMENTS

| | | | |
|---|---|---|---|
| 4,540,690 A | 9/1985 | Szmuszkovicz | |
| 4,587,258 A | 5/1986 | Gold et al. | |
| 4,738,709 A | 4/1988 | Nielsen | |
| 4,751,231 A | 6/1988 | Halczenko et al. | |
| 4,960,786 A | 10/1990 | Salituro et al. | |
| 4,981,870 A | 1/1991 | Koe | |
| 5,137,910 A | 8/1992 | Gray et al. | |
| 5,284,862 A | 2/1994 | Bigge et al. | |
| 5,373,018 A | 12/1994 | Cugola et al. | |
| 5,374,649 A | 12/1994 | Cugola et al. | |
| 5,456,919 A | 10/1995 | Patell et al. | |
| 5,523,278 A | 6/1996 | Wepplo | |
| 5,550,255 A | 8/1996 | Urbach et al. | |
| 5,578,627 A | 11/1996 | Takeda et al. | |
| 5,620,997 A | 4/1997 | Bolton et al. | |
| 5,668,162 A | 9/1997 | Domagala et al. | |
| 5,686,461 A | 11/1997 | Cugola et al. | |
| 5,760,059 A | 6/1998 | Cugola et al. | |
| 5,859,042 A | 1/1999 | Lee et al. | |
| 5,886,018 A | 3/1999 | Lodi et al. | |
| 5,922,752 A | 7/1999 | Harrison et al. | |
| 5,962,496 A | 10/1999 | Cugola et al. | |
| 5,965,591 A | 10/1999 | Kojima et al. | |
| 6,020,359 A | 2/2000 | Lodi et al. | |
| 6,069,156 A | 5/2000 | Oku et al. | |
| 6,096,771 A | 8/2000 | Kojima et al. | |
| 6,100,289 A | 8/2000 | Cugola et al. | |
| 6,297,281 B1 | 10/2001 | Chabrier de Lassauniere et al. | |
| 6,331,636 B1 | 12/2001 | Romero et al. | |
| 6,372,919 B1 | 4/2002 | Lippa et al. | |
| 6,399,601 B1 | 6/2002 | Du Bois | |

(Continued)

FOREIGN PATENT DOCUMENTS

| BE | 616646 | 5/1962 |
|---|---|---|
| CA | 2066593 A1 | 2/1992 |
| CA | 2410077 A1 | 11/2001 |
| CA | 2474451 A1 | 8/2003 |
| CA | 2498152 A1 | 3/2004 |

(Continued)

OTHER PUBLICATIONS

Mandel et al., CNS Drugs, 2003: 17(10); 729-62.*
Cecil Textbook of Medicine, 20th edition (1996), vol. 2, pp. 2050-2057.*
Cecil Textbook of Medicine, 20th edition (1996), vol. 2, pp. 1992-1996.*

(Continued)

*Primary Examiner*—Rebecca L Anderson
(74) *Attorney, Agent, or Firm*—Morgan, Lewis & Bockius, LLP

(57) ABSTRACT

This invention provides novel inhibitors of the enzyme D-amino acid oxidase as well as pharmaceutical compositions including the compounds of the invention. The invention also provides methods for the treatment and prevention of neurological disorders, such as neuropsychiatric and neurodegenerative diseases, as well as pain, ataxia and convulsion. The compounds of the invention have the general structure:

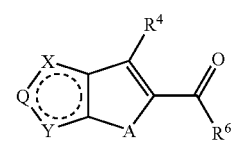

wherein A is NH or S. Q is a member selected from $CR^1$ and N. X and Y are members independently selected from O, S, $CR^2$, N and NH. $R^1$, $R^2$ and $R^4$ are members independently selected from H and F, provided that at least one member selected from $R^1$, $R^2$ and $R^4$ is F. $R^6$ is a member selected from $O^-X^+$ and OH, wherein $X^+$ is a positive ion, which is a member selected from inorganic positive ions and organic positive ions.

30 Claims, No Drawings

U.S. PATENT DOCUMENTS

| | | |
|---|---|---|
| 6,479,527 B1 | 11/2002 | Barket et al. |
| 6,576,653 B2 | 6/2003 | Du Bois |
| 6,589,949 B1 | 7/2003 | Moriwaki et al. |
| 6,603,000 B2 | 8/2003 | Yee et al. |
| 6,828,460 B2 | 12/2004 | Browning et al. |
| 6,995,144 B2 | 2/2006 | Ozaki et al. |
| 7,166,725 B2 | 1/2007 | Fang et al. |
| 7,226,938 B2 | 6/2007 | Cai et al. |
| 7,488,747 B2 | 2/2009 | Fang et al. |
| 7,579,370 B2 | 8/2009 | Heffernan et al. |
| 7,615,572 B2 | 11/2009 | Fang et al. |
| 2002/0010198 A1 | 1/2002 | Jerussi et al. |
| 2002/0085976 A1 | 7/2002 | Elomari |
| 2002/0123490 A1 | 9/2002 | Howard, Jr. |
| 2002/0183369 A1 | 12/2002 | Du Bois |
| 2003/0087803 A1 | 5/2003 | Yatvin et al. |
| 2003/0162825 A1 | 8/2003 | Heefner et al. |
| 2003/0171440 A1 | 9/2003 | Senanayake et al. |
| 2003/0195361 A1 | 10/2003 | Du Bois |
| 2003/0215523 A1 | 11/2003 | Ozawa et al. |
| 2004/0048878 A1 | 3/2004 | Cai et al. |
| 2004/0092605 A1 | 5/2004 | Jerussi et al. |
| 2004/0106681 A1 | 6/2004 | Rao et al. |
| 2004/0220229 A1 | 11/2004 | Bussolotti et al. |
| 2005/0020645 A1 | 1/2005 | Ohta et al. |
| 2005/0089935 A1 | 4/2005 | Cai et al. |
| 2005/0143434 A1 | 6/2005 | Fang et al. |
| 2005/0143443 A1 | 6/2005 | Fang et al. |
| 2006/0019944 A1 | 1/2006 | Wu et al. |
| 2006/0229286 A1 | 10/2006 | Kakigami et al. |
| 2006/0235002 A1 | 10/2006 | Nagai et al. |
| 2007/0100135 A1 | 5/2007 | Riggs et al. |
| 2007/0142452 A1 | 6/2007 | Banner et al. |
| 2007/0197588 A1 | 8/2007 | Shao et al. |
| 2007/0203111 A1 | 8/2007 | Shao et al. |
| 2008/0004328 A1 | 1/2008 | Dorsey et al. |
| 2008/0058395 A1 | 3/2008 | Heffernan et al. |
| 2009/0005456 A1 | 1/2009 | Shao et al. |
| 2009/0099248 A1 | 4/2009 | Heffernan et al. |
| 2009/0149549 A1 | 6/2009 | Zhao et al. |
| 2010/0016397 A1 | 1/2010 | Fang et al. |
| 2010/0022612 A1 | 1/2010 | Dorsey et al. |
| 2010/0029737 A1 | 2/2010 | Heffernan et al. |
| 2010/0029741 A1 | 2/2010 | Dorsey et al. |
| 2010/0120740 A1 | 5/2010 | Heffernan et al. |
| 2010/0190861 A1 | 7/2010 | Shao et al. |

FOREIGN PATENT DOCUMENTS

| | | |
|---|---|---|
| CA | 2498175 A1 | 3/2004 |
| CA | 2565852 A1 | 11/2005 |
| CA | 2566094 A1 | 12/2005 |
| CN | 1106386 A | 8/1995 |
| CN | 1709871 A | 12/2005 |
| CN | 1962656 A | 5/2007 |
| DE | 1124485 A | 3/1962 |
| DE | 3431541 A1 | 3/1986 |
| EP | 0101786 A1 | 3/1984 |
| EP | 0394905 A2 | 10/1990 |
| EP | 0396124 A2 | 11/1990 |
| EP | 1136071 A2 | 9/2001 |
| EP | 1219603 A2 | 7/2002 |
| EP | 1262181 A1 | 12/2002 |
| EP | 1362864 A1 | 11/2003 |
| EP | 1088824 B1 | 1/2004 |
| EP | 1391460 A1 | 2/2004 |
| EP | 1420028 A2 | 5/2004 |
| ES | 2081747 A1 | 3/1996 |
| JP | S54-059269 A | 5/1979 |
| JP | 01016786 A | 1/1989 |
| JP | 01172388 A | 7/1989 |
| JP | H04-077476 A | 3/1992 |
| WO | 86/00869 A1 | 2/1986 |
| WO | 92/01670 A1 | 2/1992 |
| WO | 92/16205 A2 | 10/1992 |
| WO | 95/17381 A1 | 6/1995 |
| WO | 98/14427 A1 | 4/1998 |
| WO | WO 98/42709 A1 | 10/1998 |
| WO | 99/10343 A1 | 3/1999 |
| WO | 99/18065 A1 | 4/1999 |
| WO | 99/40913 A1 | 8/1999 |
| WO | WO 99/40914 A1 | 8/1999 |
| WO | 99/48868 A2 | 9/1999 |
| WO | 99/52519 A2 | 10/1999 |
| WO | 00/25770 A1 | 5/2000 |
| WO | 01/02427 A1 | 1/2001 |
| WO | 01/09118 A2 | 2/2001 |
| WO | WO 01/27103 A1 | 4/2001 |
| WO | 01/32622 A1 | 5/2001 |
| WO | 01/32922 A2 | 5/2001 |
| WO | WO 01/79208 A1 | 10/2001 |
| WO | WO 02/12249 A2 | 2/2002 |
| WO | WO 02/20530 A1 | 3/2002 |
| WO | WO 02/31128 A1 | 4/2002 |
| WO | 02/066672 A2 | 8/2002 |
| WO | WO 03/016302 A1 | 2/2003 |
| WO | WO 03/039540 A2 | 5/2003 |
| WO | WO 03/063797 A2 | 8/2003 |
| WO | WO 03/074531 A1 | 9/2003 |
| WO | WO 03/074532 A1 | 9/2003 |
| WO | WO 03/091213 A1 | 11/2003 |
| WO | WO 03/092670 A1 | 11/2003 |
| WO | WO 2004/022537 A2 | 3/2004 |
| WO | WO 2004/031193 A1 | 4/2004 |
| WO | WO 2004/031194 A1 | 4/2004 |
| WO | WO 2004/039787 A1 | 5/2004 |
| WO | WO 2004/041780 A2 | 5/2004 |
| WO | WO 2004/089470 A2 | 10/2004 |
| WO | WO 2004/113345 A1 | 12/2004 |
| WO | WO 2005/013981 A1 | 2/2005 |
| WO | WO 2005/018637 A1 | 3/2005 |
| WO | WO 2005/020986 A1 | 3/2005 |
| WO | WO 2005/020987 A1 | 3/2005 |
| WO | WO 2005/046575 A2 | 5/2005 |
| WO | WO 2005/066135 A2 | 7/2005 |
| WO | WO 2005/066143 A2 | 7/2005 |
| WO | WO 2005/089753 A2 | 9/2005 |
| WO | WO 2005/123677 A1 | 12/2005 |
| WO | WO 2006/001958 A2 | 1/2006 |
| WO | WO 2006/004040 A1 | 1/2006 |
| WO | WO 2006/021000 A3 | 2/2006 |
| WO | WO 2006/077412 A1 | 7/2006 |
| WO | WO 2007/039773 A1 | 4/2007 |
| WO | WO 2007/068621 A1 | 6/2007 |
| WO | WO 2007/081542 A2 | 7/2007 |
| WO | WO 2007/081857 A2 | 7/2007 |
| WO | WO 2007/115185 A2 | 10/2007 |
| WO | WO 2008/005456 A2 | 1/2008 |
| WO | WO 2008/089453 A2 | 7/2008 |
| WO | WO 2008/151156 A1 | 12/2008 |
| WO | WO 2009/020814 A2 | 2/2009 |
| WO | WO 2010/017418 A1 | 2/2010 |

OTHER PUBLICATIONS

FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*

Byrn et al., Solid-State Chemistry of Drugs, Second Edition, 1999, pp. 233-247.*

Bobosik et al. Synthesis of *N*-Phenylsulfonyl Protected Furo[3,2-*b*] Pyroles, *Collect. Czech. Chem. Commun.* (vol. 59) pp. 499-502 (1994).

Cyranski et al. "Aromaticity of dihertero analogues of pentalene dianion. X-ray and ab initio studies of eight methyl furo[3,2-b]pyrrole-5-carboxylate derivatives and five methyl furo[2,3-b]pyrrole-5-carboxylate derivatives" Tetrahedon 57 8867-8873 (2001).

Dandarova, et al. "C NMR Spectra of Some Substituted Furo[3,2-b]pyrroles" Magnetic Resonance in Chemistry, vol. 28, 830-831 (1990).

Ferguson et al. "N-Acetyl-5,6-Dihydrofuro[3,2-b]Pyrid-2-One, $C_9H_9NO_3$" Cryst. Struct. Comm. 5, 911 (1976).

Fisera et al. "Correlation of Kinetic Data of 1,3-Dipolar Cycloadditions of C-Benzoyl-N-Phenylnitrones With the Homo Energies of Furan Derivatives" Collect. Czech. Chem. Commun. vol. 46, 1504-1512 (1981).

Fisera et al. "Cycloadditions of C-Benzoyl-N-Phenylnitrone with Furocondensed Derivatives" Collect. Czech. Chem. Commun. vol. 48, 2421-2427 (1981).

Fukuda, et al. "Tensidols, New Potentiators of Antifungal Miconazole Activity, Produced by *Aspergillus niger* FKI-2342" J. Antibiot 59(8): 480-485 (2006).

Gross et al. "Direct Observation of 1-Azafulven-6-one and Annelated Derivatives" J. Chem. Soc. Chem. Commun. p. 360-361 (1982).

Hemetsberger et al. "Synthese und Thermolyse von α-Azidoacrylestern" Monatshefte für Chemie, 103, 194-204, 1972.

Ilyin et al. "Synthesis of Annelated Azaheterocycles Containing a 5-Carbamoylpyrazin-3-one Fragment by a Modification of the Four-Component Ugi Reaction" Eur. J. Org. Chem. 4670-4679 (2005).

Java et al. "Chimie Organique—Synthese de selnolo, furo et pyrrolpyrroles" C.R. Acad. Sc. Paris, t. 281 (Nov. 10, 1975) Serie C—793-795.

Koren et al. "Structure of a Furo[s,2-b]pyrrole Derivative" Acta. Cryst. C44, 2032-2033 (1988).

Kralovicova et al., "Electrophilic Substitution Reactions of Furo[3,2-b]Pyrrole Derivatives" Collect. Czech. Chem. Commun. (vol. 51) 106-111 (1986).

Krutosikova et al. "Addition and Cycloaddition Reactions of Furo[3,2-b]-Pyrroles and Their Benzo[b] Analogues: an NMR Study of Structure of Products" Collect. Czech. Chem. Commun. (vol. 53) 1770-1778 (1988).

Krutosikova et al. "Reactions of Ethyl 2-(4-Chlorophenyl)-4H-Furo[3,2-b]Pyrrole-5-Carboxylate*" Collect. Czech. Chem. Commun. vol. 45, 2949-2957 (1980).

Krutosikova et al. "Reactions of furo[3,2-b]pyrroles and their benzol[b] analogues", Chem Papers 42 (1) 89-95 (1988).

Krutosikova et al. "Reactions of Methyl 2-Formylfuro[3,2-b]pyrrole-5-carboxylates" Chem Papers 50 (2)72-76 (1996).

Krutosikova et al. "Substituted 4-Benzylfuro [3,2-b] Pyrroles" Collect. Czech. Chem. Commun. (vol. 57) 1487-1494 (1992).

Krutosikova et al. "Substituted Vinyl Azides in the Synthesis of Condensed Nitrogen Heterocycles" Chem Papers 48 (4) 268-273 (1996).

Krutosikova et al. "Synthesis and reactions of 4-Oxiranylmethylfuro-[3,2-b]Pyrroles and their benzo derivatives*" Chem. of Heterocyclic Compounds vol. 37, No. 12, 1511-1517 (2001).

Krutosikova et al. "Synthesis and reactions of Furo[2,3-b]pyrroles" Molecules (2) 69-79 (1997).

Krutosikova et al. "Synthesis and Reactions of Furocondensed Derivatives*" Collect. Czech. Chem. Commun. (vol. 49) 65-70 (1984).

Krutosikova et al. "Synthesis and Reactions of Substituted Furo[3,2-b]Pyrrole Derivatives*" Collect. Czech. Chem. Commun. (vol. 46) 2564-2572 (1981).

New et al. "The Thieno [3.2-c]pyridine and Furo[3,2-c]pyridine rings: New Pharmacophonres with Potential Antipsychotic Activity" J. Med. Chem vol. 32, 1147-1156 (1989).

Ogawa et al. "Preparation of Oxygen-Bridged AZA[15]- and AZA[17]Annulene Dicarboxylates by Intramuscular Azide Cyclization" Tetrahedon Letters, vol. 29, No. 2, pp. 219-222, 1988.

Puterova et al. "Reaction of Substituted Furan-2-carboxaldehydes and Furo[b]pyrrole Type Aldehydes with Hippuric Acid" Molecules vol. 9, 11-21 (2004).

Puterova, et al. "Reactions of Substituted Furan-2-carboxaldehydes and Furo[b] pyrrole Type Aldehydes with Benzothiazolium Salts" Molecules vol. 9, 241-255 (2004).

Romanova et al. "DC Polarographic and UV Spectrometric Studies of Substituted Furo[3,2-b]- and Furo[2,3-b]Pyrroles" Collect. Czech. Chem. Commun. (vol. 66) 1615-1622 (2001).

Sleziak et al. "Furo[2,3-b]Pyrrole Derivatives, Syntheses and Reactions in the Furan and Pyrrole Ring" Polish J. Chem. vol. 74, 207-217 (2000).

Sleziak et al. "Reactions of Furo[2,3-b]Pyrrole and Furo[3,2-b]Pyrrole-Type Aldehydes" Collect. Czech. Chem. Commun. (vol. 64) 1135-1146 (1999).

Sorotskaya et al. "The Series of Substituted Butenolides and Butenolides. IV.* 4-Arylidene (Heteroarylidene)-2-Butenolides" Zhurnal Organicheskoi Khimiii, vol. 25, No. 1, pp. 175-182 (1989).

Soth et al. "Recherches en série hétérocylique. XXIX. Sur des voies d'accés á des tghiéno, sélénolo, furo et pyrrolopyrroles[1]" Can. J. Chem. vol. 56, 1429-1434, (1978).

Welch et al. "Improved Synthesis of [3,2-b] and [2,3-b]-fused Selenolo-and Thienopyrroles, and of Furo[3,2-b]pyrrole" Heterocyclic Communications vol. 5, No. 4, 305-310 (1999).

Foucaud, et al., "[1+4] Cycloaddition of Isocyanides with 1-Aryl-2-nitro-1-propenes, Methyl 2-Nitro-3-arylpropenoates, and Methyl 2-Nitro-2,4-pentadienoates. Synthesis of 1-Hydroxyindoles and 1-Hydroxypyrroles," J. Org. Chem., 48:3639-3644 (1983).

Gale, et al., "Preparation and Reactions of 5-Carbethoxythieno[3,2-b]pyrrole and Some of Its Derivatives," J. Organic Chem., 29:2160-2165, (1964).

Holmes, et al., "Reactions of N-Benzylthieno[3,2-b]pyrrole. I. Metalation and an Electrophilic Substitution," J. Org. Chem., 2155-2160 (Aug. 1964).

Keener, et al., "The Synthesis of 6-Substituted Thieno[3,2-b]pyrroles," J. Org. Chem., 33(4):1355-1359 (Apr. 1968).

Krayushkin, et a., "Synthesis of Photochromic 1,2-Dihetarylethene Using Regioselective Acylation of Thienopyrroles," Org. Letters, 4(22):3879-3881 (2002).

Krutosikova, et al., "Effect of Microwave Irradiation on Reaction of Furo[3,2-b]pyrrole and furo[2,3-b]pyrrole-2-carbaldehydes with some Active Methylene Compounds," Arkivcc, 1(Part 3):409-420 (2000).

Abarbri et al., "Les beta-cétonitriles groupes protecteurs de la fonction amine. Préparation d'amino-alcools", Helv. Chim. Acta 1995, 78(1), 109-121.

Aboul-Enein et al., "Synthesis and Antiemetic Profile of N-[1-[(diethylamino)methyl]cyclohexyl]amides", Sci. Pharm. 1990, 58(3), 273-280.

Alvaro et al., "Preparation and photolysis of diaryl esters of acetylenedicarboxylic acid", Tetrahedron 1992, 48(16), 3437-3444.

Ando et al., "3-(Arylacetylamino)-N-methylbenzamides: A Novel Class of Selective Anti-*Helicobacter pylori* Agents", J. Med. Chem. 2001, 44(25), 4468-4474.

Arya et al., "Synthesis of New Heterocycles: Part XV. Synthesis of Novel Cyclic and Acyclic Sulfamides", Indian J. Chem., Sec. B, 1976, 14B(10), 766-769.

Ashton et al., "Nonpeptide angiotensin II antagonists derived from 1H-pyrazole-5-carboxylates and 4-aryl-1H-imidazole-5-carboxylates", J. Med. Chem. 1993, 36(23), 3595-3605.

Aubert et al., "New cyclopenta[b]-pyrroles and -pyridines by reaction of 2-azido- and 2-phosphoranylideneaminocyclopent-1-ene-1-carbaldehydes with aliphatic esters", J. Chem. Soc. Perkin Trans. 1 1989(8), 1369-1373.

Azéma et al., "Efficient approach to acyloxymethyl esters of nalidixic acid and in vitro evaluation as intra-ocular prodrugs", Bioorg. Med. Chem. 2006, 14(8), 2569-2580.

Baba et al., "Structure-Based Design of a Highly Selective Catalytic Site-Directed Inhibitor of Ser/Thr Protein Phosphatase 2B (Calcineurin)", J. Am. Chem. Soc. 2003, 125(32), 9740-9749.

Babu et al., "Simple and facile oxidation of aldehydes to carboxylic acids", Org. Prep. Proced. Int. 1994, 26(1), 123-125.

Bagal et al., "Radicals from Aldehydes: A Convergent Access to Dienes and δ-Lactones", Synlett 2006(10), 1485-1490.

Balsamini et al., "(E)-3-(2-(N-phenylcarbamoyl)vinyl)pyrrole-2-carboxylic acid derivatives. A novel class of glycine site antagonists", J. Med. Chem. 1998, 41(6), 808-820.

Balsamini et al., "An improved route to cycloalka[b]pyrrole 2-carboxylates", Org. Prep. Proced. Int. 1997, 29(4), 471-473.

Bambury et al., "Trifluoromethylfurans II", J. Heterocycl. Chem. 1970, 7(2), 269-273.

Banekovich et al., "Synthesis and biological activities of novel dexibuprofen tetraacetylriboflavin conjugates", Bioorg. Med. Chem. Lett. 2007, 17(3), 683-687.

Banfi et al., "Synthesis of New Imidazole Derivatives as Potential Inhibitors of Thromboxane Synthetase", J. Heterocycl. Chem. 1990, 27, 215-219.

Bardakos et al., "Enhydrazine, 10. Einige aliphatische Enhydrazone", Chem. Ber. 1975, 108(7), 2161-2170.

Bartlett et al., "Evaluation of alternative approaches for the synthesis of macrocyclic bisindolylmaleimides", Org. Biomol. Chem. 2004, 2(19), 2874-2883.

BASF Corp., "Borane-tetrahydrofuran Complex (BTHF)" Product Bulletin, 2002, pp. 1-14.

Baumes et al., "No. 227.—Recherches sur les enehydrazines. VI.—Condensation de methylhydrazones de cetones sur les esters acetyleniques: synthese de carbomethoxypyrroles", Bull. Soc. Chim. Fr. 1974(5-6), 1147-1150.

Beaumont et al., "Design of Ester Prodrugs to Enhance Oral Absorption of Poorly Permeable Compounds: Challenges to the Discovery Scientist", Curr. Drug Metab. 2003, 4(6), 461-485.

Bedford et al., "Quaternary salts of 2-[(hydroxyimino)methyl]imidazole. 2. Preparation and in vitro and in vivo evaluaton of 1-(alkoxymethyl)-2-[(hydroxyimino)methyl]-3-methylimidazolium halides for reactivation of organophosphorus-inhibited acetylcholinesterases", J. Med. Chem. 1989, 32(2), 493-503.

Benson et al., "Aliphatic β-Chlorovinyl Aldoximes", J. Org. Chem. 1965, 30(4), 1126-1129.

Bergauer et al., "Practical ex-chiral-pool methodology for the synthesis of dopaminergic tetrahydroindoles", Tetrahedron 2004, 60(5), 1197-1204.

Bialer et al., "Pharmacokinetic analysis and antiepileptic activity of tetra-methylcyclopropane analogues of valpromide", Pharm. Res. 1996, 13(2), 284-289.

Biggadike et al., "Selective plasma hydrolysis of glucocorticoid gamma-lactones and cyclic carbonates by the enzyme paraoxonase: an ideal plasma inactivation mechanism." J. Med. Chem. 2000, 43(1), 19-21.

Birkofer et al., "The Use of Silylation in Organic Syntheses", Angew. Chem. Int. Ed. 1965, 4(5), 417-429.

Black, D., "Product Class 13: 1H-Pyrroles" in "Science of Synthesis: Houben-Weyl Methods of Molecular Transformations", vol. 9; Maas, G., ed.; Thieme Medical Publishers: Stuttgart, 2001; pp. 441-552.

Blanchfield et al., "The stability of lipidic analogues of GnRH in plasma and kidney preparations: the stereoselective release of the parent peptide", Bioorg. Med. Chem. Lett. 2005, 15(6), 1609-1612.

Bobbitt et al., "Organic Nitrosonium Salts. II. Stability Studies and Oxidations of Some Indole Derivatives", Heterocycles 1990, 30(2), 1131-1140.

Boeshagen et al., "Ueber 3-Acylimino-3H-1.2-benzodithiole", Chem. Ber. 1968, 101(7), 2472-2484.

Borza et al., "Selective NR1/2B N-Methyl-d-aspartate Receptor Antagonists among Indole-2-carboxamides and Benzimidazole-2-carboxamides" J. Med. Chem. 2007, 50(5), 901-914.

Braga et al., "Making crystals from crystals: a green route to crystal engineering and polymorphism", Chem. Commun. 2005(29), 3635-3645.

Bregant et al., "Orthogonally Protected Lanthionines: Synthesis and Use for the Solid-Phase Synthesis of an Analogue of Nisin Ring C", J. Org. Chem. 2005, 70(7), 2430-2438.

Brunner et al., "Asymmetrische Hydrierung von (Z)-α-(Acetylamino)-zimtsäure mit einem Rh/norphos-Katalysator", Angew. Chem. 1979, 91(8), 655-656.

Brunner-Guenat et al., "Esters of L-dopa: structure-hydrolysis relationships and ability to induce circling behaviour in an experimental model of hemiparkinsonism", J. Pharm. Pharmacol. 1995, 47(10), 861-869.

Bueno et al., "Dipeptides as effective prodrugs of the unnatural amino acid (+)-2-aminobicyclo[3.1.0]hexane-2,6-dicarboxylic acid (LY354740), a selective group II metabotropic glutamate receptor agonist." J. Med. Chem. 2005, 48(16), 5305-5320.

Bundgaard et al., "Esters of N,N-disubstituted 2-hydroxyacetamides as a novel highly biolabile prodrug type for carboxylic acid agents", J. Med. Chem 1987, 30(3), 451-454.

Cai et al., "Synthesis of 2,4,5-Trisubstituted Oxazoles", Synthesis 2005(10), 1569-1571.

Calderon et al., "Novel 1-Phenylcycloalkanecarboxylic Acid Derivatives Are Potent and Selective .sigma.1 Ligands", J. Med. Chem. 1994, 37(15), 2285-2291.

Callis et al., "A Tandem Horner—Emmons Olefination—Conjugate Addition Approach to the Synthesis of 1,5-Disubstituted-6-azabicyclo[3.2.1]octanes Based on the AE Ring Structure of the Norditerpenoid Alkaloid Methyllycaconitine", J. Org. Chem. 1996, 61(14), 4634-4640.

Cartoon et al., "Lithiation reactions of 1-(2'-bromophenyl)pyrrole and related compounds", J. Organomet. Chem. 1981, 212(1), 1-9.

Chakraborty et al., "Synthesis and characterization of Boc-protected 4-amino- and 5-amino-pyrrole-2-carboxylic acid methyl esters", Tetrahedron Lett. 2006, 47(27), 4631-4634.

Chapman et al., "The Analytical Reduction of Porphyrins to Pyrroles", Can. J. Chem. 1971, 49(21), 3544-3564.

Chaubey et al., "Kinetics of the Oxidation of Heterocyclic Aldehydes by Quinolinium Dichromate", Bull. Chem. Soc. Jpn. 2002, 75(10), 2215-2220.

Chen et al., "4,4-Difluoro-4-bora-3a,4a-diaza-s-indacene (BODIPY) Dyes Modified for Extended Conjugation and Restricted Bond Rotations", J. Org. Chem. 2000, 65(10), 2900-2906.

Chen et al., "Studies on the SAR and pharmacophore of milnacipran derivatives as monoamine transporter inhibitors", Bioorg. Med. Chem. Lett. 2008, 18(4), 1346-1349.

Chimichi et al., "New 5-(2-ethenylsubstituted)-3(2H)-furanones with in vitro antiproliferative activity", Tetrahedron 2003, 59(28), 5215-5223.

Cottineau et al., "Synthesis and hypoglycemic evaluation of substituted pyrazole-4-carboxylic acids", Bioorg. Med. Chem. Lett. 2002, 12(16), 2105-2108.

Crane et al., "A Novel Enantioselective Synthetic Route to Omuralide Analogues with the Potential for Species Selectivity in Proteasome Inhibition", Org. Lett. 2001, 3(9), 1395-1397.

Cuevas-Yañez et al., "Rhodium(II) catalyzed intramolecular insertion of carbenoids derived from 2-pyrrolyl and 3-indolyl α-diazo-β-ketoesters and α-diazoketones", Tetrahedron 2004, 60(7), 1505-1511.

Das et al., "Synthesis of some N-substituted carbazoles and their larvicidal studies", J. Indian Chem. Soc. 2005, 82, 158-160.

Database Beilstein, Beilstein Institute for Organic Chemistry, Frankfurt-Main, DE; Database Accession No. BRN: 10196160 Abstract; and Eur. J. Org. Chem. 2005(21), 4670-4679.

Database Beilstein, Beilstein Institute for Organic Chemistry, Frankfurt-Main, DE; Database Accession No. BRN: 1074598 Abstract; and Can. J. Chem. 1978, 56(10), 1429-1434.

Database Beilstein, Beilstein Institute for Organic Chemistry, Frankfurt-Main, DE; Database Accession No. BRN: 4185621 Abstract; and Collect. Czech. Chem. Commun. 1986, 51(1), 106-111.

Database Beilstein, Beilstein Institute for Organic Chemistry, Frankfurt-Main, DE; Database Accession No. BRN: 4429388 Abstract; and Collect. Czech. Chem. Commun. 1984, 49(1), 65-70.

Database Beilstein, Beilstein Institute for Organic Chemistry, Frankfurt-Main, DE; Database Accession No. BRN: 7812555 Abstract; and Collect. Czech. Chem. Commun. 1997, 62(10), 1612-1622.

Database CAPLUS on STN, Acc. No. 1977:83511, Koe, J. Pharmacol. Exp. Ther. 1976, 199(3), 649-661. [abstract].

De Luca et al., "A New, Simple Procedure for the Synthesis of Formyl Amides", Synlett 2004(14), 2570-2572.

Denmark et al., "Chiral fluoro ketones for catalytic asymmetric epoxidation of alkenes with oxone", J. Org. Chem. 2002, 67(10), 3479-3486.

Denmark et al., "Organocerium additions to SAMP-hydrazones: general synthesis of chiral amines", J. Am. Chem. Soc. 1987, 109(7), 2224-2225.

Dhanak et al., "Studies in the protection of pyrrole and indole derivatives", J. Chem. Soc., Perkin Trans. 1, 1986, 2181-2186.

Durrer et al., "Structure-metabolism relationships in the hydrolysis of nicotinate esters by rat liver and brain subcellular fractions", Pharm. Res. 1991, 8(7), 832-839.

Elghamry, "Synthesis of ethyl pyrrole-2-carboxylates: a regioselective cyclization of enaminones under knorr-type conditions", Synth. Commun. 2002, 32(6), 897-902.

Eliel, "Infelicitous stereochemical nomenclature", Chirality 1997, 9(5-6), 428-430.

El-Nagger et al., "Synthesis and Biological Activity of Some New Aminoacylcarbazole Derivatives. Part I", J. Heterocycl. Chem. 1982, 19, 1025-1028.

English et al., "Orally effective acid prodrugs of the beta-lactamase inhibitor sulbactam", J. Med. Chem. 1990, 33(1), 344-347.

Eras et al., "Reactivity of thienopyrroles. Synthesis of isomeric nitro and bromothienopyrroles", J. Heterocycl. Chem. 1984, 21(1), 215-217.

Estep, "An Efficient Synthesis of 4-Hydroxy-1H-indole-2-carbonitrile and Its Conversion to DPI 201-106", Synth. Commun. 1995, 25(4), 507-514.

Fagan et al., "A new approach to the core of roseophilin", Tetrahedron Lett. 1999, 40(33), 6117-6120.

Fischer et al., "On Benzisothiazolones: A Series with a Wide Range of Bacteriostatic and Fungistatic Activity", Arzneimittel-Forschung 1964, 14(12), 1301-1306.

Fischer et al., "Synthese einiger Pyrrole und ihre Umsetzungen", Justus Liebigs Ann. Chem. 1932, 492(1), 128-155.

Fischer et al., "Synthesen der Opso- und Hämopyrrolcarbonsäure. Neue Synthese von Koproporphyrin. II", Justus Liebigs Ann. Chem. 1928, 462(1), 240-250.

Fischer et al., "Synthesen von Koproporphyrin I und II, sowie Mesoporphyrin II, V und XII", Justus Liebigs Ann. Chem. 1928, 466(1), 147-178.

Flaugh et al., "Synthesis of porphyrins. Deoxophylloerythroetioporphyrin", J. Am. Chem. Soc. 1968, 90(24), 6877-6879.

Fraga-Dubreuil et al., "Grafted ionic liquid-phase-supported synthesis of small organic molecules", Tetrahedron Lett. 2001, 42(35), 6097-6100.

Franciò et al., "Asymmetric Catalysis with Chiral Phosphane/Phosphoramidite Ligands Derived from Quinoline (QUINAPHOS)", Angew. Chem. Int. Ed. 2000, 39(8), 1428-1430.

Frisell et al., "Flavoenzyme Catalysis. Substrate-Competitive Inhibition of D-Amino Acid Oxidase", J. Biol. Chem. 1956, 223, 75-83.

Fu et al., "Design and synthesis of novel bis(I-amino acid) ester prodrugs of 9-[2-(phosphonomethoxy)ethyl]adenine (PMEA) with improved anti-HBV activity", Bioorg. Med. Chem. Lett. 2007, 17(2), 465-470.

Gabbutt et al., "A Facile Synthesis of Some Benzothiopyrano[4,3-b]pyrroles", J. Chem. Res. (S) 1997(3), 102-103.

Gale et al., "Preparation and Reactions of 5-Carbethoxythieno[3,2-b]pyrrole and Some of Its Derivatives", J. Org. Chem. 1964, 29(8), 2160-2165.

Garg et al., "Development of an Enantiodivergent Strategy for the Total Synthesis of (+)- and (−)-Dragmacidin F from a Single Enantiomer of Quinic Acid", J. Am. Chem. Soc. 2005, 127(16), 5970-5978.

Gelas-Mialhe et al., "Photochemical heterocyclization of functionalized dienamines", J. Org. Chem. 1987, 52(24), 5395-5400.

Gelas-Mialhe et al., "Réactivité des N-vinylaziridines fonctionnalisées. Synthèse de dérivés des α,β-déhydro α-amino acides", Can. J. Chem. 1982, 60(22), 2830-2851.

Geraldine et al., "How an increase in the carbon chain length of the ester moiety affects the stability of a homologous series of oxprenolol esters in the presence of biological enzymes", J. Pharm. Sci. 1998, 87(7), 880-885.

Grygorenko et al., "Stereoselective synthesis of 2,4-methanoproline homologues", Tetrahedron Asymmetry 2006, 17(2), 252-258.

Guan et al., "Design and synthesis of aminopropyl tetrahydroindole-based indolin-2-ones as selective and potent inhibitors of Src and Yes tyrosine kinase", Bioorg. Med. Chem. Lett. 2004, 14(1), 187-190.

Haginoya et al., "Synthesis and conformational analysis of a non-amidine factor Xa inhibitor that incorporates 5-methyl-4,5,6,7-tetrahydrothiazolo[5,4-c]pyridine as S4 binding element", J. Med. Chem. 2004, 47(21), 5167-5182.

Haj-Yehia et al., "Pharmacokinetic analysis of the structural requirements for forming "stable" analogues of valpromide", Pharm. Res. 1992, 9(8), 1058-1063.

Haj-Yehia et al., "Structure-pharmacokinetic relationships in a series of valpromide derivatives with antiepileptic activity", Pharm. Res. 1989, 6(8), 683-689.

Harada et al., "A Simple Preparation of Chloromethyl Esters of the Blocked Amino Acids", Synth. Commun. 1994, 24(6), 767-772.

Harrak et al.,"PtCl2-Catalyzed Cycloisomerizations of 5-En-1-yn-3-ol Systems", J. Am. Chem. Soc. 2004, 126(28), 8656-8657.

Harrison et al., "Cyclopenta[b]indoles. Part 2. Model studies towards the tremorgenic mycotoxins", J. Chem. Soc. Perkin Trans. 1 1995(9), 1131-1136.

Harwood et al., "Tandem generation and intramolecular trapping of chiral stabilised azomethine ylids with alkyne dipolarophiles", Tetrahedron Lett. 1993, 34(41), 6603-6606.

Hauptmann et al., "Beiträge zum Reaktionsverhalten von 2-Aminovinylcarbonylverbindungen", Journal für Praktische Chemie 1972, 314(2), 353-364.

Hauptmann et al., "Eine neue Synthese substituierter Thiophene und Pyrrole", Tetrahedron Lett. 1968, 9(11), 1317-1319.

Hillenweck et al., "Chlorothalonil Biotransformation by Gastrointestinal Microflora: In Vitro Comparative Approach in Rat, Dog, and Human", Pestic. Biochem. Physiol. 1997, 58(1), 34-48.

Hilton et al., "Observations on the reactivity of thiyl radicals derived from 3,6-epidithiodiketopiperazine-2,5-diones and related congeners", Bioorg. Med. Chem. Lett. 2005, 15(9), 2239-2242.

Hoffman, R. V., "Organic Chemistry: An Intermediate Text, Second Edition"; Wiley: Hoboken, 2004; pp. 124 and 138-144.

Hori, M., "Syntheses of Analgesics. XIV. Aminocyclohexane Derivatives. 8.", Yakugaku Zasshi 1958, 78, 11-14.

Howarth et al., "Pyrroles and related compounds. Part XXVI. Pyrrole beta-keto-esters", J. Chem. Soc. Perkin Trans. 1 1974, 490-501.

Hu et al., "Synthesis of a Porphyrin with Fused Five- and Seven-membered Exocyclic Rings from a Cross-conjugated Tetracyclic Dipyrrole", Synlett 1994(11), 909-910.

Ikegami et al., "Synthesis and pharmacological activity of O-(5-isoxazolyl)-L-serine", Chem. Pharm. Bull. 2000, 48(2), 278-280.

Ingram et al., "Investigation of enzyme activity by SERRS using poly-functionalised benzotriazole derivatives as enzyme substrates", Org. Biomol. Chem. 2006, 4(15), 2869-2873.

Inukai et al., "Ortho-Disubstituted F-Benzenes. III. Preparation of (F-Benzo)heterocyclic Compounds from F-Benzoic Acid and F-Phenol, and the Reactions of Some Intermediary F-Benzoyl- and F-Phenoxy Compounds", Bull. Chem. Soc. Jpn. 1981, 54(11), 3447-3452.

Iranpoor et al., "A Rapid and Facile Conversion of Primary Amides and Aldoximes to Nitriles and Ketoximes to Amides with Triphenylphosphine and N-Chlorosuccinimide", Synth. Commun. 2002, 32(16), 2535-2541.

Isoherranen et al., "New CNS-active drugs which are second-generation valproic acid: can they lead to the development of a magic bullet?", Curr. Opin. Neurol. 2003, 16(2), 203-211.

Jacob et al., "Gamma-Aminobutyric acid esters. 2. Synthesis, brain uptake, and pharmacological properties of lipid esters of gamma-aminobutyric acid", J. Med. Chem. 1985, 28(1), 106-110.

Jolicoeur et al., "Pyrrole protection", Tetrahedron 2006, 62(50), 11531-11563.

Katritzky et al., "Efficient Conversion of Carboxylic Acids into N-Acylbenzotriazoles", Synthesis 2003(18), 2795-2798.

Katritzky et al., "Novel Synthesis of Bicycles with Fused Pyrrole, Indole, Oxazole, and Imidazole Rings", J. Org. Chem. 2004, 69(26), 9313-9315.

Katritzky et al., "Regiospecific C-Acylation of Pyrroles and Indoles Using N-Acylbenzotriazoles", J. Org. Chem. 2003, 68(14), 5720-5723.

Katterle et al., "A Heck-Type Coupling for the Synthesis of Novel Bridged Metallochlorin-Fullerene C60 Dyads", European J. Org. Chem. 2006(2), 414-422.

Kesel, "Synthesis of Novel Test Compounds for Antiviral Chemotherapy of Severe Acute Respiratory Syndrome (SARS)", Curr. Med. Chem. 2005, 12(18), 2095-2162.

Khanna et al., "Evaluation of glycolamide esters of indomethacin as potential cyclooxygenase-2 (COX-2) inhibitors", Bioorg. Med. Chem. 2006, 14(14), 4820-4833.

Kittredge et al., "Alpha-Helical Polypeptide Films Grown From Sulfide or Thiol Linkers on Gold Surfaces", Helv. Chim. Acta 2002, 85(3), 788-798.

Kleinspehn et al., "The Synthesis of Some β,β-Dipyrrylpropionic Esters", J. Am. Chem. Soc. 1954, 76(22), 5641-5646.

Koe, "Molecular geometry of inhibitors of the uptake of catecholamines and serotonin in synaptosomal preparations of rat brain", J. Pharmacol. Exp. Ther. 1976, 199(3), 649-661.

Kren et al., "Clustered ergot alkaloids modulate cell-mediated cytotoxicity", Bioorg. Med. Chem. 2002, 10(2), 415-424.

Krutosikova et al., "Synthesis and Reactions of 8-Hydrazinofuro[2',3':4,5]pyrrolo-[1,2-d][1,2,4]triazines", Collect. Czech. Chem. Commun. 1997, 62(10), 1612-1622.

Kukolja et al., "Orally absorbable cephalosporin antibiotics. 2. Structure-activity studies of bicyclic glycine derivatives of 7-aminodeacetoxycephalosporanic acid", J. Med. Chem. 1985, 28(12), 1896-1903.

Kumar et al., "Synthesis and biological evaluation of thiophene [3,2-b] pyrrole derivatives as potential anti-inflammatory agents", Bioorg. Med. Chem. 2004, 12(5), 1221-1230.

Kuo et al., "G-protein coupled receptors: SAR analyses of neurotransmitters and antagonists", J. Clin. Pharm. Ther. 2004, 29(3), 279-298.

Lamboley et al., "Synthesis and Properties of Conformationally Constrained Analogues of Floral-Type Odorants", Helv. Chim. Acta 2004, 87(7), 1767-1793.

Lash et al., "Influence of carbocyclic rings on porphyrin cyclizations: synthesis of geochemically significant cycloalkanoporphyrins", Energy Fuels 1990, 4(6), 668-674.

Lash et al., "Normal and Abnormal Heme Biosynthesis. 2.1 Synthesis and Metabolism of Type-III Pentacarboxylic Porphyrinogens: Further Experimental Evidence for the Enzymic Clockwise Decarboxylation of Uroporphyrinogen-III", J. Org. Chem. 1999, 64(2), 478-487.

Lash et al., "Porphyrins with exocyclic rings. 1. Chemistry of 4,5,6,7-tetrahydro-1H-indoles: synthesis of acetoxy derivatives, dihydroindoles, and novel porphyrins with four exocyclic rings", J. Org. Chem. 1992, 57(18), 4809-4820.

Lash et al., "Porphyrins with exocyclic rings. Part 3. A reassessment on the utility of cyclopenta[b]pyrroles in the synthesis of porphyrin molecular fossils. Preparation of three type II porphyrins related to deoxophylloerythroetioporphyrin (DPEP)", Tetrahedron 1993, 49(20), 4159-4172.

Lash et al., "Recent advances in the synthesis of porphyrins with five-membered exocyclic rings", Energy Fuels 1993, 7(2), 172-178.

Law et al., "The synthesis and chemistry of azolenines. Part 2. A general synthesis of pyrrole-2-carboxylic acid derivatives by the reaction of 2H-azirines with enamines, and the crystal and molecular structure of ethyl 3-phenyl-4,5,6,7-tetrahydroindole-2-carboxylate", J. Chem. Soc. Perkin Trans. 1 1984, 111-118.

Lee at al., "Amphiphilic amino acid copolymers as stabilizers for the preparation of nanocrystal dispersion", Eur. J. Pharm. Sci. 2005, 24(5), 441-449.

Lee et al., "An Effective and Convenient Esterification of Cephalosporin Derivatives by Using Quarternary Ammonium Salts as Catalysts", Synth. Commun. 1998, 28(23), 4345-4354.

Lerche et al., "Umsetzungen mit Monohydrazonen von Dicarbonylverbindungen, V: Umsetzungen von Hydrazonoethylidenammonium-Salzen und Hydrazonoaldehyden mit Grignard-Verbindungen", Chem. Ber. 1978, 111(3), 1195-1209.

Li et al., "Synthesis of deoxophylloerythroetioporphyrin (DPEP) and three ring homologs by an improved b-bilene methodology", Tetrahedron Lett. 1998, 39(47), 8571-8574.

Liederer et al., "Enzymes involved in the bioconversion of ester-based prodrugs", J. Pharm. Sci. 2006, 95(6), 1177-1195.

Liederer et al., "Stability of oxymethyl-modified coumarinic acid cyclic prodrugs of diastereomeric opioid peptides in biological media from various animal species including human", J. Pharm. Sci. 2005, 94(10), 2198-2206.

Liu et al., "Facile construction of the pentacyclic framework of subincanadine B. Synthesis of 20-deethylenylated subincanadine B and 19,20-dihydrosubincanadine B", Org. Lett. 2006, 8(1), 115-118.

Liu et al., "Indole-5-phenylcarbamate derivatives as human non-pancreatic secretory phospholipase A2 inhibitor", Bioorg. Med. Chem. Lett. 2005, 15(20), 4540-4542.

Liu et al., "The synthesis of camostat intermediate", Huaxue Shiji, 2006, 28(6), 371-372.

Ma et al., "Hydrolysis of angiotensin II receptor blocker prodrug olmesartan medoxomil by human serum albumin and identification of its catalytic active sites", Drug Metab. Dispos. 2005, 33(12), 1911-1919.

Majumdar et al., "α-(1H-Imidazol-1-yl)alkyl (IMIDA) carboxylic acid esters as prodrugs of carboxylic acid containing drugs", Tetrahedron Lett. 2007, 48(26), 4609-4611.

Mal et al., "Regioselective synthesis of 1-hydroxycarbazoles via anionic [4+2] cycloaddition of furoindolones: a short synthesis of murrayafoline-A", Tetrahedron Lett. 2006, 47(7), 1071-1075.

Mamber et al., "Tubulin polymerization by paclitaxel (taxol) phosphate prodrugs after metabolic activation with alkaline phosphatase", J. Pharmacol. Exp. Ther. 1995, 274(2), 877-883.

Marrel et al., "L-Dopa esters as potential prodrugs 1. Physicochemical properties", Eur. J. Med. Chem. 1985, 20(5), 459-465.

Marrel et al., "L-Dopa esters as potential prodrugs 2. Chemical and enzymatic-hydrolysis", Eur. J. Med. Chem. 1985, 20(5), 467-470.

Martin et al., "Das Diazo-chinon von PQQ als mögliches Reagenz für die Kartierung von Chinoproteinen mittels Photoaffinitätsmarkierung", Helv. Chim. Acta 1993, 76(4), 1674-1677.

Martin et al., "Do structurally similar molecules have similar biological activity?", J. Med. Chem. 2002, 45(19), 4350-4358.

McConnaughie et al., "Novel Acridine-Triazenes as Prototype Combilexins: Synthesis, DNA Binding, and Biological Activity" J. Med. Chem. 1995, 38(18), 3488-3501.

McLaughlin, "Suzuki-Miyaura Cross-Coupling of Benzylic Phosphates with Arylboronic Acids", Org. Lett. 2005, 7(22), 4875-4878.

Medforth et al., "Nonplanar distortion modes for highly substituted porphyrins", J. Am. Chem. Soc. 1992, 114(25), 9859-9869.

Meltzer et al., "The synthesis of bivalent 2β-carbomethoxy-3β-(3,4-dichlorophenyl)-8-heterobicyclo[3.2.1]octanes as probes for proximal binding sites on the dopamine and serotonin transporters", Bioorg. Med. Chem. 2008, 16(4), 1832-1841.

Mergen et al., "Antiepileptic activity of 1,3-dihexadecanoylamino-2-valproyl-propan-2-ol, a prodrug of valproic acid endowed with a tropism for the central nervous system", J. Pharm. Pharmacol. 1991, 43(11), 815-816.

Merisor et al., "Synthesis of New Derivatives in the Izoxazole Class with Potential Antimicrobial Activity", Rev. Chim. (Bucharest, Romania) 2001, 52(4), 206-209.

Miao et al., "Benzamide derivatives as blockers of Kv1.3 ion channel", Bioorg. Med. Chem. Lett. 2003, 13(6), 1161-1164.

Mikhaleva et al., "Expedient synthesis of 1-vinylpyrrole-2-carbaldehydes", Tetrahedron Lett. 2006, 47(22), 3693-3696.

Miki et al., "Synthesis of 3-Methoxyellipticine and Ellipticine by Friedel-Crafts Reaction of Indole-2,3-dicarboxylic Anhydride and Selective Demethylation", Heterocycles 2005, 65(11), 2693-2703.

Milkiewicz et al., "Synthesis of a novel series of tetra-substituted furan[3,2-b]pyrroles", Tetrahedron Lett. 2003, 44(22), 4257-4260.

Mishra et al., "Synthesis, characterization and pharmacological evaluation of amide prodrugs of ketorolac", Eur. J. Med. Chem. 2008, 43(11), 2464-2472.

Mokhallalati et al., "A single-pot synthesis of 1,1,2-trisubstituted 1,2-dihydronaphthalenes in high enantiomeric purity", Tetrahedron Lett. 1994, 35(25), 4267-4270.

Montero et al., "Solid-Phase Combinatorial Synthesis of Peptide-Biphenyl Hybrids as Calpain Inhibitors", Org. Lett. 2004, 6(22), 4089-4092.

Morgan et al., "Synthesis of hydrocarbon-strapped porphyrins containing quinone and phenolic groups", J. Org. Chem. 1987, 52(24), 5364-5374.

Morissette et al., "High-throughput crystallization: polymorphs, salts, co-crystals and solvates of pharmaceutical solids", Adv. Drug Deliv. Rev. 2004, 56(3), 275-300.

Mork et al., "Stereoselective enzymatic hydrolysis of various ester prodrugs of ibuprofen and flurbiprofen in human plasma", Pharm. Res. 1992, 9(4), 492-496.

Muchowski et al., "Protecting groups for the pyrrole and indole nitrogen atom. The [2-(trimethylsilyl)ethoxy]methyl moiety. Lithiation of 1-[[2-(trimethylsilyl)ethoxy]methyl]pyrrole", J. Org. Chem. 1984, 49(1), 203-205.

Murakami et al., "The Friedel-Crafts Acylation of Ethyl Pyrrole-2-carboxylate. Scope, Limitations, and Application to Synthesis of 7-Substituted Indoles", Heterocycles 1988, 27(8), 1855-1860.

Nacci et al., "Polycondensed Heterocycles. I. Synthesis of 11-Oxo-5H,11H-pyrrolo[2,1-c][1,4]benzothiazepine, Derivative of a Novel Ring System", J. Heterocycl. Chem. 1985, 22(2), 259-263.

Nacci et al., "Polycondensed Heterocycles. II. A New Preparative Route to 11-Oxo-5H,11H-pyrrolo[2,1-c][1,4]benzothiazepine", J. Heterocycl. Chem. 1986, 23(3), 769-773.

Nagarathnam et al., "Design and Synthesis of Novel α1a Adrenoceptor-Selective Dihydropyridine Antagonists for the Treatment of Benign Prostatic Hyperplasia", J. Med. Chem. 1998, 41(26), 5320-5333.

Nagel et al., "Enantioselektive Katalyse, 4. Synthese N-substituierter (R,R)-3,4-Bis(diphenylphosphino)-pyrrolidine und Anwendung ihrer Rhodiumkomplexe zur asymmetrischen Hydrierung von α-(Acylamino)acrylsäure-Derivaten", Chem. Ber. 1986, 119(11), 3326-3343.

Narasimhan et al., "A QSAR approach for the prediction of stability of benzoglycolamide ester prodrugs", Chem. Pharm. Bull. 2006, 54(8), 1067-1071.

Nelson et al., "Stereoselective Synthesis of a Potent Thrombin Inhibitor by a Novel P2-P3 Lactone Ring Opening", J. Org. Chem. 2004, 69(11), 3620-3627.

Newman-Evans et al., "The influence of intramolecular dynamics on branching ratios in thermal rearrangements", J. Org. Chem. 1990, 55(2), 695-711.

Nielsen et al., "Bioreversible quaternary N-acyloxymethyl derivatives of the tertiary amines bupivacaine and lidocaine—synthesis, aqueous solubility and stability in buffer, human plasma and simulated intestinal fluid", Eur. J. Pharm. Sci. 2005, 24(5), 433-440.

Nielsen et al., "Glycolamide esters as biolabile prodrugs of carboxylic acid agents: Synthesis, stability, bioconversion, and physicochemical properties", J. Pharm. Sci. 1988, 77(4), 285-298.

Nudelman et al., "Novel anticancer prodrugs of butyric acid. 2.", J. Med. Chem. 1992, 35(4), 687-694.

Nudelman et al., "The role of intracellularly released formaldehyde and butyric acid in the anticancer activity of acyloxyalkyl esters." J. Med. Chem. 2005, 48(4), 1042-1054.

Ojida et al., "Highly Enantioselective Reformatsky Reaction of Ketones: Chelation-Assisted Enantioface Discrimination", Org. Lett. 2002, 4(18), 3051-3054.

Ouyang et al., "Steric hindrance is a key factor in the coupling reaction of (acyloxy) alkyl-α-halides with phenols to make a new promoiety for prodrugs", Tetrahedron Lett. 2002, 43(4), 577-579.

Paine et al., "Regioselectivity of pyrrole synthesis from diethyl aminomalonate and 1,3-diketones: further observations", J. Org. Chem. 1987, 52(18), 3986-3993.

Parikh et al., "The Use of Amino Acid Oxidases for the Small-scale Preparation of the Optical Isomers of Amino Acids", J. Am. Chem. Soc. 1958, 80(4), 953-958.

Paxéus et al., "Screening for non-regulated organic compounds in municipal wastewater in Göteborg, Sweden", Water Sci. Technol. 1996, 33(6), 9-15.

Pérez-Balderas et al., "Synthesis of multivalent neoglycoconjugates by 1,3 dipolar cycloaddition of nitrile oxides and alkynes and evaluation of their lectin-binding affinities", Tetrahedron 2005, 61(39), 9338-9348.

Pfeiffer et al., "Synthesen und Eigenschaften von Pyrrolindigo-Verbindungen", Liebigs Ann. Chem. 1980(4), 564-589.

Poszavacz et al., "New Synthesis of Naratriptan", Heterocycles 2006, 68(4), 713-719.

Quizon-Colquitt et al., "Porphyrins with exocyclic rings. Part 4. An improved one step synthesis of cyclopenta[b]pyrroles", J. Heterocycl. Chem. 1993, 30(2), 477-482.

Rautio et al., "Synthesis and in Vitro Evaluation of Novel Morpholinyl- and Methylpiperazinylacyloxyalkyl Prodrugs of 2-(6-Methoxy-2-naphthyl)propionic Acid (Naproxen) for Topical Drug Delivery", J. Med. Chem. 2000, 43(8), 1489-1494.

Rodriguez et al., "Conformational and molecular study of the 4-(2-carboxyethyl)-1,2,3,4-tetrahydrocyclopent[b]indole", Tetrahedron 1985, 41(18), 3813-3823.

Rosati et al., "Cephalosporins to carbapenems: 1-oxygenated carbapenems and carbapenams.", J. Med. Chem. 1990, 33(1), 291-297.

Rose et al., "Preclinical antitumor activity of water-soluble paclitaxel derivatives", Cancer Chemother. Pharmacol. 1997, 39(6), 486-492.

Salim et al., "Pharmacokinetic analysis of esteric prodrugs of valproic acid", Pharm. Res. 1990, 7(9), S222.

Sambasivarao et al., "Synthetic approach to pentaleno[2,1-b:5,4-b']diindoles", J. Org. Chem. 1990, 55(12), 3858-3866.

Sandham et al., "Synthesis and biological properties of novel glucocorticoid androstene C-17 furoate esters", Bioorg. Med. Chem. 2004, 12(19), 5213-5224.

Sandler et al., "Organic Functional Group Preparations", vol. 3; Academic Press: New York, 1972; pp. 372-381.

Satake et al., "The Reaction of Electron Excess Aromatic Heterocycle, 1,4-Dihydropyrrolo[3,2-b]pyrrole and Some Related Compounds with Chlorosulfonyl Isocyanate (CSI)", Heterocycles 1996, 43(11), 2361-2365.

Scott et al., "Preparation and Reductive Cyclization of Some Carbon-Alkylated Derivatives of Ethyl 3-Nitro-2-thienylpyruvate", J. Org. Chem. 1964, 29(8), 2165-2168.

Sergievskaya et al., "N-Bis(chloroethyl)amines with Alicyclic and Aromatic Radicals in the Molecules. II.", Zhurnal Obshchei Khimii 1958, 28, 1845-1849. [translation].

Severin et al., "Umsetzungen von Ketonen mit azavinylogen Säureamiden", Chem. Ber. 1975, 108(5), 1756-1767.

Sewald et al., "Synthesis of homochiral camphor annulated pyrrole derivatives", Tetrahedron Asymmetry 1996, 7(5), 1269-1272.

Sha et al., "Synthesis of 2,4-Dihydropyrrolo[3,4-b]pyrroles and 4,6-Dihydro-2H-dipyrrolo[3,4-b:3',4'-d]pyrroles", Heterocycles 1990, 31(4), 603-609.

Shaaya et al., "Anhydride prodrugs for nonsteroidal anti-inflammatory drugs", Pharm. Res. 2003, 20(2), 205-211.

Shek, "Chemical delivery systems and prodrugs of anticonvulsive drugs", Adv. Drug Deliv. Rev. 1994, 14(2-3), 227-241.

Shirai et al., "Reduction of 1-(m-methoxyphenyl)-4-oxocycloalkanecarbonitriles with lithium aluminum hydride", Nagoya-shiritsu Daigaku Yakugakubu Kenkyu Nenpo 1969, 17, 33-37.

Shirai et al., "Synthesis of spiro[4-hydroxycyclohexane-1,4,2',3'-dihydro-6'-methoxy-1'-substituted-2'-methyl-1'H-isoquinoline]", Chem. Pharm. Bull. 1972, 20(1), 41-46.

Shvedov et al., "Monoarylhydrazones of di- and tricarbonyl compounds in the Knorr synthesis of pyrroles", Khimiya Geterotsiklicheskikh Soedinenii 1972(3), 342-344. [translation].

Silvestri et al., "Simple, short peptide derivatives of a sulfonylindolecarboxamide (L-737,126) active in vitro against HIV-1 wild type and variants carrying non-nucleoside reverse transcriptase inhibitor resistance mutations.", J. Med. Chem. 2004, 47(15), 3892-3896.

Skolnick et al., "Antidepressant-like actions of DOV 21,947: a "triple" reuptake inhibitor", Eur. J. Pharmacol. 2003, 461(2-3), 99-104.

Slawik et al., "Lipophilicity of a series of 1,2-benzisothiazol-3(2H)-ones determined by reversed-phase thin-layer chromatography", J. Chromatogr. A 2002, 952(1-2), 295-299.

Sleath et al., "Synthesis of 7,9-didecarboxymethoxatin (4,5-dihydro-4,5-dioxo-1H-pyrrolo[2,3-f]quinoline-2-carboxylic acid) and comparison of its chemical properties with those of methoxatin and analogous o-quinones. Model studies directed toward the action of PQQ requiring bacterial oxidoreductases and mammalian plasma amine oxidase", J. Am. Chem. Soc. 1985, 107(11), 3328-3338.

Smith et al., "Deacylation and deformylation of pyrroles", J. Org. Chem. 1983, 48(24), 4779-4781.

Snyder et al., "Synthesis of the Thieno [3,2-b]pyrrole System", J. Am. Chem. Soc. 1957, 79(10), 2556-2559.

Sohma et al., "Controlled Drug Release: Design and Application of New Water-soluble Prodrugs" in "Peptide Science 2001"; Aoyagi, H., Ed.; The Japanese Peptide Society, 2002; pp. 249-252.

Sparey et al., "The discovery of fused pyrrole carboxylic acids as novel, potent d-amino acid oxidase (DAO) inhibitors", Bioorg. Med. Chem. Lett. 2008, 18(11), 3386-3391.

STN Registry File No. 67268-37-5. Registry File. Retrieved from STN Mar. 17, 2008. One page.

Stuart et al., "Cobalt-mediated Alkylation of Siloxy Furans", Heterocycles 1991, 32(5), 949-963.

Svahn et al., "Tranexamic acid derivatives with enhanced absorption", J. Med. Chem. 1986, 29(4), 448-453.

Takahashi et al., "Asymmetric α-Substituted Phenethylamines. I. Synthesis of Optically Pure 1-Aryl-N-(2'-hydroxy-1'-isopropylethyl)-2-phenylethylamines", Chem. Pharm. Bull. 1982, 30(9), 3160-3166.

Tammara et al., "Morpholinoalkyl ester prodrugs of diclofenac: synthesis, in vitro and in vivo evaluation", J. Pharm. Sci. 1994, 83(5), 644-648.

Treibs et al., "Über einige Pyrrolderivate mit angegliedertem isocyclischem Ring. Bz-Tetrahydrindole und Cyclopentenopyrrole", Justus Liebigs Ann. Chem. 1935, 517, 152-169.

Trost et al., "Palladium-Catalyzed Enantioselective C-3 Allylation of 3-Substituted-1H-Indoles Using Trialkylboranes", J. Am. Chem. Soc. 2006, 128(19), 6314-6315.

Ueda et al., "Novel water soluble phosphate prodrugs of taxol® possessing in vivo antitumor activity", Bioorg. Med. Chem. Lett. 1993, 3(8), 1761-1766.

Ueda et al., "Novel, water-soluble phosphate derivatives of 2'-ethoxy carbonylpaclitaxel as potential prodrugs of paclitaxel: Synthesis and antitumor evaluation", Bioorg. Med. Chem. Lett. 1995, 5(3), 247-252.

Urbach et al., "Eine einfache diastereoselektive Synthese von (1SR,3SR,5SR)-2-Azabicyclo [3.3.0] octan-3-carbonsäure", Tetrahedron Lett. 1985, 26(15), 1839-1842.

van Herk et al., "Pyrazole Derivatives as Partial Agonists for the Nicotinic Acid Receptor", J. Med. Chem. 2003, 46(18), 3945-3951.

Vicini et al., "Biological studies on 1,2-benzisothiazole derivatives. I. Evaluation of antibacterial, antifungal and DNA-damaging activity", Farmaco 1989, 44(5), 511-517.

Vicini et al., "Sintesi e proprieta antiflogistiche antipiretiche ed analgesiche di 5-(1,2-benzisotiazolil)tetrazoli", Farmaco Sci. 1986, 41(2), 111-118.

Vicini et al., "Sintesi e proprieta antiflogistiche antipiretiche ed analgesiche di acidi 5-benzisotiazolilalcanoici e di loro derivati funzionali", Farmaco Sci. 1984, 39(10), 817-829.

Vippagunta et al., "Crystalline solids", Adv. Drug Deliv. Rev. 2001, 48(1), 3-26.

Viswanathan et al., "Free Radical-Mediated Aryl Amination and Its Use in a Convergent [3+2] Strategy for Enantioselective Indoline α-Amino Acid Synthesis", J. Am. Chem. Soc. 2003, 125(1), 163-168.

Vitali et al., "Ricerche nella classe dei fitocidi 3-benzisotiazolacetici", Farmaco Sci. 1973, 28(1), 8-18.

Vogel et al., "Cycloalkano-2H-pyrrole als stabile Zwischenstufen bei der Umwandlung von β-Cycloalkenyl-α-azidoacrylestern in Cycloalkano-1H-pyrrole", Angew. Chem. 1993, 105(7), 1116-1117.

Vogel et al., "Cycloalkano-2H-pyrrole as a Stable Intermediate in the Conversion of beta-Cycloalkenyl-alpha-azidoacrylates to Cycloalkano-1H pyrroles", Angew. Chem. Int. Ed. Engl. 1993, 32(7), 1051-1052. [translation of Angew. Chem. 1993, 105(7), 1116-1117.].

Wang et al., "Synthesis of ethyl cyclopenteno- or cyclohexeno[b]pyrrolyl-2-carboxylates", Youji Huaxue 1997, 17(6), 524-528.

Watanabe et al., "Enantioselective addition of chirally modified allylboranes to N-(trimethylsilyl)benzaldehyde imine", Tetrahedron Asymmetry 1995, 6(7), 1531-1534.

Wen et al., "Cell differentiation enhancement by hydrophilic derivatives of 4,8-Dihydrobenzo[1,2-b:5,4-b']dithiophene-4,8-diones in HL-60 leukemia cells", Bioorg. Med. Chem. Lett. 2007, 17(10), 2908-2912.

Wensbo et al., "Indole-3-Acetic Acids and Hetero Analogues by One Pot Synthesis including Heck Cyclisation", Tetrahedron 1995, 51(37), 10323-10342.

Wensbo et al., "Indole-3-pyruvic acid oxime ethers and thieno analogues by Heck cyclisation. Application to the synthesis of thia-tryptophans", Tetrahedron 1996, 52(47), 14975-14988.

Wernly-Chung et al., "Structure-reactivity relationships in the chemical hydrolysis of prodrug esters of nicotinic acid", Int. J. Pharm. 1990, 63(2), 129-134.

West, A. R., "Solid State Chemistry and Its Applications"; Wiley: New York, 1988; pp. 358 and 365.

Wright et al., "Derivatives of 11-(1-piperazinyl)-5H-pyrrolo[2,1-c][1,4]benzodiazepine as central nervous system agents", J. Med. Chem. 1980, 23(4), 462-465.

Xue et al., "An Efficient Synthesis of Glycoprotein IIb/IIIa Inhibitor DMP728. A Novel Synthesis of N.alpha.-Methylarginine-Containing Peptide", J. Org. Chem. 1995, 60(4), 946-952.

Yardley et al., "2-Phenyl-2-(1-hydroxycycloalkyl)ethylamine derivatives: synthesis and antidepressant activity", J. Med. Chem. 1990, 33(10), 2899-2905.

Yarovenko et al., "Regioselective acylation of methyl 2-methyl-4H-thieno[3,2-b]pyrrole-5-carboxylate", Russ. Chem. Bull., Int. Ed., 2003, 52(2), 451-456.

Yasuhara et al., "Prodrugs of 3-(3,4-dichlorobenzyloxy)-2-amino-6-fluorobicyclo[3.1.0]hexane-2,6-dicarboxylic acid (MGS0039): A potent and orally active group II mGluR antagonist with antidepressant-like potential", Bioorg. Med. Chem. 2006, 14(12), 4193-4207.

Yevich et al., "Synthesis and biological evaluation of 1-(1,2-benzisothiazol-3-yl)- and (1,2-benzisoxazol-3-yl)piperazine derivatives as potential antipsychotic agents", J. Med. Chem. 1986, 29(3), 359-369.

Yu et al., "The regiospecific C-4 lithiation of 2-(tert-butyldimethylsilyl)-3-furoic acid", J. Chem. Soc., Perkin Trans. 1, 1991(10), 2600-2601.

Yudina et al., "Synthesis and alkylation of indolo[3,2-b]carbazoles", Tetrahedron 2003, 59(8), 1265-1275.

Zani et al., "Biological studies on 1,2-benzisothiazole derivatives. VI. Antimicrobial activity of 1,2-benzisothiazole and 1,2-benzisothiazolin-3-one derivatives and of some corresponding 1,2-benzisoxazoles", Farmaco 1996, 51(11), 707-713.

Zaragoza Dörwald, F., "Side Reactions in Organic Synthesis"; Wiley-VCH: Weinheim, 2005; pp. IX and 41.

Zhang et al., "Synthesize the china 3-pyridyl ester analogs of anaddicted analgesic Epibatidine", Journal of Shangqiu Teachers College (Shangqiu Shifan Xueyuan Xuebao) 2004, 20(5), 90-94.

Zhang et al., "Total synthesis of the porphyrin mineral abelsonite and related petroporphyrins with five-membered exocyclic rings", Tetrahedron Lett. 2003, 44(39), 7253-7256.

Zinoune et al., "Aminoalkylation of Aldehydes with Glyoxal N,N-Dimethlmonohydrazone Yields Stable 4-Substituted Pyrrolin-3-ones", Heterocycles 1989, 28(2), 1077-1084.

Zong et al., "A new and efficient synthetic route toward 3,4-alkylenedioxypyrrole (XDOP) derivatives via Mitsunobu chemistry", Tetrahedron Lett. 2006, 47(21), 3521-3523.

Babu et al., "Indium trichloride (InCl3)catalyzed imino Diels-Alder reactions: An efficient synthesis of cyclopentaquinolines, azabicyclooctanones and azabicyclononanones", Tetrahedron 1998, 54(8), 1627-1638.

Bertolini et al., "Dopamine receptor agonists. I. Synthesis and pharmacological evaluation of 4-aryl-substituted analogues of 6,7-dihydroxy-2-amino tetralin (6,7-ADTN) and related indane compounds", Eur. J. Med. Chem. 1992, 27(7), 663-672.

Database CAPLUS on STN, Acc. No. 1993:233604, Bertolini et al., Eur. J. Med. Chem. 1992, 27(7), 663-672. [abstract].

Di Fabio et al., "Synthesis and pharmacological characterization of a conformationally restrained series of indole-2-carboxylates as in vivo potent glycine antagonists", Farmaco 2001, 56(10), 791-798.

Fonda et al., "D-Amino Acid Oxidase: II. Studies of Substrate-Competitive Inhibitors", J. Biol. Chem. 1968, 243(8), 1931-1935.

Hamilton et al., "The inhibition of mammalian D-amino acid oxidase by metabolites and drugs. Inferences concerning physiological function", Bioorg. Chem. 1982, 11(3), 350-370.

Hashimoto et al., "Free D-serine, D-aspartate and D-alanine in central nervous system and serum in mutant mice lacking D-amino acid oxidase", Neurosci. Lett. 1993, 152(1-2), 33-36.

Huettner, "Indole-2-carboxylic acid: a competitive antagonist of potentiation by glycine at the NMDA receptor", Science 1989, 243(4898), 1611-1613.

Klein, "Inhibition of D-Amino Acid Oxidase by Aromatic Acids", J. Biol. Chem. 1953, 205, 725-730.

Micheli et al., "Cycloalkyl Indole-2-Carboxylates as Useful Tools for Mapping the "North-Eastern" Region of the Glycine Binding Site Associated with the NMDA Receptor", Arch. Pharm. Pharm. Med. Chem. 1999, 332(3), 73-80.

Micheli et al., "Substituted Indole-2-carboxylates as Potent Antagonists of the Glycine Binding Site Associated with the NMDA Receptor", Arch. Pharm. Pharm. Med. Chem. 1999, 332(8), 271-278.

Moreno et al., "Inhibition of D-amino acid oxidase by α-keto acids analogs of amino acids", Enzyme Microb. Technol. 1996, 18(5), 379-382.

Mothet et al., "D-Serine is an endogenous ligand for the glycine site of the N-methyl-d-aspartate receptor", Proc. Natl. Acad. Sci. U.S.A. 2000, 97(9), 4926-4931.

Mothet, "Physiological relevance of endogenous free D-serine in the mammalian brain: are scientists on a royal road for the treatment of glutamatergic-related brain disorders?", Pathol. Biol. (Paris) 2001, 49(8), 655-659.

Smith et al., "Effects of the excitatory amino acid receptor antagonists kynurenate and indole-2-carboxylic acid on behavioral and neurochemical outcome following experimental brain injury", J. Neurosci. 1993, 13(12), 5383-5392.

Snyder et al., "D-amino acids as putative neurotransmitters: focus on D-serine", Neurochem. Res. 2000, 25(5), 553-560.

Stark et al., "Struktur, Funktion und potentielle therapeutische Bedeutung von NMDA-Rezeptoren. Teil 2: Therapiekonzepte und neue Rezeptorliganden", Pharm. Unserer Zeit 2000, 29(4), 228-236.

Tanaka et al., "Interaction of Steroids with D-Amino Acid Oxidase", Biochim. Biophys. Acta 1978, 522, 43-48.

Tsai et al., "D-serine added to antipsychotics for the treatment of schizophrenia", Biol. Psychiatry 1998, 44(11), 1081-1089.

Wake et al., "Exaggerated responses to chronic nociceptive stimuli and enhancement of N-methyl-D-aspartate receptor-mediated synaptic transmission in mutant mice lacking D-amino-acid oxidase", Neurosci. Lett. 2001, 297(1), 25-28.

STN - Registry file (RN 132857-67-1, RN 109252-80-4, RN 93144-92-4, RN 92321-04-5, RN 83957-46-4, RN 83957-32-8, RN 69740-90-5, RN 69640-94-4, RN 69640-90-0, RN 69640-89-7, RN 69640-88-6, RN 69640-87-5, RN 69640-86-4, RN 69640-85-3, RN 69640-84-2, RN 69640-83-1, RN 69640-82-0, RN 69640-80-8, RN 67313-00-2, RN 67312-99-6, RN 67312-98-5, RN 60068-34-0, RN 60068-33-9, RN 60068-32-8, RN 58379-13-8, RN 57955-60-9, RN 57955-59-6, RN 51074-73-8, RN 51074-72-7, RN 51074-71-6, RN 51074-69-2, RN 36373-65-6, RN 36373-63-4, RN 34779-69-6, RN 34779-67-4, RN 33317-36-1, RN 33317-33-8). [earliest date entered STN Nov. 16, 1984].

* cited by examiner

FLUORO-SUBSTITUTED INHIBITORS OF D-AMINO ACID OXIDASE

CROSS-REFERENCES TO RELATED APPLICATIONS

This application claims priority under 35 U.S.C. §119(e) to U.S. Provisional Patent Application No. 60/806,391 filed on Jun. 30, 2006, U.S. Provisional Patent Application No. 60/842,465 filed on Sep. 5, 2006, and U.S. Provisional Patent Application No. 60/914,293 filed on Apr. 26, 2007 each of which is incorporated herein by reference in its entirety for all purposes.

FIELD OF THE INVENTION

This invention relates to enzyme inhibitors and methods of treating diseases and conditions, wherein modulation of D-amino acid oxidase activity, D-serine levels, D-serine oxidative products and NMDA receptor activity in the nervous system of a mammalian subject is effective, along with a reduction in undesirable side effects.

BACKGROUND OF THE INVENTION

The enzyme D-amino acid oxidase (DAAO) metabolizes D-amino acids, and in particular, metabolizes D-serine in vitro at physiological pH. DAAO is expressed in the mammalian brain and periphery. D-Serine's role as a neurotransmitter is important in the activation of the N-methyl-D-aspartate (NMDA) selective subtype of the glutamate receptor, an ion channel expressed in neurons, here denoted as NMDA receptor.

NMDA receptors mediate many physiological functions. NMDA receptors are complex ion channels containing multiple protein subunits that act either as binding sites for transmitter amino acids and/or as allosteric regulatory binding sites to regulate ion channel activity. D-serine, released by glial cells, has a distribution similar to NMDA receptors in the brain and acts as an endogenous ligand of the allosteric "glycine" site of these receptors (Mothet et al., *PNAS,* 97:4926 (2000)), the occupation of which is required for NMDA receptor operation. D-serine is synthesized in brain through serine racemase and degraded by D-amino oxidase (DAAO) after release.

Small organic molecules, which inhibit the enzymatic cycle of DAAO, may control the levels of D-serine, and thus influence the activity of the NMDA receptor in the brain. NMDA receptor activity is important in a variety of disease states, such as schizophrenia, psychosis, ataxias, ischemia, several forms of pain including neuropathic pain, and deficits in memory and cognition.

DAAO inhibitors may also control production of toxic metabolites of D-serine oxidation, such as hydrogen peroxide and ammonia. Thus, these molecules may influence the progression of cell loss in neurodegenerative disorders. Neurodegenerative diseases are diseases in which CNS neurons and/or peripheral neurons undergo a progressive loss of function, usually accompanied by (and perhaps caused by) a physical deterioration of the structure of either the neuron itself or its interface with other neurons. Such conditions include Parkinson's disease, Alzheimer's disease, Huntington's disease and neuropathic pain. N-methyl-D-aspartate (NMDA)-glutamate receptors are expressed at excitatory synapses throughout the central nervous system (CNS). These receptors mediate a wide range of brain processes, including synaptic plasticity, that are associated with certain types of memory formation and learning. NMDA-glutamate receptors require binding of two agonists to induce neurotransmission. One of these agonists is the excitatory amino acid L-glutamate, while the second agonist, at the so-called "strychnine-insensitive glycine site", is now thought to be D-serine. In animals, D-serine is synthesized from L-serine by serine racemase and degraded to its corresponding ketoacid by DAAO. Together, serine racemase and DAAO are thought to play a crucial role in modulating NMDA neurotransmission by regulating CNS concentrations of D-serine.

Known inhibitors of DAAO include benzoic acid, pyrrole-2-carboxylic acids, and indole-2-carboxylic acids, as described by Frisell, et al., *J. Biol. Chem.,* 223:75-83 (1956) and Parikh et al., *JACS,* 80:953 (1958). Indole derivatives and particularly certain indole-2-carboxylates have been described in the literature for treatment of neurodegenerative disease and neurotoxic injury. EP 396124 discloses indole-2-carboxylates and derivatives for treatment or management of neurotoxic injury resulting from a CNS disorder or traumatic event or in treatment or management of a neurodegenerative disease. Several examples of traumatic events that may result in neurotoxic injury are given, including hypoxia, anoxia, and ischemia, associated with perinatal asphyxia, cardiac arrest or stroke. Neurodegeneration is associated with CNS disorders such as convulsions and epilepsy. U.S. Pat. Nos. 5,373,018; 5,374,649; 5,686,461; 5,962,496 and 6,100,289, to Cugola, disclose treatment of neurotoxic injury and neurodegenerative disease using indole derivatives. None of the above references mention improvement or enhancement of learning, memory or cognition.

WO 03/039540 to Heefner et al. and U.S. Patent Application Nos. 2005/0143443 to Fang et al. and 2005/0143434 to Fang et al. disclose DAAO inhibitors, including indole-2-carboxylic acids, and methods of enhancing learning, memory and cognition as well as methods for treating neurodegenerative disorders. Patent Application No. WO/2005/089753 discloses benzisoxazole analogs and methods of treating mental disorders, such as Schizophrenia. However, a need for additional drug molecules that are effective in treating memory defects, impaired learning, loss of cognition, and other symptoms related to NMDA receptor activity, remains. The present invention addresses this and other needs.

SUMMARY OF THE INVENTION

The invention provides novel inhibitors of D-amino acid oxidase that are useful in the prevention and treatment of a variety of diseases and/or conditions including neurological disorders, pain, ataxia and convulsion.

In a first aspect, the present invention provides a compound having a structure according to Formula (I):

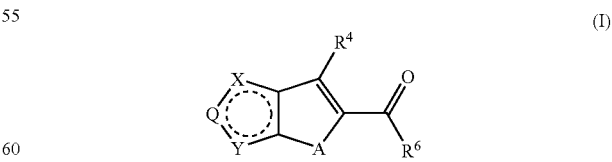

wherein A is NH or S. Q is a member selected from $CR^1$ and N. X and Y are members independently selected from O, S, $CR^2$, N and NH. $R^1$, $R^2$ and $R^4$ are members independently selected from H and F, with the proviso that at least one member selected from $R^1$, $R^2$ and $R^4$ is F. $R^6$ is a member selected from O⁻X⁺ and OH, wherein X⁺ is a positive ion, which is a member selected from inorganic positive ions and organic positive ions. In one embodiment, in which Q is CF, and one member selected from X and Y is S and the other member is CH, $R^4$ is preferably other than H.

In a second aspect, the invention provides a compound having a structure according to Formula (II):

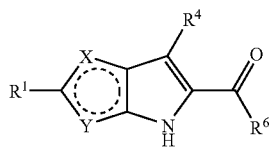

wherein one member selected from X and Y is O or S and the other member is $CR^2$. $R^1$, $R^2$ and $R^4$ are members independently selected from H and F, provided that at least one member selected from $R^1$, $R^2$ and $R^4$ is F. $R^6$ is a member selected from O⁻X⁺ and OH, wherein X⁺ is a positive ion, which is a member selected from inorganic positive ions and organic positive ions. In one embodiment, in which $R^1$ is F, X is S and Y is CH, $R^4$ is preferably other than H.

In a third aspect, the invention provides a pharmaceutical composition comprising a compound according to Formula (I) or a pharmaceutically acceptable salt, hydrate or prodrug thereof and a pharmaceutically acceptable carrier:

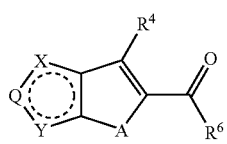

wherein A is NH or S. Q is a member selected from $CR^1$ and N. X and Y are members independently selected from O, S, $CR^2$, N and NH. $R^1$, $R^2$ and $R^4$ are members independently selected from H and F, provided that at least one member selected from $R^1$, $R^2$ and $R^4$ is F. $R^6$ is a member selected from O⁻X⁺ and OH, wherein X⁺ is a positive ion, which is a member selected from inorganic positive ions and organic positive ions.

In a fourth aspect, the invention provides a method for treating or preventing a condition, which is a member selected from a neurological disorder, pain, ataxia and convulsion. The method includes administering to a subject in need thereof a therapeutically effective amount of a compound of Formula (I) or a pharmaceutically acceptable salt, hydrate or prodrug thereof:

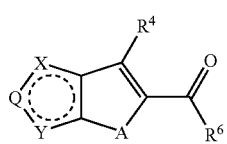

wherein A is NH or S. Q is a member selected from $CR^1$ and N. X and Y are members independently selected from O, S, $CR^2$, N and NH. $R^1$, $R^2$ and $R^4$ are members independently selected from H and F, provided that at least one member selected from $R^1$, $R^2$ and $R^4$ is F. $R^6$ is a member selected from O⁻X⁺ and OH, wherein X⁺ is a positive ion, which is a member selected from inorganic positive ions and organic positive ions.

DETAILED DESCRIPTION OF THE INVENTION

I. Definitions

Where substituent groups are specified by their conventional chemical formulae, written from left to right, they equally encompass the chemically identical substituents, which would result from writing the structure from right to left, e.g., —CH₂O— is intended to also recite —OCH₂—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl" with the difference that the heteroalkyl group, in order to qualify as an alkyl group, is linked to the remainder of the molecule through a carbon atom. Alkyl groups that are limited to hydrocarbon groups are termed "homoalkyl".

The term "alkenyl" by itself or as part of another substituent is used in its conventional sense, and refers to a radical derived from an alkene, as exemplified, but not limited, by substituted or unsubstituted vinyl and substituted or unsubstituted propenyl. Typically, an alkenyl group will have from 1 to 24 carbon atoms, with those groups having from 1 to 10 carbon atoms being preferred.

The term "alkylene" by itself or as part of another substituent means a divalent radical derived from an alkane, as exemplified, but not limited, by —CH₂CH₂CH₂CH₂—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S, B and P and wherein the nitrogen and sulfur atoms may optionally be oxidized and the nitrogen heteroatom may optionally be quaternized. The heteroatom(s) may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent may be attached to the remainder of the molecule directly or through a linker, wherein the linker is preferably alkylene. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group. Exemplary substituent groups include substituted or unsubstituted alkyl, substituted or unsubstituted heteroalkyl, substituted or unsubstituted aryl, substituted or unsubstituted heteroaryl, and substituted or unsubstituted heterocycloalkyl groups.

The phrase "therapeutically effective amount" as used herein means that amount of a compound, material, or composition comprising a compound of the present invention which is effective for producing a desired therapeutic effect, at a reasonable benefit/risk ratio applicable to any medical treatment.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When a residue is defined as "O$^-$", then the formula is meant to optionally include an organic or inorganic cationic counterion. Preferably, the resulting salt form of the compound is pharmaceutically acceptable.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. For instance, prodrugs for carboxylic acid analogs of the invention include a variety of esters. In an exemplary embodiment, the pharmaceutical compositions of the invention include a carboxylic acid ester. In another exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms ("polymorphs"). In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers and d and l isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

In the context of the present invention, compounds that are considered to possess activity as DAAO inhibitors are those displaying 50% inhibition of the enzymatic activity of DAAO ($IC_{50}$) at a concentration of not higher than about 100 µM, preferably, not higher than about 1 µM, more preferably not higher than about 100 nM and most preferably not higher than about 25 nM.

The term "neurological disorder" refers to any condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic pain" is a heterogeneous group of neurological conditions that result from damage to the nervous system. "Neuropathic" pain, as described above, refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis. Other types of pain that are meant to be included in the definition of neuropathic pain include pain from neuropathic cancer pain, HIV/AIDS induced pain, phantom limb pain, and complex regional pain syndrome. In a preferred embodiment, the compounds of the invention are of use for treating neuropathic pain.

Common clinical features of neuropathic pain include sensory loss, allodynia (non-noxious stimuli produce pain), hyperalgesia and hyperpathia (delayed perception, summation, and painful aftersensation). Pain is often a combination of nociceptive and neuropathic types, for example, mechanical spinal pain and radiculopathy or myelopathy.

"Acute pain", is the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. "Acute pain", as described above, refers to pain which is marked by short duration or sudden onset.

"Chronic pain" occurs in a wide range of disorders, for example, trauma, malignancies and chronic inflammatory diseases such as rheumatoid arthritis. Chronic pain usually lasts more than about six months. In addition, the intensity of chronic pain may be disproportionate to the intensity of the noxious stimulus or underlying process. "Chronic pain", as described above, refers to pain associated with a chronic disorder, or pain that persists beyond resolution of an underlying disorder or healing of an injury, and that is often more intense than the underlying process would predict. It may be subject to frequent recurrence.

"Inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. "Inflammatory pain", as described above, refers to pain which is produced as a symptom or a result of inflammation or an immune system disorder.

"Visceral pain", as described above, refers to pain which is located in an internal organ.

"Mixed etiology" pain, as described above, refers to pain that contains both inflammatory and neuropathic components.

"Dual mechanism" pain, as described above, refers to pain that is amplified and maintained by both peripheral and central sensitization.

"Causalgia", as described above, refers to a syndrome of sustained burning, allodynia, and hyperpathia after a traumatic nerve lesion, often combined with vasomotor and sudomotor dysfunction and later trophic changes.

"Central" pain, as described above, refers to pain initiated by a primary lesion or dysfunction in the central nervous system.

"Hyperesthesia", as described above, refers to increased sensitivity to stimulation, excluding the special senses.

"Hyperpathia", as described above, refers to a painful syndrome characterized by an abnormally painful reaction to a stimulus, especially a repetitive stimulus, as well as an increased threshold. It may occur with allodynia, hyperesthesia, hyperalgesia, or dysesthesia.

"Dysesthesia", as described above, refers to an unpleasant abnormal sensation, whether spontaneous or evoked. Special cases of dysesthesia include hyperalgesia and allodynia, "Hyperalgesia", as described above, refers to an increased response to a stimulus that is normally painful. It reflects increased pain on suprathreshold stimulation.

"Allodynia", as described above, refers to pain due to a stimulus that does not normally provoke pain.

The term "pain" includes pain resulting from dysfunction of the nervous system: organic pain states that share clinical features of neuropathic pain and possible common pathophysiology mechanisms, but are not initiated by an identifiable lesion in any part of the nervous system.

The term "Diabetic Peripheral Neuropathic Pain" (DPNP, also called diabetic neuropathy, DN or diabetic peripheral neuropathy) refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

The term "Post-Herpetic Neuralgia", also called "Postherpetic Neuralgia" (PHN), is a painful condition affecting nerve fibers and skin. It is a complication of shingles, a second outbreak of the varicella zoster virus (VZV), which initially causes chickenpox.

The term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

The term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

The term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

The term "Trigeminal Neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

The term "Complex Regional Pain Syndrome (CRPS)," formerly known as Reflex Sympathetic Dystrophy (RSD), is a chronic pain condition. The key symptom of CRPS is continuous, intense pain out of proportion to the severity of the injury, which gets worse rather than better over time. CRPS is divided into type 1, which includes conditions caused by tissue injury other than peripheral nerve, and type 2, in which the syndrome is provoked by major nerve injury, and is sometimes called causalgia.

The term "Fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

The term "convulsion" refers to a CNS disorder and is used interchangeably with "seizure," although there are many types of seizure, some of which have subtle or mild symptoms instead of convulsions. Seizures of all types may be caused by disorganized and sudden electrical activity in the brain. Convulsions are a rapid and uncontrollable shaking. During convulsions, the muscles contract and relax repeatedly.

II. Introduction

The present invention relates to novel inhibitors of the enzyme D-amino acid oxidase. These compounds are useful for treating or preventing any disease and/or condition, wherein modulation of D-serine levels, and/or its oxidative products, is effective in ameliorating symptoms. Inhibition of the enzyme can lead to increases in D-serine levels and a reduction in the formation of toxic D-serine oxidation products. Thus, the invention provides methods for the treatment or prevention of neurological disorders. For example, the invention provides methods of enhancing learning, memory and/or cognition, for treating or preventing loss of memory and/or cognition associated with neurodegenerative diseases (e.g., Alzheimer's disease) and for preventing loss of neuronal function characteristic of neurodegenerative diseases. Further, methods are provided for the treatment or prevention of pain, ataxia, and convulsion.

III. Compositions

A. Fluoro-Substituted Fused Heterocycles

The heterocyclic inhibitors of the invention are characterized by a variety of fluoro-substituted core-moieties. In an exemplary embodiment, the core-moiety includes a fused heterocyclic ring system of two 5-membered rings. Exemplary 5-membered rings include heteroaromatic rings, such as oxazoles, isoxazoles, thiazoles, isothiazoles, imidazoles and pyrazoles and preferably pyrroles, thiophenes and furans.

In one embodiment, the invention provides fluoro-substituted compounds having a structure according to Formula (I):

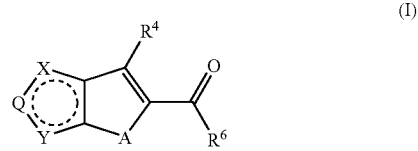

wherein A is $NR^7$, O or S. In a preferred example, A is a member selected from NE and S. Q is a member selected from O, S, $CR^1$, N and $NR^{3a}$. Q is preferably $CR^1$ or N. X and Y are members independently selected from O, S, $CR^2$, N and $NR^3$, wherein each $R^2$ is independently selected.

$R^3$, $R^{3a}$ and $R^7$ are members independently selected from H, $OR^{12}$, acyl, $SO_2R^{13}$, $SOR^{13}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{12}$ and $R^{13}$ are members independently selected from substituted or unsubstituted alkyl, substituted or unsubstituted heteroalkyl, substituted or unsubstituted aryl, substituted or unsubstituted heteroaryl and substituted or unsubstituted heterocycloalkyl. $R^3$ and $R^{3a}$ are preferably members independently selected from H and substituted or unsubstituted alkyl.

In Formula (I), $R^1$, $R^2$ and $R^4$ are members independently selected from H, F, Cl, Br, CN, $CF_3$, acyl, $OR^{14}$, $S(O)_2OR^{14}$, $S(O)_2R^{14}$, $NR^{14}R^{15}$, $SO_2NR^{14}R^{15}$, substituted or unsubstituted alkyl, substituted or unsubstituted heteroalkyl, substituted or unsubstituted aryl, substituted or unsubstituted heteroaryl and substituted or unsubstituted heterocycloalkyl, provided that at least one member selected from $R^1$, $R^2$ and $R^4$ is F. $R^1$ and $R^2$, together with the atoms to which they are attached, are optionally joined to form a 5- to 7-membered ring. In a particularly preferred embodiment, $R^1$, $R^2$ and $R^4$ are members independently selected from H and F, provided that at least one of $R^1$, $R^2$ and $R^4$ is F.

In one embodiment, in which Q is CF, and one member selected from X and Y is S and the other member is CH, $R^4$ is preferably other than H. In another embodiment, in which A is NH, Q is CF, X is S and Y is CH, $R^4$ is preferably other than H. In another embodiment, in which A is NH, Q is CF, X is CH and Y is S, $R^4$ is preferably other than H. In yet another embodiment, in which A is S, Q is CF, Y is S and X is CH, $R^4$ is preferably other than H. In a further embodiment, in which A is S, Q is CF, X is S and Y is CH, $R^4$ is preferably other than H.

$R^{14}$ and $R^{15}$ are members independently selected from H, substituted or unsubstituted alkyl, substituted or unsubstituted heteroalkyl, substituted or unsubstituted aryl, substituted or unsubstituted heteroaryl, substituted and unsubstituted cycloalkyl, and substituted or unsubstituted heterocycloalkyl. $R^{14}$ and $R^{15}$, together with the nitrogen atoms to which they are attached, are optionally joined to form a 5- to 7-membered ring.

In Formula (I), $R^6$ is a member selected from $O^-X^+$, $OR^8$, $NR^9R^{10}$, $NR^8NR^9R^{10}$, $NR^8OR^9$, $NR^8SO_2R^{11}$, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl, wherein $X^+$ is a positive ion, which is a member selected from inorganic positive ions and organic positive ions. $R^6$ is preferably a member selected from $O^-X^+$ and $OR^8$. $R^6$ and $R^4$, together with the atoms to which they are attached, are optionally joined to form a 5- to 7-membered ring.

$R^8$, $R^9$ and $R^{10}$ are members independently selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl. $R^8$ is preferably H or $C_1$-$C_4$ alkyl (e.g., Me, Et, Pr, iso-Pr, n-Bu, iso-Bu). $R^{11}$ is a member selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl. At least two of $R^8$, $R^9$, $R^{10}$ and $R^{11}$, together with the atoms to which they are attached, are optionally joined to form a 5- to 7-membered ring.

In another embodiment, the compound of the invention has a structure according to Formula (II):

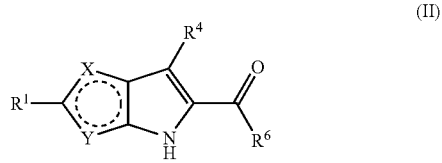

wherein one member selected from X and Y is O or S and the other member is $CR^2$.

In Formula (II), $R^1$, $R^2$ and $R^4$ are members independently selected from H and F, provided that at least one member selected from $R^1$, $R^2$ and $R^4$ is F. $R^6$ is a member selected from $O^-X^+$ and $OR^8$, wherein $X^+$ is a positive ion, which is a member selected from inorganic positive ions and organic positive ions, and wherein $R^8$ is preferably H or $C_1$-$C_4$ alkyl (e.g., Me, Et, Pr, iso-Pr, n-Bu, iso-Bu). In one embodiment, in which $R^1$ is F, X is S and Y is CH, $R^4$ is preferably other than H. In another embodiment, in which $R^1$ is F, Y is S and X is CH, $R^4$ is preferably other than H.

In yet another embodiment, the compound of the invention has a structure according to Formula (III):

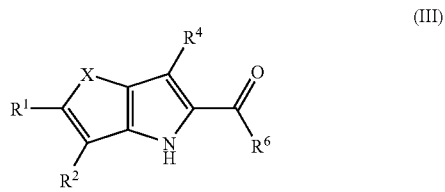

wherein X is a member selected from O and S. $R^1$, $R^2$ and $R^4$ are members independently selected from H and F, provided that at least one member selected from $R^1$, $R^2$ and $R^4$ is F. $R^6$ is a member selected from $O^-X^+$ and $OR^8$, wherein $X^+$ is a positive ion, which is a member selected from inorganic positive ions and organic positive ions, and wherein $R^8$ is preferably H or $C_1$-$C_4$ alkyl (e.g., Me, Et, Pr, iso-Pr, n-Bu, iso-Bu). In one example according to this embodiment, in which $R^1$ is F, X is S and $R^2$ is H, $R^4$ is preferably other than H.

Exemplary compounds according to this embodiment include:

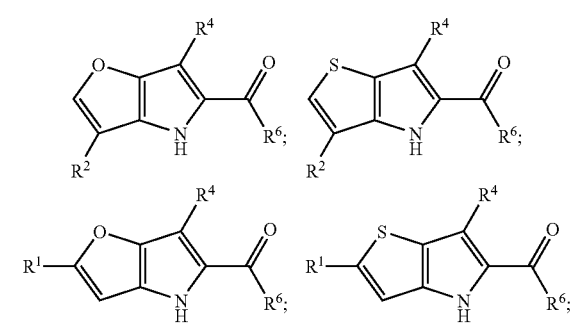

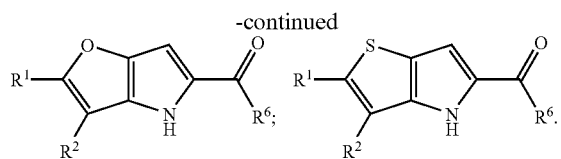

wherein $R^1$, $R^2$ and $R^4$ are selected from H and F.

In a further embodiment, the compound of the invention has a structure according to Formula (IV):

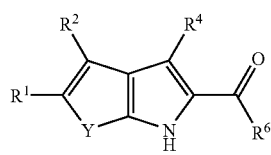
(IV)

wherein Y is a member selected from O and S. $R^1$, $R^2$ and $R^4$ are members independently selected from H and F, provided that at least one member selected from $R^1$, $R^2$ and $R^4$ is F. $R^6$ is a member selected from $O^-X^+$ and $OR^8$, wherein $X^+$ is a positive ion, which is a member selected from inorganic positive ions and organic positive ions, and wherein $R^8$ is preferably H or $C_1$-$C_4$ alkyl (e.g., Me, Et, Pr, iso-Pr, n-Bu, iso-Bu). In one example according to this embodiment, in which the moiety —C(O)$R^6$ is an ester group, $R^1$ is F. $R^2$ is H and Y is S. $R^4$ is other than H.

Exemplary compounds according to this embodiment include:

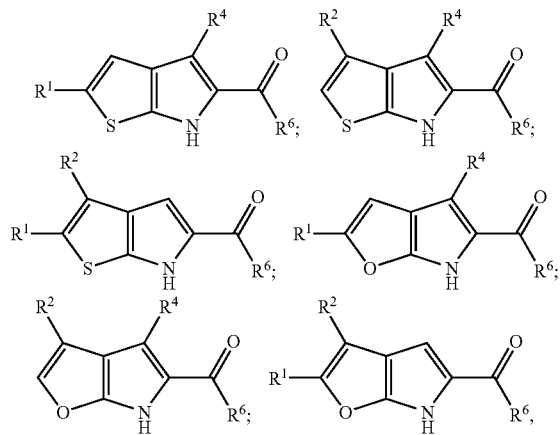

wherein $R^1$, $R^2$ and $R^4$ are selected from H and F.

In an exemplary embodiment, in Formulae (I), (II), (III) and (IV), $R^1$ is F. Compounds according to this embodiment include, for example:

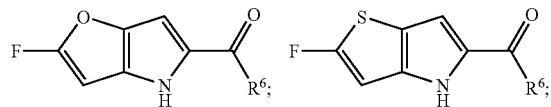

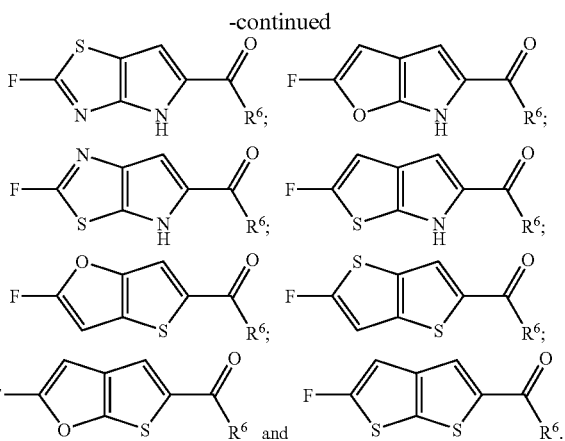

In another exemplary embodiment, in Formulae (I), (II), (III) and (IV), $R^2$ is F. Exemplary compounds according to this embodiment include:

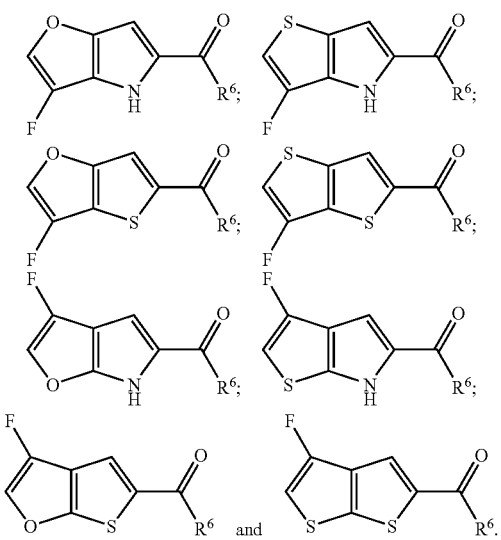

In yet another embodiment, in Formulae (I), (II), (III) and (IV), $R^4$ is F. Exemplary compounds according to this embodiment include:

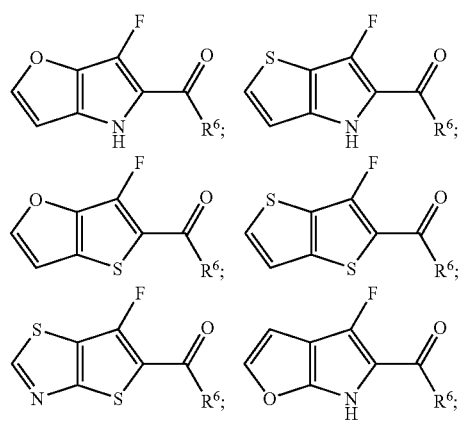

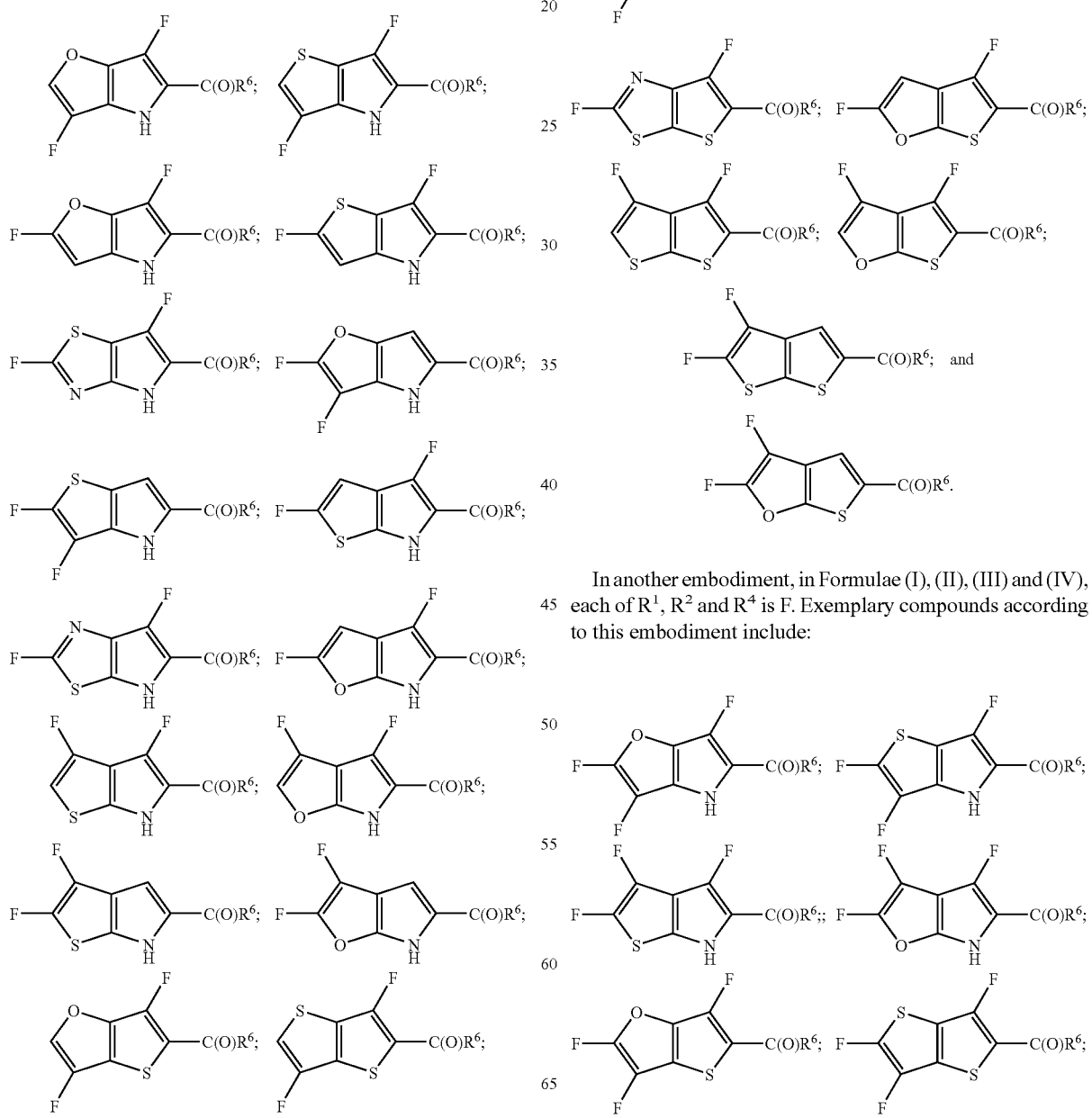
In a further embodiment, in Formulae (I), (II), (III) and (IV), at least two of $R^1$, $R^2$ and $R^4$ are F. Exemplary compounds according to this embodiment include:
In another embodiment, in Formulae (I), (II), (III) and (IV), each of $R^1$, $R^2$ and $R^4$ is F. Exemplary compounds according to this embodiment include:

-continued

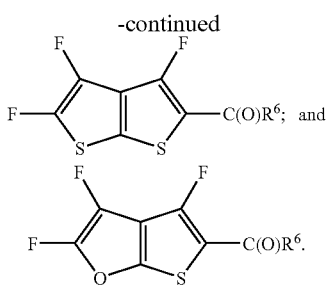

The inventors have discovered that certain fluoro-substituted (F-substituted) compounds of the invention are associated with unexpectedly high in vitro and in vivo activities. Some compounds of the invention, are significantly more active than their respective Cl- or Br-substituted counterparts. Compounds of the invention are evaluated in Examples 8 and 9. Supporting data is summarized in Table 2.

In one embodiment, the F-substituted analog has an $IC_{50}$ (DAAO inhibition) below about 1 μM, preferably below about 100 nM and more preferably below about 50 nM. In a particularly preferred embodiment, the F-substituted analog has an $IC_{50}$ below about 25 nM. In another example, the F-substituted analog has an $IC_{50}$ that is at least about one order of magnitude lower than the $IC_{50}$ measured for at least one of the respective Br- or Cl-substituted analogs. In one example, the $IC_{50}$ is measured using an in vitro DAAO enzyme inhibition assay described herein (Example 8).

In another example, the F-substituted compound of the invention increases D-serine levels in the cerebellum of a test animal. D-Serine levels may be determined following the experimental procedures described herein (e.g., Example 9). In an exemplary embodiment, the F-substituted analog (at 50 mg/kg) increases D-serine levels in the cerebellum of mice (measured 2 hours after i.p. dosing) between about 1.5 fold and 2 fold and preferably more than 2 fold when compared to vehicle. Several of the analyzed fluoro-substituted analogs of the invention (at 50 mg/kg) increased D-serine levels by at least 2 fold, while none of the respective Cl- or Br-substituted analogs that were analyzed had this activity.

Particularly preferred are those F-substituted compounds of the invention that are capable of maintaining an elevated D-serine level for at least 6 hours. For example, those F-substituted compounds that (at 50 mg/kg) increase D-serine levels between about 1.5 fold and 2 fold and preferably more than 2 fold even when measured 6 hours after dosing, are generally preferred.

Even more preferred are those F-substituted compounds that increase D-serine levels at a lower dose of 10 mg/kg between about 1.5 fold and 2 fold and preferably more than 2 fold when measured 2 hours after dosing. Most preferred are F-substituted compounds that increase D-serine levels (at a lower dose of 10 mg/kg) between about 1.5 fold and about 2 fold and preferably more than 2 fold even when measured 6 hours after dosing.

When the increases in D-serine levels are significantly (e.g., at least about 20%, preferably at least about 40%, more preferably about 60% and most preferably at least about 80% or at least about 100%) higher for the F-substituted analogs when compared to the increases measured for at least one of the respective Br- or Cl-substituted analogs, then those F-substituted analogs are generally preferred. For example, when under the same test conditions, the F-substituted analog causes an increase in the D-serine level of 2.7 fold, and the respective Cl-substituted analog causes an increase of 1.5 fold, then the F-substituted analog has an activity that is 80% higher than the activity measured for the Cl-substituted analog.

Also generally preferred are those compounds of the invention that show activity in a pain model, such as those described herein (e.g., Chung model) as well as a model of cognition, such as those described herein (e.g., a contextual fear conditioning model. Such experiments are described herein for compounds 1 and 11 (e.g., Examples 10 and 11) but are equally useful for the analysis of the compounds of the invention.

For a fluoro-substituted compound of the invention to be useful as a DAAO inhibitor, which is suitable for pharmaceutical product development, candidate compounds must demonstrate acceptable activity against the enzyme D-amino acid oxidase (DAAO).

In one example, the compounds activity is measured using an in vitro DAAO enzyme inhibition assay. Such assays are known in the art. An exemplary assay format is described herein (e.g., Example 8). The fluoro-substituted compounds of the invention are judged to be sufficiently potent if they have an $IC_{50}$ below about 25 nM. This level of activity is particularly important for the treatment of pain, such as neuropathic pain and other types of pain described herein.

In another example, the compounds activity is determined by measuring D-serine levels in vivo. Elevation of the D-serine level in a certain brain area (e.g., the cerebellum) of a test animal (e.g., mouse, rat, pig and the like) is indicative of DAAO inhibition in vivo. An exemplary assay format, which measures D-serine levels (LC/MS/MS) in the cerebellum of mice two hours and six hours after intraperitoneal (i.p.) dosing, is described herein (e.g., Example 9). Increases in D-serine levels were determined through comparison with vehicle. Useful variations of this assay will be apparent to those of skill in the art. Compounds of the invention are judged to be sufficiently active in this assay when at least one, preferably at least two, more preferably at least three and most preferably all four of the following criteria are met:

1) At a dose of 50 mg/kg, compounds must cause an elevation of D-serine level (measured about 2 hours after dosing) of greater than about 2 fold when compared to vehicle.

2) At a dose of 50 mg/kg, compounds must cause an elevated D-serine level (measured about 6 hours after dosing) of greater than about 2 fold when compared to vehicle.

3) At a dose of 10 mg/kg, compounds must cause an elevation of D-serine level (measured 2 hours after dosing) of greater than about 2 fold when compared to vehicle.

4) At a dose of 10 mg/kg, compounds must cause an elevation of D-serine level (measured 6 hours after dosing) of greater than about 2 fold when compared to vehicle.

Activity of the test compounds in this in vivo assay is particularly important for the treatment of pain, such as neuropathic pain and other types of pain described herein.

Particularly preferred for pharmaceutical development are those fluoro-substituted compounds of the invention, which demonstrate sufficient activity against the enzyme DAAO both in vitro (e.g., DAAO enzyme inhibition assay) and in vivo (e.g., elevation of D-serine levels in the cerebellum of mice).

B. Synthesis

The compounds of the present invention, including compounds of Formula (I) to Formula (IV), may be prepared by methods known in the art. One of ordinary skill in the art will know how to modify procedures to obtain the analogs of the present invention. Suitable procedures are described e.g., in WO2004/031194 to Murray, P. et al.; Yarovenko, V. N., *Russian Chemical Bulletin, International Edition* (2003), 52(2): 451-456; Krayushkin M. M et al., *Organic Letters* (2002), 4(22): 3879-3881; Eras J. et al., *Heterocyclic Chem*. (1984), 21: 215-217, each of which is incorporated herein by reference in its entirety. In addition, compounds may be prepared using the methods described below and in Examples 1 through 7 or modified versions thereof.

In an exemplary embodiment, the fused pyrrole analogs of the present invention may be prepared according to Schemes 1-2 by condensation of an appropriate five-membered heteroaromatic aldehyde and 2-azidoacetate, followed by cyclization and saponification of the resulting ester to afford the carboxylic acid analog.

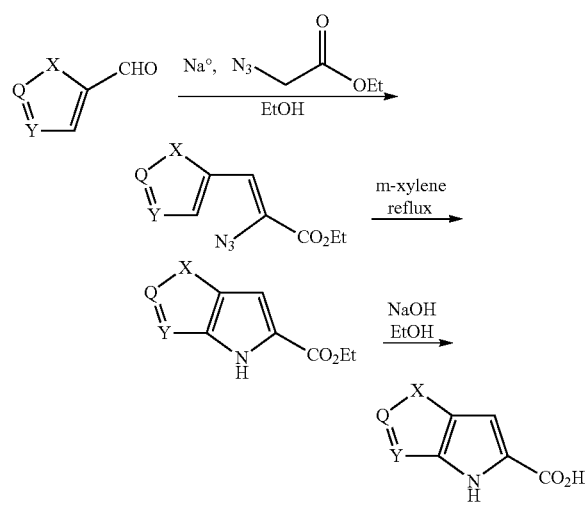

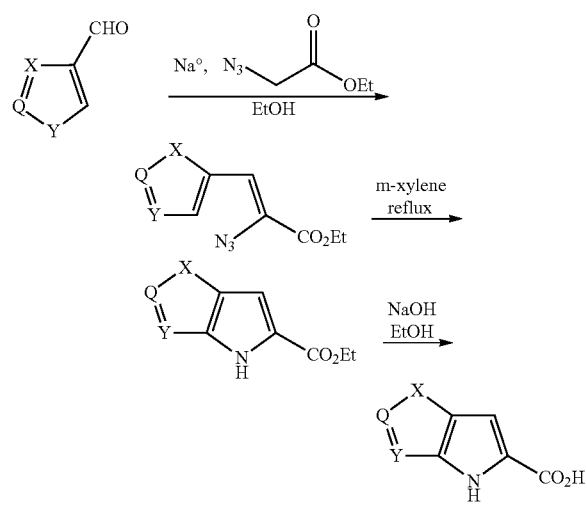

Substituted (e.g., alkyl and aryl-substituted) aldehydes, used as starting materials for these syntheses, may be prepared from a halogenated (e.g., Br, I) precursor through Suzuki coupling with an appropriate boronic acid.

$R^4$-Substitution of the pyrrole ring with a halogen (e.g., I), followed by Suzuki coupling of the resulting halogenated carboxylic acid ester and saponification, affords a $R^4$-substituted analog as outlined in Scheme 3. Alternatively, the iodine may be replaced with F, affording the F-substituted analog.

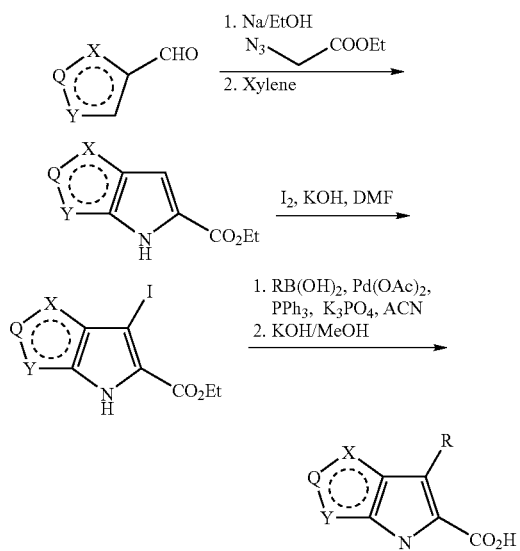

In another exemplary embodiment, the fused thiophene analogs of the invention can be prepared by condensation of the appropriate aldehyde and rhodanine, followed by hydrolysis of the rhodanine ring and cyclization as outlined below in Scheme 4.

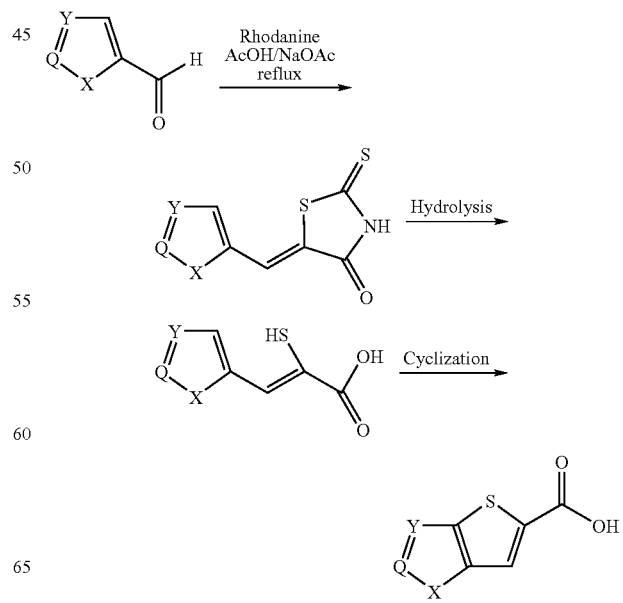

-continued

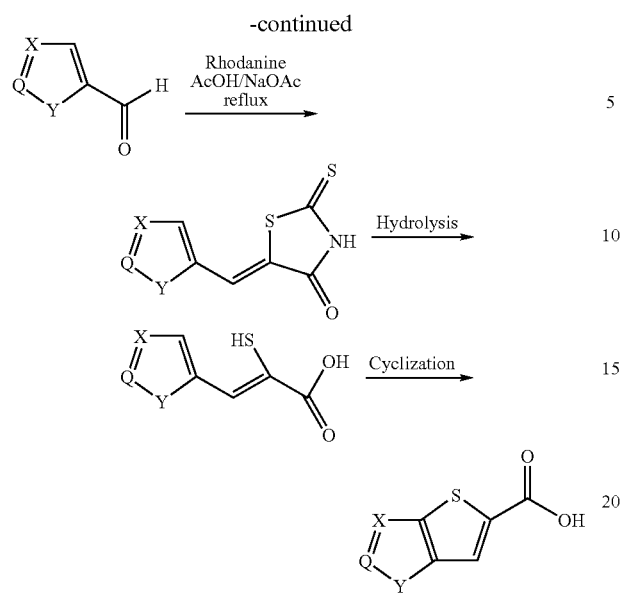

B.1. Synthesis of Fused Pyrazole Pyrrole Analogs

In an exemplary embodiment, fused pyrrole-pyrazole analogs of the invention are prepared following a procedure outlined in Scheme 5 or Scheme 6 below.

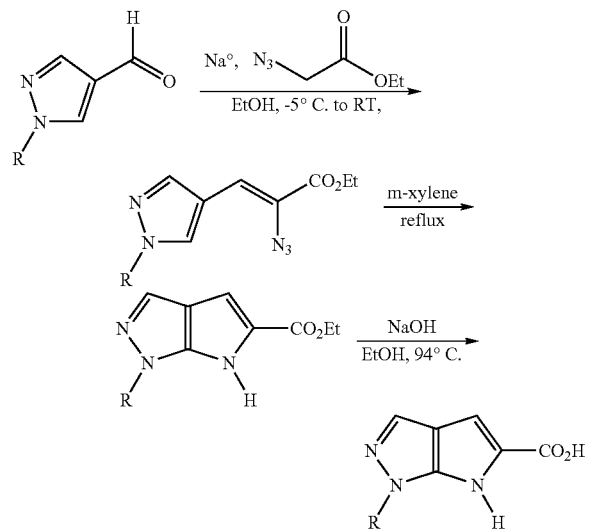

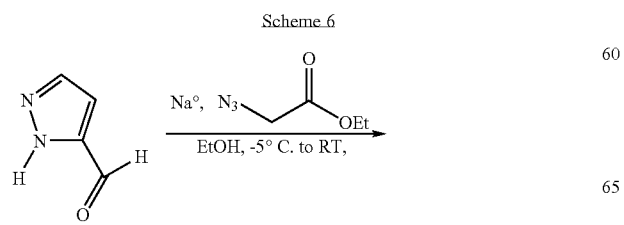

-continued

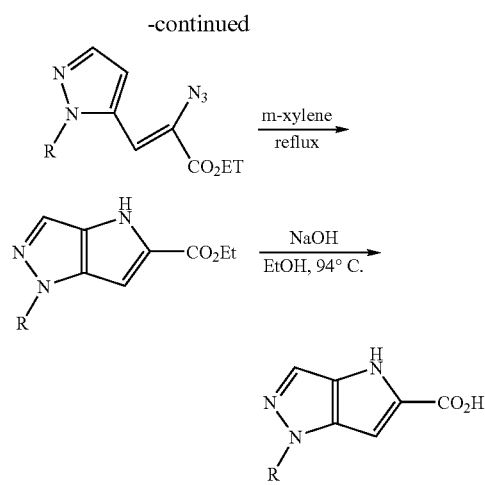

Generally, these compounds can be prepared by condensation of the appropriate pyrazole aldehyde and 2-azidoacetate, followed by cyclization. The resulting ester is then saponified to afford the carboxylic acid analog.

B.2. Synthesis of Fused Thiophene Pyrrole Analogs

Fused pyrrole-thiophene analogs of the present invention may be prepared using a procedure such as those outlined in Schemes 7 to 10 below.

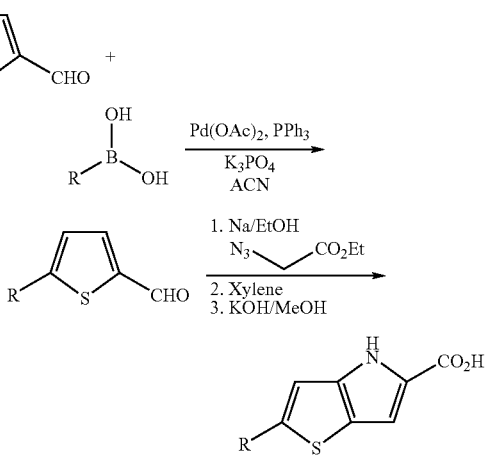

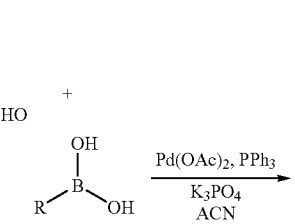

-continued

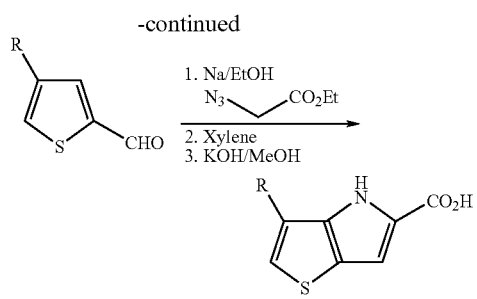

conditions (such as with nBuLi or tBuLi) followed by fluorination (e.g., with N-fluorobenzenesulfonimide (NFSI) or Selectfluor®)

B.3. Synthesis of Fused Furan Pyrrole Analogs

In another exemplary embodiment, fused furan pyrrole analogs of the present invention are prepared using a procedure such as those outlined in Schemes 11 and 12 below.

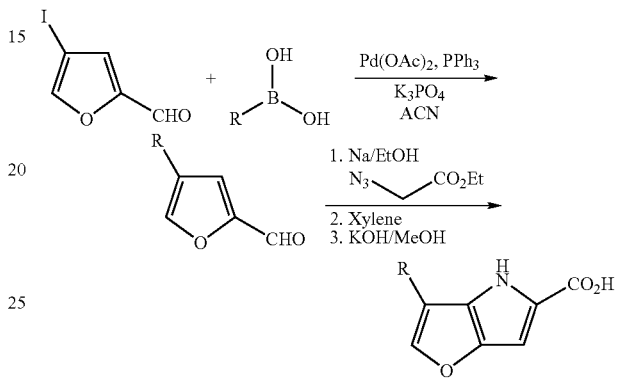

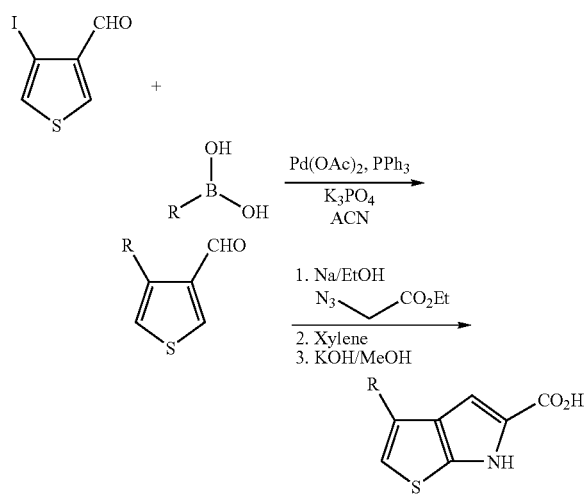

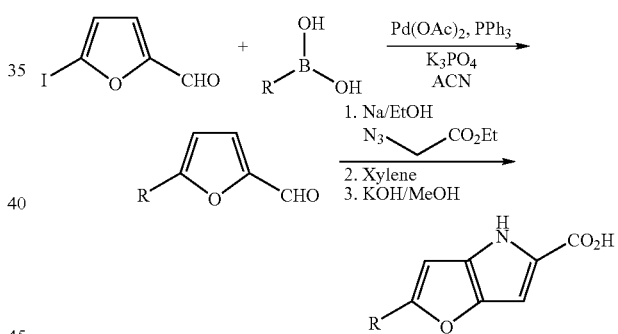

In analogy to the corresponding thiophene analogs, the fused furan pyrrole derivatives of the invention may be prepared by Suzuki coupling of a halogenated furan aldehyde and an appropriate boronic acid. Condensation of the resulting furan intermediate and 2-azidoacetate, followed by cyclization and saponification of the ester group affords the desired carboxylic acid analog.

B.4. Synthesis of Fused Pyrrole Analogs

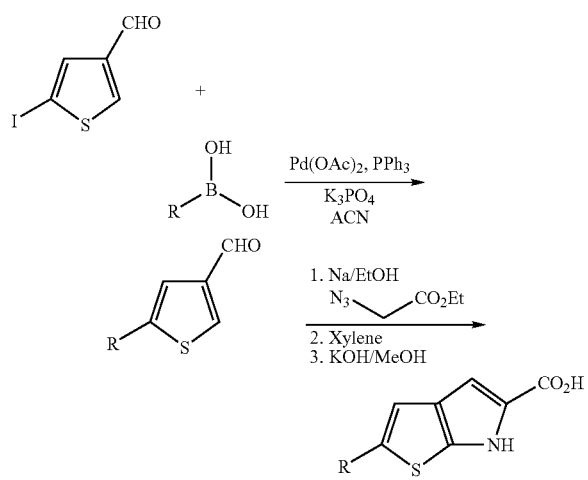

In an exemplary embodiment, the thiophene derivative, carrying a desired R-group, is prepared by Suzuki coupling of a halogenated thiophene aldehyde and the appropriate boronic acid analog. Condensation of the resulting thiophene intermediate and 2-azidoacetate, followed by cyclization and saponification of the ester group affords the carboxylic acid analog. In one example, iodine or bromine in the starting aldehyde may be replaced by fluorine using transmetalation In another exemplary embodiment, fused pyrrole-pyrrole analogs of the current invention are prepared using the synthetic approach outlined in Scheme 13 below. Similarly to the above described compounds, fused pyrrole-pyrrole analogs can be prepared by condensation of the appropriate pyrrole aldehyde and 2-azidoacetate, followed by cyclization and saponification of the ester group. Substituted pyrrole aldehydes may be prepared by Suzuki coupling of a halogenated pyrrole aldehyde and the appropriate boronic acid analog.

Scheme 13

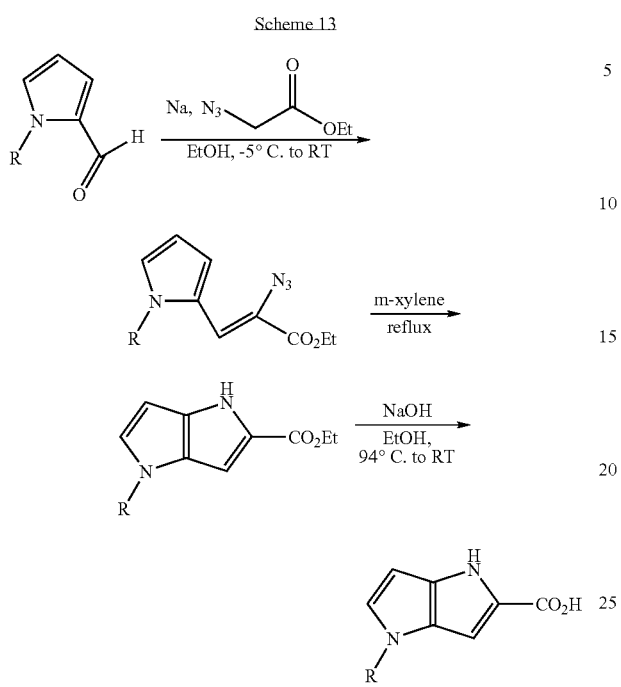

B.5. Synthesis of Fused Thiazole Pyrrole Analogs

In another exemplary embodiment, fused thiazole-pyrrole analogs of the current invention are prepared using the synthetic approach outlined in Scheme 14 below. Similarly to the above described compounds, fused thiazole-pyrrole analogs can be prepared by condensation of the appropriate thiazole aldehyde and 2-azidoacetate, followed by cyclization and saponification of the ester group. Substituted thiazole aldehydes may be prepared by Suzuki coupling of a halogenated thiazole aldehyde and the appropriate boronic acid analog.

Scheme 14

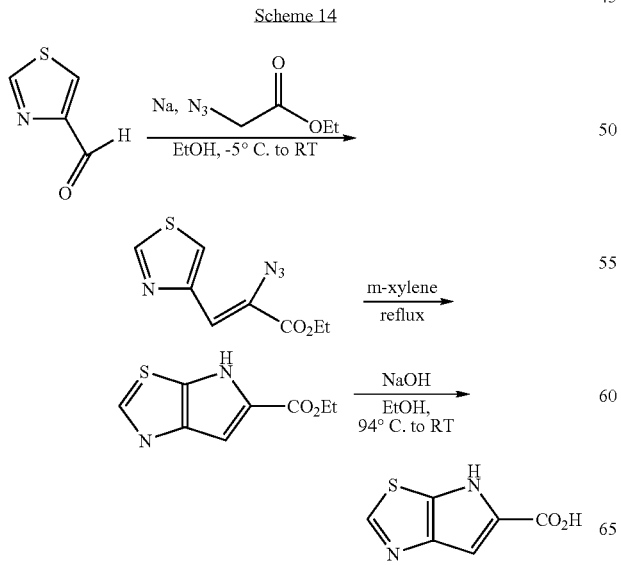

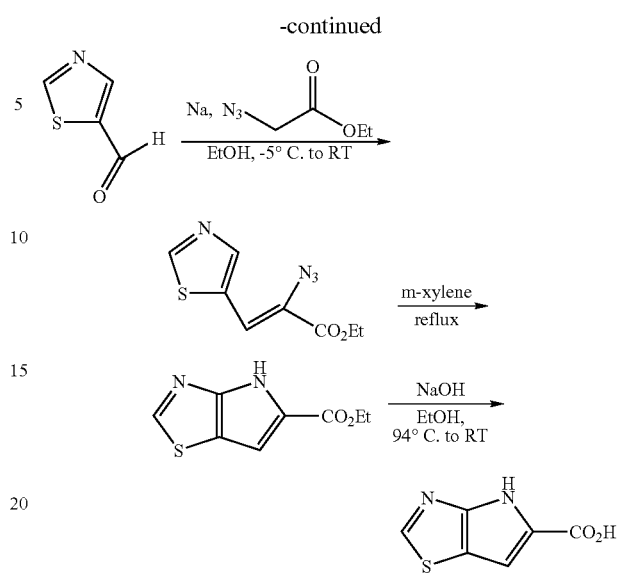

B.6. Synthesis of Fused Thiophene Analogs

In a further embodiment, the fused thiophene-thiophene analogs of the invention are synthesized using a procedure such as those outlined in Schemes 15 and 16.

Scheme 15

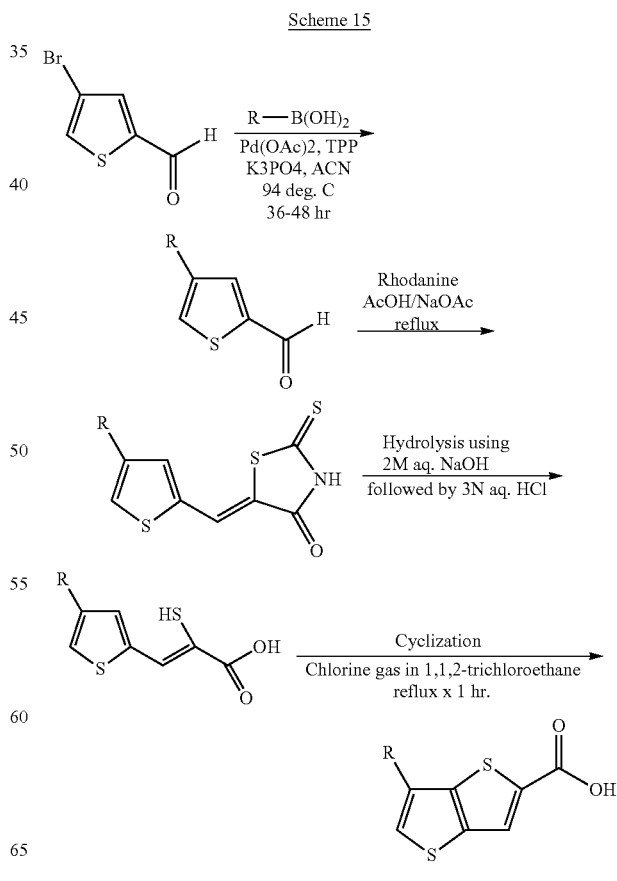

29

Scheme 16

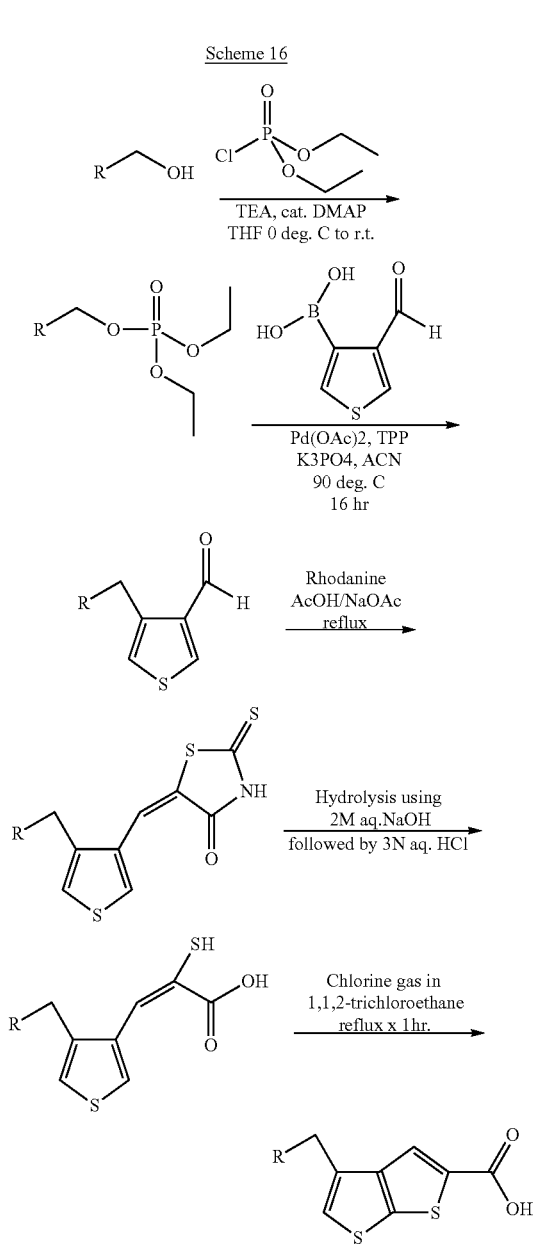

B.8. Synthesis of 1,5-dihydropyrrolo[2,3-c]pyrrole Analogs 1,5-dihydropyrrolo[2,3-c]pyrrole-2-carboxylic acid analogs of the invention can be prepared following a procedure outlined in Scheme 17.

Scheme 17

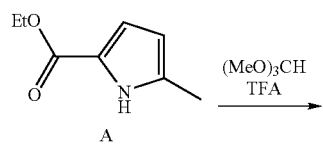

30

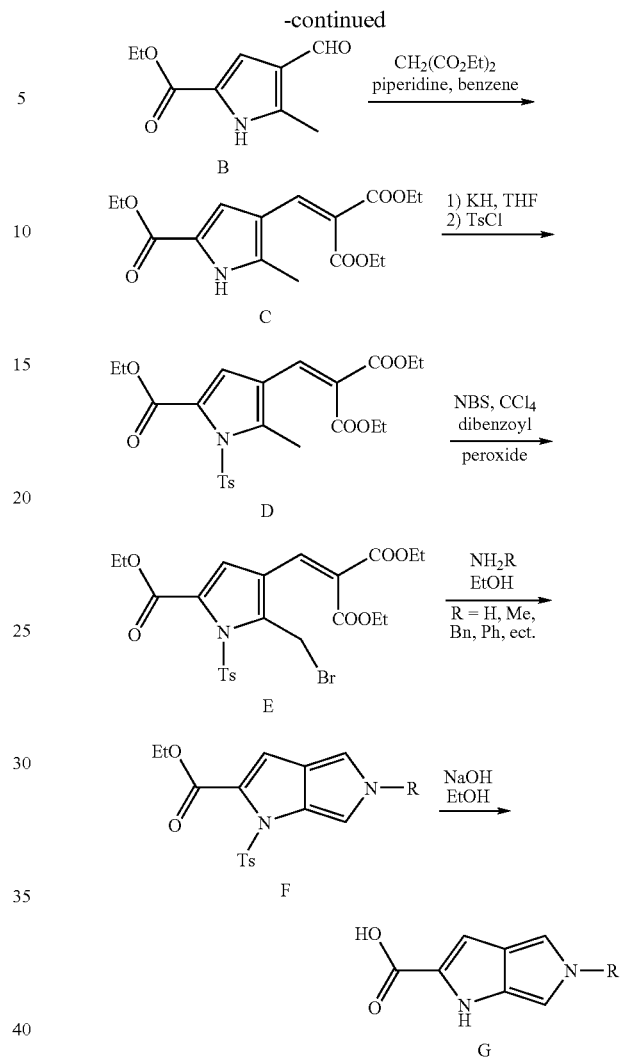

Generally, these compounds can be prepared from commercially available compounds such as A and B. For example, formylation of A, such as with trimethyl orthoformate and trifluoroacetic acid provides aldehyde B. Knoevenagel condensation of B provides C, which is protected by standard tosylation conditions to provide compounds such as D. Bromination of D, such as with N-bromosuccinimide and dibenzoyl peroxide, provides E, which is then reacted with ammonia or with amines such as methyl amine or benzyl amine to form cyclized products such as F. Standard deprotection of the N-tosyl group and saponification affords the desired carboxylic acid analog. Relevant references, which are incorporated by reference, include Sha, Chin-Kang, et al. *Heterocycles* 1990, 31, 603-609.

B.9. Synthesis of 1H-thieno[3,4-b]pyrrole and 1H-furo[3,4-b]pyrrole Analogs

In an exemplary embodiment, 1H-thieno[3,4-b]pyrrole-2-carboxylic acid and 1H-furo[3,4-b]pyrrole-2-carboxylic acid analogs of the invention are prepared following a procedure outlined in Scheme 18.

Scheme 18

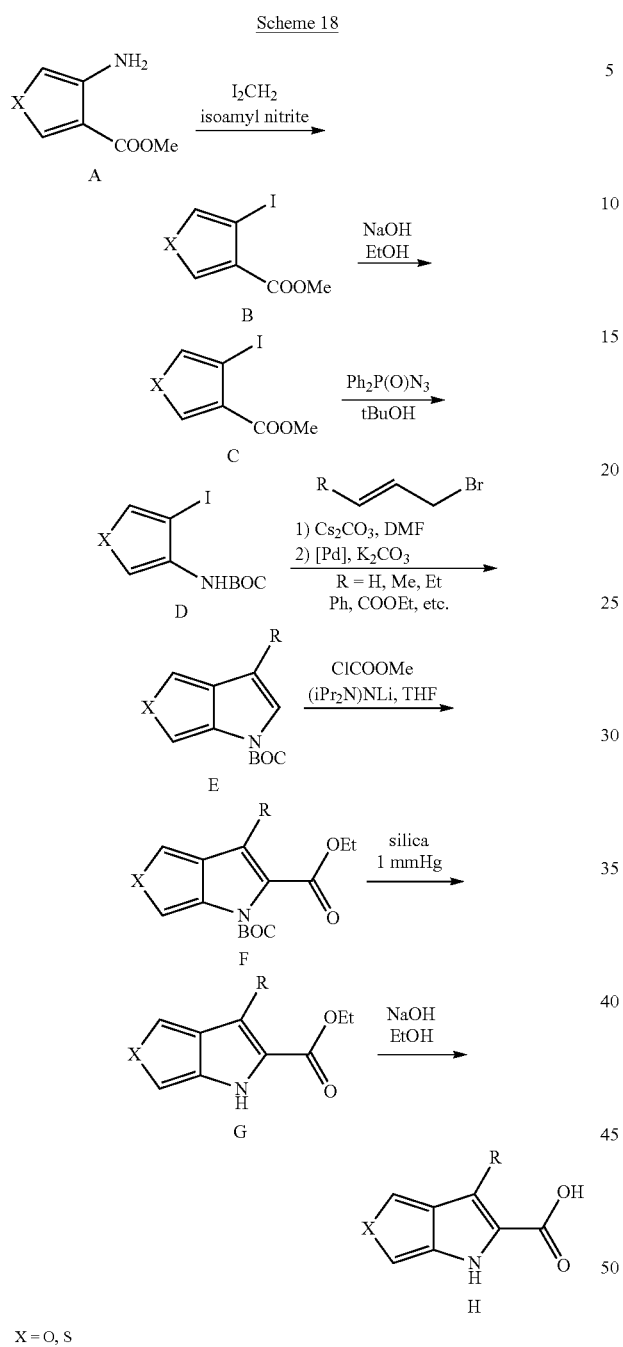

X = O, S

Generally, these compounds can be prepared from appropriately substituted furans and thiophenes such as A, B, or C, which are easily synthesized using standard literature procedures such as those listed below. Curtius rearrangement of C provides D, which can be allylated and subjected to Heck conditions to afford bicyclic compound E. Standard functional group manipulation, such as acylation, BOC deprotection, and saponification affords the desired carboxylic acid analogs. Relevant references, which are incorporated by reference, include Yu, Shuyuan et al *J. Chem. Soc., Perkin Transactions* 1 1991, 10, 2600-2601. Wensbo, D.; et al *Tetrahedron* 1995, 51, 10323-10342; Wensbo, D.; Gronowitz, S. *Tetrahedron* 1996, 52, 14975-14988, and references cited therein.

B.9. Synthesis of Fluorinated Thiophene Pyrrole and Furan Pyrrole Analogs

In an exemplary embodiment, fluoro-substituted analogs of the invention may be prepared following procedures outlined in Schemes 19 to 24.

In an exemplary embodiment, fluoro-substituted fused pyrrole analogs of the invention may be prepared following adaptations to procedures outlined in Schemes 1 to 18. Fluorine may be incorporated early, such as in the aldehyde starting materials of Scheme 1 and Scheme 2. Fluorinated five membered heteroaromatic aldehydes may be prepared from the corresponding bromo, chloro- or iodo substituted aldehydes, as shown in Schemes 19 and 20, by protecting the aldehyde as an acetal, then subjecting the bromo-, chloro-, or iodo-acetal to transmetalation conditions (such as, for example, with nBuLi or tBuLi) followed by fluorination (for example, with N-fluorobenzenesulfonimide (NFSI) or Selectfluor®). Deprotection of the acetal under standard conditions provides fluorinated aldehydes, which may be converted to the fused pyrrole analogs of the invention as outlined in Schemes 1 and 2.

Scheme 19

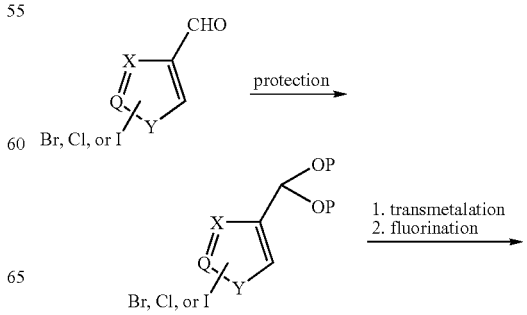

Scheme 20

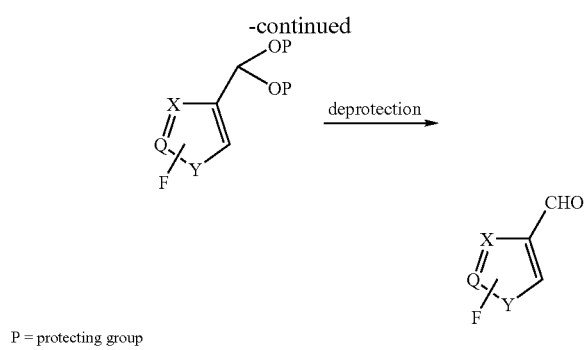

P = protecting group

Fluorinated, five membered heteroaromatic aldehydes may also be prepared from the corresponding bromo- or iodo-substituted protected methyl alcohols following the transmetalation, fluorination protocol used for acetals, as shown in Schemes 21 and 22. Standard deprotection of the alcohol, followed by oxidation (such as, for example, with $MnO_2$ or pyridinium chlorochromate) provides fluorinated five membered heteroaromatic aldehydes, which may be converted, as shown in Schemes 1 and 2, to the fused pyrrole analogs of the invention.

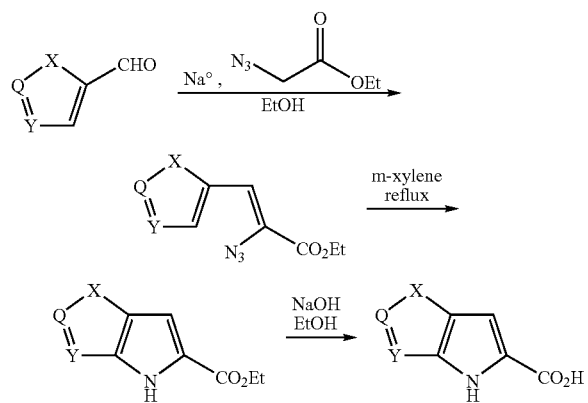

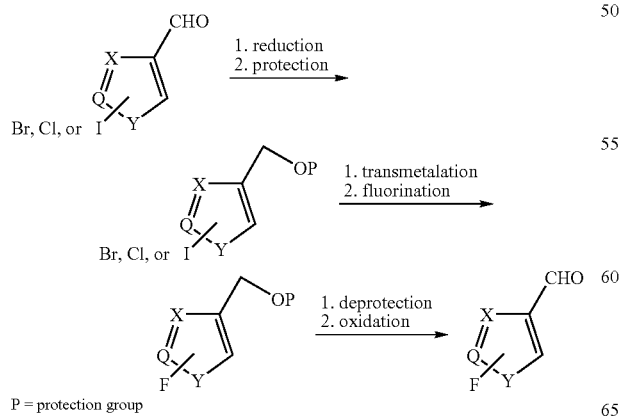

P = protection group

Alternatively, fluoro-substituted five membered heteroaromatic aldehydes may be obtained by direct fluorination of a five-membered heteroaromatic aldehyde, protected five-membered heteroaromatic aldehyde, or protected five-membered heteroaromatic methyl alcohol (such as, for example, with nBuLi or tBuLi, or LDA), followed by fluorination conditions (for example, with N-fluorobenzenesulfonimide (NFSI) or Selectfluor®) and optional deprotection to provide fluorinated aldehydes, which may be taken on, as in Scheme 1 and Scheme 2, to the fused pyrrole analogs of the invention. Alternatively, fluorinated aldehydes may be obtained by fluorodecarboxylation of a carboxylic acid containing five-membered heteroaromatic precursor.

Fluoro-substituted five membered heteroaromatic aldehydes may also be obtained by synthesis of the heteroaromatic ring following incorporation of fluorine. One example is described, in Example 2, for the synthesis of 4-fluorofuran-2-carbaldehyde starting from (4-bromo-4,4-difluoro-but-2-ynyloxy)-tert-butyl-dimethyl-silane.

Fluorine may also be incorporated into the azide intermediates of Schemes 1 and 2, from the corresponding bromo-, chloro-, or iodo-compound, as described above, or from the corresponding carboxylic acid, by fluorodecarboxylation (such as in the synthesis of ethyl 2-azido-3-(5-fluorofuran-2-yl)prop-2-enoate from 5-(2-azido-3-ethoxy-3-oxoprop-1-enyl)furan-2-carboxylic acid in Example 2.

In addition, fluorine may be incorporated later in the synthesis, into the fused pyrrole esters or acids. As shown in Schemes 23 and 24, fused pyrrole esters or acids of Schemes 1 and 2 may be subjected to standard bromination, chlorination or iodination conditions (for example, $Br_2$, KOH, I2, KOH, NBS, NCS), followed by transmetalation conditions (for example, nBuLi or tBuLi), then fluorination conditions (e.g., N-fluorobenzenesulfonimide (NFSI) or Selectfluor®), to provide fluorinated fused pyrrole esters or acids. Alternatively, the fused pyrrole esters or acids of Schemes 1 and 2 may be subjected to direct deprotonation conditions (e.g., nBuLi or tBuLi, or LDA), then fluorination conditions (e.g., N-fluorobenzenesulfonimide (NFSI) or Selectfluor®), to provide fluorinated fused pyrrole esters or acids.

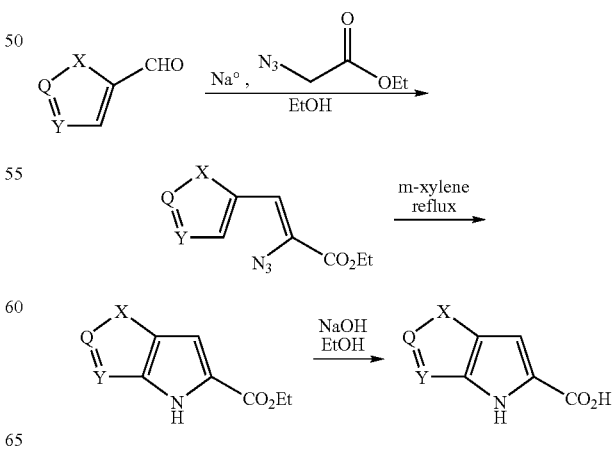

Scheme 24

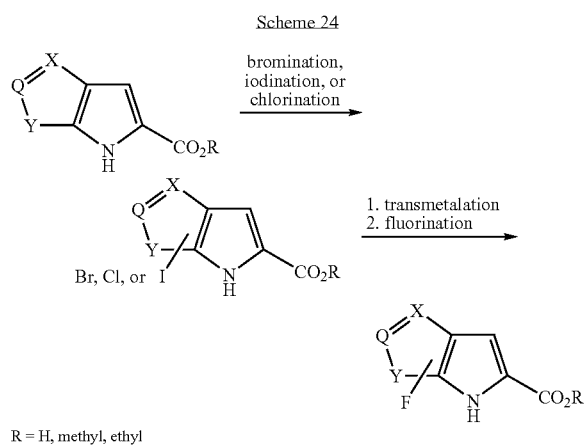

R = H, methyl, ethyl

In Schemes 1-24, X, Y and Q are defined as above for Formula (I). The reagents and reaction conditions, such as those given in Schemes 1 to 24 are exemplary and can be replaced with other suitable reagents and conditions, known to those of skill in the art. Representative examples for synthetic routes incorporating fluorine into fused pyrrole analogs may be found in Examples 1 and 2.

C. Pharmaceutical Compositions

While it may be possible for compounds of the present invention to be administered as the raw chemical, it is preferable to present them as a pharmaceutical composition. According to a further aspect, the present invention provides a pharmaceutical composition comprising a compound of Formula (I) to Formula (IV) or a pharmaceutically acceptable salt, solvate, hydrate or prodrug thereof, together with one or more pharmaceutical carrier and optionally one or more other therapeutic ingredients. The carrier(s) must be "acceptable" in the sense of being compatible with the other ingredients of the formulation and not deleterious to the recipient thereof. The term "pharmaceutically acceptable carrier" includes vehicles and diluents.

The formulations include those suitable for oral, parenteral (including subcutaneous, intradermal, intramuscular, intravenous and intraarticular), rectal and topical (including dermal, buccal, sublingual and intraocular) administration, as well as those for administration by inhalation. The most suitable route may depend upon the condition and disorder of the recipient. The formulations may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Oral formulations are well known to those skilled in the art, and general methods for preparing them are found in any standard pharmacy school textbook, for example, Remington: THE SCIENCE AND PRACTICE OF PHARMACY, 21st Ed. (1995), the entire disclosure of which is incorporated herein by reference.

Pharmaceutical compositions containing compounds of Formula (I) to Formula (IV) may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 7000 mg per day, preferably about 1 mg per day to about 100 mg per day, and more preferably, from about 10 mg per day to about 100 mg per day, and even more preferably from about 20 mg to about 100 mg, to about 80 mg or to about 60 mg. In some embodiments, the total daily dose may range from about 50 mg to about 500 mg per day, and preferably, about 100 mg to about 500 mg per day. It is further recommended that children, patients over 65 years old, and those with impaired renal or hepatic function, initially receive low doses and that the dosage be titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

It should be understood that in addition to the ingredients particularly mentioned above, the formulations of this invention may include other agents conventional in the art having regard to the type of formulation in question, for example those suitable for oral administration may include flavoring agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally using one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. Oral and parenteral sustained release drug delivery systems are well known to those skilled in the art, and general methods of achieving sustained release of orally or parenterally administered drugs are found, for example, in Remington: THE SCIENCE AND PRACTICE OF PHARMACY, 21st Ed. (1995), pages 1660-1675.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The pharmaceutically acceptable carrier may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Exemplary formulations, are well known to those skilled in the art, and general methods for preparing them are found in any standard pharmacy school textbook, for example, Remington: THE SCIENCE AND PRACTICE OF PHARMACY, 21st Ed., Lippincott.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

IV. Methods

A. Methods for Treatment or Prevention

In a further aspect the invention provides a method for treating or preventing a disease or condition which is a member selected from a neurological disorder, pain, ataxia and convulsion. The method includes administering to a subject in need thereof a therapeutically effective amount of a compound of Formulae (I) to (IV) or a pharmaceutically acceptable salt, solvate, hydrate or prodrug thereof.

In an exemplary embodiment, the subject is preferably not in need of treatment for a condition, which is a member selected from a $H_4$-receptor mediated disease, a monocyte chemoattractant protein-1 (MCP-1) receptor mediated disease, type-2 diabetes, insulin resistance, syndrome X, hyperinsulinaemia, hyperglucagonaemia, cardiac ischemia, obesity, artherosclerosis, diabetic neuropathy, diabetic nephropathy, diabetic retinopathy, cataracts, hypercholesterolemia, hypertriglyceridemia, hyperlipidemia, hyperglycemia, hypertension, tissue ischemia and myocardial ischemia.

In another embodiment, the subject is preferably not in need of inhibiting glycogen phosphorylase.

Subjects for treatment according to the present invention include humans (patients) and other mammals in need of therapy for the stated condition.

Compounds of the invention possess unique pharmacological characteristics with respect to inhibition of DAAO and influence the activity of the NMDA receptor in the brain, particularly by controlling the levels of D-serine. Therefore, these compounds are effective in treating conditions and disorders (especially CNS-related disorders), which are modulated by DAAO, D-serine and/or NMDA receptor activity. In one embodiment, compounds of the invention are associated with diminished side effects compared to administration of the current standards of treatment.

Accordingly, the present invention relates to methods for increasing the concentration of D-serine and/or decreasing the concentration of toxic products of D-serine oxidation by DAAO in a mammal. Each of the methods comprises administering to a subject in need thereof a therapeutically effective amount of a compound of the invention, for example those of Formulae (I)-(IV) or a pharmaceutically acceptable salt, solvate, hydrate or prodrug thereof.

Compounds of the invention are typically more selective than known DAAO inhibitors, including indole-2-carboxylates, and demonstrate higher selectivity for DAAO inhibition relative to binding at the NMDA receptor's D-serine binding site. The compounds also exhibit an advantageous profile of activity including good bioavailability. Accordingly, they offer advantages over many art-known methods for treating disorders modulated by DAAO, D-serine or NMDA receptor activity. For example, unlike many conventional antipsychotic therapeutics, DAAO inhibitors can produce a desirable reduction in the cognitive symptoms of schizophrenia. Conventional antipsychotics often produce undesirable side effects, including tardive dyskinesia (irreversible involuntary movement disorder), extra pyramidal symptoms, and akathesia, and these may be reduced or eliminated by administering compounds of the invention.

Compounds of the present invention may also be used in conjunction with therapy involving administration of D-serine or an analog thereof, such as a salt of D-serine, an ester of D-serine, alkylated D-serine, D-cycloserine or a precursor of D-serine, or can be used in conjunction with therapy involving administration of antipsychotics, antidepressants, psychostimulants, and/or Alzheimer's disease therapeutics.

The compounds of the invention may also be used in conjunction with therapy involving administration of antipsychotics (for treating schizophrenia and other psychotic conditions), psychostimulants (for treating attention deficit disorder, depression, or learning disorders), antidepressants, nootropics (for example, piracetam, oxiracetam or aniracetam), acetylcholinesterase inhibitors (for example, the physostigmine related compounds, tacrine or donepezil), GABA analogs (e.g., gabapentin) or GABA receptor modulators, Alzheimer's disease therapeutics (e.g., nemantine hydrochloride) and/or analgesics (for treating of persistent or chronic pain, e.g. neuropathic pain). Such methods for conjoint therapies are included within the invention.

Conditions and Disorders

In one embodiment, the compounds of the present invention are useful for the treatment of neurological disorders, pain (e.g., neuropathic pain), ataxia and convulsion. Neurological disorders include neurodegenerative diseases (e.g., Alzheimers disease) and neuropsychiatric disorders (e.g., schizophrenia).

Neuropsychiatric Disorders

Neuropsychiatric disorders include schizophrenia, autism, and attention deficit disorder. Clinicians recognize a distinction among such disorders, and there are many schemes for categorizing them. The Diagnostic and Statistical Manual of Mental Disorders, Revised, Fourth Ed., (DSM-IV-R), published by the American Psychiatric Association, provides a standard diagnostic system upon which persons of skill rely, and is incorporated herein by reference. According to the framework of the DSM-IV, the mental disorders of Axis I include: disorders diagnosed in childhood (such as Attention Deficit Disorder (ADD) and Attention Deficit-Hyperactivity Disorder (ADHD)) and disorders diagnosed in adulthood.

The disorders diagnosed in adulthood include (1) schizophrenia and psychotic disorders; (2) cognitive disorders; (3) mood disorders; (4) anxiety related disorders; (5) eating disorders; (6) substance related disorders; (7) personality disorders; and (8) "disorders not yet included" in the scheme.

ADD and ADHD are disorders that are most prevalent in children and are associated with increased motor activity and a decreased attention span. These disorders are commonly treated by administration of psychostimulants such as methylphenidate and dextroamphetamine sulfate.

The compounds (and their mixtures) of the present invention are also effective for treating disruptive behavior disorders, such as attention deficit disorder (ADD) and attention deficit disorder/hyperactivity (ADHD), which is in accordance with its accepted meaning in the art, as provided in the DSM-IV-TR™. These disorders are defined as affecting one's behavior resulting in inappropriate actions in learning and social situations. Although most commonly occurring during childhood, disruptive behavior disorders may also occur in adulthood.

Schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates. So-called negative symptoms of schizophrenia include affect blunting, anergia, alogia and social withdrawal, which can be measured using SANS (Andreasen, 1983, Scales for the Assessment of Negative Symptoms (SANS), Iowa City, Iowa). Positive symptoms of schizophrenia include delusion and hallucination, which can be measured using PANSS (Positive and Negative Syndrome Scale) (Kay et al., 1987, *Schizophrenia Bulletin* 13:261-276). Cognitive symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, *J. Nerv. Ment. Dis.* 182:631-638) or with cognitive tasks such as the Wisconsin Card Sorting Test. Conventional antipsychotic drugs, which act on the dopamine $D_2$ receptor, can be used to treat the positive symptoms of schizophrenia, such as delusion and hallucination. In general, conventional antipsychotic drugs and atypical antipsychotic drugs, which act on the dopamine $D_2$ and $5HT_2$ serotonin receptor, are limited in their ability to treat cognitive deficits and negative symptoms such as affect blunting (i.e., lack of facial expressions), anergia, and social withdrawal.

Disorders treatable with the compounds of the present invention include, but are not limited to, depression, bipolar disorder, chronic fatigue disorder, seasonal affective disorder, agoraphobia, generalized anxiety disorder, phobic anxiety, obsessive compulsive disorder (OCD), panic disorder, acute stress disorder, social phobia, posttraumatic stress disorder, premenstrual syndrome, menopause, perimenopause and male menopause.

Compounds and compositions of the present invention are also effective for treating eating disorders. Eating disorders are defined as a disorder of one's appetite or eating habits or of inappropriate somatotype visualization. Eating disorders include, but are not limited to, anorexia nervosa; bulimia nervosa, obesity and cachexia.

In addition to their beneficial therapeutic effects, compounds of the present invention provide the additional benefit of avoiding one or more of the adverse effects associated with conventional mood disorder treatments. Such side effects include, for example, insomnia, breast pain, weight gain, extrapyramidal symptoms, elevated serum prolactin levels and sexual dysfunction (including decreased libido, ejaculatory dysfunction and anorgasmia).

Learning, Memory and Cognition

Generally, compounds of the invention can be used for improving or enhancing learning and memory in subjects without cognitive deficits or patients suffering from cognitive deficits. Patients, who may benefit from such treatment, include those exhibiting symptoms of dementia or learning and memory loss. Individuals with an amnesic disorder are impaired in their ability to learn new information or are unable to recall previously learned information or past events. The memory deficit is most apparent on tasks to require spontaneous recall and may also be evident when the examiner provides stimuli for the person to recall at a later time. The memory disturbance must be sufficiently severe to cause marked impairment in social or occupational functioning and must represent a significant decline from a previous level of functioning. The memory deficit may be age-related or the result of disease or other cause. Dementia is characterized by multiple clinically significant deficits in cognition that represent a significant change from a previous level of functioning, including memory impairment involving inability to learn new material or forgetting of previously learned material. Memory can be formally tested by measuring the ability to register, retain, recall and recognize information. A diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

Compounds of the invention are useful for preventing loss of neuronal function, which is characteristic of neurodegenerative diseases. Therapeutic treatment with a compound of the invention improves and/or enhances memory, learning and cognition. In one embodiment, the compounds of the invention can be used to treat a neurodegenerative disease such as Alzheimer's, Huntington's disease, Parkinson's disease and amyotrophic lateral sclerosis, as well as MLS (cerebellar ataxia), Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, and closed head injury.

Compounds of the invention are useful for treating or preventing loss of memory and/or cognition associated with a neurodegenerative disease. The compounds also ameliorate cognitive dysfunctions associated with aging and improve catatonic schizophrenia Alzheimer's disease is manifested as a form of dementia that typically involves mental deterioration, reflected in memory loss, confusion, and disorientation. In the context of the present invention, dementia is defined as a syndrome of progressive decline in multiple domains of cognitive function, eventually leading to an inability to maintain normal social and/or occupational performance. Early symptoms include memory lapses and mild but progressive deterioration of specific cognitive functions, such as language (aphasia), motor skills (apraxia) and perception (agnosia). The earliest manifestation of Alzheimer's disease is often memory impairment, which is required for a diagnosis of dementia in both the National Institute of Neurological and Communicative Disorders and Stroke-Alzheimer's Disease- and the Alzheimer's Disease and Related Disorders Association (NINCDS-ADRDA) criteria (McKhann et al., 1984, Neurology 34:939-944), which are specific for Alzheimer's disease, and the American Psychiatric Association's Diagnostic and Statistical Manual of Mental Disorders, Fourth Edition (DSM-IV) criteria, which are applicable for all forms of dementia. The cognitive function of a patient may also be assessed by the Alzheimer's disease Assessment Scale-cognitive subscale (ADAS-cog; Rosen et al., 1984, *Am. J. Psychiatry* 141:1356-1364). Alzheimer's disease is typically treated by acetylcholine esterase inhibitors such as tacrine hydrochloride or donepezil. Unfortunately, the few forms of treatment for memory loss and impaired learning available at present are not considered effective enough to make any significant difference to a patient, and there is currently a lack of a standard nootropic drug for use in such treatment.

Other conditions that are manifested as deficits in memory and learning include benign forgetfulness and closed head injury. Benign forgetfulness refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale. Closed head injury refers to a clinical condition after head injury or trauma. Such a condition, which is characterized by cognitive and memory impairment, can be diagnosed as "amnestic disorder due to a general medical condition" according to DSM-IV.

Compounds and compositions of the invention are also effective for treating cerebral function disorders. The term cerebral function disorder, as used herein, includes cerebral function disorders involving intellectual deficits, and may be exemplified by senile dementia, Alzheimer's type dementia, memory loss, amnesia/amnestic syndrome, epilepsy, disturbances of consciousness, coma, lowering of attention, speech disorders, Parkinson's disease and autism.

Pain

The compounds of the invention are useful to treat any kind of acute or chronic pain. In a preferred embodiment, the compounds of the invention are useful to treat chronic pain. In a particularly preferred embodiment, the compounds of the invention are useful to treat neuropathic pain. The term neuropathic "pain" includes central neuropathic pain, involving damage to the brain or spinal cord, such as may occur following stroke, spinal cord injury, and as a result of multiple sclerosis. It also includes peripheral neuropathic pain, which includes diabetic peripheral neuropathic pain, post-herpetic neuralgia (PHN), and trigeminal neuralgia (TN). It also includes dysfunctions of the nervous system such as Complex Regional Pain Syndrome (CRPS), formerly known as Reflex Sympathetic Dystrophy (RSD), and causalgia, and neuropathic pain symptoms such as sensory loss, allodynia, hyperalgesia and hyperpathia. It further includes mixed nociceptive and neuropathic pain types, for example, mechanical spinal pain and radiculopathy or myelopathy, and the treatment of chronic pain conditions such as fibromyalgia, lower back pain and neck pain due to spinal nerve root compression, neuropathic cancer pain, HIV/AIDS induced pain, and phantom limb pain. In another preferred embodiment, the compounds of the invention are useful for chronic migraine prophylaxis.

Other conditions and disorders include, but are not limited to, autism, childhood learning disorders, depressions, anxieties, sleep disorders, Compounds of the invention may also be useful for the treatment of neurotoxic injury that follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest.

The term "treating" when used in connection with the foregoing disorders means amelioration, prevention or relief from the symptoms and/or effects associated with these disorders and includes the prophylactic administration of a compound of the invention, a mixture thereof, or a pharmaceutically acceptable salt of either, to substantially diminish the likelihood or seriousness of the condition.

B. Models of Disease

In animals, several established models of learning and memory are available to examine the beneficial cognitive enhancing effects and potential related side effects of treatment. Descriptions of tests that may be employed to assess changes in cognition in non-human species are given in the following references and references cited therein. Each of the following references is incorporated by reference into this application in their entirety: Sarter, M., *Intern. J. Neuroscience*, 1987, 32:765-774; *Methods and Findings in Experimental and Clinical Pharmacology* 1998, 20(3), 249-277; *Indian Journal of Pharmacology* 1997, 29(4), 208-221. The tests include the Morris water maze (Stewart and Morris, In "*Behavioral Neuroscience. A Practical Approach*. Volume I", 1993, R. Saghal, Ed., 107-122; Morris, R. *Journal of neuroscience methods* 1984, 11(1), 47-60), delayed non-match to sample (Bontempi, B, et al, *Journal of Pharmacology and Experimental Therapeutics* 2001, 299(1), 297-306.; Alvarez, P; Zola-Morgan, S; Squire, L. R. *Proc Natl Acad Sci USA.* 1994 7; 91(12), 5637-41.), delayed Alternation (also called delayed non-matching to position; Roux, S; Hubert, I; Lenegre, A; Milinkevitch, D; Porsolt, R D. *Pharmacol Biochem Behav.* 1994 49(3), 83-8; Ohta, H; Ni, X. H.; Matsumoto, K; Watanabe, H, *Jpn J Pharmacol.* 1991, 56(3), 303-9), social discrimination models (Engelmann, M; Wotjak, C. T; Landgraf R. *Physiol Behav.* 1995, 58(2), 315-21), social recognition test (also called delay-induced forgetting; Lemaire, M; Bohme, G. A.; Piot. O; Roques, B. P.; Blanchard, J. C. *Psychopharmacology (Berl).* 1994, 115(4):435-40), contextual fear conditioning (Barad, M; Bourtchouladze, R; Winder, D G; Golan, H; Kandel, E. *Proc Natl Acad Sci USA.* 1998, 95(25), 15020-5; Bourtchouladze, R.; Frenguelli, B.; Blendy, J.; Cioffi, D.; Schutz, G.; Silva, A. J. *Cell,* 1994, 79, 59-68), and conditioned fear extinction (Walker, D L; Ressler, K J; Lu, K. T., Davis, M., *J Neurosci.* 2002, 22(6), 2343-51; Davis, M.; Ressler, K.; Rothbaum, B. O.; Richardson, R. *Biol. Psychiatry,* 2006, 60, 369-375).

The Morris water maze is one of the best-validated models of learning and memory, and it is sensitive to the cognitive enhancing effects of a variety of pharmacological agents. The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia. In addition, this animal paradigm accurately models the increasing degree of impairment with advancing age and the increased vulnerability of the memory trace to pre-test delay or interference which is characteristic of amnesiac patients.

Contextual fear conditioning is a form of associative learning in which animals learn to fear a new environment (or an emotionally neutral conditioned stimulus) because of its temporal association with an aversive unconditioned stimulus (US), such as a foot shock. When exposed to the same context or conditioned stimulus at a later time, conditioned animals show a variety of conditioned fear responses, including freezing behavior. Because robust learning can be triggered with a single training trial, contextual fear conditioning has been used to study temporally distinct processes of short-term and long-term memory. Contextual fear conditioning is believed to be dependent on both the hippocampus and amygdale function.

Another example of learning is called fear extinction, a process exhibited in both human and animals, including rodents. Extinction of fear refers to the reduction in the measured level of fear to a cue previously paired with an aversive event when that cue is presented repeatedly in the absence of the aversive event. Extinction of fear is not the erasure of the original fear memory, but instead results from a new form of learning that acts to inhibit or suppress the original fear memory (Bouton, M. D.; Bolles, R. C. *J. Exp. Psychol. Anim. Behav. Process.* 1979, 5, 368-378; Konorski, J. *Inegrative Activity of the Brain: An Interdiscipinary Approach,* 1967, Chicago: The University of Chicago Press; Pavlov, I. P. *Conditioned Reflexes.* 1927, Oxford, United Kingdom: Oxford University Press.). The literature also suggests that glutamate acting at the N-methyl D-aspartate (NMDA) receptor is critically involved in learning and memory (Bear, M. F. *Proc. Nat. Acad. Sci.* 1996, 93, 13453-13459; Castellano, C.; Cestari, V.; Ciamei, A. *Curr. Drug Targets,* 2001, 2, 273-283; Morris, R. G.; Davis, S.; Butcher, S. P. *Philos. Trans. R Soc. Lond. B Biol. Sci.* 1990. 329, 187-204; Newcomer, J. W.; Krystal, J. H. *Hippocampus,* 2001, 11, 529-542.). There is also evidence that the NMDA receptor is involved with extinction of fear. For example, NMDA antagonists such as 2-amino-5-phosphopentanoic acid (APV) are known to block fear extinction (Davis, M.; Ressler, K.; Rothbaum, B. O.; Richardson, R. *Biol. Psychiatry,* 2006, 60, 369-375; Kehoe, E. J.; Macrae, M.; Hutchinson, C. L. *Psychobiol.* 1996, 24, 127-135; Lee, H.; Kim, J. J. *J. Neurosci.* 1998, 18, 8444-8454; Szapiro, G.; Vianna, M. R.; McGaugh, J. L.; Medina, J. H.; Izquierdo, I. *Hippocampus,* 2003, 13, 53-58.), and NMDA agonists (such as the partial agonist D-cycloserine), are known to facilitate fear extinction (Davis, M.; Ressler, K.; Rothbaum, B. O.; Richardson, R. *Biol. Psychiatry,* 2006, 60, 369-375; Ledgerwood, L.; Richardson, R.; Cranney, J. *Behav. Neurosci.* 2003, 117 341-349; Walker, D. L.; Ressler, K. J.; Lu K.-T.; Davis, M. *J. Neurosci.* 2002, 22, 2343-2351). Additional experimental conditions for fear extinction tests may be found in the references cited in this paragraph, and are incorporated by reference.

In human exposure therapy, a patient is repeatedly exposed for prolonged periods to a feared object or situation in the absence of aversive consequences. As a result, the patient is often able to face their feared cues or situations with less fear and avoidance (extinction retention) due to the learning that took place during exposure therapy (extinction training). It has been shown that agents, such as D-cycloserine, that improve extinction in animals also improve the effectiveness of exposure-based psychotherapy. Examples of exposure based cognitive-behavioral therapy (CBT) improved by agents that improve extinction include exposure to phobic objects as therapy for phobia disorders (For acrophobia, see Davis, M.; Ressler, K.; Rothbaum, B. O.; Richardson, R. *Biol. Psychiatry*, 2006, 60, 369-375; Ressler, K. J.; Rothbaum, B. O.; Tannenbaum, L.; Anderson, P.; Graap, K.; Zimand, E.; Hodges, L.; Davis, M. *Archives Gen. Psychiatry* 2004, 61, 1136-1144.), exposure to phobic situations as therapy for panic disorders (For social anxiety disorder, see Hoffmann, S. G.; Meuret, A. E.; Smits, J. A.; Simon, N. M.; Pollack, M. H.; Eisenmenger, K.; Shiekh, M.; Otto, M. W. *Arch. Gen. Psychiatry* 2006, 63, 298-304; Hofmann, S. G.; Pollack, M. H.; Otto, M. W. *CNS Drug Reviews* 2006, 12, 208-217), recollection of traumatic memories as therapy for Post-Traumatic Stress Disorder, exposure to cues associated with drug cravings as therapy for drug addiction, and exposure to cues associated with smoking as therapy for smoking cessation. Because of the cognitive, learning aspects associated with psychotherapy based treatment for disorders such as phobias, anxiety, Post-Traumatic Stress Disorder, and Addiction, compounds of the invention are useful as an adjunct with psychotherapy for the treatment of these conditions. Clinically, compounds of the invention are useful as an adjunct to shorten the number of therapy sessions required or improve the therapeutic outcome of therapy.

In humans, methods for improving learning and memory may be measured by such tests as the Wechsler Memory Scale and the Minimental test. A standard clinical test for determining if a patient has impaired learning and memory is the Minimental Test for Learning and Memory (Folstein et al., J. Psychiatric Res. 12:185, 1975), especially for those suffering from head trauma, Korsakoffs disease or stroke. The test result serves as an index of short-term, working memory of the kind that deteriorates rapidly in the early stages of dementing or amnesiac disorders. Ten pairs of unrelated words (e.g., army-table) are read to the subject. Subjects are then asked to recall the second word when given the first word of each pair. The measure of memory impairment is a reduced number of paired-associate words recalled relative to a matched control group. Improvement in learning and memory constitutes either (a) a statistically significant difference between the performance of treated patients as compared to members of a placebo group; or (b) a statistically significant change in performance in the direction of normality on measures pertinent to the disease model. Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task. Another potential application for therapeutic interventions against memory impairment is suggested by age-related deficits in performance which are effectively modeled by the longitudinal study of recent memory in aging mice.

The Wechsler Memory Scale is a widely used pencil-and-paper test of cognitive function and memory capacity. In the normal population, the standardized test yields a mean of 100 and a standard deviation of 15, so that a mild amnesia can be detected with a 10-15 point reduction in the score, a more severe amnesia with a 20-30 point reduction, and so forth. During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/memory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (DSM IV, 1994). As noted above, "improvement" in learning and memory within the context of the present invention occurs when there is a statistically significant difference in the direction of normality in the paired-associate test, for example, between the performance of therapeutic agent treated patients as compared to members of the placebo group or between subsequent tests given to the same patient.

In animals, many established models of schizophrenia are available to examine the beneficial effects of treatment; many of which are described in the following references, as well as references cited within, and are incorporated by reference: Saibo *Kogaku* 2007, 26(1), 22-27; Cartmell, J.; Monn, J. A.; Schoepp, D. D. *J. Pharm. Exp. Ther.* 1999, 291(1), 161-170; Rowley, M; Bristow, L. J.; Hutson, P. H. *J. Med. Chem.* 2001 15; 44(4), 477-501; Geyer, M. A.; Ellenbroek, B; *Prog Neuropsychopharmacol Biol Psychiatry* 2003, 27(7):1071-9; Geyer, M. A.; Krebs-Thomson, K; Braff, D. L.; Swerdlow, N. R. *Psychopharmacology (Berl)*. 2001 156(2-3):117-54; Jentsch, J. D.; Roth, R. H. *Neuropsychopharmacology* 1999, 20(3):201-25. The tests include Prepulse Inhibition (Dulawa, S. C.; Geyer, M. A. *Chin J Physiol*. 1996, 39(3):139-46), PCP stereotypy test (Meltzer et al (In "PCP (Phencyclidine): Historical and Current Perspectives", ed. E. F. Domino, NPP Books, Ann Arbor, 1981, 207-242), Amphetamine stereotypy test (Simon and Chemat, *J. Pharmacol. (Paris)*, 1972, 3, 235-238), PCP hyperactivity (Gleason, S. D.; Shannon, H. E. *Psychopharmacology (Berl)*. 1997, 129(1):79-84) and MK-801 hyperactivity (Corbett, R; Camacho, F; Woods, A. T.; Kerman, L. L.; Fishkin, R. J.; Brooks, K; Dunn, R. W. *Psychopharmacology (Berl)*. 1995, 120(1):67-74.

The prepulse inhibition test may be used to identify compounds that are effective in treating schizophrenia. The test is based upon the observations that animals or humans that are exposed to a loud sound will display a startle reflex and that animals or humans exposed to a series of lower intensity sounds prior to the higher intensity test sound will no longer display as intense of a startle reflex. This is termed prepulse inhibition. Patients diagnosed with schizophrenia display defects in prepulse inhibition, that is, the lower intensity prepulses no longer inhibit the startle reflex to the intense test sound. Similar defects in prepulse inhibition can be induced in animals via drug treatments (scopolamine, ketamine, PCP or MK-801) or by rearing offspring in isolation. These defects in prepulse inhibition in animals can be partially reversed by drugs known to be efficacious in schizophrenia patients. It is felt that animal prepulse inhibition models have face value for predicting efficacy of compounds in treating schizophrenia patients.

In animals, many established models of pain are available to examine the beneficial effects of treatment; many of which are reviewed in Methods in Pain Research, CRC Press, 2001, Kruger, L. (Editor). Tests of acute pain include the tail flick (d'Amour and Smith, *J. Pharmacol. Exp. Ther.* 1941, 72, 74-79), hot plate (Eddy, N. B.; Leimbach, D. *J Pharmacol Exp Ther.* 1953, 107(3):385-93), and paw withdrawal tests. The phenylbenzoquinone writhing assay is a measure of peritoneovisceral or visceral pain. Persistent pain tests, which use an irritant or foreign chemical agent as the nociceptive stimulus, include the formalin test (Wheeler-Aceto, H; Cowan, A Psychopharmacology (Berl). 1991, 104(1):35-44), Freund's adjuvant (Basile, A. S. et al Journal of Pharmacology and Experimental Therapeutics 2007, 321(3), 1208-1225; Ackerman, N. R. et al; Arthritis & Rheumatism 1979, 22(12), 1365-74), capsaicin (Barrett, A. C. et al Journal of Pharmacology and Experimental Therapeutics 2003, 307(1), 237-245), and carrageenin models. These models have an initial, acute phase, followed by a second, inflammatory phase.

Neuropathic pain models are reviewed in Wang and Wang, Advanced Drug Delivery Reviews 2003, and include the Spinal Nerve Ligation (SNL) model (also called the Chung Model; Kim, S. H.; Chung, J. M. *Pain* 1992 50(3):355-63; Chaplan et al., *Journal of Neuroscience Methods* 1994, 53(1): 55-63; Chaplan S R, Bach F W, Pogrel J W.), Chronic Constriction Injury (CCI) model (also called the Bennett Model; Bennett, G. J; Xie, Y. K *Pain* 1988 33(1):87-107.), Progressive Tactile Hypersensitivity (PTH) model (Decosterd, I. *Pain*, 2002, 100(1), 155-162; *Anesth. Analg.* 2004, 99, 457-463), Spared Nerve Injury (SNI) model (Decosterd, I. *Pain*, 2002, 100(1), 155-162; *Anesth. Analg.* 2004, 99, 457-463), the lumbar nerve ligation model (Ringkamp, M; Eschenfelder, S; Grethel, E. J.; Häbler, H. J., Meyer, R. A., Jänig, W., Raja, S. N. *Pain*, 1999, 79(2-3), 143-153), and streptozocin- or chemotherapy induced diabetic neuropathy (Courteix, C.; Eschalier, A.; Lavarenne, J. *Pain*, 1993, 53(1), 81-88; Aubel, B. et al *Pain* 2004, 110(1-2), 22-32.).

Opioids, such as morphine, display robust efficacy in models of acute pain, such as the tail flick and hot plate tests, as well as in both the initial, acute phase and the second, inflammatory phase of persistent pain tests, such as the formalin test. Opioids also display efficacy in neuropathic pain models, such as the Spinal Nerve Ligation (SNL) model. The general analgesic effects of opiate compounds such as morphine in neuropathic pain models, however, are suggested by the increase in paw withdrawal threshold (PWT) in both the injured and the contralateral (uninjured) paw. Compounds that are useful specifically for the treatment of persistent or chronic pain states (e.g., neuropathic pain), such as gabapentin, tend to display efficacy in models of persistent inflammatory and neuropathic pain, such as the formalin (second phase) and SNL models. Compounds of this type, however, tend to increase PWT in the SNL model in only the injured paw. In addition, these compounds fail to display efficacy in acute tests such as the tail flick test and the hot plate test, and also fail to display efficacy in the initial, acute phase of the formalin test. The lack of effect of compounds in the acute pain tests supports the notion that the antinociceptive action of these compounds is related to specific mechanisms associated with a central sensitized state following injury. As a result, compounds that are efficacious in neuropathic pain model(s), such as the SNL (Chung) model, and the second phase of the formalin test, but are not efficacious in acute pain models, such as hot plate and tail flick, or in the first phase of the formalin test suggest that these compounds are more likely to be effective in persistent and chronic, rather than acute, pain states (see Table 1). In addition, their ability to increase PWT in the SNL model should be specific for the ipsilateral (injured) paw. Relevant references follow, and are included by reference. Singh, L. et al, *Psychopharmacology*, 1996, 127, 1-9. Field, M. J. et al *Br. J. Pharmacol.* 1997, 121, 1513-1522. Iyengar, S. et al, *J. Pharmacology and Experimental Therapeutics*, 2004, 311, 576-584. Shimoyama, N. et al *Neuroscience Letters*, 1997, 222, 65-67. Laughlin, T. M. et al *J. Pharmacology and Experimental therapeutics*, 2002, 302, 1168-1175. Hunter, J. C. et al *European J. Pharmacol.* 1997, 324, 153-160. Jones, C. K. et al *J. Pharmacology and Experimental therapeutics*, 2005, 312, 726-732. Malmberg, A. B.; Yaksh, T. L. *Anesthesiology*, 1993, 79, 270-281. Bannon, A W et al *Brain Res.*, 1998, 801, 158-63.

In a preferred embodiment, the compounds of the invention are useful for the treatment of persistent or chronic pain states (e.g., neuropathic pain). As described above, such compounds may be profiled in vivo by evaluating their efficacy in models of both acute and neuropathic pain. Preferred compounds demonstrate efficacy in neuropathic pain models, but not in acute pain models.

TABLE 1

Profile of morphine and gabapentin in a variety of animal models

| Animal Model | Morphine | Gabapentin |
|---|---|---|
| Acute Pain | | |
| Hot plate | + | − |
| Tail flick | + | − |
| Formalin (early phase) | + | − |
| Tissue Injury/Inflammatory Pain | | |
| Formalin (second phase) | + | + |
| Carrageenan | + | + |
| Nerve Injury/Neuropathic Pain | | |
| Spinal Nerve Ligation (SNL; Chung) | + | + |
| Chronic Constriction Injury (CCI; Bennet) | + | + |

There are various animal models with chronic brain dysfunctions thought to reflect the processes underlying human epilepsy and seizures/convulsions, such as those described in *Epilepsy Res.* 2002 June; 50(1-2):105-23. Such chronic models include the kindling model of temporal lobe epilepsy (TLE), post-status models of TLE in which epilepsy develops after a sustained status epilepticus, and genetic models of different types of epilepsy. Currently, the kindling model and post-status models, such as the pilocarpine or kainate models, are the most widely used models for studies on epileptogenic processes and on drug targets by which epilepsy can be prevented or modified. Furthermore, the seizures in these models can be used for testing of antiepileptic drug effects. A comparison of the pharmacology of chronic models with models of acute (reactive or provoked) seizures in previously healthy (non-epileptic) animals, such as the maximal electroshock seizure test, demonstrates that drug testing in chronic models of epilepsy yields data which are more predictive of clinical efficacy and adverse effects.

The following examples are provided to illustrate selected embodiments of the invention and are not to be construed as limiting its scope.

EXAMPLES

General Procedures

General Procedure 1

Synthesis of Fused Pyrrole Analogs

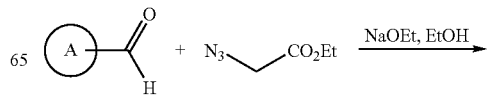

-continued

In the above Scheme, ring A represents any substituted or unsubstituted 5-membered, aromatic ring. Exemplary aromatic rings include thiophenes, furans, thiazoles and pyrroles.

A) Condensation of an Aldehyde with Ethyl Azidoacetate

A solution of the aldehyde (e.g., 1.61 g, 8.41 mmol) and about 4 to 7 equivalents of ethyl azidoacetate (e.g., 4.34 g, 33.7 mmol) in anhydrous EtOH (e.g., 10.5 mL) was added dropwise to a solution of sodium ethoxide prepared from sodium (e.g., 0.8 g) in anhydrous EtOH (e.g., 50.0 mL) at a temperature between about 0° C. and about −45° C. (typically between about −10 and about −5° C. (e.g., NaCl/ice)). The reaction mixture was stirred for about 1 hour (h) while the temperature was maintained below 0° C. and was then allowed to warm to ambient temperature (also called room temperature, rt) (e.g., overnight). The mixture was quenched with a cold solution of saturated aqueous $NH_4Cl$ or was diluted with water (e.g., 0.5 L). The product was extracted with diethyl ether or ethyl acetate (EtOAc) (e.g., 3×0.2 L) and the combined organic phases were washed with saturated aqueous NaCl solution (2×0.1 L), dried (e.g., over $Na_2SO_4$) and filtered. The solvent was removed in vacuo to give the ethyl azidoacrylate. Alternatively, the solvent was reduced in vacuo (e.g., to about 50 mL) and the resulting solution was used in the next reaction step.

B) Cyclization of the Ethyl Azidoacrylate

A solution of the above ethyl azidoacrylate in o- or m-xylene (e.g., 150 mL) was heated to reflux for a time period between about 5 minutes (min) and 14 h (typically about 1 h). The reaction mixture was then allowed to cool to ambient temperature. The solution was concentrated in vacuo and the crude product was purified (e.g., silica gel column chromatography) to give the fused pyrrole ethyl ester.

General Procedure 2

Saponification of Ethyl and Methyl-Esters

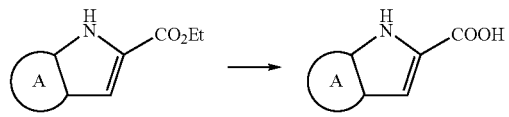

To a solution or suspension of the ester (e.g., 0.33 g, 1.2 mmol) in MeOH or EtOH (e.g., 16.5 mL) was added an aqueous base, such as 10M NaOH (e.g., 0.6 mL, 6 mmol), 5M KOH (e.g., 1.2 mL, 6 mmol) or 1M LiOH (e.g., 6 mL). The solution was heated to a temperature between about 50° C. and reflux for a time period between about 30 min and about 20 h (e.g., 5 h). The reaction mixture was cooled to rt and was then acidified. In one example, the mixture was poured into water (e.g., 200 mL) and the pH of the resulting mixture was adjusted to about pH 1-2 with HCl. In another example, excess solvent was removed in vacuo and the residue was dissolved in 5% citric acid (e.g., 15 mL). In yet another example, the solvent was removed in vacuo and the residue was dissolved in a saturated solution of $NH_4Cl$ (e.g., 15 mL). The acidified solution was then extracted (e.g., 3×100 mL EtOAc) and the combined organic layers were washed (e.g., with brine), dried (e.g., over $Na_2SO_4$), filtered and concentrated in vacuo to give the carboxylic acid.

Example 1

Synthesis of Fused Thiophene Pyrrole Analogs 1.1. Synthesis of Intermediate Aldehydes 1.1.a) Synthesis of 4-(4-Chlorobenzyl)thiophene-2-carbaldehyde

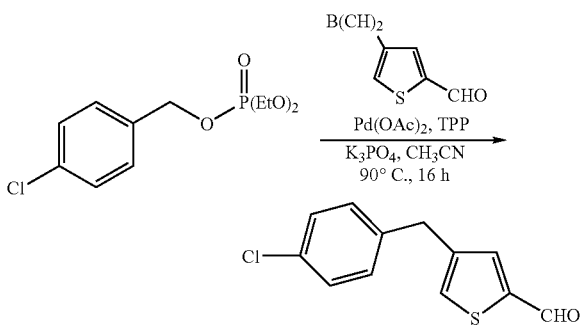

A solution mixture of $Pd(OAc)_2$ (144 mg, 0.64 mmol) and triphenylphosphine (TPP) (136 mg, 0.52 mmol) were weighed into a vial, dissolved in acetonitrile and transferred into a 40 mL Wheaton vial containing diethyl 4-chlorobenzyl phosphate (*Org. Lett.* 2005, 7, 4875-4878; 3.08 g, 11.6 mmol), 5-formylthiophen-3-ylboronic acid (2.0 g, 12.8 mmol), $K_3PO_4$ (2.72 g, 12.8 mmol) and a stir-bar. Nitrogen gas was bubbled through the mixture. The vial was closed tightly and heated to 90° C. and vigorously stirred for 16 h. The reaction was diluted with water and extracted with dichloromethane (DCM) (3×100 mL). The combined extracts were washed with brine, dried over $Na_2SO_4$, filtered and concentrated. Purification by flash chromatography (Isco CombiFlash) (0-20% heptane/EtOAc) yielded 4-(4-chlorobenzyl)thiophene-2-carbaldehyde: 835 mg, 28% yield. $^1$H NMR (400 MHz, $CDCl_3$) δ ppm: 10.10 (d, 1H), 7.80 (d, 1H), 7.63 (m, 1H), 7.55 (m, 2H), 7.40 (m, 2H), 4.23 (s, 2H).

1.1.b) Synthesis of 4-Phenethylthiophene-2-carbaldehyde

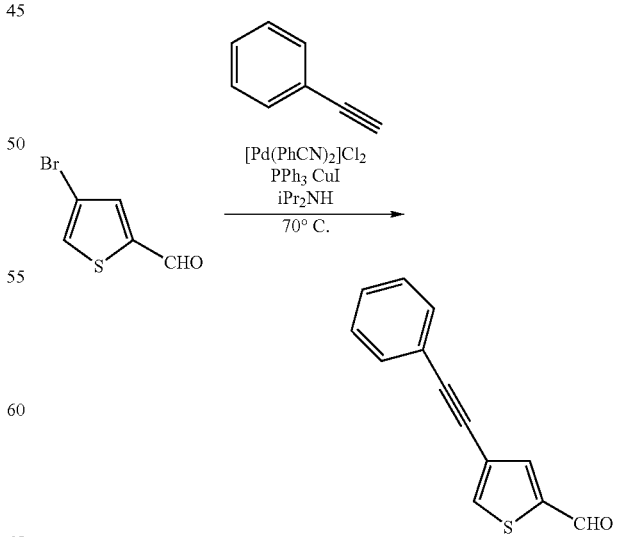

Under a $N_2$ atmosphere, 4-bromothiophene-2-carbaldehyde (1.0 g, 5.2 mmol) was taken up in diisopropylamine (20 mL). TPP (549 mg, 2.1 mmol), bis(benzonitrile)palladium chloride ([Pd(PhCN)$_2$]Cl$_2$) (400 mg, 1.0 mmol), and copper iodide (199 mg, 1.0 mmol) were added. The mixture was degassed with N$_2$ before phenylacetylene (1.15 mL, 10.4 mmol) was added, and the reaction was stirred at 70° C. for 16 h. The mixture was concentrated to a dark brown solid and chromatographed in 0-15% EtOAc in heptane to yield 4-(phenylethynyl)thiophene-2-carbaldehyde (981 mg, 88%). $^1$H NMR (400 MHz, CDCl$_3$) δ (ppm): 9.93 (d, 1H), 7.88 (t, 1H), 7.85 (d, 1H), 7.53 (m, 2H), 7.38 (m, 3H).

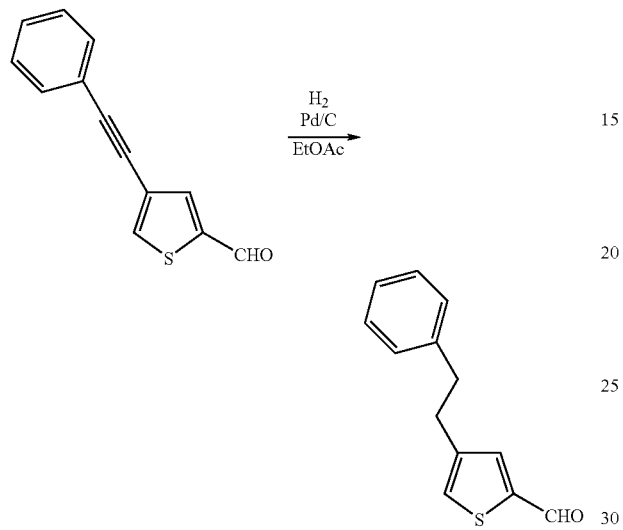

Under a N$_2$ atmosphere, 4-(phenylethynyl)thiophene-2-carbaldehyde (386 mg, 1.8 mmol) was dissolved EtOAc (6 mL), and palladium on carbon (Pd/C) (44 mg) was added. The flask was evacuated and flushed with H$_2$ (3×). The reaction stirred at rt overnight with a balloon of H$_2$. The mixture was filtered through a plug of Celite® and the filtrate was concentrated to give 4-phenethylthiophene-2-carbaldehyde (373 mg, 95%). $^1$H NMR (400 MHz, CDCl$_3$) δ (ppm): 9.87 (d, 1H), 7.56 (d, 1H), 7.33 (m, 1H), 7.29 (m, 2H), 7.23 (m, 1H), 7.16 (m, 2H), 2.97 (m, 4H).

1.1.c) Synthesis of 4-[2-(4-Chlorophenyl)-ethyl]-thiophene-3-carbaldehyde

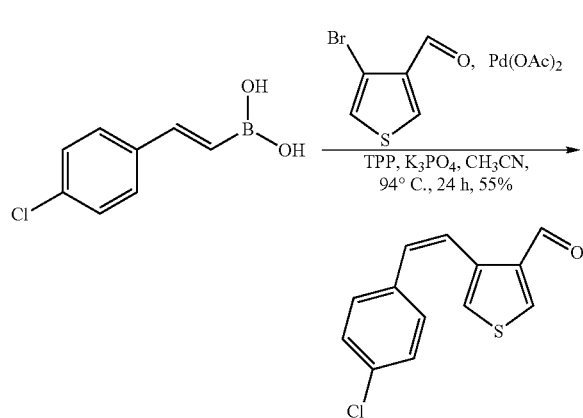

To a 40-mL scintillation vial containing trans-2-(4-chlorophenyl)vinylboronic acid (0.42 g, 2.30 mmol), 3-bromo-4-formylthiophene (0.40 g, 2.09 mmol), K$_3$PO$_4$ (0.490 g, 2.30 mmol), TPP (22 mg, 0.08 mmol, 4 mol %), Pd(OAc)$_2$ (4.7 mg, 0.02 mmol, 1 mol %) and a stir-bar, was added acetonitrile (2.5 mL). The vial was purged with N$_2$, capped tightly and heated at 94° C. (aluminum multi-reaction block) while vigorously stirred for 32 h. The reaction was diluted with water and extracted with EtOAc (3×50 mL). The combined extracts were washed with brine, dried over Na$_2$SO$_4$, filtered and concentrated. Purification by flash chromatography (Isco CombiFlash) 0-10% EtOAc in heptane afforded the desired 4-[2-(4-chlorophenyl)-vinyl]-thiophene-3-carbaldehyde (285 mg, 54%). $^1$H NMR (400 MHz, CDCl$_3$) δ ppm 6.99 (d, J=16.38 Hz, 1H), 7.31-7.36 (m, 2H), 7.45-7.49 (m, 2H), 7.50 (d, J=3.20 Hz, 1H), 7.76 (dd, J=16.34, 0.78 Hz, 1H), 8.13 (d, J=3.20 Hz, 1H), 10.07 (d, J=0.82 Hz, 1H).

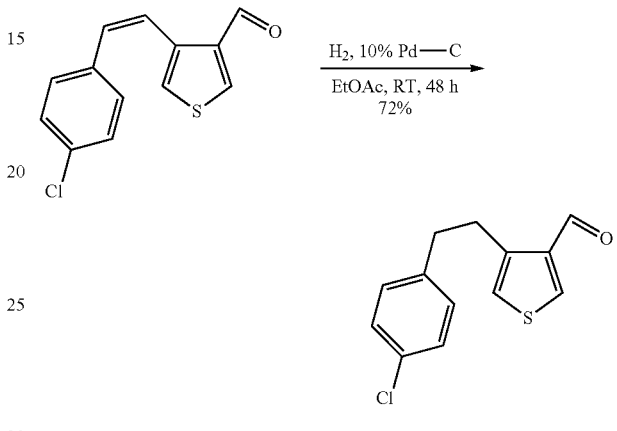

4-(4-Chlorophenethyl)thiophene-3-carbaldehyde was synthesized from 4-[2-(4-chlorophenyl)-vinyl]-thiophene-3-carbaldehyde (260 mg, 1.04 mmol) following the conditions used to hydrogenate 4-(phenylethynyl)thiophene-2-carbaldehyde to 4-phenethylthiophene-2-carbaldehyde (Example 1.1.b). Purification by flash chromatography (0-10% EtOAc/heptane) yielded 4-(4-chlorophenethyl)thiophene-3-carbaldehyde (188 mg, 72%). $^1$H NMR (400 MHz, CDCl$_3$) δ ppm 2.86-2.92 (m, 2H), 3.16-3.22 (m, 2H), 6.91 (dd, J=3.20, 0.82 Hz, 1H), 7.10-7.15 (m, 2H), 7.22-7.27 (m, 2H), 8.11 (d, J=3.11 Hz, 2H), 10.00 (d, J=0.82 Hz, 1H).

1.1.d) Synthesis of 5-Phenethylthiophene-2-carbaldehyde

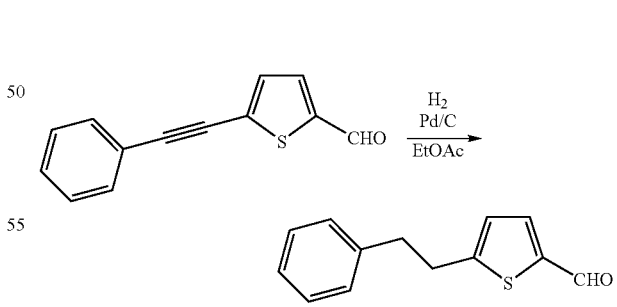

5-Phenethylthiophene-2-carbaldehyde was synthesized from 5-(phenylethynyl)thiophene-2-carbaldehyde (4.0 g, 18.8 mmol) following the conditions used to hydrogenate 4-(phenylethynyl)thiophene-2-carbaldehyde to 4-phenethylthiophene-2-carbaldehyde (Example 1.1.b). 5-Phenethylthiophene-2-carbaldehyde (3.8 g, 93%) was used in the next step without further purification $^1$H NMR (400 MHz, CDCl$_3$)

δ (ppm): 9.83 (s, 1H), 7.60 (d, 1H), 7.30 (m, 2H), 7.23 (m, 1H), 7.19 (m, 2H), 6.86 (dt, 1H), 3.21 (t, 2H), 3.03 (t, 2H).

1.1.e) Synthesis of 5-(4-chlorobenzyl)thiophene-2-carbaldehyde

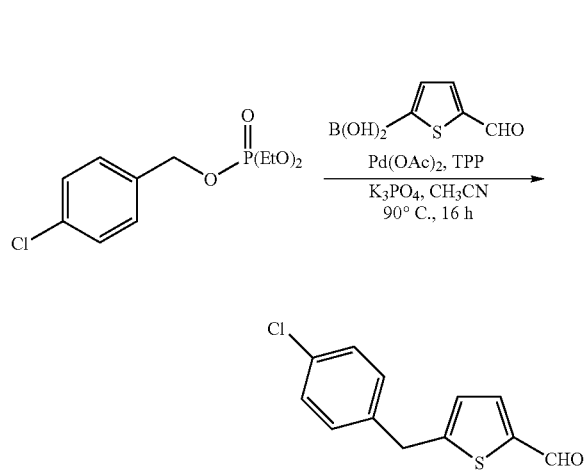

The title compound was synthesized from 5-formylthiophen-2-ylboronic acid and diethyl 4-chlorobenzyl phosphate using the conditions to synthesize 4-(4-chlorobenzyl)thiophene-2-carbaldehyde (Example 1.1.a). Purification by flash chromatography (0-20% heptane/EtOAc) yielded 5-(4-chlorobenzyl)thiophene-2-carbaldehyde (730 mg, 48%). $^1$H NMR (400 MHz, CDCl$_3$) δ ppm 9.82 (s, 1H), 7.62 (d, 1H), 7.31 (m, 2H), 7.18 (m, 2H), 6.90 (m, 1H), 4.17 (s, 2H).

1.1.f) Synthesis of 4-Benzyl-thiophene-3-carbaldehyde

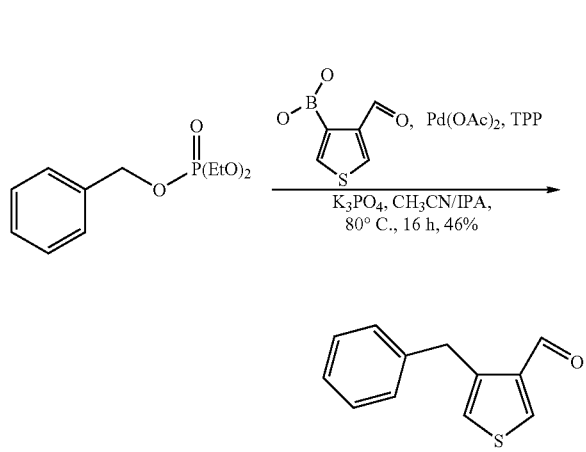

The title compound was synthesized from diethyl benzyl phosphate (*Org. Lett.* 2005, 7, 4875-4878) and 4-formylthiophen-3-ylboronic acid using the conditions to synthesize 5-(4-chlorobenzyl)thiophene-2-carbaldehyde (Example 1.1.a). Purification by prep-TLC (10% heptane/DCM, eluting 3×) yielded 4-benzylthiophene-3-carbaldehyde (204 mg, 46%). $^1$H NMR (400 MHz, CDCl$_3$) δ ppm 4.29 (s, 2H), 6.83-6.86 (m, 1H), 7.20-7.26 (m, 3H), 7.29-7.34 (m, 2H), 8.12 (d, J=3.22 Hz, 1H), 9.98 (d, J=0.73 Hz, 1H).

1.1.g) Synthesis of 4-phenylthiophene-3-carbaldehyde

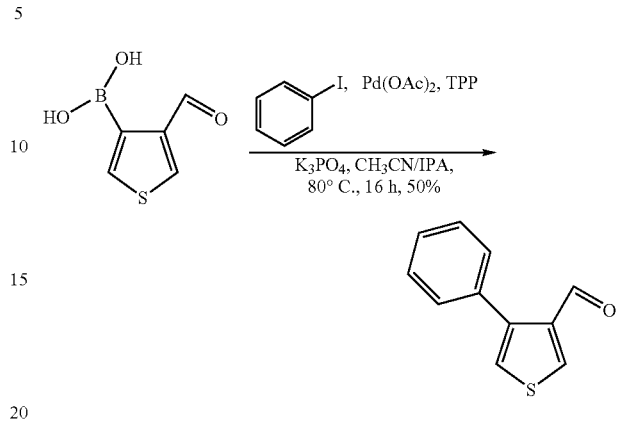

The title compound was synthesized from iodobenzene and 4-formylthiophen-3-ylboronic acid using the conditions to synthesize 5-(4-chlorobenzyl)thiophene-2-carbaldehyde. Double elution by prep-TLC (10% heptane/DCM) allowed for the isolation of 4-phenylthiophene-3-carbaldehyde (300 mg, 48% yield). $^1$H NMR (400 MHz, CDCl$_3$) δ ppm 7.32 (d, J=3.29 Hz, 1H), 7.39-7.50 (m, 5H), 8.27 (d, J=3.29 Hz, 1H), 9.87 (s, 1H); $^{13}$C NMR (100 MHz, CDCl$_3$) δ 185.80, 143.82, 138.91, 134.68, 134.28, 129.30, 128.58, 128.05, 124.76.

1.1.h) Synthesis of 4-(4-Chlorobenzyl)-thiophene-3-carbaldehyde

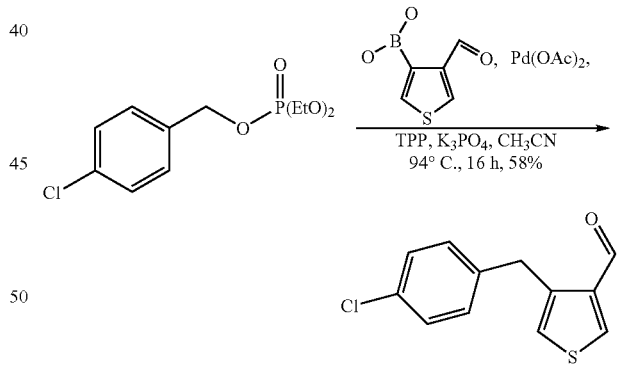

The title compound was synthesized from 4-chlorobenzyl diethyl phosphate and 4-formylthiophen-3-ylboronic acid using the conditions to synthesize 5-(4-chlorobenzyl)thiophene-2-carbaldehyde (Example 1.1.a). Purification by prep-TLC (50% heptane/DCM, double elution) yielded 266 mg of 4-(4-chlorobenzyl)thiophene-3-carbaldehyde (58%). $^1$H NMR (400 MHz, CDCl$_3$) δ ppm 4.25 (s, 2H), 6.84-6.88 (m, 1H), 7.14-7.19 (m, 2H), 7.25-7.30 (m, 2H), 8.12 (d, J=3.17 Hz, 1H), 9.96 (s, 1H); $^{13}$C NMR (100 MHz, CDCl$_3$) δ 185.52, 140.84, 140.28, 140.02, 138.06, 132.10, 130.31, 128.58, 124.75, 34.70; LCMS-MS (ESI+) 236.68 (M+H).

1.1.i) Synthesis of 4-fluoro-thiophene-2-carboxaldehyde and 5-fluoro-thiophene-2-carboxaldehyde

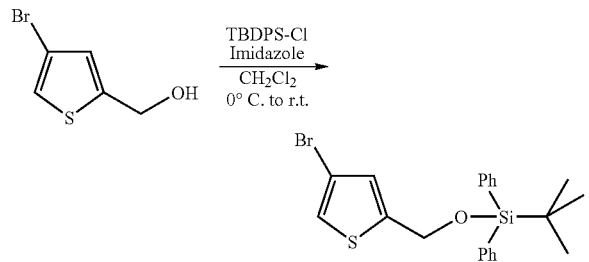

To a 250-mL round bottom flask fitted with a magnetic stir bar under a $N_2$ atmosphere was added (4-bromothiophen-2-yl)methanol (2.0 g, 10 mmol, 1 equiv) and 30 mL of anhydrous DCM. The reaction mixture was then cooled to 0° C. and the tert-butyl-diphenylsilyl chloride (3.4 g, 3.2 mL, 12.4 mmol, 1.2 equiv) was added followed by imidazole (1.06 g, 15.5 mmol, 1.5 equiv). The reaction was stirred for 16 h and was allowed to equilibrate to rt. The reaction mixture was subsequently taken up in 75 mL DCM and washed with water (100 mL). The organic layer was then dried ($Na_2SO_4$), filtered, and evaporated in vacuo. The resulting residue was chromatographed over silica gel (0-10% EtOAc in heptane over 18 min.-retention time ($t_R$) of product: 4-12 min) to give the desired ((4-bromothiophen-2-yl)methoxy)-tert-butyl diphenyl silane (4.3929 g, 98%). $^1$H-NMR (400 MHz, $CD_3CN$) δ ppm 7.66-7.71 (m, 4H), 7.39-7.51 (m, 6H), 7.29 (d, J=1.46 Hz, 1H), 6.77-6.81 (m, 1H), 4.89 (d, J=0.93 Hz, 2H), 1.06 (s, 9H).

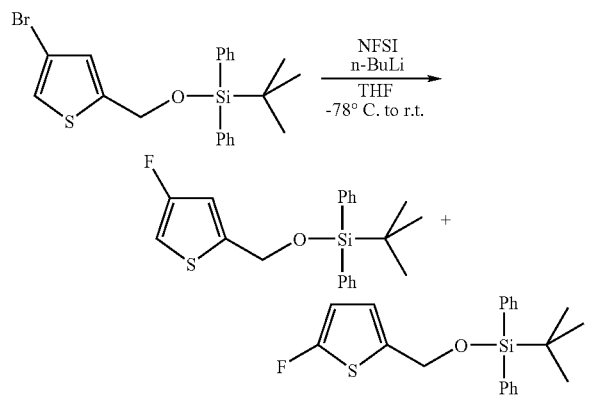

To a 40-mL vial fitted with a magnetic stir bar under a $N_2$ atmosphere was added ((4-bromothiophen-2-yl)methoxy)-tert-butyl diphenyl silane (2.9 g, 6.7 mmol, 1 equiv) and 15 mL of anhydrous tetrahydrofuran (THF). The reaction vial was cooled to −78° C. and n-BuLi in hexanes (3.2 mL, 2.5 M, 8 mmol, 1.2 equiv) was added slowly, dropwise. Stirring was continued at −78° C. for 1 h. N-fluorobenzenesulfonimide (NFSI) (2.54 g, 8 mmol, 1.2 equiv) was dissolved in 7 mL of anhydrous THF (0.9 mL/mmol reagent) in a separate vessel under inert atmosphere, and was then added dropwise over 10 to 15 min to the reaction vial. The reaction temperature was maintained at −78° C. for 4 h, and was subsequently allowed to equilibrate to rt overnight. The reaction was quenched by the addition of approx. 30 mL of saturated aqueous ammonium chloride solution. The resulting aqueous mixture was extracted with ether (4×20 mL). The combined organic layers were dried ($Na_2SO_4$), filtered, and evaporated. The resulting residue was chromatographed over silica gel (0-10% EtOAc in heptane over 20 min; $t_R$ of product: 5-15 min) to give a mixture which was qualitatively shown by $^1$H and $^{19}$F NMR to contain tert-butyl(((4-fluorothiophen-2-yl)methoxy)methyl)diphenylsilane and tert-butyl(((5-fluorothiophen-2-yl)methoxy)methyl)diphenylsilane. 2.6 g isolated as a mixture. $^1$H NMR (400 MHz, $CD_3CN$) showed signature peaks at 7.68, 7.44, and 4.78 ppm that were indicative of the desired product. $^{19}$F NMR (376 MHz, $CD_3CN$) showed a multiplet at approx. −134 to 133 ppm. The material was carried on without further purification.

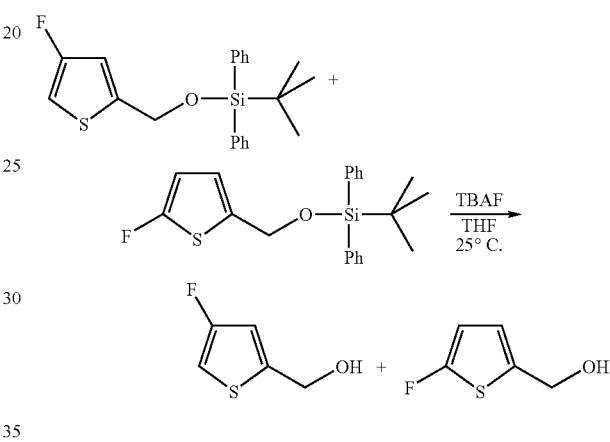

To a 100 mL round bottom flask fitted with a magnetic stir bar under a $N_2$ atmosphere was added tert-butyl(((4-fluorothiophen-2-yl)methoxy)methyl)diphenylsilane and tert-butyl(((5-fluorothiophen-2-yl)methoxy)methyl)diphenylsilane mixture (2.6 g, 7 mmol, 1 equiv) and 20 mL of anhydrous THF. A tetra n-butyl ammonium fluoride (TBAF) solution (14 mL, 1 M, 14 mmol, 2 equiv) in THF was then added in one portion and stirring continued for 16 h at 25° C. The reaction mixture was taken up into an equal volume of ether and washed with water, brine, and dried over anhydrous $Na_2SO_4$. The mixture was filtered and evaporated. The resulting residue was chromatographed over silica gel (gradient of 0-40% EtOAc in pentane over 20 min. ($t_R$ of product: 10-12 min.). The isolated fractions were consolidated and evaporated carefully to give a yellow oil (0.791 g, 85%) as a mixture which was qualitatively shown by $^1$H and $^{19}$F NMR to contain the desired (4-fluorothiophene-2-yl)methanol and (5-fluorothiophene-2-yl)methanol. $^1$H NMR (400 MHz, $CD_3CN$) showed signature peaks at 6.97, 6.39, 4.71 and 3.37 ppm that were indicative of the desired product. $^{19}$F NMR (376 MHz, $CD_3CN$) showed a strong signal at −130 ppm. The material was carried on without further purification.

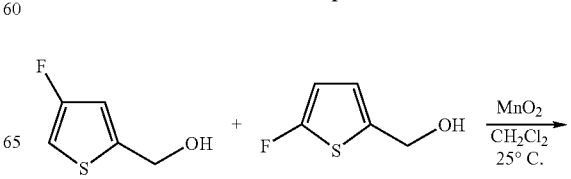

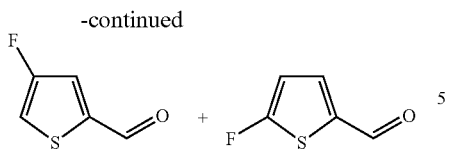

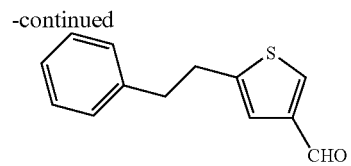

To a 250-mL round bottom flask fitted with a magnetic stir bar under a N₂ atmosphere at 25° C. was added the (4-fluorothiophene-2-yl)methanol and (5-fluorothiophene-2-yl) methanol mixture (0.79 g, 6.05 mmol, 1 equiv) and 50 mL of anhydrous DCM. Manganese (IV) oxide (5.26 g, 60.5 mmol, 10 equiv) was added in one portion, and stirring was continued overnight at 25° C. The reaction material was subsequently filtered through a short pad of Celite®, and the resulting plug was washed thoroughly with DCM. The organics were evaporated to give a light brown oil (0.60 g, 77%) as a mixture which was qualitatively shown by $^1$H and $^{19}$F NMR to contain 4-fluoro-thiophene-2-carboxaldehyde and 5-fluoro-thiophene-2-carboxaldehyde. $^1$H NMR (400 MHz, CD₃CN) showed a signature peak for the aldehyde at 9.75 ppm and a similar aromatic pattern as well as disappearance of the hydroxy-methyl moiety of the starting material. $^{19}$F NMR (376 MHz, CD₃CN) showed a strong signal at –119.20 ppm. The material was carried on without further purification.

1.1.j) Synthesis of 5-phenethylthiophene-3-carbaldehyde

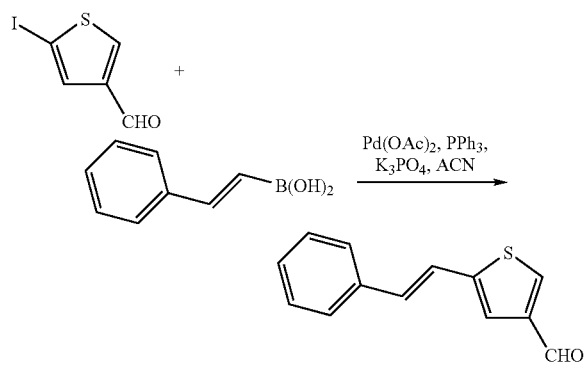

(E)-5-styrylthiophene-3-carbaldehyde was synthesized from 5-iodo-3-thiophene carboxaldehyde and (E)-styrylboronic acid using the conditions to synthesize 4-(4-chlorobenzyl)thiophene-2-carbaldehyde. The crude product was chromatographed over silica gel (0 to 25% EtOAc in heptane over 30 min) to give (E)-5-styrylthiophene-3-carbaldehyde (0.115 g, 20% yield). $^1$H NMR (400 MHz, CDCl₃) δ ppm 9.86 (s, 1H), 7.97 (s, 1H), 7.48 (m, 3H), 7.38 (m, 2H), 7.31 (m, 1H), 7.19 (d, J=16.2 Hz, 1H), 6.99 (d, J=16.2 Hz, 1H).

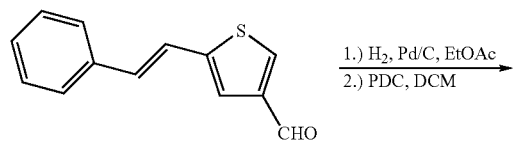

Pd/C (25% by weight) was added to a solution of (E)-5-styrylthiophene-3-carbaldehyde (0.300 g, 1.4 mmol) in EtOAc (5.0 mL). The reaction vessel was evacuated and flushed (×3) with H₂. The reaction was stirred at rt overnight under a balloon of H₂. The mixture was filtered through a Celite® plug, washed with EtOAc (0.2 L). The solution was concentrated in vacuo and chromatographed over silica gel (0 to 25% EtOAc in heptane over 30 min) to yield 0.245 g of 5-phenethylthiophene-3-methylalcohol. $^1$H NMR (400 MHz, CDCl₃) δ ppm 7.32 (m, 2H), 7.24 (m, 3H), 7.01 (m, 1H), 6.80 (s, 1H), 4.60 (d, J=0.98 Hz, 2H), 3.13 (m, 2H), 3.01 (m, 2H), 1.85 (s, 1H).

Pyridinium dichromate (PDC) (0.863 g, 2.30 mmol) was added to a solution of 5-phenethylthiophene-3-methylalcohol (0.200 g, 0.92 mmol) in DCM (5.0 mL). The mixture stirred at rt for 5 h. The mixture was filtered through a Celite® plug and washed with DCM (0.2 L). The solution was concentrated in vacuo and chromatographed over silica gel (0 to 25% EtOAc in heptane over 30 min) to give 5-phenethylthiophene-3-carbaldehyde (0.045 g). $^1$H NMR (400 MHz, CDCl₃) δ ppm 9.86 (s, 1H), 7.97 (s, 1H), 7.48 (m, 3H), 7.38 (m, 2H), 7.31 (m, 1H), 7.19 (d, J=16.2 Hz, 1H), 6.99 (d, J=16.2 Hz, 1H).

1.1.k) Synthesis of 5-Fluorothiophene-3-carboxaldehyde

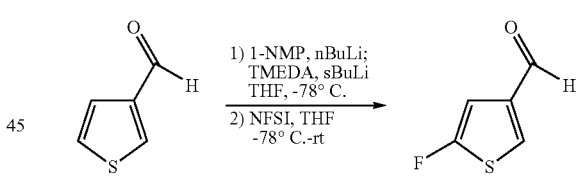

To a solution of N-methyl piperazine (1-NMP) (0.54 g, 5.4 mmol) in anhydrous THF (15 mL) cooled to –78° C. was added nBuLi (2.5 M in hexanes, 2.0 mL, 4.9 mmol) dropwise followed by the addition of 3-thiophenecarboxaldehyde (0.5 g, 4.5 mmol). The resulting mixture was stirred at –78° C. for 15 min at which time tetramethylethylenediamine (TMEDA) (1.04 g, 8.9 mmol) and sec-butyllithium (sBuLi) (1.4 M cyclohexane, 3.8 ml, 5.4 mmol) were added in sequence, dropwise. After stirring for 2 h at –78° C., a solution of NFSI (1.4 g, 4.5 mmol) in THF (5 mL) was added dropwise as a solution in THF (5 mL). Upon addition of NFSI the dry ice bath was removed and the reaction was allowed to warm to 23° C. over 1 h. After 4 h, the reaction was quenched by the addition of H₂O (20 mL) and extracted with Et₂O (3×30 mL), and the combined organic extracts were washed with brine, dried over Na₂SO₄, and filtered. The solvent was removed in vacuo. Purification by flash column chromatography (20% EtOAc in hexanes) afforded the desired aldehyde 5-fluorothiophene-3-carboxaldehyde as a mixture with starting material. The mixture was carried on to the next step without further purification.

1.2. Synthesis of Intermediate Esters

The following ethyl esters were synthesized from the indicated aldehyde according to General Procedure 1A (to yield an intermediate acrylate) followed by General Procedure 1B.

1.2.a) Synthesis of ethyl 2-bromo-4H-thieno[3,2-b]pyrrole-5-carboxylate

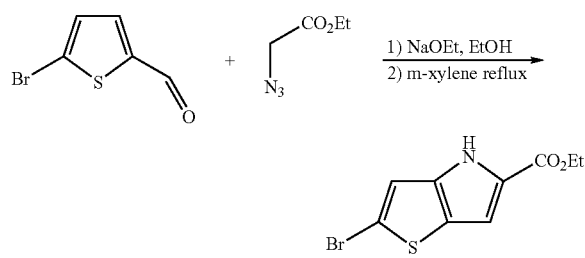

The title compound was synthesized from 5-bromothiophene-2-carboxaldehyde (1.61 g, 8.41 mmol) in two steps. The crude product was chromatographed over silica gel (gradient 0 to 25% EtOAc in heptane over 30 min) to give ethyl 2-bromo-4H-thieno[3,2-b]pyrrole-5-carboxylate as yellow needles (0.330 g, 15%). $R_f$=0.29 (25:75 heptane/EtOAc); $^1$H NMR (400 MHz, CDCl$_3$) δ (ppm) 9.03 (s, 1H) 7.05 (s, 1H) 7.03 (s, 1H) 4.37 (q, J=7.1 Hz, 2H) 1.39 (t, J=7.1 Hz, 3H).

1.2.b) Synthesis of ethyl 2,3-dibromo-4H-thieno[3,2-b]pyrrole-5-carboxylate The title compound was synthesized from 4,5-dibromothiophene-2-carboxaldehyde (2.0 g, 7.41 mmol) in two steps. The crude product was purified by silica gel column chromatography (0-25% EtOAc/heptane over 30 min) to give ethyl 2,3-dibromo-4H-thieno[3,2-b]pyrrole-5-carboxylate as a yellow solid (0.158 g, 6%). $R_f$=0.57 (50:50 heptane/EtOAc); $^1$H NMR (400 MHz, CDCl$_3$) δ (ppm) 9.02 (s, 1H) 7.09 (s, 1H) 4.39 (q, J=7.1 Hz, 2H) 1.41 (t, J=7.1 Hz, 3H).

1.2.c) Synthesis of ethyl 3-methyl-4H-thieno[3,2-b]pyrrole-5-carboxylate

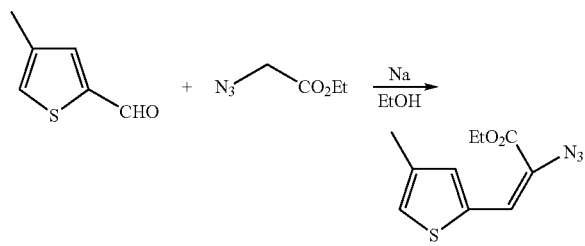

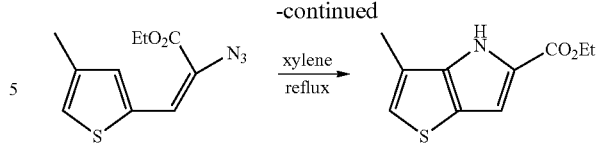

A) Ethyl 2-azido-3-(4-methylthiophen-2-yl)acrylate (orange-red oil) was synthesized from 4-methyl-2-thiophenecarbaldehyde (1.0 g, 7.9 mmol). $^1$H NMR (400 MHz, CDCl$_3$) δ (ppm): 7.15 (m, 1H), 7.10 (m, 1H), 7.09 (m, 1H), 4.35 (q, 2H), 2.26 (d, 3H), 1.39 (t, 3H).

B) The title compound was prepared from ethyl 2-azido-3-(4-methylthiophen-2-yl)acrylate and was purified by flash column chromatography (0-20% EtOAc in heptane) and recrystallization from ether/heptane to give ethyl 3-methyl-4H-thieno[3,2-b]pyrrole-5-carboxylate as an orange solid (94 mg). LCMS m/e 210 (M+H). $^1$H NMR (400 MHz, CDCl$_3$) δ (ppm): 9.04 (s, 1H), 7.08 (d, 1H), 6.94 (m, 1H), 4.38 (q, 2H), 2.35 (d, 3H), 1.40 (t, 3H).

1.2.d) Synthesis of ethyl 2-methyl-4H-thieno[3,2-b]pyrrole-5-carboxylate

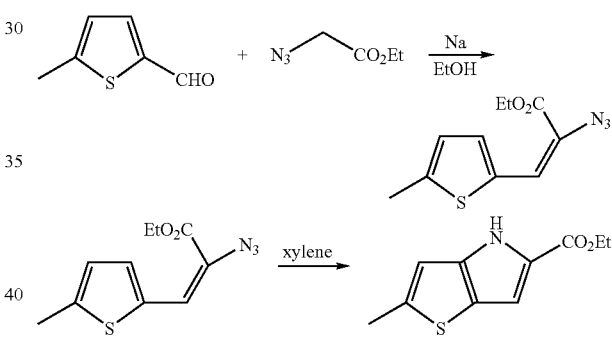

A) Ethyl 2-azido-3-(5-methylthiophen-2-yl)acrylate (1.9 g) was synthesized from 5-methyl-2-thiophenecarbaldehyde (2.0 g, 15.9 mmol) and was isolated as an orange solid after purification by flash column chromatography (100% heptane). $^1$H NMR (400 MHz, CDCl$_3$) δ (ppm): 7.14 (m, 1H), 7.10 (s, 1H), 6.74 (m, 1H), 4.35 (q, 2H), 2.54 (d, 3H), 1.39 (t, 3H).

B) The title compound was prepared from ethyl 2-azido-3-(5-methylthiophen-2-yl)acrylate and was isolated to give ethyl 2-methyl-4H-thieno[3,2-b]pyrrole-5-carboxylate as a pale yellow solid (965 mg). LCMS m/e 210 (M+H). $^1$H NMR (400 MHz, CDCl$_3$) δ (ppm): 8.95 (s, 1H), 7.06 (dd, 1H), 6.65 (m, 1H), 4.36 (q, 2H), 2.56 (d, 3H), 1.39 (t, 3H).

1.2.e) Synthesis of ethyl 2-chloro-4H-thieno[3,2-b]pyrrole-5-carboxylate

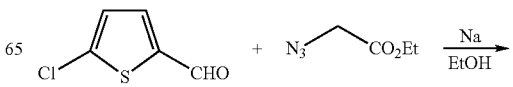

-continued

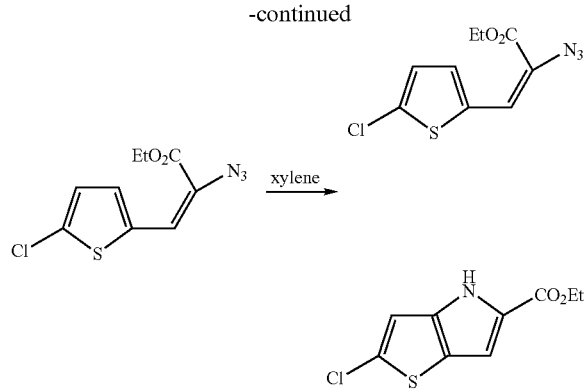

A) Ethyl 2-azido-3-(5-chlorothiophen-2-yl)acrylate (1.13 g) was synthesized from 5-chloro-2-thiophene-carboxaldehyde (2.0 g, 10.5 mmol) and was isolated as an orange solid after purification by flash column chromatography (100% heptane). $^1$H NMR (400 MHz, CDCl$_3$) δ (ppm): 7.06 (m, 1H), 7.02 (s, 1H), 6.89 (d, 1H), 4.36 (q, 2H), 1.39 (t, 3H).

B) The title compound was prepared from ethyl 2-azido-3-(5-chlorothiophen-2-yl)acrylate and was purified by flash column chromatography (0-20% EtOAc in heptane) to give ethyl 2-chloro-4H-thieno[3,2-b]pyrrole-5-carboxylate (418 mg) as a yellow solid. $^1$H NMR (400 MHz, CDCl$_3$) δ (ppm): 9.10 (s, 1H), 7.05 (m, 1H), 6.90 (m, 1H), 4.38 (q, 2H), 1.39 (t, 3H).

1.2.f) Synthesis of ethyl 3-bromo-6H-thieno[2,3-b]pyrrole-5-carboxylate

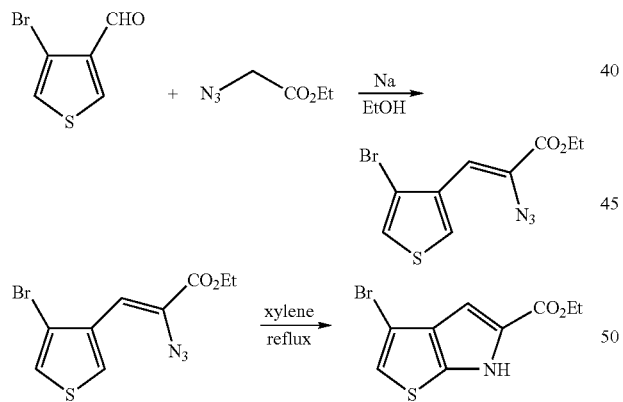

A) Ethyl 2-azido-3-(4-bromothiophen-3-yl)acrylate was synthesized from 4-bromo-3-thiophene-carbaldehyde (2.0 g, 10.5 mmol) and was isolated as an orange oil after purification by flash column chromatography (100% heptane). $^1$H NMR (400 MHz, CDCl$_3$) δ (ppm): 8.31 (m, 1H), 7.30 (m, 1H), 7.03 (m, 1H), 4.40 (q, 2H), 1.42 (t, 3H).

B) The title compound was prepared from ethyl 2-azido-3-(4-bromothiophen-3-yl)acrylate and was purified by flash column chromatography (0-20% EtOAc in heptane) to give ethyl 3-bromo-6H-thieno[2,3-b]pyrrole-5-carboxylate (971 mg) as a pale yellow solid. LCMS m/e 275 (M+H). $^1$H NMR (400 MHz, CDCl$_3$) δ (ppm): 9.38 (s, 1H), 7.07 (m, 1H), 6.85 (s, 1H), 4.39 (q, 2H), 1.41 (t, 3H).

1.2.g) Synthesis of ethyl 3-(4-chlorobenzyl)-4H-thieno[3,2-b]pyrrole-5-carboxylate

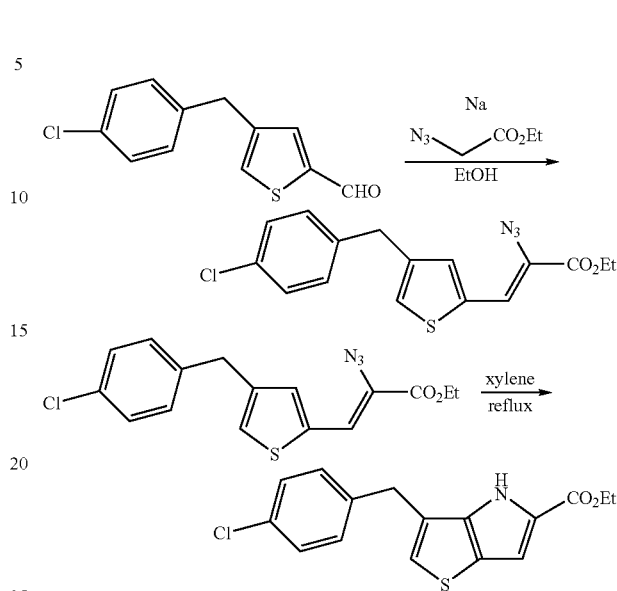

A) Ethyl 2-azido-3-(4-(4-chlorobenzyl)thiophen-2-yl)acrylate was synthesized from 4-(4-chlorobenzyl)thiophene-2-carbaldehyde (835 mg, 3.5 mmol) and was isolated as a yellow oil (657 mg, 54%) after purification by flash column chromatography (100% heptane). $^1$H NMR (400 MHz, CDCl$_3$) δ (ppm): 7.20 (m, 2H), 7.04 (m, 2H), 7.02 (s, 2H), 6.99 (s, 1H), 4.27 (q, 2H), 3.84 (s, 2H), 1.30 (t, 3H).

B) The title compound was synthesized from ethyl 2-azido-3-(4-(4-chlorobenzyl)thiophen-2-yl)acrylate and was purified by flash column chromatography (0-20% EtOAc in heptane) to give ethyl 3-(4-chlorobenzyl)-4H-thieno[3,2-b]pyrrole-5-carboxylate (350 mg, 58%). $^1$H NMR (400 MHz, CDCl$_3$) δ (ppm): 8.56 (s, 1H), 7.31 (m, 2H), 7.19 (m, 2H), 7.10 (d, 1H), 6.97 (m, 1H), 4.34 (q, 2H), 4.04 (s, 2H), 1.37 (t, 3H).

1.2.h) Synthesis of ethyl 3-phenethyl-4H-thieno[3,2-b]pyrrole-5-carboxylate

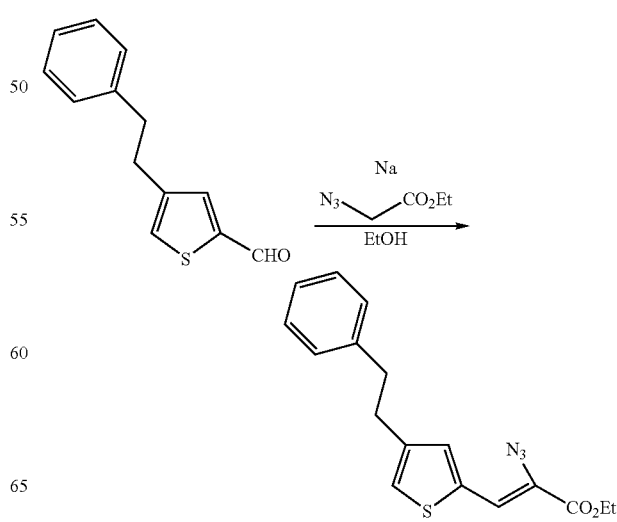

-continued

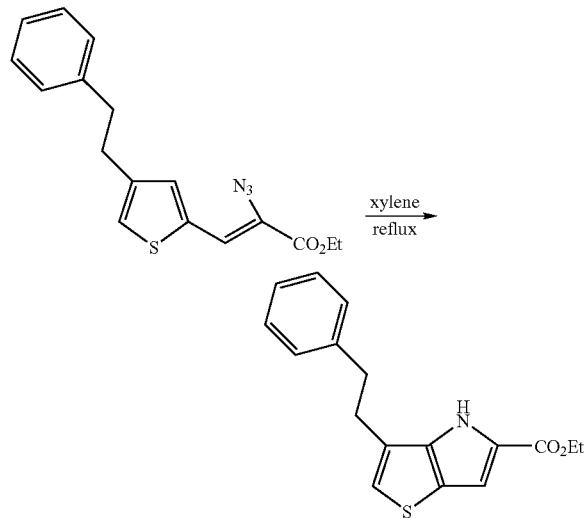

A) Ethyl 2-azido-3-(4-phenethylthiophen-2-yl)acrylate (334 mg, 56%) was synthesized from 4-phenethyl-thiophene-2-carbaldehyde (373 mg, 1.7 mmol) and was isolated as a yellow solid after purification by flash column chromatography (100% heptane). ¹H NMR (400 MHz, CDCl₃) δ (ppm): 7.29 (m, 2H), 7.22 (m, 1H), 7.17 (m, 3H), 7.10 (s, 1H), 7.09 (s, 1H), 4.36 (q, 2H), 2.93 (s, 4H), 1.40 (t, 3H).

B) The title compound was prepared from ethyl 2-azido-3-(4-phenethylthiophen-2-yl)acrylate and was purified by flash column chromatography (0-20% EtOAc in heptane) to give ethyl 3-phenethyl-4H-thieno[3,2-b]pyrrole-5-carboxylate (188 mg) as a yellow-orange solid. ¹H NMR (400 MHz, CDCl₃) δ (ppm): 8.46 (s, 1H), 7.31 (m, 2H), 7.25 (m, 1H), 7.19 (m, 2H), 7.07 (d, 1H), 6.95 (m, 1H), 4.33 (q, 2H), 3.03 (m, 4H), 1.38 (t, 3H).

1.2.i) Synthesis of 3-[2-(4-chlorophenyl)-ethyl]-6H-thieno[2,3-b]pyrrole-5-carboxylic acid ethyl ester

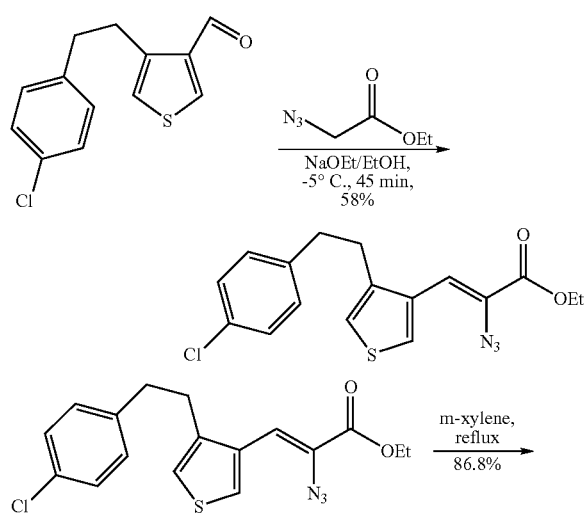

-continued

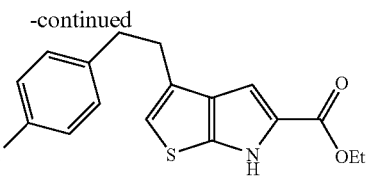

A) Ethyl 2-azido-3-{4-[2-(4-chlorophenyl)-ethyl]-thiophen-3-yl}-acrylate (142 mg, 58%) was synthesized from 4-[2-(4-chlorophenyl)-ethyl]-thiophene-3-carbaldehyde (170 mg, 0.68 mmol) and isolated after purification by flash chromatography (Isco CombiFlash, 0-5% EtOAc/heptane). ¹H NMR (400 MHz, CDCl₃) δ ppm 1.41 (t, J=7.14 Hz, 3H), 2.84-2.96 (m, 4H), 4.38 (q, J=7.14 Hz, 2H), 6.83 (d, J=0.55 Hz, 1H), 6.91 (d, J=3.11 Hz, 1H), 7.05-7.10 (m, 2H), 7.23-7.27 (m, 2H), 8.26 (d, J=3.20 Hz, 1H); LCMS-MS (ESI+) 333.71 (M-N₂).

B) The title compound was prepared from ethyl 2-azido-3-{4-[2-(4-chlorophenyl)-ethyl]-thiophen-3-yl}-acrylate and was purified by flash chromatography (Isco CombiFlash, 0-5% EtOAc/heptane) to afford ethyl 3-[2-(4-chlorophenyl)-ethyl]-6H-thieno[2,3-b]pyrrole-5-carboxylate (112 mg, 87%) as a straw-colored solid. ¹H NMR (400 MHz, CDCl₃) δ ppm 1.41 (t, J=7.14 Hz, 3H), 2.97-3.01 (m, 4H), 4.39 (q, J=7.08 Hz, 2H), 6.46 (s, 1H), 7.05 (d, J=1.92 Hz, 1H), 7.08-7.12 (m, 2H), 7.23-7.27 (m, 2H), 9.37 (s, 1H); LCMS-MS (ESI+) 333.71 (M+H).

1.2.j) Synthesis of ethyl 2-phenethyl-4H-thieno[3,2-b]pyrrole-5-carboxylate

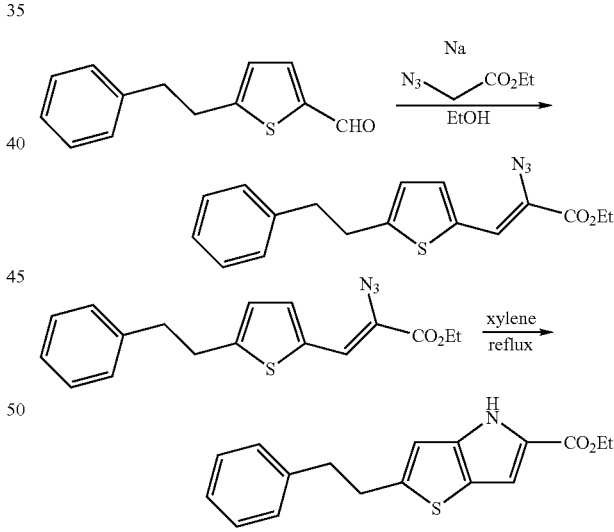

A) Ethyl 2-azido-3-(5-phenethylthiophen-2-yl)acrylate was synthesized from 5-phenethylthiophene-2-carbaldehyde (1.5 g, 6.9 mmol) and was isolated as an orange oil (832 mg, 37%) after purification by flash column chromatography (100% heptane). ¹H NMR (400 MHz, CDCl₃) δ (ppm): 7.30 (m, 2H), 7.22 (m, 3H), 7.14 (d, 1H), 7.10 (s, 1H), 6.73 (dt, 1H), 4.36 (q, 2H), 3.16 (t, 2H), 3.02 (t, 2H), 1.39 (t, 3H).

B) The title compound was prepared from ethyl 2-azido-3-(5-phenethylthiophen-2-yl)acrylate and was purified by flash column chromatography (0-20% EtOAc in heptane) to afford ethyl 2-phenethyl-4H-thieno[3,2-b]pyrrole-5-carboxylate (502 mg, 66%) as a pale yellow solid. $^1$H NMR (400 MHz, CDCl$_3$) δ (ppm): 8.86 (s, 1H), 7.30 (m, 2H), 7.22 (m, 3H), 7.07 (dd, 1H), 6.62 (dd, 1H), 4.36 (q, 2H), 3.17 (t, 2H), 3.03 (t, 2H), 1.38 (t, 3H).

1.2.k) Synthesis of ethyl 2-(4-chlorobenzyl)-4H-thieno[3,2-b]pyrrole-5-carboxylate

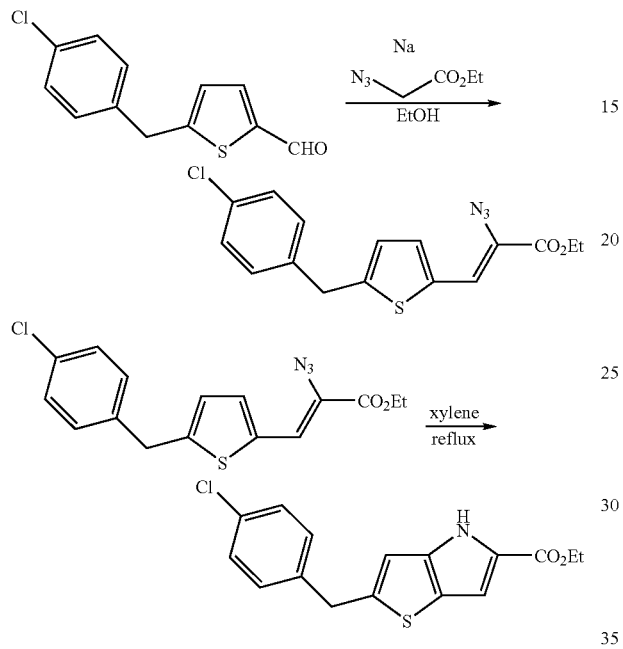

A) Ethyl 2-azido-3-(5-(4-chlorobenzyl)thiophen-2-yl)acrylate was synthesized from 5-(4-chlorobenzyl)thiophene-2-carbaldehyde (730 mg, 3.1 mmol) and was isolated as a yellow oil (84 mg, 8%) after purification by flash column chromatography (100% heptane). $^1$H NMR (400 MHz, CDCl$_3$) δ (ppm): 7.30 (m, 2H), 7.19 (m, 2H), 7.15 (d, 1H), 7.08 (s, 1H), 6.76 (m, 1H), 4.35 (q, 2H), 4.14 (s, 2H), 1.39 (t, 3H).

B) The title compound was prepared from ethyl 2-azido-3-(5-(4-chlorobenzyl)thiophen-2-yl)acrylate and was purified by flash column chromatography (0-20% EtOAc in heptane) to afford ethyl 2-(4-chlorobenzyl)-4H-thieno[3,2-b]pyrrole-5-carboxylate (42 mg, 55%). $^1$H NMR (400 MHz, CDCl$_3$) δ (ppm): 8.86 (s, 1H), 7.30 (m, 2H), 7.21 (m, 2H), 7.06 (dd, 1H), 6.67 (d, 1H), 4.36 (q, 2H), 4.15 (s, 2H), 1.38 (t, 3H).

1.2.l) Synthesis of ethyl 3-benzyl-6H-thieno[2,3-b]pyrrole-5-carboxylate

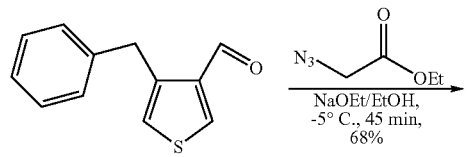

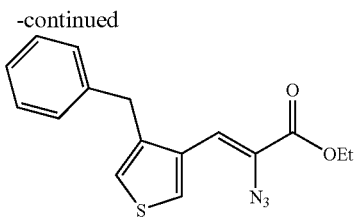

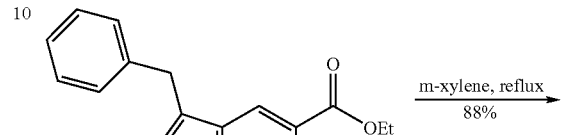

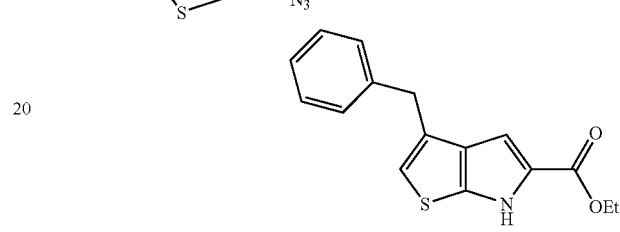

A) Ethyl 2-azido-3-(4-benzylthiophen-3-yl)acrylate was synthesized from 4-benzyl-thiophene-3-carbaldehyde (200 mg, 0.99 mmol) and was isolated after purification by flash chromatography (Isco CombiFlash, 0-5% EtOAc/heptane) (210 mg, 68%). $^1$H NMR (400 MHz, CDCl$_3$) δ ppm 1.36 (t, J=7.13 Hz, 3H), 4.01 (s, 2H), 4.32 (q, J=7.16 Hz, 2H), 6.86-6.91 (m, 2H), 7.16-7.21 (m, 2H), 7.21-7.25 (m, 1H), 7.27-7.33 (m, 2H), 8.28 (d, J=3.17 Hz, 1H).

B) The title compound was prepared from ethyl 2-azido-3-(4-benzylthiophen-3-yl)acrylate and was purified by flash chromatography (Isco CombiFlash, 0-5% EtOAc/heptane) to afford ethyl 3-benzyl-6H-thieno[2,3-b]pyrrole-5-carboxy-late (169 mg, 88%) as an off-white solid. $^1$H NMR (400 MHz, CDCl$_3$) δ ppm 1.37 (t, J=7.14 Hz, 3H), 4.04 (s, 2H), 4.34 (q, J=7.14 Hz, 2H), 6.52 (t, J=1.10 Hz, 1H), 6.90 (d, J=1.92 Hz, 1H), 7.20-7.26 (m, 1H), 7.28-7.34 (m, 4H), 9.11 (s, 1H); LCMS-MS (ESI+) 285.78 (M+H).

1.2.m) Synthesis of ethyl 3-phenyl-6H-thieno[2,3-b]pyrrole-5-carboxylate

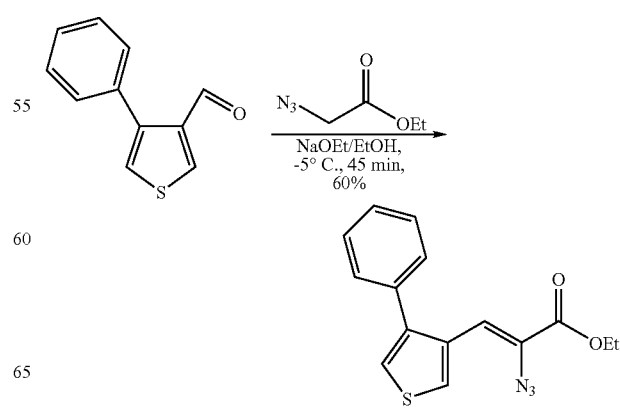

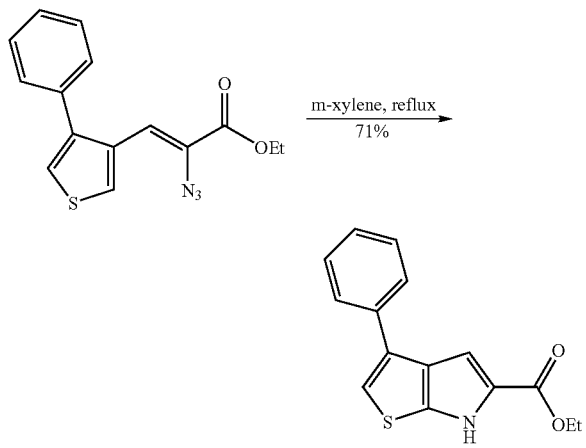

A) Ethyl 2-azido-3-(4-phenylthiophen-3-yl)acrylate was synthesized from 4-formylthiophen-3-ylboronic acid (300 mg, 1.59 mmol) and was isolated after purification by flash chromatography (Isco CombiFlash, 0-5% EtOAc/heptane) (270 mg, 60%). $^1$H NMR (400 MHz, CDCl$_3$) δ 1.30 (t, J=7.13 Hz, 3H), 4.29 (q, J=7.13 Hz, 2H), 6.89 (s, 1H), 7.25 (d, J=3.27 Hz, 1H), 7.27 (s, 1H), 7.34-7.37 (m, 2H) 7.38-7.48 (m, 3H), 8.38 (d, J=3.22 Hz, 1H).

B) The title compound was prepared from ethyl 2-azido-3-(4-phenylthiophen-3-yl)acrylate and was purified by flash chromatography (Isco CombiFlash, 0-10% EtOAc/heptane) to afford ethyl 3-phenyl-6H-thieno[2,3-b]pyrrole-5-carboxylate (170 mg, 71%) as an off-white solid. $^1$H NMR (400 MHz, CD$_3$OD) δ ppm 1.40 (t, J=7.13 Hz, 3H), 4.35 (q, J=7.13 Hz, 2H), 7.19 (s, 1H), 7.27 (s, 1H), 7.28-7.34 (m, 1H), 7.41-7.47 (m, 2H), 7.73-7.78 (m, 2H); LCMS-MS (ESI+) 272.0 (M+H).

1.2.n) Synthesis of ethyl 3-(4-chlorobenzyl)-6H-thieno[2,3-b]pyrrole-5-carboxylate

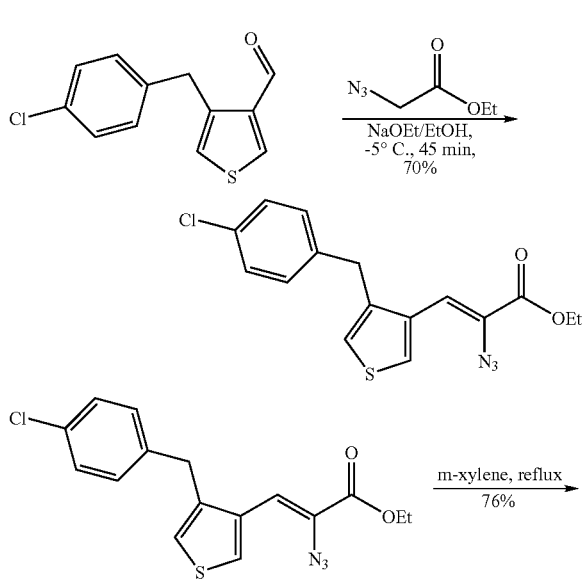

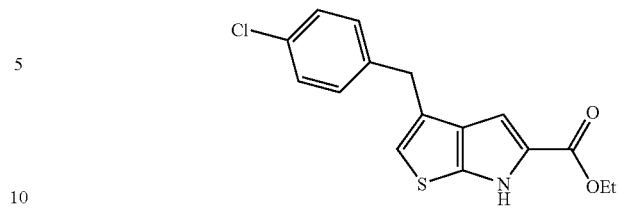

A) Ethyl-2-azido-3-(4-(4-chlorobenzyl)thiophene-3-yl)acrylate (230 mg, 60%) was prepared from 4-(4-chlorobenzyl)-thiophene-3-carbaldehyde (260 mg, 1.1 mmol) and was isolated after purification by flash chromatography (Isco CombiFlash, 0-5% EtOAc/heptane). $^1$H NMR (400 MHz, CDCl$_3$) δ ppm 1.37 (t, J=7.15 Hz, 3H), 3.98 (s, 2H), 4.32 (q, J=7.13 Hz, 2H), 6.80 (s, 1H), 6.89 (d, J=3.12 Hz, 1H), 7.08-7.13 (m, 2H), 7.24-7.29 (m, 2H), 8.29 (d, J=3.12 Hz, 1H); $^{13}$C NMR (100 MHz, CDCl$_3$) δ 163.36, 140.46, 137.94, 132.58, 132.20, 130.01, 129.58, 128.69, 125.19, 122.45, 116.63, 62.10, 34.69, 14.16; LCMS-MS (ESI+) 319.75 (M-N$_2$).

B) The title compound was prepared from ethyl-2-azido-3-(4-(4-chlorobenzyl)thiophene-3-yl)acrylate and was purified by flash chromatography (Isco CombiFlash, 0-5% EtOAc/heptane) to afford ethyl 3-(4-chlorobenzyl)-6H-thieno[2,3-b]pyrrole-5-carboxylate (158 mg, 76%) as a straw-colored solid. $^1$H NMR (400 MHz, CDCl$_3$) δ ppm 1.37 (t, J=7.14 Hz, 3H), 4.00 (s, 2H), 4.35 (q, J=7.14 Hz, 2H), 6.53 (t, J=1.10 Hz, 1H), 6.87 (d, J=1.92 Hz, 1H), 7.18-7.23 (m, 2H), 7.25-7.30 (m, 2H), 9.16 (s, 1H); $^{13}$C NMR (100 MHz, CDCl$_3$) δ 161.47, 137.90, 137.79, 132.08, 131.64, 131.08, 130.06, 128.56, 128.04, 116.59, 106.77, 60.71, 35.25, 14.43; LCMS-MS (ESI+) 319.72 (M+H).

1.2.o) Synthesis of ethyl 6H-thieno[2,3-b]pyrrole-5-carboxylate

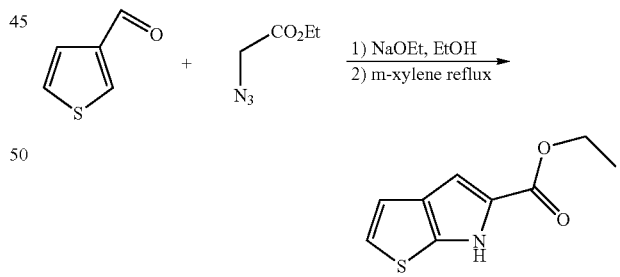

A) Ethyl 2-azido-3-(thiophen-3-yl)acrylate was synthesized from thiophene-3-carboxaldehyde (4.50 g, 40.0 mmol) and isolated by silica gel column chromatography (0 to 25% EtOAc in heptane over 30 min.). 2.8 g of the purified intermediate were used in the next step.

B) The title compound was prepared from ethyl 2-azido-3-(thiophen-3-yl)acrylate and was purified by recrystallization from DCM to give ethyl 6H-thieno[2,3-b]pyrrole-5-carboxylate (1.0 g) as a white solid. R$_f$=0.51 (50:50 heptane/EtOAc); $^1$H NMR (400 MHz, CDCl$_3$) δ ppm 1.40 (t, J=7.15

Hz, 3H) 4.39 (q, J=7.14 Hz, 2H) 6.92 (d, J=5.37 Hz, 1H) 7.01 (d, J=5.37 Hz, 1H) 7.11 (d, J=1.90 Hz, 1H) 9.48 (s, 1H).

1.2.p) Synthesis of ethyl 3-bromo-4H-thieno[3,2-b]pyrrole-5-carboxylate

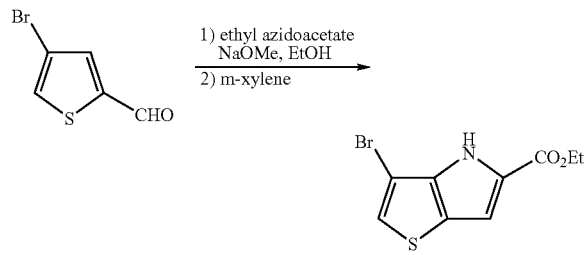

A) Ethyl 2-azido-3-(4-bromothiophen-2-yl)acrylate was synthesized from 4-bromothiophene-2-carboxaldehyde (2.0 g, 10.47 mmol) as a dark brown residue (1.8 g) after purification by silica gel column chromatography (heptane and EtOAc).

B) The title compound was prepared from ethyl 2-azido-3-(4-bromothiophen-2-yl)acrylate and was purified by silica gel column chromatography to give ethyl 3-bromo-4H-thieno[3,2-b]pyrrole-5-carboxylate (27.6 mg, 0.102 mmol). $^1$H NMR (400 MHz, acetone) δ ppm 1.34 (t, J=7.13 Hz, 2H) 3.88 (s, 2H) 4.34 (q, J=7.13 Hz, 1H) 7.70 (t, J=1.34 Hz, 1H) 7.86 (dd, J=3.90, 1.51 Hz, 1H).

1.2.q) Synthesis of 2-fluoro-4H-thieno[3,2-b]pyrrole-5-carboxylate ethyl ester and 3-fluoro-4H-thieno[3,2-b]pyrrole-5-carboxylate ethyl ester

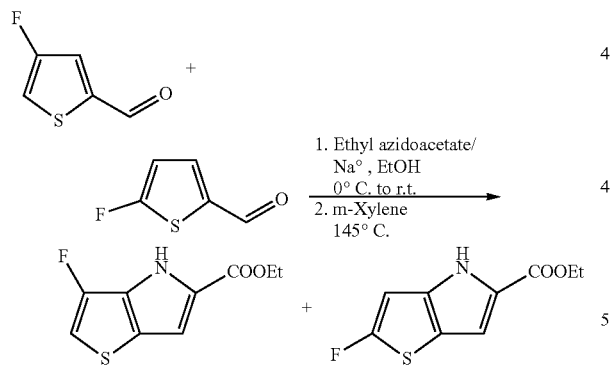

A) The intermediate acrylates (ethyl 2-azido-3-(4-fluorothiophen-2-yl)acrylate and ethyl 2-azido-3-(5-fluorothiophen-2-yl)acrylate) were obtained from a mixture of 4-fluoro-thiophene-2-carboxaldehyde and 5-fluoro-thiophene-2-carboxaldehyde (1.4 g, 10.8 mmol, 1 equiv). The mixture was purified by silica gel column chromatography (0-15% EtOAc in heptane over 20 min, $t_R$ of product: 3-5 min.) to give a pale oil (0.37 g, 14%). $^1$H NMR (400 MHz, CD$_3$CN) showed signature peaks in the aromatic region from 6.5-7.8 ppm and an ethyl ester pattern at 4.3 ppm and 1.3 ppm. $^{19}$F NMR (376 MHz, CD$_3$CN) showed a strong signal at −127.60 ppm.

B) A mixture of ethyl 2-azido-3-(4-fluorothiophen-2-yl)acrylate and ethyl 2-azido-3-(5-fluorothiophen-2-yl)acrylate (0.37 g) was dissolved in m-xylene (~10 mL) and heated at 145° C. for 20 min in a capped 40-mL vial. The m-xylene was evaporated in vacuo and the resulting residue was chromatographed over silica gel (0 to 40% EtOAc in heptane over 30 min) to give two products: (a) 0.15 g of an impure pale oil with an $R_f$=0.25 (10:90 EtOAc/heptane), which stained a bright violet color when developed using anisaldehyde and heat, which was further purified via preparative HPLC using a Chromeleon purification system (methanol/0.1% formic acid-1% acetonitrile mixture in water, 50 mm Dynamax C-18, 28 mL/min (initial gradient of 20% methanol and increasing to 100% over 7 min) to give ethyl 2-fluoro-4H-thieno[3,2-b]pyrrole-5-carboxylate (48.9 mg, 3%). $t_R$ of product: 4.2-4.4 min. $^1$H NMR (400 MHz, CD$_3$CN) δ ppm 10.10 (s, 1H), 6.98-7.05 (m, 1H), 6.69 (dd, J=2.05, 0.49 Hz, 1H), 4.29 (q, J=7.09 Hz, 2H), 1.33 (t, J=7.13 Hz, 3H). $^{19}$F NMR (376 MHz, CD$_3$CN) δ ppm −122.18 (d, J=2.29 Hz, 1F). (b) 10.5 mg of an impure pale oil with an $R_f$=0.30 (10:90 EtOAc/heptane), which stained a bright red color when developed using anisaldehyde and heat, was further purified via preparative HPLC as described above (40%-100% methanol over 7 min) to give ethyl 3-fluoro-4H-thieno[3,2-b]pyrrole-5-carboxylate (5.4 mg, 0.3%). $t_R$ of product: 3-3.4 min. $^1$H NMR (400 MHz, CD$_3$CN) δ ppm 10.30 (s, 1H), 7.06 (t, J=2.05 Hz, 1H), 6.90 (d, J=2.54 Hz, 1H), 4.32 (q, J=7.09 Hz, 2H), 1.34 (t, J=7.10 Hz, 3H). $^{19}$F NMR (376 MHz, CD$_3$CN) δ ppm −144.16 (t, J=2.29 Hz, 1F).

1.2.r) Synthesis of ethyl 2-phenethyl-6H-thieno[2,3-b]pyrrole-5-carboxylate

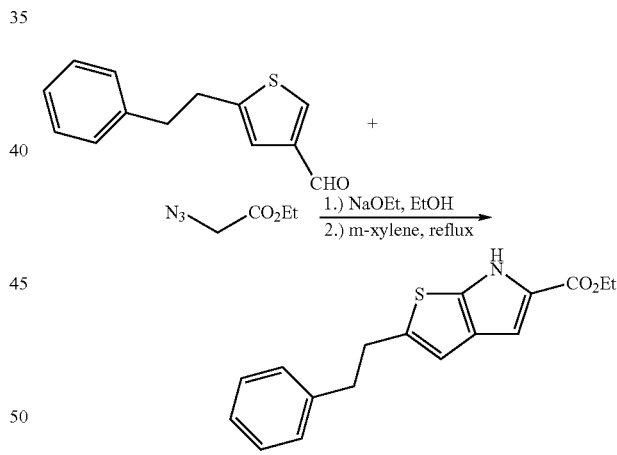

A) Ethyl 2-azido-3-(5-phenethylthiophen-3-yl)acrylate was prepared from 5-phenethylthiophene-3-carboxaldehyde (0.106 g, 0.49 mmol) in EtOH (2.0 mL) and chromatographed over silica gel (0 to 10% EtOAc in heptane over 20 min).

B) The title compound was synthesized from ethyl 2-azido-3-(5-phenethylthiophen-3-yl)acrylate and purified by silica gel column chromatography (0 to 25% EtOAc in heptane over 30 min) to give ethyl-2-phenethyl-6H-thieno[2,3-b]pyrrole-5-carboxylate as yellow solid (0.013 g, 9%). $^1$H NMR (400 MHz, CDCl$_3$) δ (ppm) 9.09 (s, 1H), 7.30 (m, 2H), 7.22 (m, 3H), 6.98 (d, J=1.95 Hz, 1H), 6.66 (d, J=0.6 Hz, 1H), 4.36 (q, J=7.0 Hz, 2H), 3.13 (m, 2H), 3.00 (m, 2H), 1.38 (t, J=7. Hz, 3H).

1.2.s) Synthesis of ethyl 2-fluoro-6H-thieno[2,3-b]pyrrole-5-carboxylate

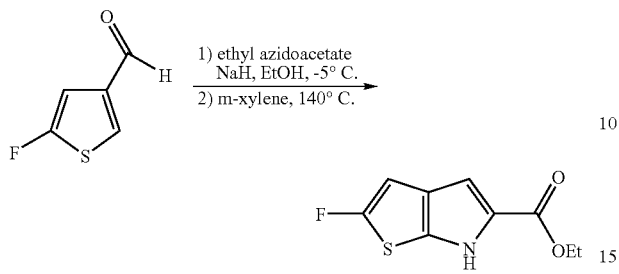

A) Ethyl 2-azido-3-(5-fluorothiophen-3-yl)acrylate was prepared from 5-fluorothiophene-3-carbaldehyde (as a mixture with 3-thiophenecarboxaldehyde, 0.29 g, ~2.2 mmol) in EtOH (8.5 mL) and used without purification in the next reaction step.

B) The title compound was synthesized from the above intermediate and purified by preparative RP-HPLC (10-100% gradient 0.1% formic acid in $H_2O$ to $CH_3CN$ over 10 min) to afford pure ethyl 2-fluoro-6H-thieno[2,3-b]pyrrole-5-carboxylate as a white solid (0.030 g, 15%). $^1$H NMR (400 MHz, $CD_3OD$) δ (ppm) 6.99 (m, 1H), 6.56 (m, 1H), 4.31 (q, J=7.3 Hz, 2H) 1.36 (t, J=7.3 Hz, 3H). $^{19}$F NMR (282 MHz, $CD_3OD$) δ ppm −132.24 (1F). LCMS m/e 214 (M+H).

1.2.t) Synthesis of methyl 3-fluoro-6H-thieno[2,3-b]pyrrole-5-carboxylate

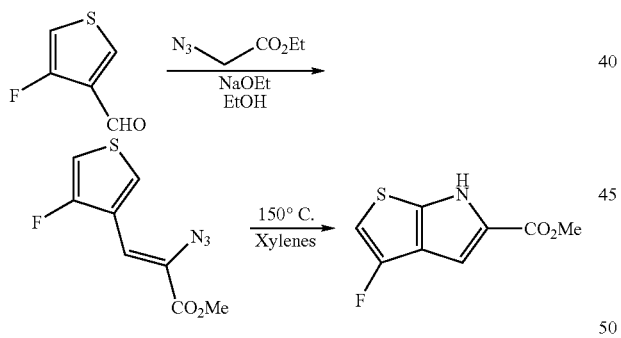

A) Methyl 2-azido-3-(4-fluorothiophen-3-yl)acrylate was prepared from 4-fluorothiophene-3-carbaldehyde (Ozaki et al U.S. Pat. No. 6,995,144 B2 (2006)) and purified by chromatography (0.53 g, 37%).

B) The title compound was synthesized from methyl 2-azido-3-(4-fluorothiophen-3-yl)acrylate and purified by preparative RP-HPLC. The acetonitrile was removed under vacuum and the aqueous layer was extracted with methyl tert-butyl ether (MTBE). The residue was then taken up in DCM and washed with ammonium chloride solution, water, and brine. The organic layer was dried with sodium sulfate, filtered, and the filtrate was evaporated to afford methyl 3-fluoro-6H-thieno[2,3-b]pyrrole-5-carboxylate (170 mg, 36%) as a pale-yellow solid. $^1$H NMR (400 MHz, $CD_3OD$) δ (ppm) 7.04 (d, J=5.5 Hz, 1H), 6.90 (d, J=5.5 Hz, 1H).

1.3. Synthesis of ethyl 2-(4-chlorobenzyl)-6H-thieno[2,3-b]pyrrole-5-carboxylate

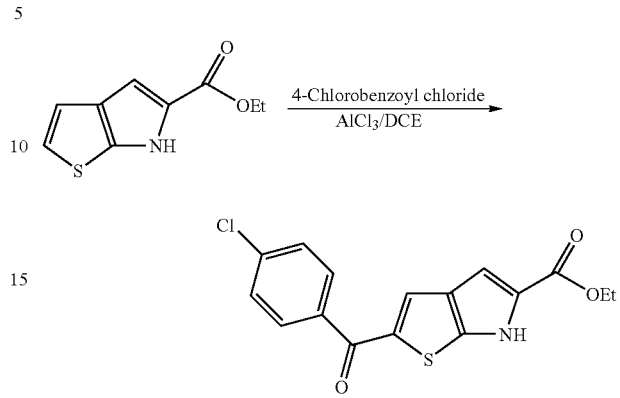

Under a $N_2$ atmosphere and at 0° C., to a 40-mL scintillation vial fitted with a magnetic stir bar was added solid aluminum chloride (0.7 g 5.28 mmol) and a solution of ethyl 6H-thieno[2,3-b]pyrrole-5-carboxylate (0.61 g, 3.14 mmol, 0.9 equiv) in solution in 10 mL dichloroethane (DCE). 4-Chlorobenzoyl chloride (0.92 g, 5.28 mmol) was then added at 0° C. and stirring was continued for 2 h as the reaction was allowed to warm to rt. The reaction was cooled and was added to an ice-filled beaker. The aqueous mixture was extracted ×3 with EtOAc. The organic layers were combined, dried over anhydrous sodium sulfate, filtered and evaporated in vacuo. The resulting residue was purified via ISCO Companion (0-30% gradient EtOAc/heptane over 30 min) to give ethyl 2-(4-chlorobenzoyl)-6H-thieno[2,3-b]pyrrole-5-carboxylate (0.34 g). $^1$H NMR (400 MHz, $CDCl_3$) δ ppm 1.42 (t, J=7.13 Hz, 3H) 4.43 (q, J=7.13 Hz, 2H) 7.17 (d, J=1.81 Hz, 1H) 7.50 (d, J=8.44 Hz, 2H) 7.59 (s, 1H) 7.77-7.86 (m, 2H) 10.03 (s, 1H).

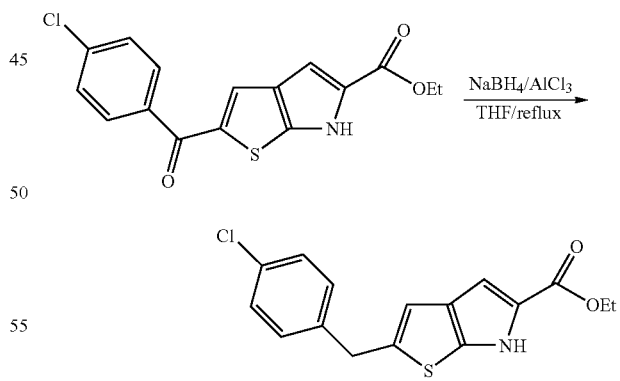

Under a $N_2$ and at rt, to a 40-mL scintillation vial fitted with a magnetic stir bar was added ethyl 2-(4-chlorobenzoyl)-6H-thieno[2,3-b]pyrrole-5-carboxylate (0.203 g, 0.61 mmol) in solution in 5 mL in THF. $AlCl_3$ (0.22 g, 1.67 mmol, 2.75 equiv) and $NaBH_4$ (0.116 g, 3.0 mmol, 5 eq.) are added in the same time. The mixture was heated to reflux for 2 h. The reaction was cooled to rt and solvent was evaporated. The crude product was purified via ISCO Companion (0-30%

EtOAc/heptane over 30 min) to give ethyl 2-(4-chlorobenzyl)-6H-thieno[2,3-b]pyrrole-5-carboxylate (0.050 g). $^1$H NMR (400 MHz, CDCl$_3$) δ ppm 1.39 (t, J=7.13 Hz, 3H) 4.11 (s, 2H) 4.37 (q, J=7.13 Hz, 2H) 6.71 (s, 1H) 7.00 (d, J=1.76 Hz, 1H) 7.18-7.23 (m, 2H) 7.27-7.32 (m, 2H) 9.41 (s, 1H).

1.4. Synthesis of methyl 6-methyl-4H-thieno[3,2-b]pyrrole-5-carboxylate

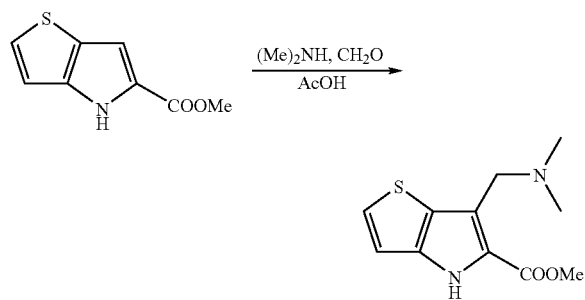

Under N$_2$, to 9 mL of glacial acetic acid were added N,N-dimethylamine (40% aqueous solution) (437 mg, 9.94 mmol), formaldehyde (37% aqueous solution) (283 mg, 9.90 mmol), and methyl 4H-thieno[3,2-b]pyrrole-5-carboxylate (1.8 g, 9.94 mmol). The temperature was kept between 0-5° C. while the components were added. The reaction mixture was heated at reflux for 1 h, and then allowed to stand at rt for 12 h. The mixture was poured onto 30 g of ice, and was brought to pH 10 by careful addition of 10% sodium hydroxide. The temperature was not allowed to exceed 10° C. while the base was added. The gummy substance that precipitated solidified when stored in the refrigerator overnight. The solid was collected and dried in a vacuum. It was recrystallized from petroleum ether (30-60° C.) to yield methyl 6-[(dimethylamino)methyl]-4H-thieno[3,2-b]pyrrole-5-carboxylate (1.65 g, 70%). $^1$H NMR (400 MHz, CDCl$_3$) δ ppm 2.36 (s, 6H) 3.86 (s, 3H) 3.89 (s, 2H) 6.85 (d, J=5.32 Hz, 1H) 7.28 (d, J=5.32 Hz, 1H) 9.84 (s, 1H).

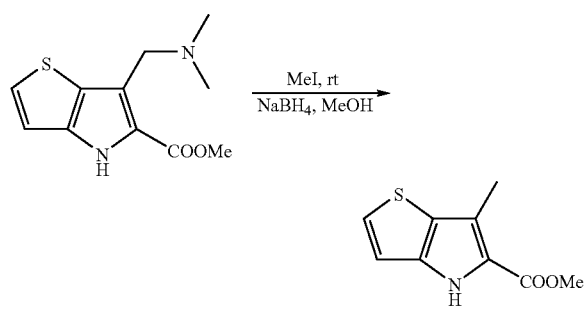

Under N$_2$, to methyl 6-[(dimethylamino)methyl]-4H-thieno[3,2-b]pyrrole-5-carboxylate (0.34 g, 1.45 mmol) was added methyl iodide (1.48 mL, 2.37 mmol). The mixture was allowed to stand at rt for 1 h, and then the methyl iodide was removed. The resulting salt was dissolved in absolute methanol (5 mL). To this solution was carefully added sodium borohydride (1.23 g, 3.25 mmol) in small portions. After the addition was complete, the reaction mixture was diluted to a volume of 25 mL by the addition of 3N hydrochloric acid. The mixture was stored in the refrigerator overnight, and then the blue precipitate was dissolved in boiling methylcyclohexane, and the solution was treated with Darco (activated carbon) and filtered. The filtrate was evaporated and purified by chromatography over silica gel (0 to 40% EtOAc in heptane over 30 min) to give methyl 6-methyl-4H-thieno[3,2-b]pyrrole-5-carboxylate (0.12 g, 43%). $^1$H NMR (400 MHz, CDCl$_3$) δ ppm 2.53 (s, 3H) 3.91 (s, 3H) 6.92 (d, J=5.27 Hz, 1H) 7.32 (d, J=5.32 Hz, 1H) 8.81 (s, 1H).

1.5. Synthesis of methyl 6-fluoro-4H-thieno[3,2-b]pyrrole-5-carboxylate

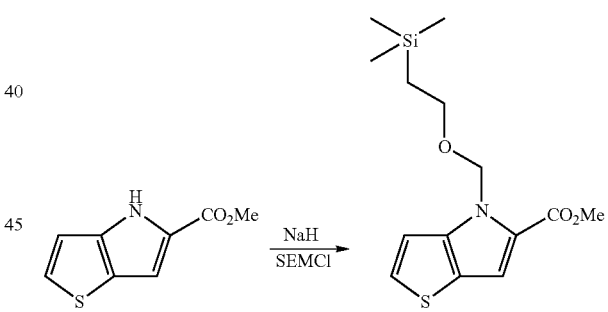

4H-thieno[3,2-b]pyrrole-5-carboxylic acid (3.0 g, 17.9 mmol) was dissolved in anhydrous MeOH (50.0 mL) and cooled to 0° C. A solution (45.0 mL, 2 M in hexanes) of trimethylsilyldiazomethane (45 mL) was added in portions and the yellow color of the TMSCH$_2$N$_2$ remained. Stirring was continued for 10 min and then the excess TMSCH$_2$N$_2$ was quenched with acetic acid (5.0 mL). The solvent was removed with N$_2$ stream, and the residue was chromatographed over silica gel (5%-40%, 30 min, EtOAc in heptane) to give methyl 4H-thieno[3,2-b]pyrrole-5-carboxylate (2.8 g, 86% yield). $^1$H NMR (400 MHz, CD$_3$Cl) δ ppm 3.90 (s, 3H) 6.95 (dd, J=5.32, 0.78 Hz, 1H) 7.13 (dd, J=1.88, 0.76 Hz, 1H) 7.33 (d, J=5.37 Hz, 1H) 9.02 (br. s, 1H).

Methyl 4H-thieno[3,2-b]pyrrole-5-carboxylate (2.8 g, 15.45 mmol) was dissolved in 150 mL anhydrous THF. NaH (3.0 g, 60% oil dispersion, 75 mmol) was added and the reaction stirred for 15 min at rt. SEMCl [(2-trimethylsilyl)-ethoxymethyl chloride] (0.7 mL, 3.95 mmol) was added dropwise over 5 min. The reaction was stirred 1 h at rt and then CAUTIOUSLY poured onto 25 g crushed ice with stirring. The aqueous was extracted with EtOAc, dried (Na$_2$SO$_4$), filtered and evaporated in vacuo to give a green residue. The residue was chromatographed over silica gel (EtOAc in heptane, 3%-10%, 3 h, TLC visualized with KMnO$_4$ with heat) to give methyl 4-(2-trimethylsilanyl-ethoxymethyl)-4H-thieno[3,2-b]pyrrole-5-carboxylate (3.85 g, 80% yield). $^1$H NMR (400 MHz, (CD$_3$)$_2$CO) δ ppm −0.08 (s, 9H) 0.84 (t, J=7.83 Hz, 2H) 3.54 (t, J=7.88 Hz, 2H) 3.83 (s, 3H) 5.94 (s, 2H) 7.21-7.25 (m, 1H) 7.26 (s, 1H) 7.55 (d, J=5.37 Hz, 1H).

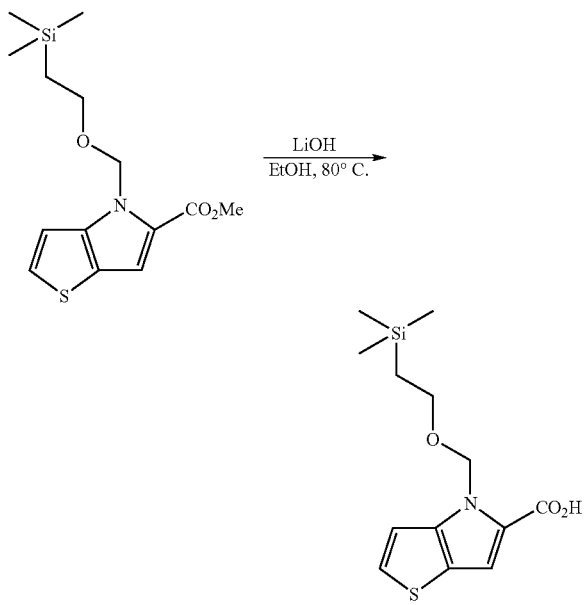

Methyl 4-(2-trimethylsilanyl-ethoxymethyl)-4H-thieno[3,2-b]pyrrole-5-carboxylate (2.89 g, 9.27 mmol) was dissolved in 60 mL EtOH. A 2.0 M solution of LiOH (46 mL) was added and the reaction was heated to 75° C. for 30 min. EtOH was removed with a $N_2$ stream. The residue was taken up in 300 mL water and acidified to pH 2 with conc. HCl, which gave a white precipitate. The precipitate was extracted into EtOAc. The solution was dried ($Na_2SO_4$), filtered and evaporated in vacuo to give 4-(2-trimethylsilanyl-ethoxymethyl)-4H-thieno[3,2-b]pyrrole-5-carboxylic acid (2.57 g, 93% yield). $^1$H NMR (400 MHz, $(CD_3)_2CO$) δ ppm −0.08 (s, 9H) 0.77-0.91 (m, 2H) 3.55 (t, 2H) 5.96 (s, 2H) 7.23 (d, J=5.37 Hz, 1H) 7.31 (s, 1H) 7.55 (d, J=5.37 Hz, 1H).

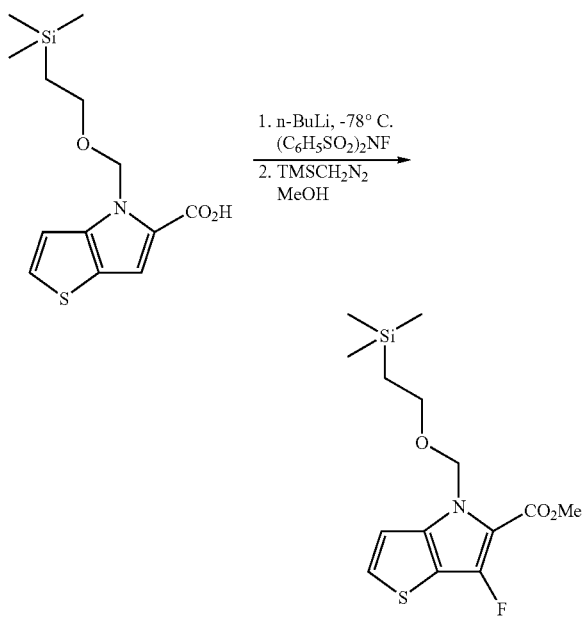

4-(2-Trimethylsilanyl-ethoxymethyl)-4H-thieno[3,2-b]pyrrole-5-carboxylic acid (1.9 g, 6.4 mmol) was dissolved in anhydrous THF (250 mL) and cooled to −78° C. n-BuLi (1.6 M in hexanes, 12 mL, 19.2 mmol, 3 equiv) was added over 5 min and stirred at −78° C. for 60 min. A solution of NFSI (3.1 g, 9.6 mmol, 1.5 equiv) in 15 mL anhydrous THF was added over 15 min and the reaction was stirred at −78° C. for 5 h and then allowed to warm to rt overnight. The reaction was cooled in an ice bath, quenched with 6N HCl, and then extracted with EtOAc and evaporated in vacuo to give 5.5 g of dark residue. The residue was chromatographed over silica gel (DCM in EtOAc) to give a more pure residue. This residue was further purified via prep reverse phase HPLC (RP-HPLC) to give 360 mg of the 2-fluoro isomer (2-fluoro-4-((2-(trimethylsilyl)ethoxy)methyl)-4H-thieno[3,2-b]pyrrole-5-carboxylic acid) and a separate mixture of starting material and 6-fluoro isomer (6-fluoro-4-((2-(trimethylsilyl)ethoxy)methyl)-4H-thieno[3,2-b]pyrrole-5-carboxylic acid). This latter mixture was converted to the corresponding methyl ester via $TMSCH_2N_2$. The mixture of esters was chromatographed over silica gel (EtOAc in heptane, 5%-20%) to give methyl 6-fluoro-4-((2-(trimethylsilyl)ethoxy)methyl)-4H-thieno[3,2-b]pyrrole-5-carboxylate (16 mg, 0.0485 mmol, 0.8% yield). $^1$H NMR (400 MHz, $(CD_3)_2CO$) δ ppm −0.08 (s, 9H) 0.80-0.87 (m, 2H) 3.49-3.57 (m, 2H) 3.87 (s, 3H) 5.88 (s, 2H) 7.29 (dd, J=5.32, 2.20 Hz, 1H) 7.66 (d, J=5.32 Hz, 1H).

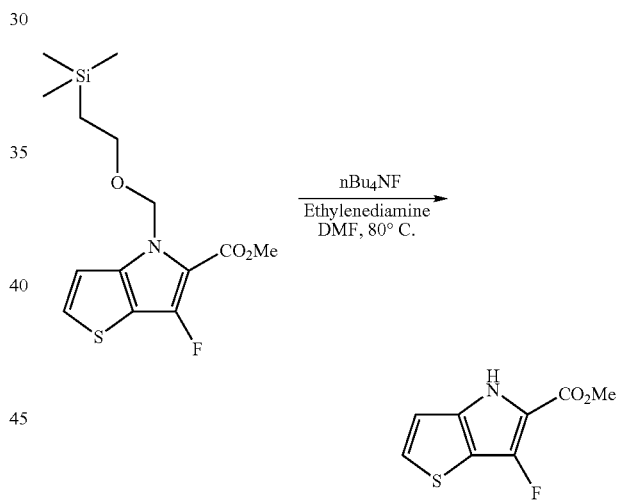

Methyl 6-fluoro-4-((2-(trimethylsilyl)ethoxy)methyl)-4H-thieno[3,2-b]pyrrole-5-carboxylate (16 mg, 0.0485 mmol) was dissolved in 3 mL anhydrous DMF. TBAF (1.0 M in THF, 0.485 mL, 10 equiv) and ethylenediamine (0.10 mL, 87.45 mg, 1.455 mmol, 30 equiv) were added, and the reaction was heated to 80° C. for 1 h and then allowed to cool to rt overnight. TLC (1/1 EtOAc in heptane, visualized with anisaldehyde and heat) indicated complete reaction. The product was partitioned with LiCl saturated solution and EtOAc, dried ($Na_2SO_4$), filtered, evaporated in vacuo the organic layer to give a residue. The residue was passed through a 5 g silica gel cartridge (1/1 EtOAc in heptane) to give methyl 6-fluoro-4H-thieno[3,2-b]pyrrole-5-carboxylate (9 mg, 94% yield) as a white solid. The regiochemistry of fluorine was determined via NMR-NOE experiments. $^1$H NMR (400 MHz, $(CD_3)_2CO$) δ ppm 3.86 (s, 3H) 7.03 (dd, J=5.27, 2.29 Hz, 1H) 7.55 (d, J=5.27 Hz, 1H) 10.81 (br. s., 1H). $^{19}$F NMR (376 MHz, (CD$_3$)$_2$CO) δ ppm −155.88 (dd, J=27.47, 2.29 Hz, 1F).

1.6. Synthesis of ethyl 4-bromo-6H-thieno[2,3-b]pyrrole-5-carboxylate

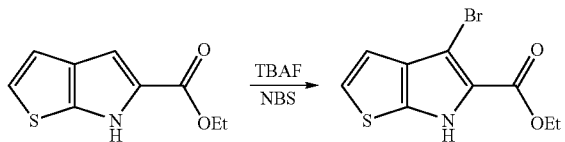

To a solution of ethyl 6H-thieno[2,3-b]pyrrole-5-carboxylate (0.06 g, 0.31 mmol) in dichloromethane (1 mL) was added TBAF (1M THF, 0.46 mL) followed by N-bromosuccinimide (NBS) (0.07 g, 0.4 mmol). The resulting mixture was allowed to stir at 23° C. for 16 h at which time the entire reaction mixture was placed on a silica gel column. Flash column chromatography (20% EtOAc in hexanes) affords one major peak containing a mixture of 4-bromo and 2,4-dibromo products. Separation of the desired product from the byproduct by RP-HPLC (10-100% gradient 0.1% formic acid in H$_2$O to CH$_3$CN over 10 min) afforded ethyl 4-bromo-6H-thieno[2,3-b]pyrrole-5-carboxylate (0.03 g, 35% yield).

1.7. Synthesis of ethyl 2-bromo-6H-thieno[2,3-b]pyrrole-5-carboxylate

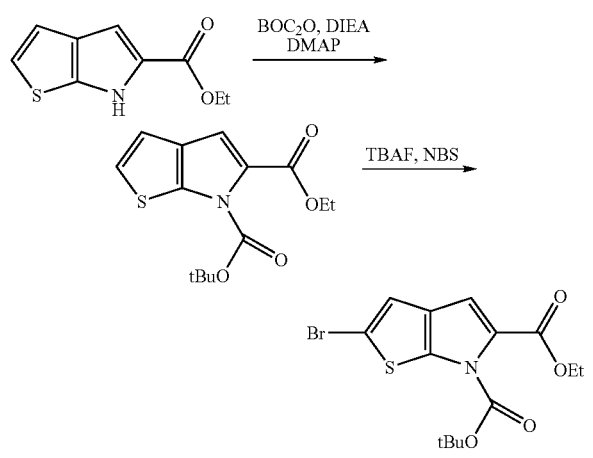

To ethyl 6H-thieno[2,3-b]pyrrole-5-carboxylate (0.12 g, 0.62 mmol) dissolved in dichloromethane (4 mL) was added N,N-diisopropylethylamine (DIPEA) (0.32 mL, 1.85 mmol) followed by t-butyl dicarbonate (BOC$_2$O) (0.20 g, 0.92 mmol) and 4-(N,N-dimethylamino)pyridine (DMAP) (0.015 g, 0.12 mmol). The combined reaction mixture was allowed to stir at 23° C. for 3 h at which time the reaction mixture was transferred directly to a silica gel column. Flash column chromatography (20% ethyl acetate in hexanes) afforded the carbamate-protected intermediate 6-tert-butoxycarbonyl-6H-thieno[2,3-b]pyrrole-5-carboxylic acid ethyl ester in quantitative yield.

To 6-tert-butoxycarbonyl-6H-thieno[2,3-b]pyrrole-5-carboxylic acid ethyl ester (0.09 g, 0.31 mmol) as a solution in dichloromethane (1 mL) was added TBAF (1M THF, 0.46 mL) followed by N-bromosuccinimide (NBS) (0.07 g, 0.4 mmol). The resulting mixture was allowed to stir at 23° C. for 16 h, after which time the entire reaction mixture was placed directly on a silica gel column. Flash column chromatography (20% ethyl acetate in hexanes) afforded 6-tert-butoxycarbonyl-2-bromo-6H-thieno[2,3-b]pyrrole-5-carboxylic acid ethyl ester (0.04 g, 36% yield).

1.8. Synthesis of ethyl 3-chloro-4H-thieno[3,2-b]pyrrole-5-carboxylate

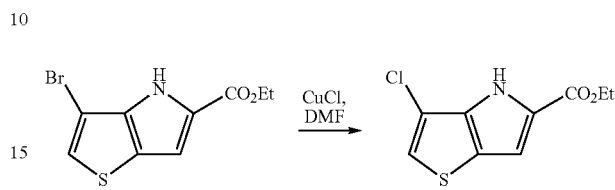

Ethyl 3-bromo-4H-thieno[3,2-b]pyrrole-5-carboxylate (200 mg, 0.730 mmol) was dissolved in 20 mL anhydrous DMF. Copper chloride (150 mg, 1.52 mmol, 2 equiv) was added, and the reaction was heated to 140° C. for 16 h. The reaction was cooled, partitioned between water and EtOAc, and the organic layer was dried (MgSO$_4$), filtered, and evaporated in vacuo. The resulting residue was chromatographed (silica gel, heptane/ethyl acetate) and yielded ethyl 3-chloro-4H-thieno[3,2-b]pyrrole-5-carboxylate (112 mg, 74% yield). $^1$H NMR (400 MHz, (CD$_3$)$_2$C(O)) δ ppm 1.33 (t, J=7.13 Hz, 3H) 4.31 (q, J=7.11 Hz, 2H) 7.17 (s, 1H) 7.39 (s, 1H) 11.45 (br. s., 1H).

1.9 Synthesis of ethyl 4-chloro-6H-thieno[2,3-b]pyrrole-5-carboxylate

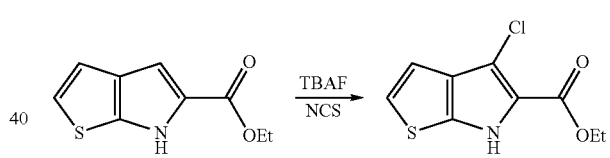

The title compound was synthesized from ethyl 6H-thieno[2,3-b]pyrrole-5-carboxylate (0.20 g, 1.02 mmol) and N-chlorosuccinimide (NCS) (0.17 g, 1.2 mmol) using the halogenation conditions to synthesize ethyl 4-bromo-6H-thieno[2,3-b]pyrrole-5-carboxylate. Separation of the desired product by RP-HPLC (10-100% gradient 0.1% formic acid in H$_2$O to CH$_3$CN over 10 min) afforded ethyl 4-chloro-6H-thieno[2,3-b]pyrrole-5-carboxylate (0.044 g, 19% yield). $^1$H NMR (400 MHz, CD$_3$OD) δ (ppm): 9.96 (br s, 1H), 6.98 (d, J=5.4 Hz, 1H), 6.92 (d, J=5.4 Hz, 1H), 4.43 (q, J=7.1 Hz, 2H), 1.43 (t, J=7.1 Hz, 3H). $^{13}$C NMR (101 MHz, CD$_3$OD) δ (ppm): 161.1, 136.8, 131.3, 124.4, 123.5, 121.5, 116.5, 61.3, 14.6. LCMS m/e 230 (M+H).

1.10 Synthesis of ethyl 2-chloro-6H-thieno[2,3-b]pyrrole-5-carboxylate

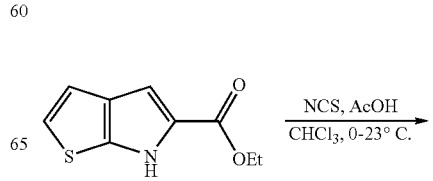

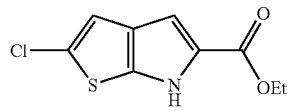

To a solution of ethyl 6H-thieno[2,3-b]pyrrole-5-carboxylate (0.21 g, 1.1 mmol) in CHCl$_3$ (2.0 mL) cooled in an ice bath to 0° C., was added AcOH (glacial, 2.0 mL) followed by portionwise addition of N-chlorosuccinimide (NCS) (0.14 g, 1.1 mmol) over 2 h. After the addition of NCS was complete, the ice bath was removed and the reaction was allowed to stir at 23° C. for 5 h. After 5 h the CHCl$_3$ was removed in vacuo and the remaining mixture was combined with aqueous 4N NaOH (10 mL) and extracted with EtOAc (3×30 mL). The combined organics were dried over Na$_2$SO$_4$, filtered and the solvent removed in vacuo. Purification by flash column chromatography (25% EtOAc in hexanes) afforded ethyl 2-chloro-6H-thieno[2,3-b]pyrrole-5-carboxylate (0.16 g, 66% yield).

1.11 Synthesis of ethyl 3-chloro-6H-thieno[2,3-b]pyrrole-5-carboxylate

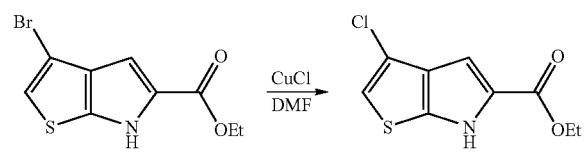

To a solution of ethyl 3-bromo-6H-thieno[2,3-b]pyrrole-5-carboxylate (0.25 g, 0.93 mmol) in DMF (37.5 mL) was added CuCl (178 mg, 1.85 mmol). The combined reactants were heated to reflux for 7 h, at which time the cooled mixture was diluted with a saturated solution of NH$_4$Cl (20 mL) and extracted with Et$_2$O (3×40 mL). The combined organic fractions were dried over Na$_2$SO$_4$, filtered and the solvent was removed in vacuo. Purification of the crude oil by flash column chromatography (25% EtOAc in hexanes) afforded ethyl 3-chloro-6H-thieno[2,3-b]pyrrole-5-carboxylate (0.18 g, 86% yield).

1.12 Synthesis of ethyl 4-fluoro-6H-thieno[2,3-b]pyrrole-5-carboxylate

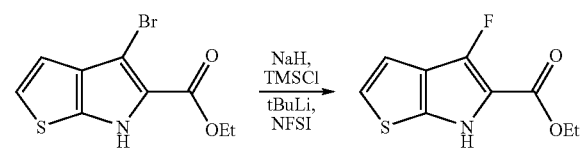

To a suspension of sodium hydride (24 mg, 1.0 mmol) in THF (10 mL) at −20° C. was added ethyl 4-bromo-6H-thieno[2,3-b]pyrrole-5-carboxylate (0.186 g, 0.678 mmol) as a solution in THF over about 2 min. After 20 min, trimethylsilyl chloride (0.090 mL, 0.71 mmol) was added and the solution was stirred at 0° C. After 30 min, the flask was chilled to −78° C. and t-BuLi (1.2 mL, 1.7M in hexanes, 2.0 mmol) was added dropwise over about 5 min. After 10 min, NFSI (428 mg, 1.36 mmol) was added as a solution in 2 mL of THF. The reaction was stirred at −78° C. for 30 min at ambient temperature for 1 h. The reaction was quenched with saturated ammonium chloride and extracted with methyl t-butyl ether. The organic phase was washed with water and brine and evaporated to give a crude brown oil. The residue was filtered through silica gel and evaporated. The resultant oil was purified using a C18 column (10-100% ACN/H$_2$O/0.1% HCOOH) followed by Chiracel OD column (95% hexane, 5% IPA, 0.1% DEA to give the pure ethyl 4-fluoro-6H-thieno[2,3-b]pyrrole-5-carboxylate (14.4 mg, 10% yield) as a white solid. $^1$H NMR (400 MHz, CDCl$_3$) δ (ppm) 9.3 (br s, 1H), 6.98 (d, J=5.4 Hz, 1H), 6.85 (d, J=5.4 Hz, 1H), 4.42 (q, J=7.1 Hz, 2H), 1.41 (t, J=7.1 Hz, 3H). $^{19}$F NMR (282 MHz, CDCl$_3$) δ ppm: −151.30 (s, 1F). $^{13}$C NMR (101 MHz, CD$_3$OD) δ (ppm) 160.7, 147.4, 144.8, 120.6, 119.9, 119.8, 115.5, 115.5, 112.7, 112.5, 60.9, 14.4. LCMS m/e=214 (M+H).

1.13 Synthesis of ethyl 2,4-dibromo-6H-thieno[2,3-b]pyrrole-5-carboxylate

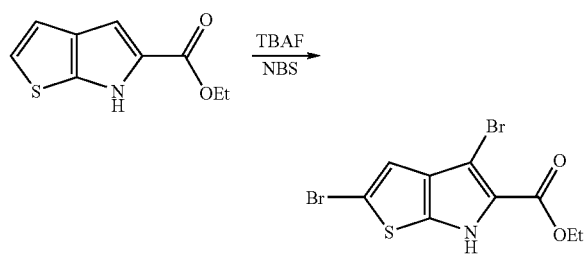

To a solution of ethyl 6H-thieno[2,3-b]pyrrole-5-carboxylate (0.55 g, 2.82 mmol) in DCM (10 mL) was added TBAF (1.0 M THF, 4.2 mL) followed by NBS (0.55 g, 3.1 mmol). The resulting mixture was allowed to stir at 23° C. for 1 h in the dark at which time the entire reaction mixture was placed on a silica gel column. Flash column chromatography (0-100% EtOAc in hexanes) affords one major peak containing a mixture of starting material, ethyl 4-bromo-6H-thieno[2,3-b]pyrrole-5-carboxylate, and 2,4-dibromo products. Separation of the desired products from the byproduct by RP-HPLC (10-100% gradient 0.1% formic acid in H$_2$O to CH$_3$CN over 10 min) afforded ethyl 4-bromo-6H-thieno[2,3-b]pyrrole-5-carboxylate (0.30 g, 39% yield) and ethyl 2,4-dibromo-6H-thieno[2,3-b]pyrrole-5-carboxylate (183 mg, 18%). Ethyl 2,4-dibromo-6H-thieno[2,3-b]pyrrole-5-carboxylate: $^1$H NMR (400 MHz, CD$_3$OD) δ (ppm) 6.95 (s, 1H), 4.32 (q, J=4.6 Hz, 2H), 1.36 (t, J=7.0 Hz, 3H). LCMS m/e=351 (M+H).

1.14. Synthesis of Carboxylic Acids from Esters

The following compounds were synthesized via saponification of their corresponding esters, for example according to General Procedure 2.

1.14.a) Synthesis of 3-methyl-4H-thieno[3,2-b]pyrrole-5-carboxylic acid (2)

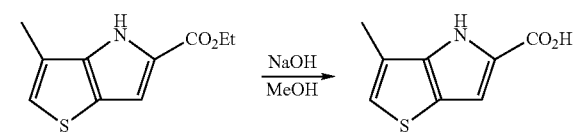

81

The title compound was synthesized from ethyl 3-methyl-4H-thieno[3,2-b]pyrrole-5-carboxylate (94 mg, 1.1 mmol) according to General Procedure 2. The crude product was purified by silica gel chromatography to give 3-methyl-4H-thieno[3,2-b]pyrrole-5-carboxylic acid 2 (57 mg). LCMS m/e 182 (M+H). $^1$H NMR (400 MHz, CD$_3$OD) δ (ppm): 7.04 (s, 1H), 6.94, (m, 1H), 2.32 (d, 3H).

1.14.b) Synthesis of 2-methyl-4H-thieno[3,2-b]pyrrole-5-carboxylic acid (3)

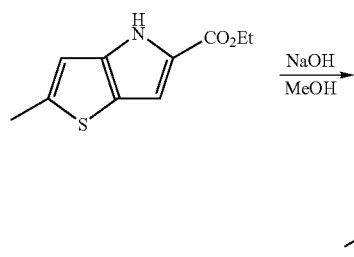

The title compound was prepared from ethyl 2-methyl-4H-thieno[3,2-b]pyrrole-5-carboxylate (250 mg, 1.2 mmol) according to General Procedure 2 and was purified by silica gel chromatography to give 2-methyl-4H-thieno[3,2-b]pyrrole-5-carboxylic acid 3 (117 mg). LCMS m/e 182 (M+H). $^1$H NMR (400 MHz, CD$_3$OD) δ (ppm): 6.98 (m, 1H), 6.68 (m, 1H), 2.52 (d, 3H).

1.14.c) Synthesis of 2-chloro-4H-thieno[3,2-b]pyrrole-5-carboxylic acid (4)

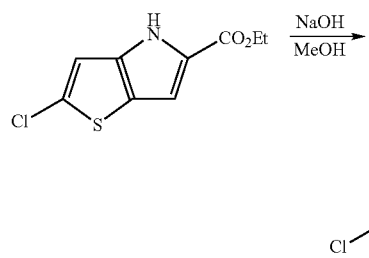

The title compound was synthesized from ethyl 2-chloro-4H-thieno[3,2-b]pyrrole-5-carboxylate (250 mg, 1.1 mmol) according to General Procedure 2 and was purified by silica gel chromatography to give 2-chloro-4H-thieno[3,2-b]pyrrole-5-carboxylic acid 4 (164 mg, 75%). $^1$H NMR (400 MHz, CD$_3$OD) δ (ppm): 7.01 (m, 1H), 6.97 (m, 1H).

1.14.d) Synthesis of 2-bromo-4H-thieno[3,2-b]pyrrole-5-carboxylic acid (5)

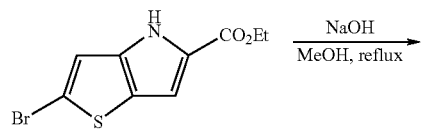

82

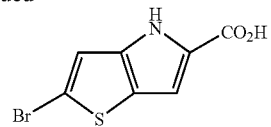

The title compound was prepared from ethyl 2-bromo-4H-thieno[3,2-b]pyrrole-5-carboxylate (General Procedure 2) and was purified by silica gel column chromatography (25 to 100% EtOAc in heptane over 30 min) to give 2-bromo-4H-thieno[3,2-b]pyrrole-5-carboxylic acid 5 as a light green solid (0.09 g, 30%). R$_f$=0.06 (50:50 heptane/EtOAc); $^1$H NMR (400 MHz, (CD$_3$)$_2$SO) δ (ppm) 12.65 (s, 1H) 12.04 (s, 1H) 7.16 (s, 1H) 6.99 (s, 1H). LCMS m/e 246 (M+H).

1.14.e) Synthesis of 2,3-dibromo-4H-thieno[3,2-b]pyrrole-5-carboxylic acid (6)

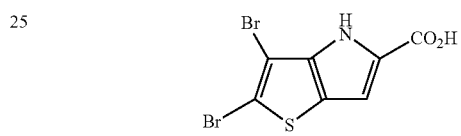

The title compound was synthesized from ethyl 2,3-dibromo-4H-thieno[3,2-b]pyrrole-5-carboxylate (0.158 g, 0.45 mmol) according to (General Procedure 2) and was purified by silica gel column chromatography (0-100% EtOAc/heptane) to give 2,3-dibromo-4H-thieno[3,2-b]pyrrole-5-carboxylic acid 6 as a light brown solid (0.054 g, 38%). R$_f$=0.07 (1:1 heptane/EtOAc); $^1$H NMR (400 MHz, (CD$_3$)$_2$SO) δ (ppm) 12.80 (s, 1H) 12.55 (s, 1H) 7.08 (s, 1H). LCMS m/e 324 (M+H).

1.14.f) Synthesis of 6H-thieno[2,3-b]pyrrole-5-carboxylic acid (7)

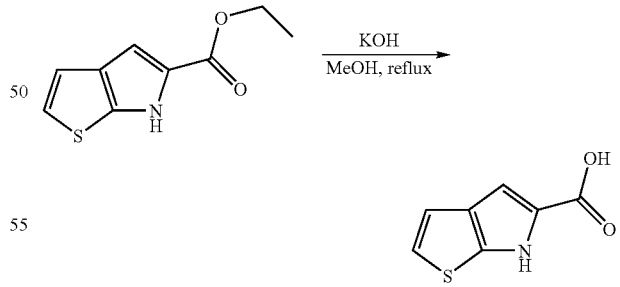

The title compound was synthesized from ethyl 6H-thieno[2,3-b]pyrrole-5-carboxylate (0.140 g, 0.72 mmol) according to General Procedure 2 and purified by silica gel column chromatography (0 to 100% EtOAc in heptane over 30 min) to give 6H-thieno[2,3-b]pyrrole-5-carboxylic acid 7 as a white solid (9 mg, 7.5%). R$_f$=0.15 (50:50 heptane/EtOAc). $^1$H NMR (400 MHz, CD$_3$OD) δ ppm 6.95 (dd, J=5.42 Hz and J=8.0 Hz, 2H) 7.01 (s, 1H). LCMS m/e 168 (M+H).

1.14.g) Synthesis of 3-bromo-6H-thieno[2,3-b]pyrrole-5-carboxylic acid (8)

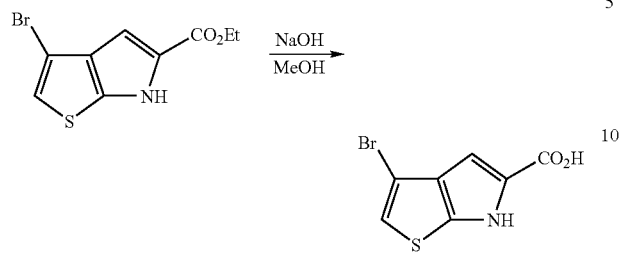

The title compound was synthesized from ethyl 3-bromo-6H-thieno[2,3-b]pyrrole-5-carboxylate (300 mg, 1.1 mmol) according to General Procedure 2. The crude product was purified by silica gel column chromatography to give 3-bromo-6H-thieno[2,3-b]pyrrole-5-carboxylic acid 8 (164 mg, 61. $^1$H NMR (400 MHz, CD$_3$OD) δ (ppm): 6.96 (s, 1H), 6.92 (s, 1H).

1.14.h) Synthesis of 3-benzyl-6H-thieno[2,3-b]pyrrole-5-carboxylic acid (9)

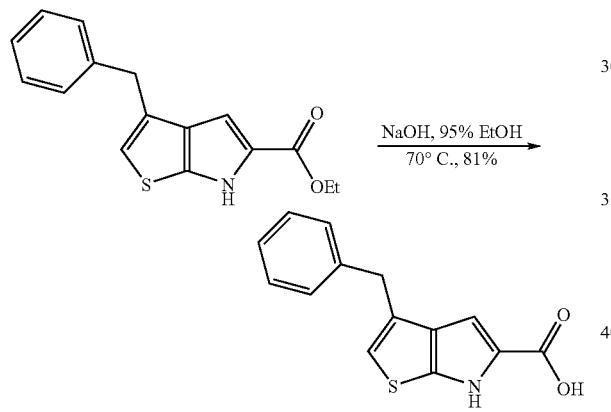

The title compound was prepared from ethyl 3-benzyl-6H-thieno[2,3-b]pyrrole-5-carboxylate (167 mg, 0.585 mmol) according to General Procedure 2 and was purified by flash chromatography (Isco CombiFlash, 0-100% EtOAc/heptane) to give 3-benzyl-6H-thieno[2,3-b]pyrrole-5-carboxylic acid 9 (122 mg, 81%) as a pale yellow solid. $^1$H NMR (400 MHz, CD$_3$OD) δ ppm 4.00 (s, 2H), 6.58 (t, J=1.00 Hz, 1H), 6.79 (s, 1H), 7.14-7.31 (m, 5H); LCMS-MS (ESI+) 257.9 (M+H); HPLC (UV=100%), (ELSD=100%).

1.14.i) Synthesis of 3-phenyl-6H-thieno[2,3-b]pyrrole-5-carboxylic acid (10)

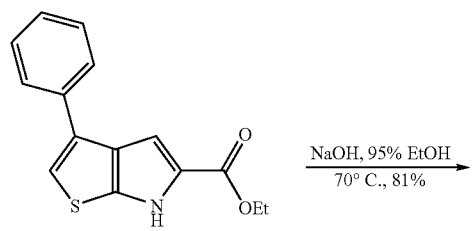

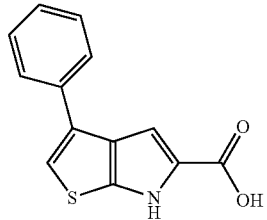

The title compound was prepared from ethyl 3-phenyl-6H-thieno[2,3-b]pyrrole-5-carboxylate (165 mg, 0.61 mmol) according to General Procedure 2 and was purified by flash chromatography (Isco CombiFlash, 0-100% EtOAc/heptane) to afford 3-phenyl-6H-thieno[2,3-b]pyrrole-5-carboxylic acid 10 (120 mg, 81%) as a pale yellow solid. $^1$H NMR (400 MHz, CD$_3$OD) δ ppm 7.18 (s, 1H), 7.27 (s, 1H), 7.28-7.34 (m, 1H), 7.44 (t, J=7.66 Hz, 2H), 7.74-7.78 (m, 2H); LCMS-MS (ESI+) 244.0 (M+H); HPLC (UV=100%), (ELSD=100%).

1.14.j) Synthesis of 3-(4-chlorobenzyl)-4H-thieno[3,2-b]pyrrole-5-carboxylic acid (14)

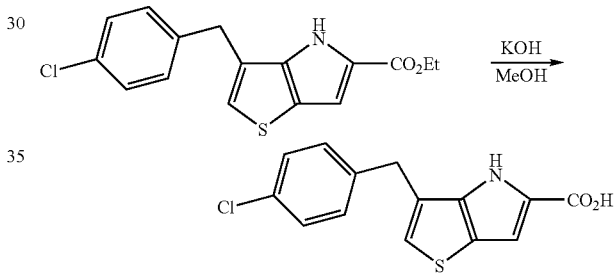

The title compound was synthesized from ethyl 3-(4-chlorobenzyl)-4H-thieno[3,2-b]pyrrole-5-carboxylate (170 mg, 0.53 mmol) according to General Procedure 2. The crude product was purified by silica gel chromatography to give 3-(4-chlorobenzyl)-4H-thieno[3,2-b]pyrrole-5-carboxylic acid 14. LC/MS: m/e 292 (M+H). $^1$H NMR (400 MHz, CD$_3$OD) δ (ppm): 7.25 (m, 4H), 7.06 (s, 1H), 6.87 (m, 1H), 4.04 (s, 2H).

1.14.k) Synthesis of 3-phenethyl-4H-thieno[3,2-b]pyrrole-5-carboxylic acid (15)

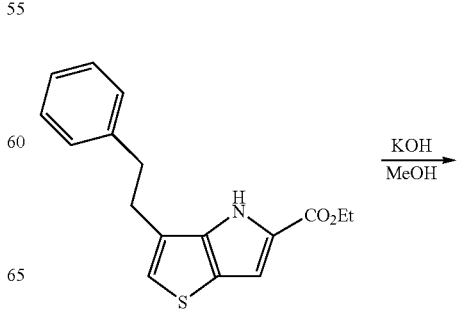

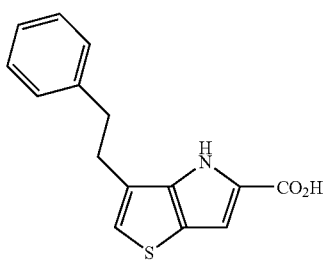

The title compound was synthesized from ethyl 3-phenethyl-4H-thieno[3,2-b]pyrrole-5-carboxylate (188 mg, 0.63 mmol) according to General Procedure 2 and was purified by silica gel column chromatography to give 3-phenethyl-4H-thieno[3,2-b]pyrrole-5-carboxylic acid 15 (118 mg, 69%). LCMS m/e 272 (M+H). $^1$H NMR (400 MHz, CD$_3$OD) δ (ppm): 7.22 (m, 4H), 7.15 (M, 1H), 7.05 (s, 1H), 6.92 (s, 1H), 3.02 (m, 4H).

1.14.l) Synthesis of 3-(4-chlorophenethyl)-6H-thieno[2,3-b]pyrrole-5-carboxylic acid (16)

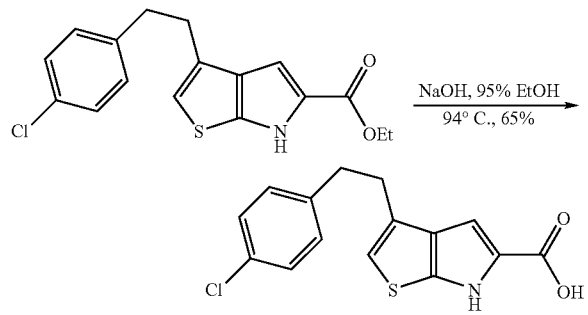

The title compound was synthesized from ethyl 3-(4-chlorophenethyl)-6H-thieno[2,3-b]pyrrole-5-carboxylate (110 mg, 0.33 mmol) according to General Procedure 2 and was purified by flash chromatography (Isco CombiFlash, 0-100% EtOAc/heptane) to afford 3-(4-chlorophenethyl)-6H-thieno[2,3-b]pyrrole-5-carboxylic acid 16 (66 mg, 65%) as an off-white solid. $^1$H NMR (400 MHz, CD$_3$OD) δ ppm 2.93-3.03 (m, 4H), 6.50 (s, 1H), 7.01 (s, 1H), 7.12-7.17 (m, 2H), 7.20-7.24 (m, 2H); LCMS-MS (ESI+) 305.72 (M+H); HPLC (UV=98%), (ELSD=100%).

1.14.m) Synthesis of 2-phenethyl-4H-thieno[3,2-b]pyrrole-5-carboxylic acid (18)

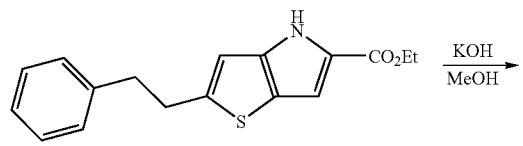

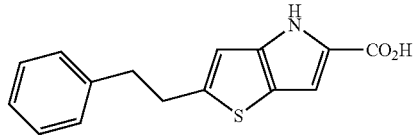

The title compound was synthesized from ethyl 2-phenethyl-4H-thieno[3,2-b]pyrrole-5-carboxylate (290 mg, 0.97 mmol) according to General Procedure 2. The crude product was purified by silica gel chromatography and recrystallization (EtOAc) to give 2-phenethyl-4H-thieno[3,2-b]pyrrole-5-carboxylic acid 18 (70 mg). LC/MS: m/e 272 (M+H). $^1$H NMR (400 MHz, CD$_3$OD) δ (ppm): 7.21 (m, 5H), 6.99 (d, 1H), 6.65 (dd, 1H), 3.14 (m, 2H), 2.99 (m, 2H).

1.14.n) Synthesis of 2-(4-chlorobenzyl)-6H-thieno[2,3-b]pyrrole-5-carboxylic acid (19)

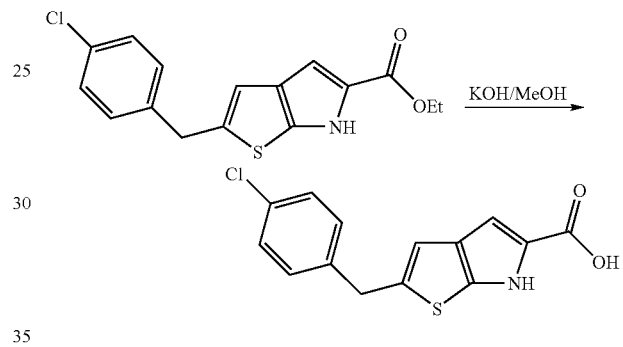

The title compound was prepared from ethyl 2-(4-chlorobenzyl)-6H-thieno[2,3-b]pyrrole-5-carboxylate (50 mg, 0.15 mmol) according to General Procedure 2. The crude product was purified by silica gel chromatography to give 2-(4-chlorobenzyl)-6H-thieno[2,3-b]pyrrole-5-carboxylic acid 19 (9 mg). LC/MS: m/e 290 (M−H). $^1$H NMR (400 MHz, CD$_3$OD) δ ppm 4.13 (s, 2H), 6.75 (s, 1H), 6.94 (s, 1H), 7.23-7.35 (m, 4H).

1.14.o) Synthesis of 2-(4-chlorobenzyl)-4H-thieno[3,2-b]pyrrole-5-carboxylic acid (20)

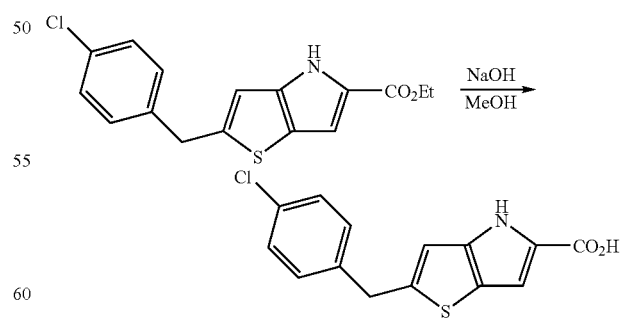

The title compound was prepared from ethyl 2-(4-chlorobenzyl)-4H-thieno[3,2-b]pyrrole-5-carboxylate (42 mg, 0.13 mmol) according to General Procedure 2. The crude product was purified by silica gel column chromatography and HPLC to afford 2-(4-chlorobenzyl)-4H-thieno[3,2-b]

pyrrole-5-carboxylic acid 20 (12 mg). LC/MS: m/e 290 (M–H). ¹H NMR (400 MHz, CD₃OD) δ (ppm): 7.28 (m, 4H), 6.96 (d, 1H), 6.73 (d, 1H), 4.15 (s, 2H).

1.14.p) Synthesis of 3-(4-chlorobenzyl)-6H-thieno[2,3-b]pyrrole-5-carboxylic acid (29)

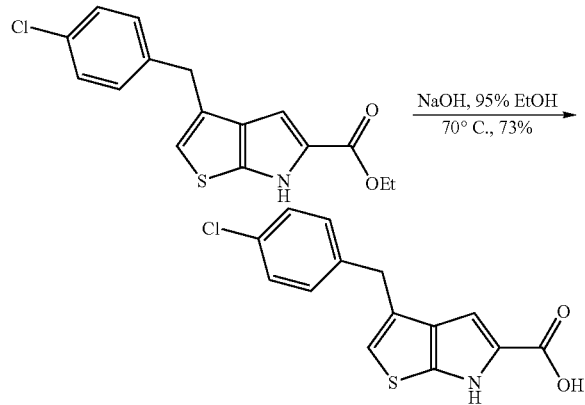

The title compound was prepared from ethyl 3-(4-chlorobenzyl)-6H-thieno[2,3-b]pyrrole-5-carboxylate (152 mg, 0.475 mmol) according to General Procedure 2 and was purified by flash chromatography (Isco CombiFlash, 0-100% EtOAc/heptane) to give 3-(4-chlorobenzyl)-6H-thieno[2,3-b]pyrrole-5-carboxylic acid 29 (102 mg, 73%) as a pale yellow solid. ¹H NMR (400 MHz, CD₃OD) δ ppm 4.00 (s, 2H), 6.62 (t, J=0.96 Hz, 1H), 6.79 (s, 1H), 7.23-7.30 (m, 4H); ¹³C NMR (100 MHz, CD₃OD) δ 164.59, 140.11, 139.87, 133.12, 132.61, 132.37, 131.53, 129.55, 129.47, 117.51, 108.00, 36.19; LCMS-MS (ESI+) 291.72 (M+H); HPLC (UV=99.2%), (ELSD=100%).

1.14.q) Synthesis of 3-bromo-4H-thieno[3,2-b]pyrrole-5-carboxylic acid (49)

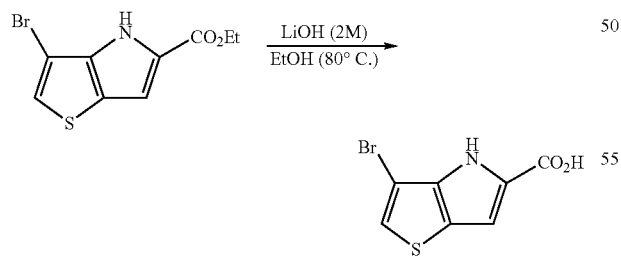

The title compound was synthesized from ethyl 3-bromo-4H-thieno[3,2-b]pyrrole-5-carboxylate (27.6 mg, 0.102 mmol) according to General Procedure 2 to give 3-bromo-4H-thieno[3,2-b]pyrrole-5-carboxylic acid (15.6 mg, 62%). ¹H NMR (400 MHz, (CD₃)₂CO) δ ppm 7.22 (s, 1H) 7.49 (s, 1H) 11.33 (br. s., 0.05H). LCMS m/e 246 (M+H).

1.14.r) Synthesis of 6-methyl-4H-thieno[3,2-b]pyrrole-5-carboxylic acid (52)

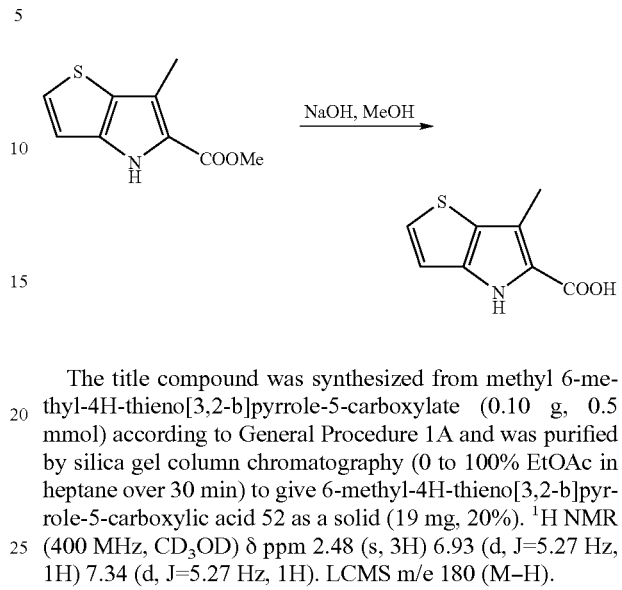

The title compound was synthesized from methyl 6-methyl-4H-thieno[3,2-b]pyrrole-5-carboxylate (0.10 g, 0.5 mmol) according to General Procedure 1A and was purified by silica gel column chromatography (0 to 100% EtOAc in heptane over 30 min) to give 6-methyl-4H-thieno[3,2-b]pyrrole-5-carboxylic acid 52 as a solid (19 mg, 20%). ¹H NMR (400 MHz, CD₃OD) δ ppm 2.48 (s, 3H) 6.93 (d, J=5.27 Hz, 1H) 7.34 (d, J=5.27 Hz, 1H). LCMS m/e 180 (M–H).

1.14.s) Synthesis of 6-fluoro-4H-thieno[3,2-b]pyrrole-5-carboxylic acid (54)

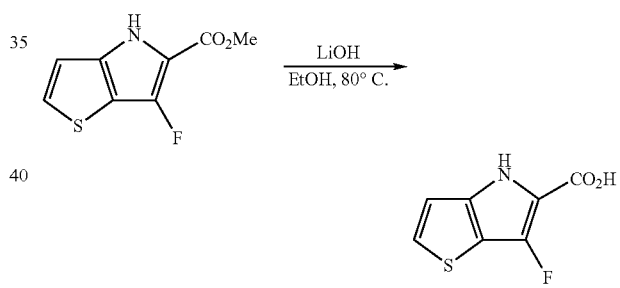

The title compound was synthesized from methyl 6-fluoro-4H-thieno[3,2-b]pyrrole-5-carboxylate (9 mg, 0.0451 mmol) according to General Procedure 2 and was purified using a 5 g silica gel cartridge (DCM/EtOAc) to give 6-fluoro-4H-thieno[3,2-b]pyrrole-5-carboxylic acid 54 (3.3 mg, 41%). ¹H NMR (400 MHz, CD₃OD) δ ppm 6.92 (dd, J=5.22, 2.25 Hz, 1H) 7.35 (d, J=5.27 Hz, 1H). ¹⁹F NMR (376 MHz, CD₃OD) δ ppm –158.76 (br. s., 1F).

1.14.t) Synthesis of 2-fluoro-4H-thieno[3,2-b]pyrrole-5-carboxylic acid (55)

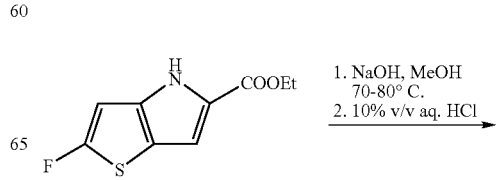

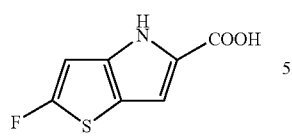

The title compound was synthesized from ethyl 2-fluoro-4H-thieno[3,2-b]pyrrole-5-carboxylate (0.0489 g, 0.23 mmol) according to General Procedure 2 to give 2-fluoro-4H-thieno[3,2-b]pyrrole-5-carboxylic acid 55 (38.6 mg, 91%) as a cream-colored solid. LC/MS m/e 183.7 (M–H). $^1$H NMR (400 MHz, CD$_3$OD) δ ppm 7.03 (s, 1H), 6.64 (d, J=1.66 Hz, 1H). $^{19}$F NMR (376 MHz, CD$_3$OD) δ ppm –123.29 (d, J=1.91 Hz, 1F).

1.14.u) Synthesis of
3-fluoro-4H-thieno[3,2-b]pyrrole-5-carboxylic acid
(56)

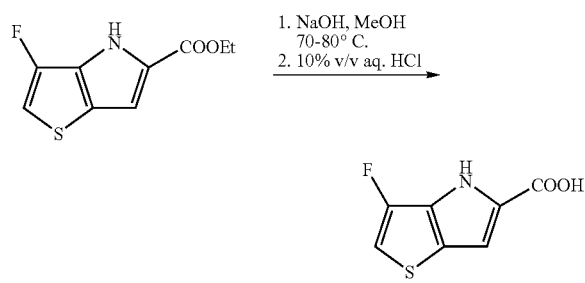

The title compound was synthesized from ethyl 3-fluoro-4H-thieno[3,2-b]pyrrole-5-carboxylate (0.0054 g, 0.023 mmol) according to General Procedure 2 and was purified by preparative HPLC using a Chromeleon purification system (30% to 100% over 7 min methanol/0.1% formic acid-1% acetonitrile in water, 50 mm Dynamax C-18, 28 mL/min) to give 3-fluoro-4H-thieno[3,2-b]pyrrole-5-carboxylic acid 56 (0.8 mg, 17%). LC/MS m/e 184 (M–H). Retention time of product: 2.5-2.8 min. $^1$H NMR (400 MHz, CD$_3$OD) δ ppm 7.01 (d, J=2.25 Hz, 1H), 6.84 (d, J=2.49 Hz, 1H). $^{19}$F NMR (376 MHz, CD$_3$OD) δ ppm –145.73 (t, J=2.29 Hz, 1F).

1.14.v) Synthesis of
2-phenethyl-6H-thieno[2,3-b]pyrrole-5-carboxylic acid (59)

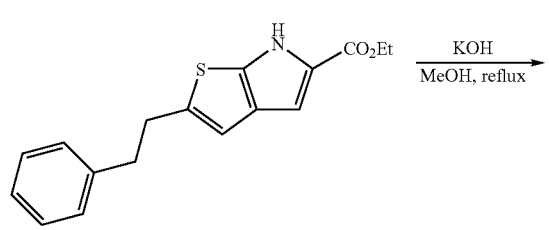

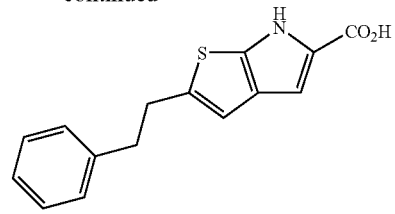

The title compound was synthesized from ethyl 2-phenethyl-6H-thieno[2,3-b]pyrrole-5-carboxylate (0.33 g, 1.2 mmol) according to General Procedure 2 and was purified by silica gel column chromatography (25 to 100% EtOAc in heptane over 30 min) to give 2-phenethyl-6H-thieno[2,3-b]pyrrole-5-carboxylic acid 59 (13 mg, 3%) as an off-white solid. $^1$H NMR (400 MHz, CD$_3$OD) δ (ppm) 7.21 (s, 1H), 6.88 (s, 1H), 6.61 (s, 1H), 3.09 (m, 1H), 2.97 (m, 1H). LCMS m/e 270 (M–H).

1.14.w) Synthesis of
4-bromo-6H-thieno[2,3-b]pyrrole-5-carboxylic acid
(64)

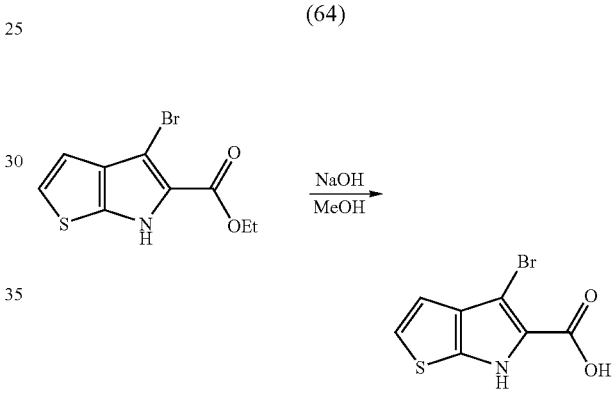

The title compound was synthesized from ethyl 4-bromo-6H-thieno[2,3-b]pyrrole-5-carboxylate (0.03 g, 0.11 mmol) according to General Procedure 2, and was purified by RP-HPLC (10-100% gradient 0.1% formic acid in H$_2$O to CH$_3$CN over 10 min) to give 4-bromo-6H-thieno[2,3-b]pyrrole-5-carboxylic acid 64 as an off-white solid (0.022 g, 78% yield). $^1$H NMR (400 MHz, CD$_3$OD) δ (ppm) 7.04 (d, J=5.5 Hz, 1H), 6.90 (d, J=5.5 Hz, 1H).

1.14.x) Synthesis of
2-bromo-6H-thieno[2,3-b]pyrrole-5-carboxylic acid
(65)

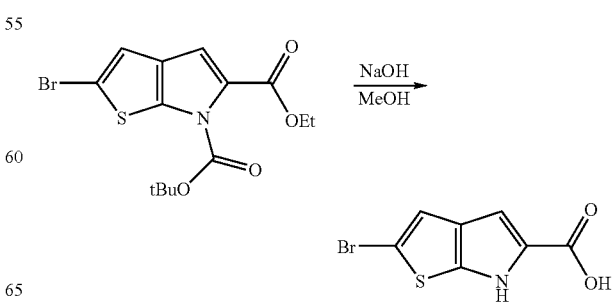

The title compound was synthesized from 6-tert-butoxy-carbonyl-2-bromo-6H-thieno[2,3-b]pyrrole-5-carboxylic acid ethyl ester (0.04 g, 0.11 mmol) according to General Procedure 2 and was purified by RP-HPLC (10-100% gradient 0.1% formic acid in H$_2$O to CH$_3$CN over 10 min) afforded 2-bromo-6H-thieno[2,3-b]pyrrole-5-carboxylic acid 65 as an off-white solid (0.020 g, 70% yield). Note that the tert-butyloxycarbonyl group was removed under the reaction conditions. $^1$H NMR (400 MHz, CD$_3$OD) δ (ppm) 7.07 (s, 1H), 6.96 (s, 1H).

1.14.y) Synthesis of 2-fluoro-6H-thieno[2,3-b]pyrrole-5-carboxylic acid (66)

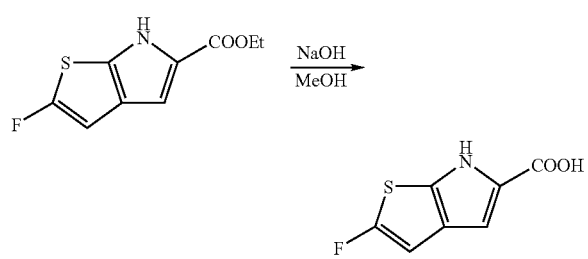

The title compound was synthesized from ethyl 2-fluoro-6H-thieno[2,3-b]pyrrole-5-carboxylate (0.03 g, 0.14 mmol) according to General Procedure 2 and was purified by RP-HPLC (10-100% gradient 0.1% formic acid in H$_2$O to CH$_3$CN over 10 min) to afford 2-fluoro-6H-thieno[2,3-b]pyrrole-5-carboxylic acid 66 as a light pink solid (0.019 g, 73%). $^1$H NMR (400 MHz, CD$_3$OD) δ (ppm) 6.98 (s, 1H), 6.56 (d, J=2.6 Hz, 1H). $^{19}$F NMR (282 MHz, CD$_3$OD) δ ppm −132.58 (1F). LCMS m/e 186 (M+H).

1.14.z) Synthesis of 3-chloro-4H-thieno[3,2-b]pyrrole-5-carboxylic acid (67)

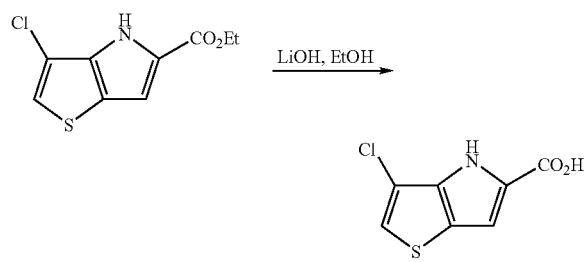

The title compound was synthesized from ethyl 3-chloro-4H-thieno[3,2-b]pyrrole-5-carboxylate (100 mg, 0.4353 mmol) according to General Procedure 2. 3-Chloro-4H-thieno[3,2-b]pyrrole-5-carboxylic acid 67 was isolated pure without purification (35.3 mg, 40% yield). $^1$H NMR (400 MHz, CD$_3$OD) δ ppm 7.08 (s, 1H) 7.22 (s, 1H).

1.14.aa) Synthesis of 3-fluoro-6H-thieno[2,3-b]pyrrole-5-carboxylic acid (68)

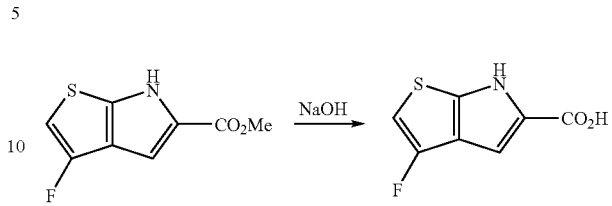

The title compound was synthesized from methyl 3-fluoro-6H-thieno[2,3-b]pyrrole-5-carboxylate (53.7 mg, 0.2518 mmol) according to General Procedure 2 and was purified by RP-HPLC to afford 3-fluoro-6H-thieno[2,3-b]pyrrole-5-carboxylic acid 68 (30 mg, 65%) as a slight pink solid. $^1$H NMR (300 MHz, CD$_3$OD) δ (ppm): 6.97 (d, J=0.48 Hz, 1H), 6.43 (d, J=2.93, 1H), 4.9 (br s, 2H). $^{19}$F NMR (282 MHz, CD$_3$OD) δ ppm: −134.56 (s, 1F). $^{13}$C NMR (75.4 MHz, CD$_3$OD) δ (ppm): 164.1, 152.5, 149.0, 105.9, 105.8, 98.9, 98.5. LCMS m/e=186 (M+H).

1.14.bb) Synthesis of 4-chloro-6H-thieno[2,3-b]pyrrole-5-carboxylic acid (69)

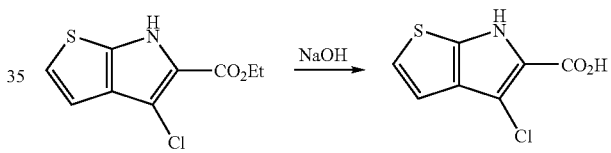

The title compound was synthesized from ethyl 4-chloro-6H-thieno[2,3-b]pyrrole-5-carboxylate (0.04 g, 0.11 mmol) according to General Procedure 2 and was purified by RP-HPLC (10-100% gradient 0.1% formic acid in H$_2$O to CH$_3$CN over 10 min). The desired fraction was treated under vacuum to remove the acetonitrile, and the remainder was extracted with MTBE. The organic layer was washed with saturated ammonium chloride, water, and brine; dried over sodium sulfate; filtered and evaporated to afford 4-chloro-6H-thieno[2,3-b]pyrrole-5-carboxylic acid 69 as a white solid (0.013 g, 37% yield). $^1$H NMR (400 MHz, CD$_3$OD) δ (ppm): 7.04 (d, J=5.5 Hz, 1H), 6.94 (d, J=5.5 Hz, 1H). $^{13}$C NMR (101 MHz, CD$_3$OD) δ (ppm): 163.2, 138.1, 131.8, 124.6, 122.7, 116.8, 111.5. LCMS m/e=202 (M+H).

1.14.cc) Synthesis of 2-chloro-6H-thieno[2,3-b]pyrrole-5-carboxylic acid (80)

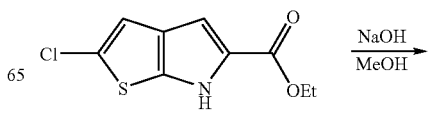

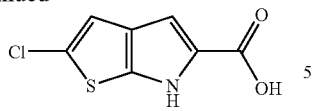

The title compound was synthesized from ethyl 2-chloro-6H-thieno[2,3-b]pyrrole-5-carboxylate according to General Procedure 2 and was purified by RP-HPLC (10-100% gradient 0.1% formic acid in $H_2O$ to $CH_3CN$ over 10 min) to give 2-chloro-6H-thieno[2,3-b]pyrrole-5-carboxylic acid 80 as an off-white solid (0.068 g, 97% yield). $^1$H NMR (400 MHz, $CD_3OD$) δ (ppm) 6.96 (dd, J=2.2 Hz, 1H), 6.92 (dd, J=2.2 Hz, 1H). $^{13}$C NMR (100 MHz, $CD_3OD$) δ (ppm) 163.0, 135.0, 128.4, 127.9, 123.9, 117.4, 107.2.

1.14.dd) Synthesis of 3-chloro-6H-thieno[2,3-b]pyrrole-5-carboxylic acid (81)

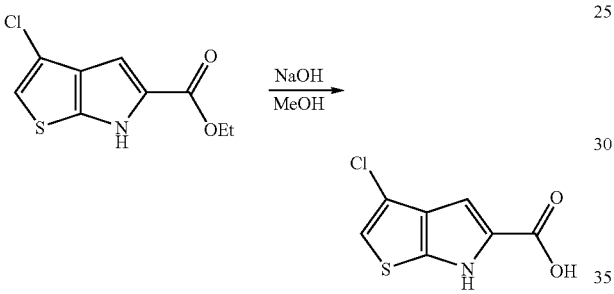

The title compound was synthesized from ethyl 3-chloro-6H-thieno[2,3-b]pyrrole-5-carboxylate (0.1 g, 0.44 mmol) according to General Procedure 2 and was purified by RP-HPLC (10-100% gradient 0.1% formic acid in $H_2O$ to $CH_3CN$ over 10 min) to give 3-chloro-6H-thieno[2,3-b]pyrrole-5-carboxylic acid 81 as an off-white solid (0.077 g, 88% yield). $^1$H NMR (400 MHz, $CD_3OD$) δ (ppm) 6.97 (dd, J=1.4 Hz, 1H), 6.81 (dd, J=1.4 Hz, 1H). $^{13}$C NMR (100 MHz, $CD_3OD$) δ (ppm) 163.0, 136.6, 129.2, 128.8, 116.4, 114.5, 105.4.

1.14.ee) Synthesis of 4-fluoro-6H-thieno[2,3-b]pyrrole-5-carboxylic acid (82)

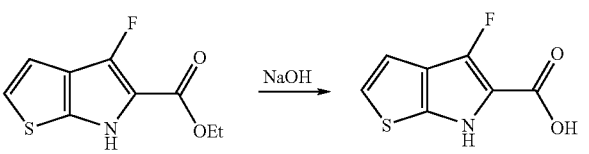

The title compound was synthesized from ethyl 4-fluoro-6H-thieno[2,3-b]pyrrole-5-carboxylate (0.020 g, 0.094 mmol) according to General Procedure 2. 4-Fluoro-6H-thieno[2,3-b]pyrrole-5-carboxylic acid 82 was obtained as an off-white solid without further purification (0.012 g, 69% yield). $^1$H NMR (300 MHz, $CD_3OD$) δ (ppm) 6.09 (s, 2H). $^{19}$F NMR (282 MHz, $CD_3OD$) δ ppm: −155.09 (s, 1F). LCMS m/e=186 (M+H).

1.14.ff) Synthesis of 2,4-dibromo-6H-thieno[2,3-b]pyrrole-5-carboxylic acid (84)

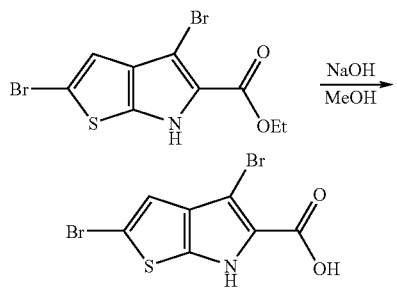

The title compound was synthesized from 2,4-dibromo-6H-thieno[2,3-b]pyrrole-5-carboxylate (0.087 g, 0.025 mmol) according to General Procedure 2, and was purified by RP-HPLC (10-100% gradient 0.1% formic acid in $H_2O$ to $CH_3CN$ over 10 min) to afford 2,4-dibromo-6H-thieno[2,3-b]pyrrole-5-carboxylic acid 84 as a white solid (0.071 g, 88% yield). $^1$H NMR (400 MHz, $CD_3OD$) δ (ppm) 7.01 (s, 1H). $^{13}$C NMR (101 MHz, $CD_3OD$) δ (ppm) 161.6, 151.4, 131.1, 119.4, 107.5, 104.5, 93.8. LCMS m/e=328 (M+H).

1.15. Synthesis of 6-chloro-4H-thieno[3,2-b]pyrrole-5-carboxylic acid (70)

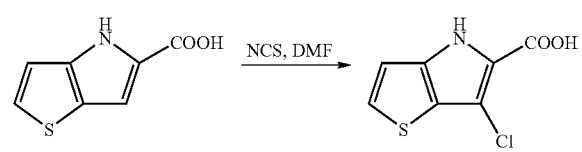

To a 20 mL vial fitted with a magnetic stir bar at 25° C. was added 4H-thieno[3,2-b]pyrrole-5-carboxylic acid (0.1 g, 0.599 mmol, 1 equiv) and 2 mL of anhydrous DMF. N-chlorosuccinimide (NCS) (0.08 g, 0.599 mmol, 1 equiv) was subsequently added and the reaction vessel contents stirred for 1 h at 25° C. before heating the reaction vial to 55° C. for 12 h. The reaction was then allowed to cool to 25° C. and was diluted with EtOAc (10 mL). The resulting mixture was then washed with water) 3×5 mL). The organic phase was dried over anhydrous $MgSO_4$, filtered, and evaporated in vacuo. The resulting residue was dissolved in a small volume of methanol, filtered through a 0.45 micron syringe filter, and further purified via preparative HPLC using the Chromeleon purification system. A 0.1% formic acid/1% acetonitrile mixture in water (aqueous phase) and methanol (no modifier added—organic phase) using a 50 mm Dynamax HPLC C-18 column at 28 mL/min (initial gradient of 40% methanol and increasing to 100% over 7 min) afforded the desired 6-chloro-4H-thieno[3,2-b]pyrrole-5-carboxylic acid 70 (5.5 mg, 5%).

LC/MS m/e 199.9 (M–H). $t_R$ of product: 2.3-2.7 min. $^1$H NMR (400 MHz, CD$_3$OD) δ ppm 7.41 (d, J=5.32 Hz, 1H), 6.97 (d, J=5.27 Hz, 1H).

1.16. Synthesis of 6-bromo-4H-thieno[3,2-b]pyrrole-5-carboxylic acid (71)

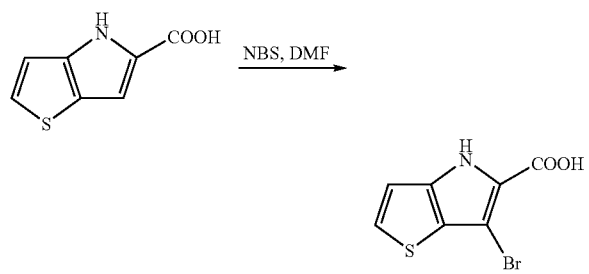

The title compound was synthesized from 4H-thieno[3,2-b]pyrrole-5-carboxylic acid (0.1 g, 0.60 mmol, 1 equiv) and N-bromosuccinimide (NBS) (0.107 g, 0.599 mmol, 1 equiv) according to the halogenation method reported for the chlorination of 4H-thieno[3,2-b]pyrrole-5-carboxylic acid (with NCS) to 6-chloro-4H-thieno[3,2-b]pyrrole-5-carboxylic acid, providing the desired 6-bromo-4H-thieno[3,2-b]pyrrole-5-carboxylic acid 71 (15.5 mg, 10.5%). LC/MS m/e 243.9 (M–H). $t_R$ of product: 2.5-2.8 min. $^1$H NMR (400 MHz, CD$_3$OD) δ ppm 7.42 (d, J=5.32 Hz, 1H), 7.01 (d, J=5.32 Hz, 1H).

Example 2

Synthesis of Fused Furan Pyrrole Analogs

2.1. Synthesis of Intermediate Aldehydes

2.1.a) Synthesis of 4-phenethyl-furan-2-carbaldehyde

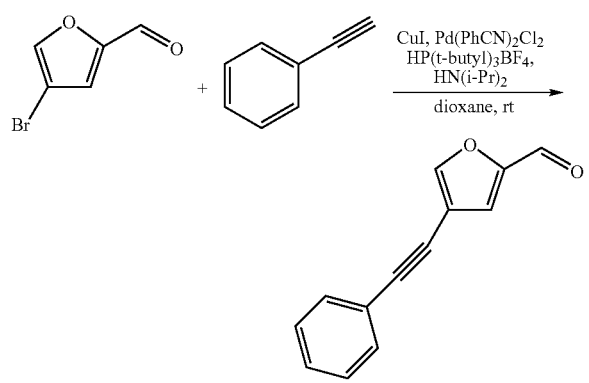

A solid mixture of 4-bromo-2-furaldehyde (1.50 g, 8.57 mmol), PdCl$_2$(PhCN)$_2$ (197 mg, 0.514 mmol) and CuI (65.0 mg, 0.343 mmol) was flushed under an argon stream for 1 min. A solution of HP(t-butyl)$_3$BF$_4$ (298 mg, 1.03 mmol) and diisopropylamine (1.80 mL, 12.9 mmol) in dioxane (9 mL) was added to the solid mixture followed by phenylacetylene (1.13 mL, 10.3 mmol). The reaction was allowed to stir at rt under an atmosphere of argon for 15 h before being filtered through a plug of silica gel with EtOAc. The solution was then concentrated in vacuo and chromatographed over silica gel to give 4-phenylethynyl-furan-2-carbaldehyde as a colorless oil (1.54 g, 92%). $R_f$=0.35 (1:9 heptane/EtOAc); $^1$H NMR (400 MHz, CDCl$_3$) δ ppm 9.68 (d, J=0.5 Hz, 1H) 7.90 (s, 1H) 7.48-7.55 (m, 2H) 7.35-7.40 (m, 3H) 7.33 (d, J=0.7 Hz, 1H).

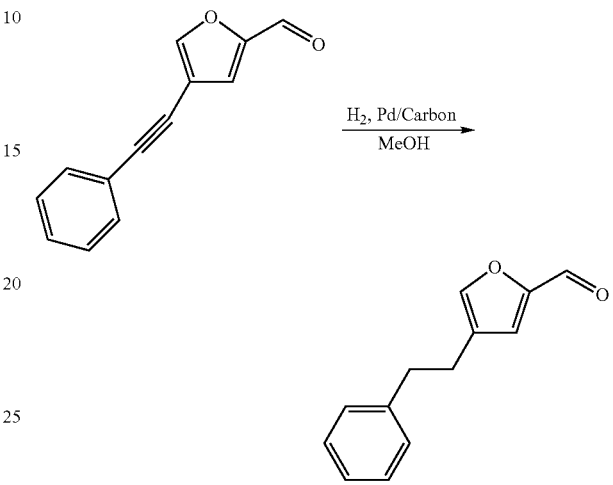

To a solution of 4-phenylethynyl-furan-2-carbaldehyde (1.54 g, 7.84 mmol) in MeOH was added Pd/C (154 mg, 10% Pd by weight). A vacuum was applied to the reaction mixture and back filled (×4) with H$_2$. The reaction was then allowed to stir at rt for 14 h under an atmosphere of H$_2$ before being filtered through a plug of Celite® with EtOAc. The reaction was then concentrated in vacuo to give 4-phenethyl-furan-2-carbaldehyde as a colorless oil (1.53 g, 97%). $^1$H NMR (400 MHz, CDCl$_3$) δ ppm 9.59 (d, J=0.6 Hz, 1H) 7.40 (d, J=0.8 Hz, 1H) 7.28-7.34 (m, 2H) 7.20-7.26 (m, 1H) 7.14-7.20 (m, 2H) 7.05 (d, J=0.6 Hz, 1H) 2.87-2.94 (m, 2H) 2.78-2.85 (m, 2H).

2.1.b) Synthesis of 5-benzyl-furan-2-carbaldehyde

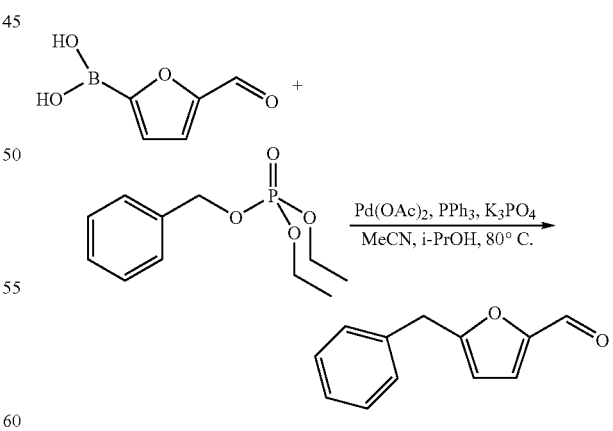

The title compound was synthesized from 5-formylfuran-2-ylboronic acid (0.80 g, 5.7 mmol) and benzyl diethyl phosphate (1.5 g, 6.3 mmol) using the same conditions used to synthesize 4-(4-chlorobenzyl)thiophene-2-carbaldehyde. Purification by flash chromatography yielded 5-benzyl-furan-2-carbaldehyde as a brown solid (0.37 g, 65%). $^1$H NMR (400 MHz, CDCl₃) δ ppm 9.56 (s, 1H) 7.29-7.38 (m, 3H) 7.24-7.28 (m, 2H) 7.17 (d, J=3.5 Hz, 1H) 6.19 (d, J=3.6 Hz, 1H) 4.07 (s, 2H).

2.1.c) Synthesis of 4-benzyl-furan-2-carbaldehyde

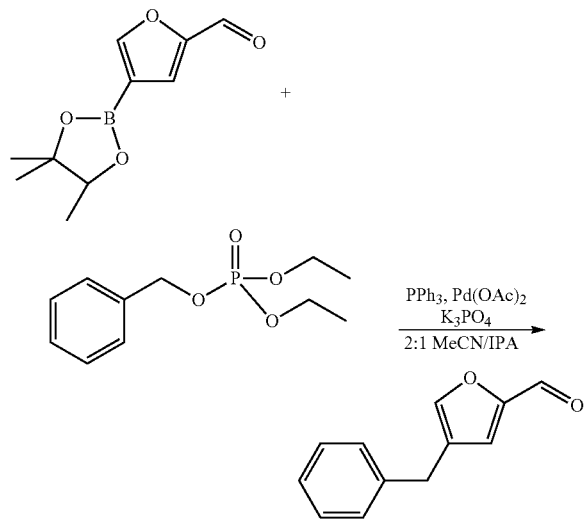

The title compound was synthesized from 5-formylfuran-3-boronic acid pinacol ester (878 mg, 3.95 mmol), and benzyl diethyl phosphate (1.25 g, 5.14 mmol) using the same conditions used to synthesize 4-(4-chlorobenzyl)thiophene-2-carbaldehyde, with the exception that triphenylphosphine and Pd(OAc)₂ were dissolved in 2:1 CH₃CN/isopropyl alcohol. Purification by flash chromatography yielded 4-benzyl-furan-2-carbaldehyde as a white solid (300 mg, 41%). ¹H NMR (400 MHz, CDCl₃) δ ppm 9.56 (s, 1H) 7.29-7.38 (m, 3H) 7.24-7.28 (m, 2H) 7.17 (d, J=3.5 Hz, 1H) 6.19 (d, J=3.6 Hz, 1H) 4.07 (s, 2H).

2.1.d) Synthesis of 4-vinylfuran-2-carbaldehyde

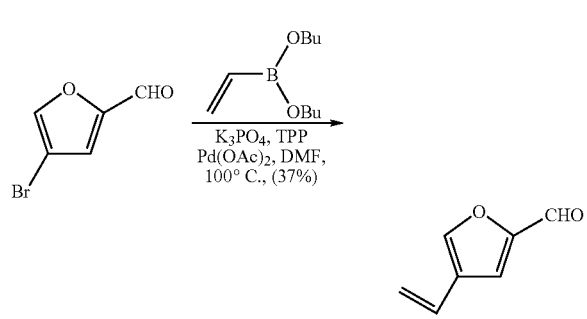

The title compound was synthesized from 4-bromo-furan-2-carbaldehyde (1.1 g, 6.29 mmol) and vinylboronic acid dibutyl ester (1.67 mL, 7.54 mmol) using the same conditions used to synthesize 4-(4-chlorobenzyl)thiophene-2-carbaldehyde, with the exception that the reaction was run in DMF (20 mL). Purification by flash chromatography (0-30% EtOAc in heptane) provided 4-vinylfuran-2-carbaldehyde as an orange oil; Yield 282 mg (37%). ¹H NMR (400 MHz, CDCl₃) δ ppm 5.31 (dd, J=10.88, 0.93 Hz, 1H), 5.61 (dd, J=17.57, 0.54 Hz, 1H), 6.56 (dd, J=17.55, 10.91 Hz, 1H), 7.37 (s, 1H), 7.67 (s, 1H), 9.66 (d, J=0.59 Hz, 1H).

2.1.e) Synthesis of 4-cyclopropylfuran-2-carbaldehyde

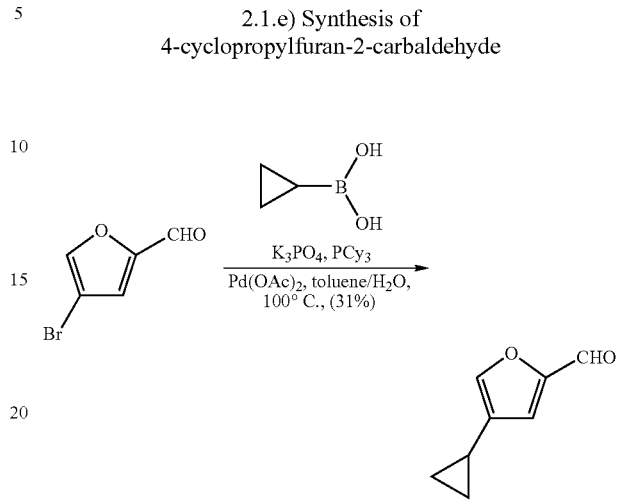

The title compound was synthesized from 4-bromo-furan-2-carbaldehyde (300 mg, 1.71 mmol) and cyclopropylboronic acid (171 mg, 1.99 mmol), using the conditions to synthesize 4-(4-chlorobenzyl)thiophene-2-carbaldehyde, with the exception that the reaction was run in toluene (7.5 mL) and water (0.5 mL), and triphenylphosphine was replaced with tricyclohexylphosphine (48 mg, 0.17 mmol). Purification by flash chromatography (0-60% EtOAc in heptane) provided 4-cyclopropylfuran-2-carbaldehyde as an orange oil 72 mg (31%). ¹H NMR (400 MHz, CDCl₃) δ ppm 0.55-0.61 (m, 2H), 0.90-0.97 (m, 2H), 1.69-1.77 (m, 1H), 7.00 (d, J=0.78 Hz, 1H), 7.49 (d, J=0.59 Hz, 1H), 9.58 (d, J=0.49 Hz, 1H).

2.1.f) Synthesis of 4-isopropylfuran-2-carbaldehyde

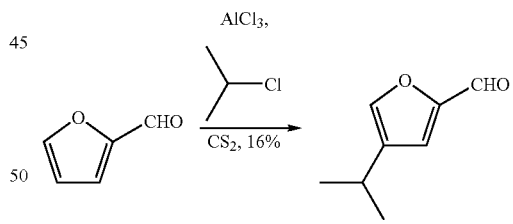

To a suspension containing aluminium chloride (24 g, 180 mmol) in 100 mL of CS₂ was added 2-furaldehyde (9.8 mL, 156 mmol). To this mixture was added dropwise isopropyl chloride (14.3 mL, 156 mmol), and the resulting mixture stirred at rt for 24 h. The dark mixture was carefully poured into a vigorously stirred 250 g of ice, and then extracted with ether (5×100 mL). The combined organic layers were washed with water, brine, dried (Na₂SO₄), filtered through a pad of silica gel, and concentrated. The residue was purified by flash chromatography (0-5% EtOAc in heptane) to give 4-isopropylfuran-2-carbaldehyde as an orange oil: Yield 3.5 g (16%). ¹H NMR (400 MHz, CDCl₃) δ ppm 1.25 (d, J=6.88 Hz, 6H), 2.80-2.91 (m, 1H), 7.16-7.18 (m, 1H), 7.47 (q, J=0.91 Hz, 1H), 9.61 (d, J=0.59 Hz, 1H).

2.1.g) Synthesis of (Z)-4-(prop-1-enyl)furan-2-carbaldehyde

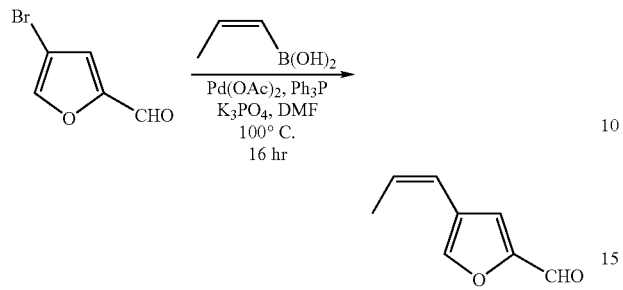

The title compound was synthesized from 4-bromo-furan-2-carboxaldehyde (1.1 g, 6.3 mmol, 1 equiv) and cis-propene boronic acid (0.65 g, 7.5 mmol, 1.2 equiv) using the conditions to synthesize 4-(4-chlorobenzyl)thiophene-2-carbaldehyde, with the exception that the reaction was run in DMF (20 mL). The resulting residue was purified via ISCO Companion (0-25% EtOAc/heptane over 30 min, retention time of product: 23-26 min) to give (Z)-4-(prop-1-enyl)furan-2-carbaldehyde (0.4130 g, 48% yield). LC/MS m/e 136.8 (M+H). $^1$H NMR (400 MHz, CD$_3$CN) δ (ppm): 9.59 (d, J=0.63 Hz, 1H), 7.83 (s, 1H), 7.42 (s, 1H), 6.23 (dd, J=11.40, 1.68 Hz, 1H), 5.79-5.89 (m, 1H), 1.87 (dd, J=7.10, 1.78 Hz, 3H).

2.1.h) Synthesis of 4-(trifluoromethyl)furan-2-carbaldehyde

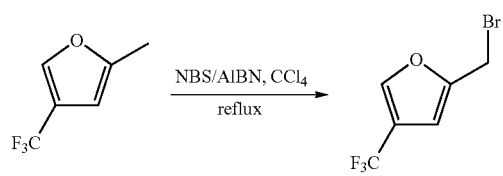

A solution of 2-methyl-4-trifluoromethyl-furan (*J. Heterocyclic Chemistry* 1970, 7, 269-272) (340 mg, 2.26 mmol), N-bromosuccinimide (423 mg, 2.38 mmol) and azobisisobutyronitrile (19 mg, 0.11 mmol) in carbon tetrachloride (10 mL) was refluxed for 1.5 h, then allowed to cool to rt and filtered through a cotton plug. The solvent was evaporated to give 2-(bromomethyl)-4-(trifluoromethyl)furan as an orange oil (508 mg, 98%). The product was pure enough by proton NMR that no further purification was necessary. $^1$H NMR (400 MHz, CDCl$_3$) δ ppm 4.46 (d, J=0.44 Hz, 2H), 6.56 (d, J=0.49 Hz, 1H), 7.77 (m, 1H).

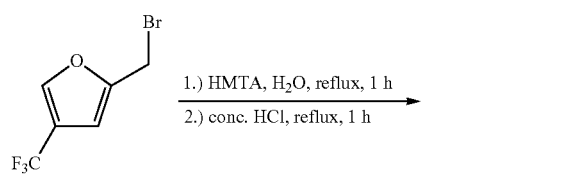
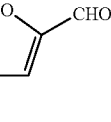

A mixture of 2-bromomethyl-4-trifluoromethyl-furan (500 mg, 3.57 mmol), hexamethylenetetramine (HMTA) (637 mg, 4.54 mmol) and water (2.6 mL) were placed in a 50 mL pear-shaped flask equipped with a vigreaux column atop of which is attached to dry-ice condenser chilled at −78° C. The mixture was heated at reflux for 1 h, and then treated with concentrated HCl (1.7 mL). Reflux was maintained for an additional 1 h before the reaction was cooled to rt, diluted with water and extracted with DCM (4×50 mL). The combined organic extracts were washed with water, brine, dried (Na$_2$SO$_4$) and carefully concentrated to give 4-(trifluoromethyl)furan-2-carbaldehyde. $^1$H NMR (400 MHz, CDCl$_3$) δ ppm 7.37 (m, 1H), 8.01 (m, 1H), 9.74 (d, J=0.54 Hz, 1H).

2.1.i) Synthesis of (E)-4-styrylfuran-2-carbaldehyde

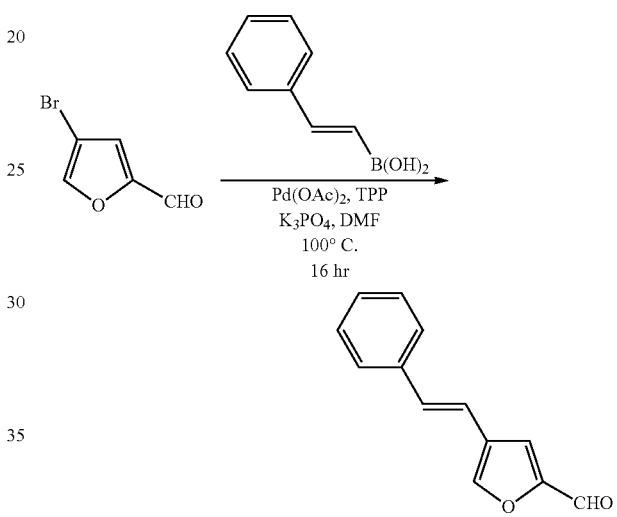

The title compound was synthesized from 4-bromo-furan-2-carboxaldehyde (1.1 g, 6.3 mmol, 1 equiv) and trans-phenylvinyl-boronic acid (1.4 g, 9.4 mmol, 1.5 equiv) using the conditions used to synthesize 4-(4-chlorobenzyl)thiophene-2-carbaldehyde, with the exception that the reaction was run in DMF (25 mL). The resulting residue was purified via ISCO Companion (0-30% EtOAc/heptane) and preparative HPLC using the Chromeleon purification system (0.1% formic acid/1% acetonitrile mixture in water (aqueous phase) and methanol (no modifier added—organic phase) using a 50 mm Dynamax HPLC C-18 column at 28 mL/min (initial gradient of 40% methanol and increasing to 100% over 7 min)) afforded a clean product, retention time of product: 3.4-3.6 min. Amount of (E)-4-styrylfuran-2-carbaldehyde isolated: 89.1 mg (7% yield). $^1$H NMR (400 MHz, CD$_3$CN) δ (ppm): 9.62 (d, J=0.59 Hz, 1H), 7.91 (s, 1H), 7.63 (d, J=0.63 Hz, 1H), 7.50-7.55 (m, 2H), 7.35-7.42 (m, 2H), 7.26-7.32 (m, 1H), 7.08 (s, 2H).

2.1.j) Synthesis of 4-methyl-2-furaldehyde

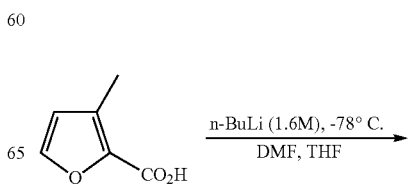

-continued

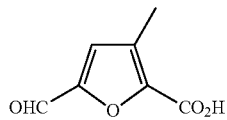

Under N$_2$, a solution of 3-methyl-2-furoic acid (2.0 g, 15.9 mmol) in THF (80 mL) was cooled to −78° C. and n-BuLi (1.6 M in hexane) (20.8 mL, 33.3 mmol, 2.1 equiv) was added dropwise. The mixture was kept for 30 min at −78° C., then a solution of DMF (6.11 mL, 79.4 mmol, 5 equiv) in THF (20 mL) was added. After being stirred for 3 h at −78° C., the reaction mixture was allowed to warm to rt. The reaction was quenched with saturated aqueous ammonium chloride then the reaction mixture was partitioned between water and ether. The ether layer was washed with water, and then dried over sodium sulfate, filtered, and the solvent was evaporated. The residue was purified by chromatography over silica gel (0 to 30% EtOAc in heptane over 30 min) to give 5-formyl-3-methyl-2-furoic acid (0.9 g, 37%). $^1$H NMR (400 MHz, CD$_3$OD) δ ppm 2.39 (s, 3H) 7.29 (s, 1H) 9.67 (s, 1H).

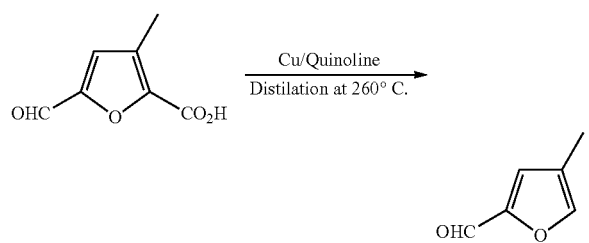

Under N$_2$, 5-formyl-3-methyl-2-furoic acid (0.83 g, 0.54 mmol) was heated in distillation apparatus at 250-260° C. in presence of copper (0.17 g, 0.27 mmol, 0.5 equiv) and quinoline (1.5 mL). After 45 min, the system was cooled down and the distillate gave 4-methyl-2-furaldehyde (0.32 g, 54%). $^1$H NMR (400 MHz, CDCl$_3$) δ ppm 2.04-2.18 (m, 3H) 7.09 (s, 1H) 7.46 (d, J=0.78 Hz, 1H) 9.45-9.71 (m, 1H).

2.1.k) Synthesis of 4-fluorofuran-2-carbaldehyde

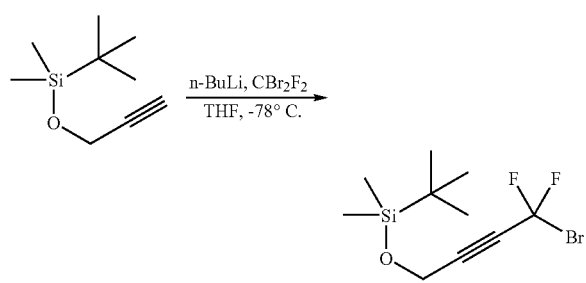

To a solution of tert-butyl-dimethyl-prop-2-ynyloxy-silane (11.6 g, 6.78 mmol) in dry THF (190 mL) was added nBuLi (46.6 mL, 1.6 M solution in hexanes) dropwise (via an addition funnel) over 30 min at 0° C. under N$_2$. The reaction mixture was stirred at rt for 1.5 h before being cooled to −78° C. Then, CF$_2$Br$_2$ (18.8 mL, 20.3 mmol) was added dropwise over 30 min. After stirring for 2.5 h at −78° C., the reaction mixture was quenched with a saturated solution of NH$_4$Cl and was extracted with ether. The combined organic extracts were washed with brine, dried over anhydrous Na$_2$SO$_4$, filtered, and concentrated. Vacuum distillation (0.35-0.7 Torr) provided (4-bromo-4,4-difluoro-but-2-ynyloxy)-tert-butyl-dimethyl-silane (15.4 g, 76% yield) as a yellow liquid (55-70° C.): $^1$H NMR (400 MHz, CDCl$_3$) δ 0.15 (s, 6H), 0.93 (s, 9H), 4.46 (t, J=4.08 Hz, 2H); $^{19}$F NMR (376.19 MHz, CDCl$_3$) δ −33.01 (t, J=4.1 Hz, 2F).

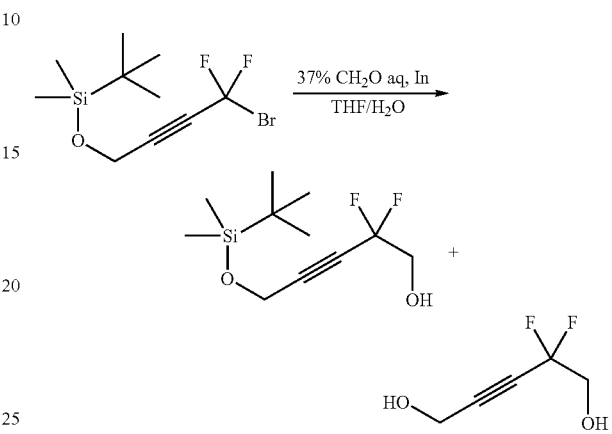

To a stirred solution of (4-bromo-4,4-difluoro-but-2-ynyloxy)-tert-butyl-dimethyl-silane (9.0 g, 30.1 mmol) and HCHO (37 wt % solution in water, 3.36 mL, 45.1 mmol) in THF/H$_2$O (38.6 mL, 4/1, v/v) was added indium powder (4.14 g, 36.1 mmol) at rt. After stirring vigorously for 22 h, the reaction mixture was filtered through Celite®, and the filter cake was washed sequentially with a saturated solution of NH$_4$Cl and EtOAc. After separation of the layers, the aqueous layer was extracted with EtOAc, and the combined organic extracts were washed with brine, dried over anhydrous Na$_2$SO$_4$, filtered, and concentrated. The residue was purified by flash chromatography on silica gel eluting with 0-100% EtOAc in heptane to afford 5-(tert-butyldimethylsilyloxy)-2,2-difluoropent-3-yn-1-ol (3.3 g, 44%, light pale oil) and free propargyl alcohol 4,4-difluoropent-2-yne-1,5-diol (0.85 g 21%, clear pale oil). Silylated alcohol 5-(tert-butyldimethylsilyloxy)-2,2-difluoropent-3-yn-1-ol: $^1$H NMR (400 MHz, CDCl$_3$) δ 0.14 (s, 6H), 0.92 (s. 9H), 3.88 (t, J=12.23, Hz, 2H) 4.41 (t, J=4.47, 2H); $^{19}$F NMR (376.19 MHz, CDCl$_3$) δ −96.15 (tt, J=12.21, 4.29, 1F).

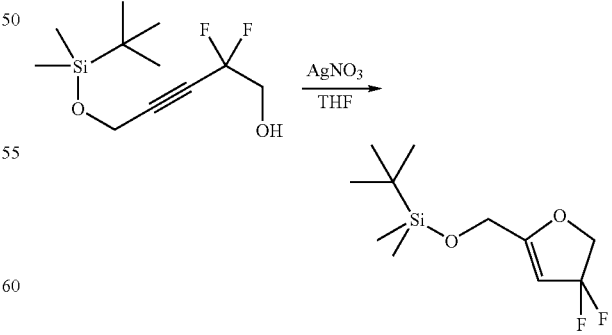

AgNO$_3$ (31 mg, 0.184 mmol) was added to a solution of 5-(tert-butyldimethylsilyloxy)-2,2-difluoropent-3-yn-1-ol (0.46 g, 1.84 mmol) in THF (18 mL) under N$_2$. The resulting mixture was then refluxed for 2.5 h, cooled to rt and diluted with a saturated solution of NH₄Cl. The layers were separated and the aqueous phase extracted with EtOAc (3×30 mL). The combined organic extracts were washed with water, brine, dried (Na₂SO₄), filtered and concentrated to a light oil tert-butyl((4,4-difluoro-4,5-dihydrofuran-2-yl)methoxy)dimethylsilane that was used as is without further purification. ¹H NMR (400 MHz, CDCl₃) δ 0.11 (s, 6H), 0.93 (s, 9H), 4.24 (tt, J=3.69, 0.63 Hz, 2H), 4.44 (td, J=17.29, 0.46, Hz, 2H), 5.29 (t, J=1.32, 1H); ¹⁹F NMR (376.19 MHz, CDCl₃) δ −83.15 (tt, J=17.28, 3.67, 1F).

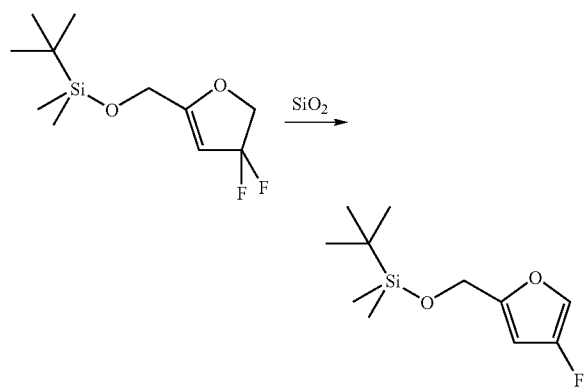

tert-Butyl((4,4-difluoro-4,5-dihydrofuran-2-yl)methoxy)dimethylsilane was diluted with DCM and treated with silica gel (5 g SiO₂/1 g of compound). The flask was swirled around to ensure an even mix, DCM was allowed to air dry and the flask left at rt overnight. The silica gel was transferred to a fritted funnel and eluted with DCM until no more product could be detected by TLC. The filtrate was concentrated to provide an orange oil tert-butyl((4-fluorofuran-2-yl)methoxy)dimethylsilane. ¹H NMR (400 MHz, CDCl₃) δ 0.09 (s, 6H), 0.91 (s, 9H), 4.55 (br s, 2H), 6.20 (m, 1H), 7.31 (dd, J=5.03, 0.63 Hz, 1H); ¹⁹F NMR (376.19 MHz, CDCl₃) δ −170.53 (dd, J=4.95, 1.32, 1F).

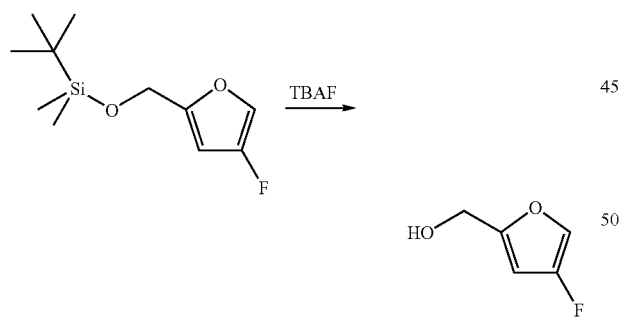

A solution of TBAF in THF (1 M, 2.5 mL, 2.54 mmol) was added to a solution of tert-butyl-(4-fluoro-furan-2-yl-methoxy)-dimethyl-silane (0.39 g, 1.69 mmol) in THF (10 mL). After stirring for 4 h, the reaction was diluted with a saturated solution of NH₄Cl and extracted with EtOAc (3×50 mL). The combined extracts were washed with brine, dried (Na₂SO₄) filtered, and concentrated. Purification by flash chromatography on silica gel 0-50% EtOAc/heptane afforded (4-fluorofuran-2-yl)methanol (190 mg, 97%) as an orange oil: ¹H NMR (400 MHz, CDCl₃) δ 4.54 (s, 2H), 6.27 (m, 1H), 7.34 (dd, J=5.08, 0.83 Hz, 1H); ¹³C NMR (100 MHz, CDCl₃) δ 57.36 (d, J=1.3 Hz), 100.39 (d, J=19.8 Hz), 125.69 (d, J=29.4 Hz), 152.8 (d, J=7.5 Hz), 153.26 (d, J=249.6 Hz); ¹⁹F NMR (376.19 MHz, CDCl₃) δ −170.17 (ddd, J=5.11, 1.49, 1.32 Hz, 1F).

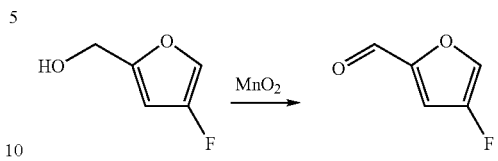

Activated MnO₂ (1.68 g, 16.4 mmol, 85% pure) was added to a solution of (4-fluorofuran-2-yl)methanol (0.19 g, 1.64 mmol) in DCM (15 mL). After stirring the heterogeneous mixture at rt overnight, an additional 500 mg of MnO₂ was added. The reaction was continued for an additional h, then the oxidant was filtered off over Celite® and the cake washed with DCM. The solvent was carefully stripped off at 5° C. to a residual volume of about 5 mL. This orange solution of 4-fluorofuran-2-carbaldehyde in DCM was used without further purification: ¹H NMR (400 MHz, CDCl₃) δ 7.10 (dd, J=1.46, 0.98, 1H); 7.63 (dd, J=5.27, 0.49, 1H), 9.59 (m, 1H); ¹⁹F NMR (376.19 MHz, CDCl₃) δ −166.04 (d, J=5.28 Hz, 1F).

2.2. Synthesis of Esters

The following ethyl esters were synthesized from the indicated aldehyde according to General Procedure 1A (to yield an intermediate acrylate) followed by General Procedure 1B.

2.2.a) Synthesis of ethyl 4H-furo[3,2-b]pyrrole-5-carboxylate

The title compound was synthesized from 2-furaldehyde (1.44 g, 15.0 mmol) and was purified by silica gel column chromatography (0 to 25% EtOAc in heptane over 25 min) to give ethyl 4H-furo[3,2-b]pyrrole-5-carboxylate as a pink solid (0.330 g, 12%). R_f=0.42 (50:50 heptane/EtOAc); ¹H NMR (400 MHz, CDCl₃) δ (ppm) 8.63 (s, 1H) 7.53 (s, 1H) 6.81 (s, 1H) 6.47 (s, 1H) 4.36 (q, J=7.1 Hz, 2H) 1.38 (t, J=7.1 Hz, 3H).

2.2.b) Synthesis of ethyl 3-phenethyl-4H-furo[3,2-b]pyrrole-5-carboxylate

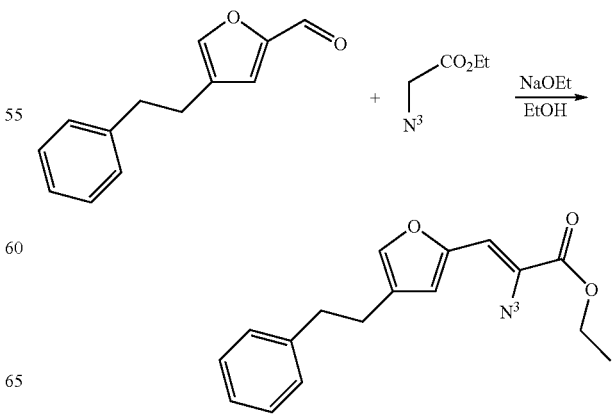

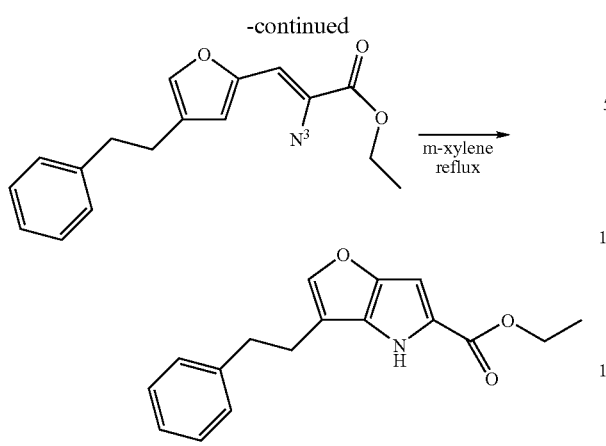

A) Ethyl 2-azido-3-(4-phenethyl-furan-2-yl)-acrylate was synthesized from 4-phenethyl-furan-2-carbaldehyde (1.53 g, 7.64 mmol) to give a colorless oil (0.718 g, 30%) after purification by silica gel column chromatography. $^1$H NMR (400 MHz, CDCl$_3$) δ ppm 7.28-7.34 (m, 2H) 7.17-7.25 (m, 4H) 6.99 (s, 1H) 6.81 (s, 1H) 4.35 (q, J=7.1 Hz, 2H) 2.86-2.94 (m, 2H) 2.73-2.80 (m, 2H) 1.38 (t, J=7.1 Hz, 3H).

B) The title compound was prepared from ethyl 2-azido-3-(4-phenethyl-furan-2-yl)-acrylate and was purified by silica gel column chromatography to give ethyl 3-phenethyl-4H-furo[3,2-b]pyrrole-5-carboxylate as a white solid (613 mg, 94%). $^1$H NMR (400 MHz, CDCl$_3$) δ ppm 7.48 (br s., 1H) 7.28-7.39 (m, 4H) 7.23-7.26 (m, 2H) 6.67 (d, J=1.8 Hz, 1H) 4.30 (q, J=7.1 Hz, 2H) 2.90-2.99 (m, 4H) 1.36 (t, J=7.2 Hz, 3H).

2.2.c) Synthesis of ethyl 2-benzyl-4H-furo[3,2-b]pyrrole-5-carboxylate

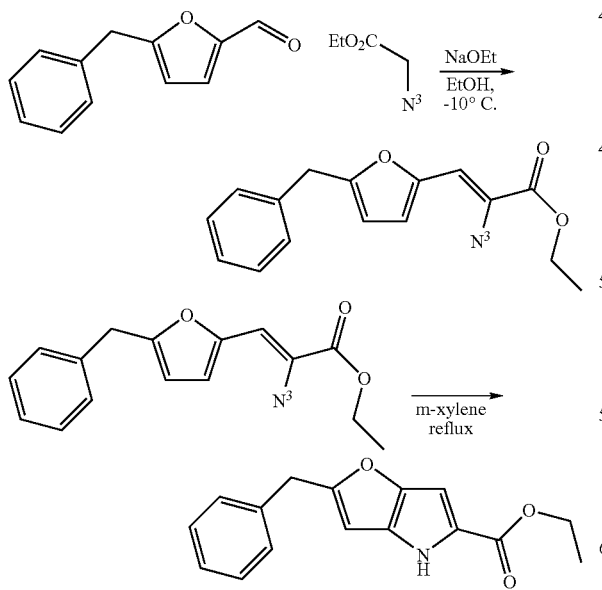

A) Ethyl 2-azido-3-(5-benzyl-furan-2-yl)-acrylate was prepared from 5-benzyl-furan-2-carbaldehyde (295 mg, 1.58 mmol) and was purified by silica gel column chromatography to give a brown oil (35.0 mg, 7%). $^1$H NMR (400 MHz, CDCl$_3$) δ ppm 7.30-7.36 (m, 3H) 7.24 (d, J=0.6 Hz, 2H) 7.09 (dd, J=3.4, 0.4 Hz, 1H) 6.21-6.24 (m, 1H) 6.05-6.08 (m, 1H) 4.35 (q, J=7.1 Hz, 2H) 4.05 (s, 2H) 1.35-1.39 (m, 3H).

B) The title compound was prepared from ethyl 2-azido-3-(5-benzyl-furan-2-yl)-acrylate and was purified by silica gel column chromatography to afford ethyl 2-benzyl-4H-furo[3,2-b]pyrrole-5-carboxylate as a tan solid (17 mg, 53%). $^1$H NMR (400 MHz, CDCl$_3$) δ ppm 8.61 (br. s., 1H) 7.31-7.37 (m, 2H) 7.23-7.31 (m, 3H) 6.74 (dd, J=1.6, 0.9 Hz, 1H) 6.10 (d, J=0.9 Hz, 1H) 4.34 (q, J=7.1 Hz, 2H) 4.07 (s, 2H) 1.37 (t, J=7.1 Hz, 3H).

2.2.d) Synthesis of ethyl 3-benzyl-4H-furo[3,2-b]pyrrole-5-carboxylate

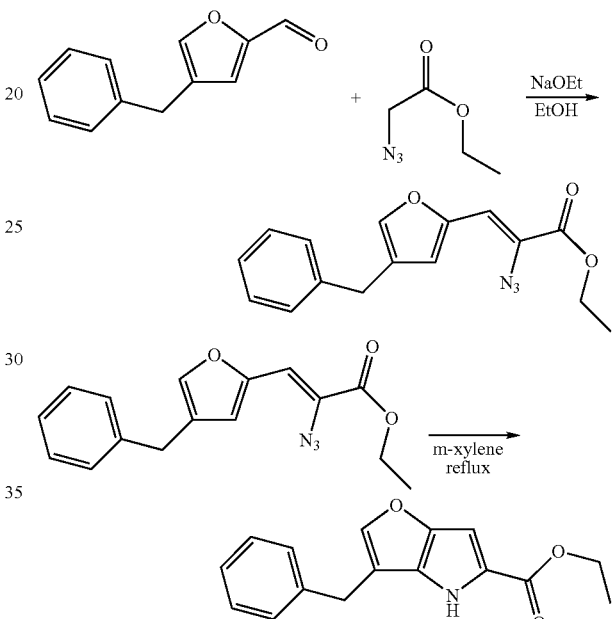

A) Ethyl 2-azido-3-(4-benzyl-furan-2-yl)-acrylate was synthesized from 4-benzyl-furan-2-carbaldehyde (0.300 g, 1.61 mmol) and purified to give a pale yellow oil (135 mg, 28%). $^1$H NMR (400 MHz, CD$_3$CN) δ ppm 7.42 (d, J=0.9 Hz, 1H) 7.30 (d, J=7.1 Hz, 2H) 7.19-7.28 (m, 3H) 7.00 (s, 1H) 6.75 (s, 1H) 4.29 (q, J=7.1 Hz, 2H) 3.79 (s, 2H) 1.32 (t, J=7.1 Hz, 3H).

B) The title compound was prepared from ethyl 2-azido-3-(4-benzyl-furan-2-yl)-acrylate and was purified by silica gel column chromatography to afford ethyl 3-benzyl-4H-furo [3,2-b]pyrrole-5-carboxylate as a brown solid (52 mg, 43%). $^1$H NMR (400 MHz, CD$_3$CN) δ ppm 9.57 (br. s., 1H) 7.40 (s, 1H) 7.28-7.35 (m, 4H) 7.19-7.27 (m, 1H) 6.68 (d, J=1.8 Hz, 1H) 4.26 (q, J=7.1 Hz, 2H) 3.92 (s, 2H) 1.27-1.34 (m, 3H).

2.2.e) Synthesis of ethyl 3-vinyl-4H-furo[3,2-b]pyrrole-5-carboxylate

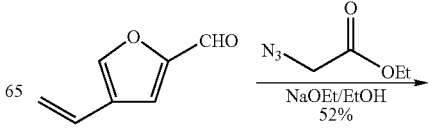

-continued

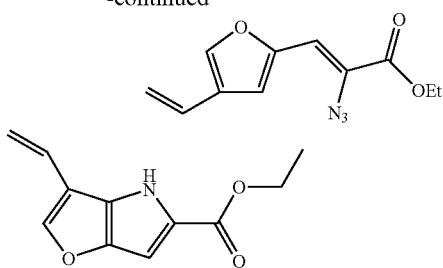

A) Ethyl 2-azido-3-(4-vinylfuran-2-yl)acrylate (398 mg, 52%) was synthesized from 4-vinylfuran-2-carbaldehyde (0.4 g, 3.28 mmol) and was purified by flash chromatography (Isco CombiFlash, 0-5% EtOAc/heptane). $^1$H NMR (400 MHz, CDCl$_3$) δ ppm 1.39 (t, J=7.13 Hz, 3H), 4.36 (q, J=7.13 Hz, 2H), 5.23 (dd, J=10.88, 1.22 Hz, 1H), 5.58 (dd, J=17.52, 1.17 Hz, 1H), 6.55 (dd, J=17.57, 10.88 Hz, 1H), 6.81 (s, 1H), 7.25 (s, 1H), 7.46 (s, 1H); LCMS-MS (ESI+) 205.86 (M-N$_2$).

B) The title compound was synthesized from ethyl 2-azido-3-(4-vinylfuran-2-yl)acrylate and was purified by flash column chromatography (Isco CombiFlash, 0-30% EtOAc/heptane) to afford ethyl 3-vinyl-4H-furo[3,2-b]pyrrole-5-carboxylate as a white solid (215 mg, 62%). $^1$H NMR (400 MHz, CDCl$_3$) δ ppm 1.40 (t, J=7.13 Hz, 3H), 4.38 (q, J=7.13 Hz, 2H), 5.35 (d, J=10.93, Hz, 1H), 5.52 (d, J=17.57 Hz, 1H), 6.63 (dd, J=17.57, 10.88 Hz, 1H), 6.80 (d, J=1.66 Hz, 1H), 7.53 (s, 1H); LCMS-MS (ESI+) 205.85 (M+H).

2.2.f) Synthesis of ethyl 3-cyclopropyl-4H-furo[3,2-b]pyrrole-5-carboxylate

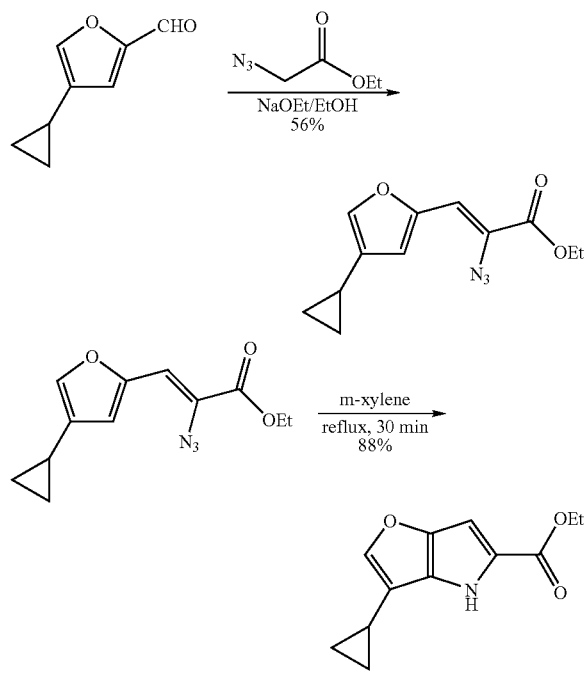

A) Ethyl 2-azido-3-(4-cyclopropylfuran-2-yl)acrylate (148 mg, 56%) was synthesized from 4-cyclopropylfuran-2-carbaldehyde (145 mg, 1.06 mmol) and was purified by flash chromatography (Isco CombiFlash, 0-20% EtOAc/heptane). $^1$H NMR (400 MHz, CDCl$_3$) δ ppm 0.56-0.61 (m, 2H), 0.85-0.91 (m, 2H), 1.38 (t, J=7.15 Hz, 3H), 1.66-1.75 (m, 1H), 4.34 (q, J=7.16 Hz, 2H), 6.79 (s, 1H), 6.87 (s, 1H), 7.30 (s, 1H); LCMS-MS (ESI+) 219.84 (M-N$_2$).

B) The title compound was synthesized from ethyl 2-azido-3-(4-cyclopropylfuran-2-yl)acrylate and was purified by flash chromatography (Isco CombiFlash) eluting with 0-15% EtOAc/heptane to afford ethyl 3-cyclopropyl-4H-furo[3,2-b]pyrrole-5-carboxylate as a white solid (114 mg, 88%). $^1$H NMR (400 MHz, CDCl$_3$) δ ppm 0.66-0.71 (m, 2H), 0.88-0.94 (m, 2H), 1.38 (t, J=7.13 Hz, 3H), 1.72-1.80 (m, 1H), 4.36 (q, J=7.13 Hz, 2H), 6.75 (d, J=1.66 Hz, 1H), 7.31 (d, J=0.88 Hz, 1H); LCMS-MS (ESI+) 219.82 (M+H).

2.2.g) Synthesis of ethyl 3-bromo-4H-furo[3,2-b]pyrrole-5-carboxylate

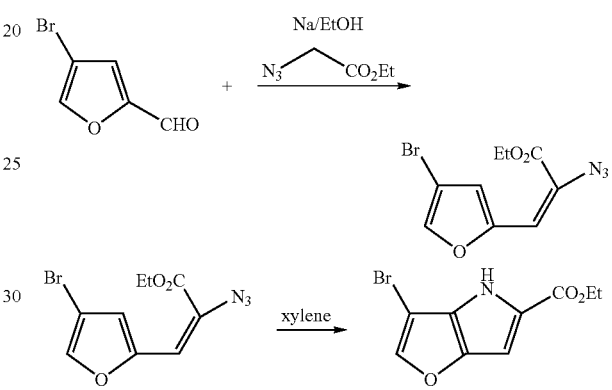

A) Ethyl 2-azido-3-(4-bromofuran-2-yl)acrylate was synthesized from 4-bromo-2-furaldehyde (2.0 g, 11.4 mmol) and was purified by flash column chromatography (100% heptane) to give an orange oil. $^1$H NMR (400 MHz, CDCl$_3$) δ (ppm): 7.47 (d, 1H), 7.17 (s, 1H), 6.77 (s, 1H), 4.36 (q, 2H), 1.39 (t, 3H).

B) The title compound was synthesized from ethyl 2-azido-3-(4-bromofuran-2-yl)acrylate and was purified by flash column chromatography (0-20% EtOAc in heptane) to give ethyl 3-bromo-4H-furo[3,2-b]pyrrole-5-carboxylate (400 mg) as a light brown solid. LCMS m/e 259 (M+H). $^1$H NMR (400 MHz, CDCl$_3$) δ (ppm): 8.71 (s, 1H), 7.51 (s, 1H), 6.82 (d, 1H), 4.37 (q, 2H), 1.39 (t, 3H).

2.2.h) Synthesis of ethyl 3-isopropyl-4H-furo[3,2-b]pyrrole-5-carboxylate

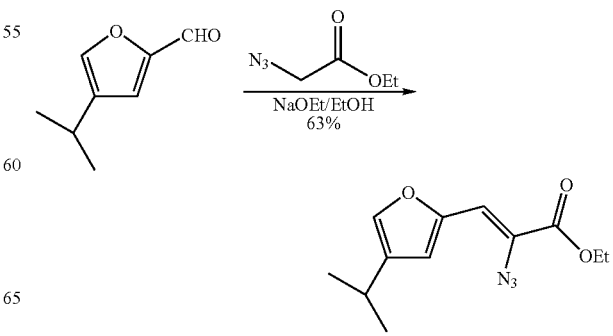

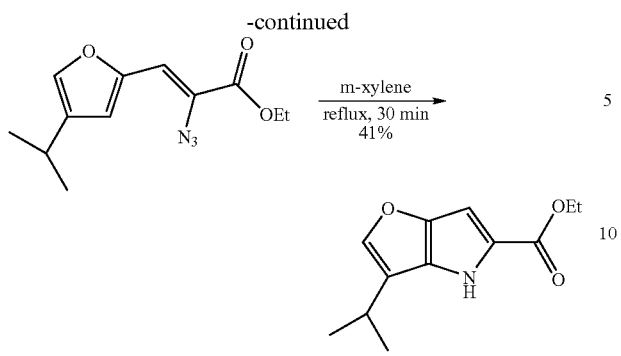

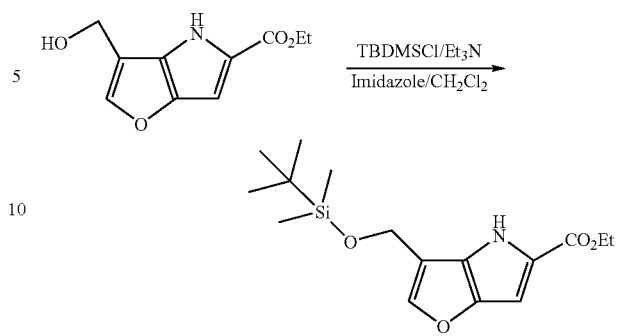

A) Ethyl 2-azido-3-(4-isopropylfuran-2-yl)-acrylate (1.36 g, 63%) was synthesized from 4-isopropylfuran-2-carbaldehyde (1.2 g, 8.69 mmol) and was purified by flash chromatography (Isco CombiFlash, 0-1% EtOAc/heptane). $^1$H NMR (400 MHz, CDCl$_3$) δ ppm 1.22-1.25 (m, 6H), 1.35-1.41 (m, 3H), 2.82 (m, 1H), 4.30-4.38 (m, 2H), 6.82 (d, J=0.44 Hz, 1H), 7.04 (d, J=0.34 Hz, 1H), 7.26 (t, J=0.90 Hz, 1H); LCMS-MS (ESI+) 221.83 (M-N$_2$).

B) The title compound was synthesized from ethyl 2-azido-3-(4-isopropylfuran-2-yl)-acrylate (1.3 g, 5.22 mmol) and was purified by flash chromatography (Isco CombiFlash, 0-5% EtOAc/heptane) and reverse phase semi-preparative HPLC (MeOH:H$_2$O) to give a pure fraction of ethyl 3-isopropyl-4H-furo[3,2-b]pyrrole-5-carboxylate (436 mg, 47% based on the purity of the starting material). $^1$H NMR (400 MHz, CDCl$_3$) δ ppm 1.32 (d, J=6.88 Hz, 6H), 1.39 (t, J=7.15 Hz, 3H), 2.92-3.01 (m, 1H), 4.36 (q, J=7.09 Hz, 2H), 6.76 (d, J=1.66 Hz, 1H), 7.28 (d, J=1.12 Hz, 1H), 8.79 (s, 1H); LCMS-MS (ESI+) 221.83 (M+H).

2.2.i) Synthesis of ethyl 3-(tert-butyl-dimethyl-silanyloxymethyl)-4H-furo[3,2-b]pyrrole-5-carboxylate

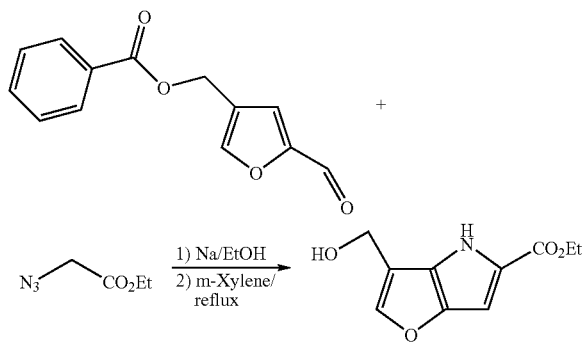

A) Ethyl 2-azido-3-(4-hydroxylmethyl-furan-2-yl)-acrylate was synthesized from 4-benzoyloxymethyl-2-furaldehyde (*J. Am. Chem. Soc.* 2003, 125, 9740-9749) (10.0 g, 43.4 mmol) and was purified by silica gel column chromatography (0 to 30% EtOAc in heptane over 30 min) to give 5.0 g of a reddish solid.

B) Ethyl 2-azido-3-(4-hydroxylmethyl-furan-2-yl)-acrylate was converted to ethyl 3-hydroxymethyl-4H-furo[3,2-b]pyrrole-5-carboxylate according to General Procedure 1B and was purified by silica gel column chromatography (0 to 40% EtOAc in heptane over 30 min) to give a light reddish solid (0.50 g, 30% in 2 steps). $^1$H NMR (400 MHz, CDCl$_3$) δ ppm 1.38 (t, J=7.13 Hz, 3H) 2.11 (t, J=6.15 Hz, 1H) 4.35 (q, J=7.22 Hz, 2H) 4.69 (d, J=5.86 Hz, 2H) 6.38 (s, 1H) 6.77 (dd, J=1.66, 0.88 Hz, 1H) 8.80 (br. s., 1H).

To a solution of ethyl 3-hydroxymethyl-4H-furo[3,2-b]pyrrole-5-carboxylate (1.75 g, 8.37 mmol) in CH$_2$Cl$_2$ (50 mL) was added imidazole (0.85 g, 12.55 mmol) and Et$_3$N (1.16 mL, 8.37 mmol) and then cooled to 0° C. t-butyldimethylsilyl chloride (1.64 g, 10.88 mmol) was added slowly and the mixture was stirred at rt for 3 h and then poured into 50 mL H$_2$O. The product was extracted with CH$_2$Cl$_2$ (3×50 mL) and the combined organic layers were washed with saturated aq NaCl, dried over Na$_2$SO$_4$, filtered and concentrated in vacuo to give ethyl 3-(tert-butyl-dimethyl-silanyloxymethyl)-4H-furo[3,2-b]pyrrole-5-carboxylate as a solid. The solid was clean enough to be used in next step. $^1$H NMR (400 MHz, CDCl$_3$) δ ppm 0.12 (s, 6H) 0.93 (s, 9H) 1.38 (t, J=7.13 Hz, 3H) 4.35 (q, J=7.13 Hz, 2H) 4.72 (d, J=0.59 Hz, 2H) 6.33 (d, J=0.49 Hz, 1H) 6.77 (dd, J=1.59, 0.85 Hz, 1H) 8.63 (br. s., 1H).

2.2j) Synthesis of (Z)-ethyl 3-(prop-1-enyl)-4H-furo[3,2-b]pyrrole-5-carboxylate

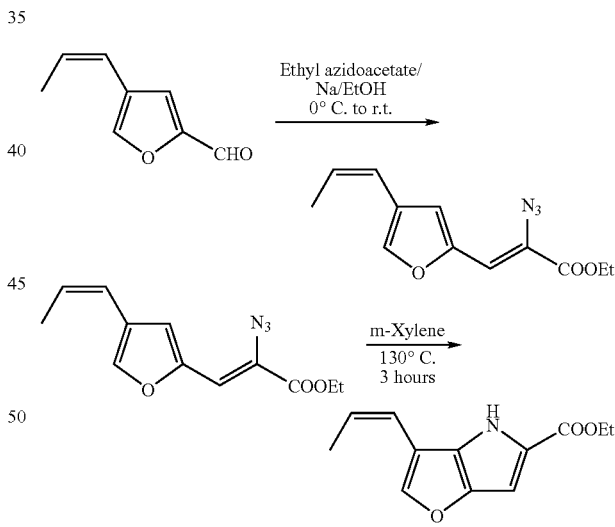

A) Ethyl 2-azido-3-(4-((Z)-prop-1-enyl)furan-2-yl)acrylate (663 mg, 87%) was synthesized from (Z)-4-(prop-1-enyl)furan-2-carbaldehyde (0.4130 g, 3.7 mmol, 1 eq.) and was purified via ISCO Companion (0-20% EtOAc/heptane over 19 min, t$_R$: 3-6 min). $^1$H NMR (400 MHz, CD$_3$CN) δ (ppm): 7.63 (s, 1H), 7.21 (s, 1H), 6.78 (s, 1H), 6.20 (dd, J=11.37, 1.61 Hz, 1H), 5.71-5.82 (m, 1H), 4.31 (q, J=7.13 Hz, 2H), 1.86 (dd, J=7.13, 1.76 Hz, 3H), 1.33 (t, J=7.13 Hz, 3H).

B) The title compound was synthesized from ethyl 2-azido-3-(4-((Z)-prop-1-enyl)furan-2-yl)acrylate (0.6633 g) and purified via ISCO Companion (0-30% EtOAc/heptane over 30 min, retention time: 26-29 min) to give (Z)-ethyl 3-(prop-1-enyl)-4H-furo[3,2-b]pyrrole-5-carboxylate (145 mg, 25%). LC/MS m/e 219.8 (M+H). $^1$H NMR (400 MHz, CD$_3$CN) δ (ppm): 9.70 (s, 1H), 7.65 (s, 1H), 6.72 (d, J=1.71 Hz, 1H), 6.30-6.37 (m, 1H), 5.82-5.94 (m, 1H), 4.24-4.34 (m, 2H), 1.88 (dd, J=7.05, 1.78 Hz, 3H), 1.30-1.36 (m, 3H).

2.2.k) Synthesis of ethyl 3-(trifluoromethyl)-4H-furo[3,2-b]pyrrole-5-carboxylate

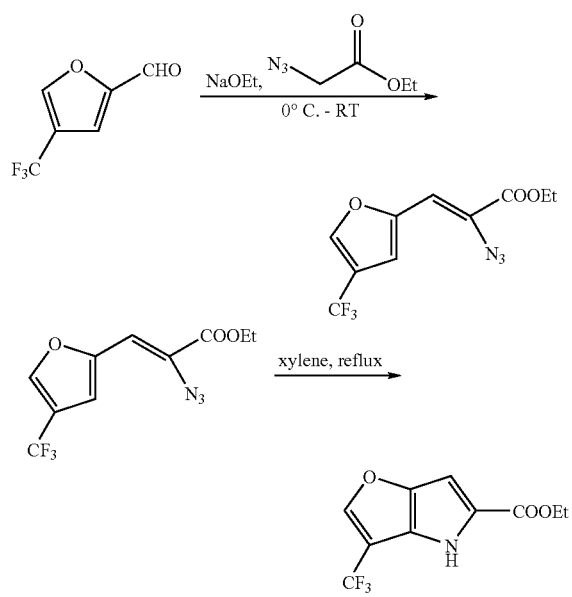

A) Ethyl 2-azido-3-(4-(trifluoromethyl)furan-2-yl)acrylate (43 mg, 10%) was synthesized from 4-trifluoromethyl-furan-2-carbaldehyde (373 mg, 2.27 mmol) and was purified by flash chromatography (Isco CombiFlash, 0-40% EtOAc/heptane). $^1$H NMR (400 MHz, CDCl$_3$) δ ppm 1.40 (t, J=7.15 Hz, 3H), 4.38 (q, J=7.13 Hz, 2H), 6.80 (d, J=0.34 Hz, 1H), 7.25 (s, 1H), 7.78 (dd, J=1.44, 0.85 Hz, 1H); LCMS-MS (ESI+) 247.82 (M-N$_2$).

B) The title compound was prepared from ethyl 2-azido-3-(4-(trifluoromethyl)furan-2-yl)acrylate (45 mg, 0.16 mmol) and was purified by flash chromatography (Isco CombiFlash, 0-30% EtOAc/heptane) to afford ethyl 3-(trifluoromethyl)-4H-furo[3,2-b]pyrrole-5-carboxylate as a white solid (30 mg, 76%). $^1$H NMR (400 MHz, CDCl$_3$) δ ppm 1.40 (t, J=7.13 Hz, 3H), 4.39 (q, J=7.13 Hz, 2H), 6.85 (d, J=1.71 Hz, 1H), 7.84 (q, J=1.56, 1H), 9.08 (s, 1H); LCMS-MS (ESI+) 247.8 (M+H).

2.2.l) Synthesis of (E)-ethyl 3-styryl-4H-furo[3,2-b]pyrrole-5-carboxylate

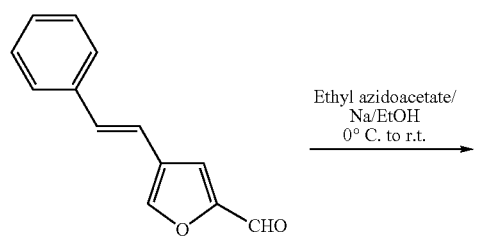

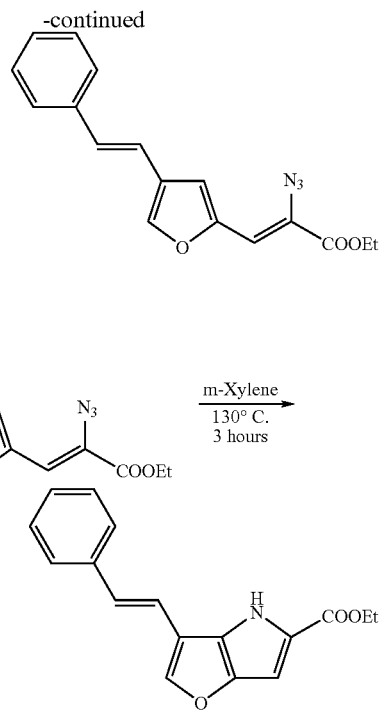

A) (E)-Ethyl 2-azido-3-(4-styrylfuran-2-yl)acrylate (36.1 mg, 26%) was synthesized from (E)-4-styrylfuran-2-carbaldehyde (0.0891 g, 0.5 mmol) and was purified via ISCO Companion (0-50%, EtOAc/heptane, over 35 min, retention time: 3-8 min). $^1$H NMR (400 MHz, CD$_3$CN) δ (ppm): 7.71 (s, 1H), 7.47-7.54 (m, 3H), 7.34-7.40 (m, 2H), 7.24-7.30 (m, 1H), 6.99-7.10 (m, 2H), 6.79 (s, 1H), 4.32 (q, J=7.13 Hz, 2H), 1.34 (t, J=7.10 Hz, 3H).

B) The title compound was prepared from (E)-ethyl 2-azido-3-(4-styrylfuran-2-yl)acrylate (36.1 mg) and was purified via preparative HPLC using the Chromeleon purification system (60-100% methanol/0.1% formic acid-1% acetonitrile in water, 50 mm Dynamax C-18 column at 28 mL/min over 7 min, t 3.5-3.8 min) to give (E)-ethyl 3-styryl-4H-furo[3,2-b]pyrrole-5-carboxylate (18.1 mg, 55% yield). $^1$H NMR (400 MHz, CD$_3$CN) δ (ppm): 10.07 (s, 1H), 7.75 (s, 1H), 7.57-7.62 (m, 2H), 7.40 (t, J=7.61 Hz, 2H), 7.26-7.32 (m, 1H), 7.09-7.22 (m, 2H), 6.78 (d, J=1.71 Hz, 1H), 4.33 (q, J=7.13 Hz, 2H), 1.36 (t, J=7.13 Hz, 3H).

2.2.m) Synthesis of ethyl 3-methyl-4H-furo[3,2-b]pyrrole-5-carboxylate

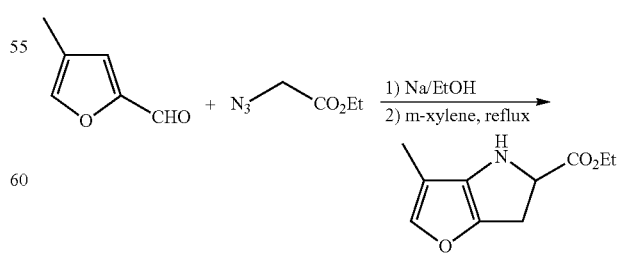

A) Ethyl 2-azido-3-(4-methyl-2-furyl)acrylate (0.25 g, 42%) was synthesized from 4-methyl-2-furaldehyde (0.3 g, 2.7 mmol) and was purified by silica gel column chromatography (0 to 30% EtOAc/heptane over 30 min). $^1$H NMR (400 MHz, CD$_3$OD) δ ppm 1.33 (t, J=7.13 Hz, 3H) 2.02 (d, J=0.78 Hz, 3H) 4.28 (q, J=7.13 Hz, 2H) 6.69 (s, 1H) 6.93 (s, 1H) 7.31 (s, 1H).

B) The title compound was synthesized from ethyl 2-azido-3-(4-methyl-2-furyl)acrylate and was purified by silica gel column chromatography (0 to 40% EtOAc in heptane over 30 min) to give ethyl 3-methyl-4H-furo[3,2-b]pyrrole-5-carboxylate (0.17 g, 78%). $^1$H NMR (400 MHz, CD$_3$OD) δ ppm 1.36 (t, J=7.13 Hz, 3H) 2.15 (d, J=1.32 Hz, 3H) 4.31 (q, J=7.13 Hz, 2H) 6.65 (s, 1H) 7.24-7.44 (m, 1H). LCMS m/e 194 (M+H).

2.2.n) Synthesis of ethyl 2-(trifluoromethyl)-4H-furo[3,2-b]pyrrole-5-carboxylate

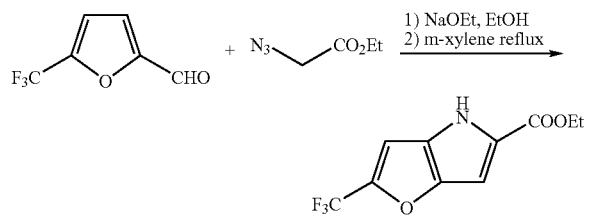

A) Ethyl 2-azido-3-(5-(trifluoromethyl)furan-2-yl)acrylate was synthesized from 5-(trifluoromethyl)furan-2-carbaldehyde (1.00 g, 6.09 mmol) and was purified by silica gel column chromatography (0 to 25% EtOAc in heptane over 20 min) to give a yellow oil (0.512 g, 30%). R$_f$=0.63 (50:50 heptane/EtOAc); $^{19}$F NMR (376 MHz, CDCl$_3$) δ (ppm) −64.63 (s, 3F); $^1$H NMR (400 MHz, CDCl$_3$) δ (ppm) 7.14 (m, 1H) 6.88 (m, 1H) 4.37 (q, J=7.1 Hz, 2H) 1.40 (t, J=7.1 Hz, 3H).

B) The title compound was synthesized from ethyl 2-azido-3-(5-(trifluoromethyl)furan-2-yl)acrylate (0.512 g) and was purified by silica gel column chromatography (0 to 30% EtOAc in heptane over 20 min) to give ethyl 2-(trifluoromethyl)-4H-furo[3,2-b]pyrrole-5-carboxylate as yellow solid (0.250 g, 55). R$_f$=0.50 (50:50 heptane/EtOAc); $^{19}$F NMR (376 MHz, CDCl$_3$) δ (ppm) −64.68 (s, 3F); $^1$H NMR (400 MHz, CDCl$_3$) δ (ppm) 6.88 (m, 1H) 6.84 (m, 1H) 4.38 (q, J=7.1 Hz, 2H) 1.40 (t, J=7.1 Hz, 3H).

2.2.o) Synthesis of ethyl 3-fluoro-4H-furo[3,2-b]pyrrole-5-carboxylate

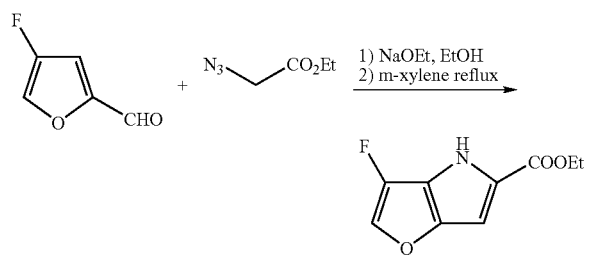

A) Ethyl 2-azido-3-(4-fluoro-furan-2-yl)-acrylate was synthesized from 4-fluorofuran-2-carbaldehyde (160 mg, 1.4 mmol) and was purified by silica gel column chromatography (0 to 30% EtOAc in heptane) to give 180 mg (91%) of ethyl 2-azido-3-(4-fluoro-furan-2-yl)-acrylate. $^1$H NMR (400 MHz, CDCl$_3$) δ ppm 1.39 (t, J=7.13 Hz, 3H), 4.36 (q, J=7.13 Hz, 2H), 6.72 (d, J=1.46 Hz, 1H) 7.03 (s, 1H), 7.41 (dd, J=5.08, 0.78 Hz, 1H); $^{19}$F NMR (376.19 MHz, CDCl$_3$) δ −167.30 (dt, J=5.03, 1.61 Hz, 1F). LCMS-MS (ESI+) 198.1 (M-N$_2$).

B) The title compound was synthesized from ethyl 2-azido-3-(4-fluoro-furan-2-yl)-acrylate (190 mg, 0.84 mmol), and was purified by silica gel column chromatography (0 to 30% EtOAc in heptane) to give ethyl 3-fluoro-4H-furo[3,2-b]pyrrole-5-carboxylate as white solid (108 mg, 65%. $^1$H NMR (400 MHz, CDCl$_3$) δ ppm 1.40 (t, J=7.15 Hz, 3H), 4.39 (q, J=7.13 Hz, 2H), 6.74 (t, J=1.95, 1H), 7.52 (d, J=4.44 Hz, 1H), 9.30 (s, 1H); $^{19}$F NMR (376.19 MHz, CDCl$_3$) δ −179.37-179.42 (m, 1F); LCMS-MS (ESI+) 198.0 (M+H).

2.2.p) Synthesis of ethyl 2-fluoro-4H-furo[3,2-b]pyrrole-5-carboxylate

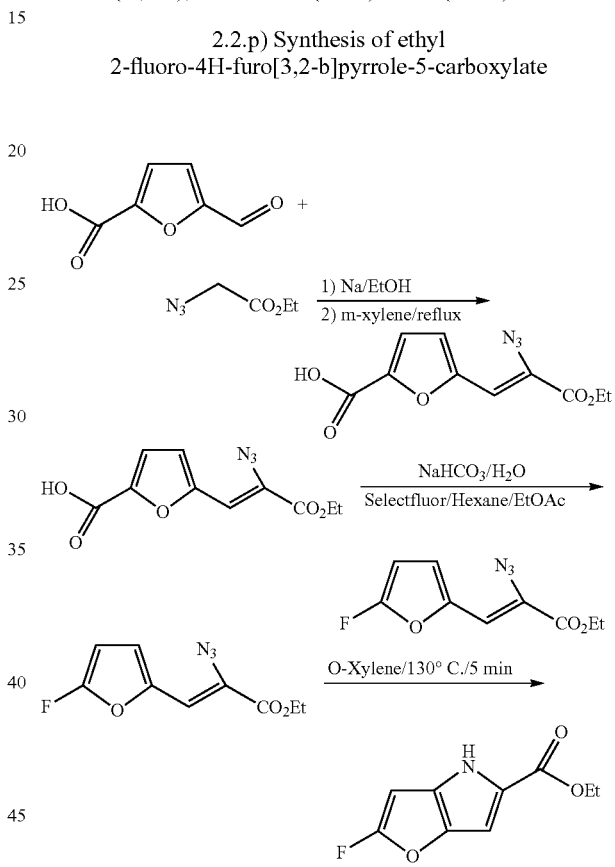

A) 5-(2-azido-3-ethoxy-3-oxoprop-1-enyl)furan-2-carboxylic acid was prepared from 5-formyl-2-furancarboxylic acid (2.0 g, 14.28 mmol) and was purified by silica gel column chromatography (0 to 30% EtOAc in heptane over 20 min) to give a yellow solid (2.40 g, 67%). $^1$H NMR (400 MHz, CD$_3$OD) δ ppm 1.38 (t, J=7.13 Hz, 3H) 4.36 (q, J=7.11 Hz, 2H) 6.82 (s, 1H) 7.22 (d, J=3.71 Hz, 1H) 7.27 (d, J=3.71 Hz, 1H).

To 5-(2-azido-3-ethoxy-3-oxoprop-1-enyl)furan-2-carboxylic acid (0.50 g, 2.03 mmol) was added a mixture of NaHCO$_3$ (0.34 g, 4.06 mmol) and Selectfluor® (1.08 g, 3.05 mmol), followed by water (4.0 mL), hexane (5.0 mL) and EtOAc (2.0 mL). The mixture was stirred at rt for 5 min. The organic layer was separated, dried (Na$_2$SO$_4$), filtered, and concentrated in vacuo. Purification by silica gel chromatography (0 to 30% EtOAc in heptane over 20 min) yielded pure ethyl 2-azido-3-(5-fluorofuran-2-yl)prop-2-enoate as a reddish oil (0.20 g, 45%). $^1$H NMR (400 MHz, CD$_3$OD) δ ppm 1.35 (t, J=7.15 Hz, 3H) 4.32 (q, J=7.16 Hz, 2H) 5.74 (dd, J=6.83, 3.66 Hz, 1H) 6.63 (s, 1H) 7.05 (t, J=3.59 Hz, 1H). $^{19}$F NMR (376 MHz, CD$_3$OD) δ ppm −115.12 (dd, J=6.60, 3.30 Hz).

B) The title compound was prepared from ethyl 2-azido-3-(5-fluorofuran-2-yl)prop-2-enoate (0.20 g, 0.88 mmol) and was purified by silica gel column chromatography (0 to 40% EtOAc in heptane over 20 min) to give pure ethyl 2-fluoro-4H-furo[3,2-b]pyrrole-5-carboxylate as white solid (0.13 g, 74%). $^1$H NMR (400 MHz, CD$_3$OD) δ ppm 1.35 (t, J=7.13 Hz, 3H) 4.30 (q, J=7.11 Hz, 2H) 5.86 (d, J=6.30 Hz, 1H) 6.72 (s, 1H). $^{19}$F NMR (376 MHz, CD$_3$OD) δ ppm −108.54 (d, J=6.60 Hz). LCMS m/e 198 (M+H).

2.3. Synthesis of ethyl 2-chloro-4H-furo[3,2-b]pyrrole-5-carboxylate

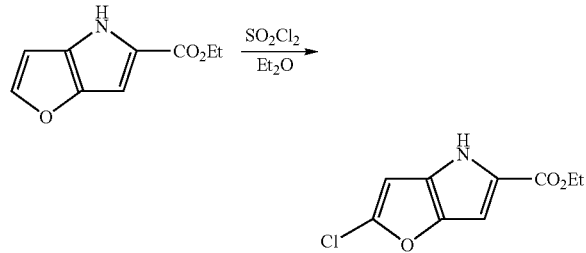

Under a N$_2$ atmosphere, sulfuryl chloride (0.15 mL, 1.85 mmol) was added dropwise over 10 min to a stirring solution of ethyl 4H-furo[3,2-b]pyrrole-5-carboxylate (300 mg, 1.67 mmol) in ether (7.5 mL). The reaction was stirred at rt for 4 h. The solvent was removed in vacuo. The residue was taken up in DCM and washed with H$_2$O (1×) and brine (1×), then dried with Na$_2$SO$_4$, filtered and concentrated. Purification by HPLC gave 160 mg of ethyl 2-chloro-4H-furo[3,2-b]pyrrole-5-carboxylate. $^1$H NMR (400 MHz, CDCl$_3$) δ (ppm): 8.98 (s, 1H), 6.76 (s, 1H), 6.34 (s, 1H), 4.35 (q, 2H), 1.38 (t, 3H).

2.4. Synthesis of ethyl 3-formyl-4H-furo[3,2-b]pyrrole-5-carboxylate

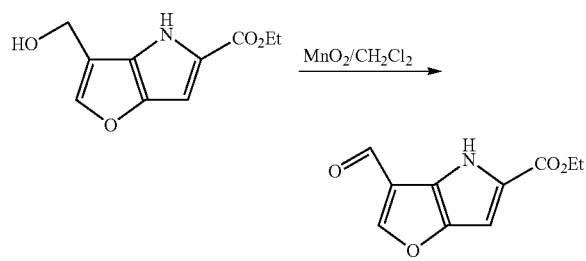

To a solution of ethyl 3-hydroxymethyl-4H-furo[3,2-b]pyrrole-5-carboxylate (1.1 g, 5.26 mmol) in CH$_2$Cl$_2$ (100 mL) was added MnO$_2$ (4.6 g, 52.6 mmol). The reaction mixture was stirred at rt overnight and was then filtered through Celite® and washed with CH$_2$Cl$_2$ (3×50 mL). The organic solution was concentrated in vacuo and chromatographed over silica gel (0 to 40% EtOAc in heptane over 30 min) to give ethyl 3-formyl-4H-furo[3,2-b]pyrrole-5-carboxylate (1.0 g, 92%) as light yellow solid. $^1$H NMR (400 MHz, CDCl$_3$) δ ppm 1.41 (t, J=7.13 Hz, 3-H) 4.40 (q, J=7.13 Hz, 2H) 6.83 (dd, J=1.54, 1.00 Hz, 1H) 7.23 (d, J=0.88 Hz, 1H) 8.98 (br. s., 1H) 9.67 (s, 1H).

2.5. Synthesis of methyl 2-methyl-4H-furo[3,2-b]pyrrole-5-carboxylate

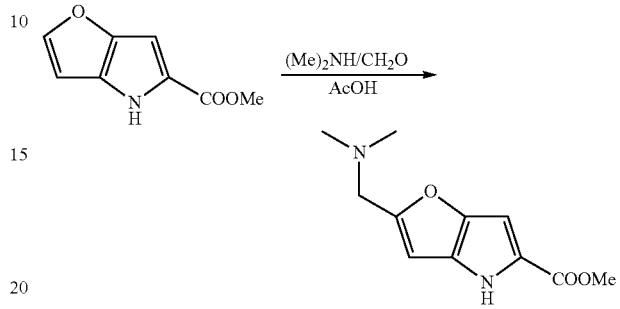

Under N$_2$, to 9 mL of glacial acetic acid were added N,N-dimethylamine (40% aqueous solution) (437 mg, 9.94 mmol), formaldehyde (37% aqueous solution) (283 mg, 9.90 mmol), and methyl 4H-thieno[3,2-b]pyrrole-5-carboxylate (1.64 g, 9.94 mmol). The temperature was kept between 0 and 5° C. while the components were added. The reaction mixture was heated at reflux for 1 h, and was then allowed to stand at rt for 12 h. The mixture was poured onto 30 g of ice, and it was brought to pH 10 by careful addition of 10% sodium hydroxide. The temperature was not allowed to exceed 10° C. while the base was added. The gummy substance solidified when stored in the refrigerator overnight. The solid was collected and dried in vacuo. It was recrystallized from petroleum ether (30-60° C.) to yield methyl 2-[(dimethylamino)methyl]-4H-furo[3,2-b]pyrrole-5-carboxylate (0.80 g, 36%). $^1$H NMR (400 MHz, CDCl$_3$) δ ppm 2.36 (s, 6H) 3.71 (s, 2H) 3.81 (s, 3H) 6.33 (s, 1H) 6.69 (s, 1H).

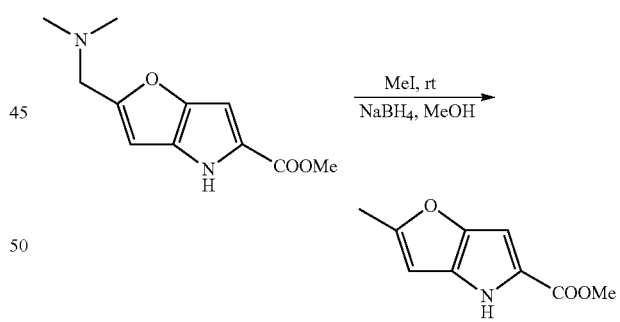

Under N$_2$, to methyl 2-[(dimethylamino)methyl]-4H-furo[3,2-b]pyrrole-5-carboxylate (0.58 g, 2.61 mmol) was added methyl iodide (3 mL, 4.82 mmol). The mixture was allowed to stand at rt for 1 h, and then the methyl iodide was removed. The resulting salt was dissolved in absolute methanol (5 mL). To this solution was carefully added sodium borohydride (2.21 g, 5.84 mmol) in small portions. After the addition was complete, the reaction mixture was dilute to a volume of 25 mL by the addition of 3N hydrochloric acid. The mixture was stored in the refrigerator overnight, and then the blue precipitate was dissolved in boiling methylcyclohexane, and the solution was treated with Darco and filtered. The filtrate was evaporated and purified by chromatography over silica gel (0 to 40% EtOAc/heptane over 30 min) to give methyl 2-methyl-4H-furo[3,2-b]pyrrole-5-carboxylate (0.25 g, 53%). $^1$H NMR (400 MHz, CDCl$_3$) δ ppm 2.42 (s, 3H) 3.87 (s, 3H) 6.09 (d, J=0.49 Hz, 1H) 6.74 (s, 1H) 8.56 (s, 1H).

2.6. Synthesis of ethyl 3-ethyl-4H-furo[3,2-b]pyrrole-5-carboxylate

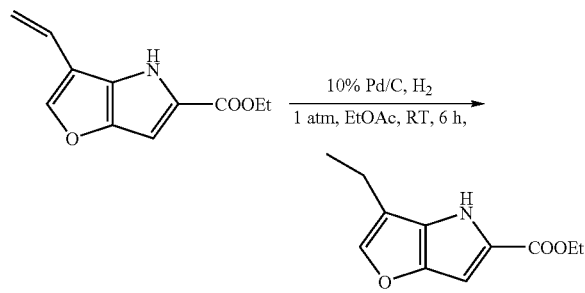

A solution of ethyl 3-vinyl-4H-furo[3,2-b]pyrrole-5-carboxylate (105 mg, 0.51 mmol) in EtOAc (8 mL) in a 40-mL scintillation vial was treated with 10% Pd/C (~15 mg) and a balloon of H$_2$. The system was evacuated and refilled three times with H$_2$ before hydrogenating at rt for 6 h. The catalyst was removed by filtration over Celite® and the filtrate was concentrated. The crude product was purified by flash chromatography (0-10% EtOAc/heptane) to give ethyl 3-ethyl-4H-furo[3,2-b]pyrrole-5-carboxylate (96 mg, 91%). $^1$H NMR (400 MHz, CDCl$_3$) δ ppm 1.30 (t, J=7.54 Hz, 3H), 1.36-1.42 (m, 3H), 2.57-2.64 (m, 2H), 4.33-4.40 (m, 2H), 6.76 (d, J=1.66 Hz, 1H), 7.31 (t, J=1.12 Hz, 1H); LCMS-MS (ESI+) 207.83 (M+H).

2.7. Synthesis of methyl 6-bromo-4H-furo[3,2-b]pyrrole-5-carboxylate

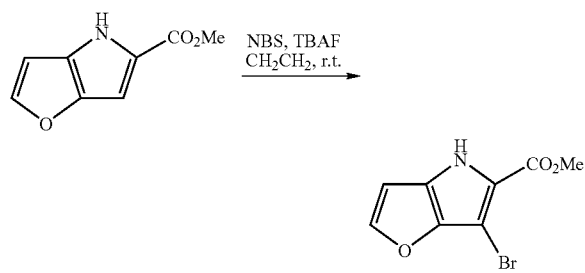

To a cold solution (ice-water bath) of methyl 4H-furo[3,2-b]pyrrole-5-carboxylate (1.0 g, 6.05 mmol) in DCM (10 mL) was added TBAF (1.0 M in THF, 9.0 mL, 9.0 mmol) and NBS (1.5 g, 7.9 mmol). The resulting dark colored solution was stirred from 0° C. to rt overnight. The reaction mixture was diluted with 50 mL of CH$_2$Cl$_2$ and washed with water (100 mL) and brine (100 mL) and dried (Na$_2$SO$_4$). After filtration, the filtrate was concentrated by evaporation and the crude product was purified by silica gel chromatography (0-5% EtOAc/hexane) to afford a white solid. $^1$H NMR (400 MHz, CDCl$_3$) δ (ppm) 8.84 (broad, 1H, NH), 7.54 (d, J=2.2 Hz, 1H), 6.48 (d, J=1.83 Hz, 1H), 3.92 (s, 3H) ppm; m+/z 244 (100%), 246 (100%).

2.8. Synthesis of 4-tert-butoxycarbonyl-2-bromo-4H-furo[3,2-b]pyrrole-5-carboxylic acid methyl ester

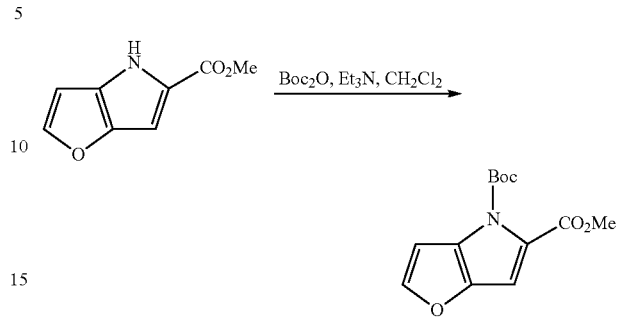

To a solution of methyl 4H-furo[3,2-b]pyrrole-5-carboxylate (1.0 g, 6.06 mmol) in CH$_2$Cl$_2$ (10 ml) was added triethyl amine (1.85 g, 18.2 mmol) and DMAP (148 mg 1.22 mol). Then BOC$_2$O (2.0 g, 9.1 mmol) was added. The resulting mixture was stirred overnight. After the reaction was complete as judged TLC analysis (10% EtOAc/hexane), the reaction mixture was washed with water and brine and dried over Na$_2$SO$_4$. After filtration, the filtrate was concentrated and the crude product was purified by silica gel chromatography (20% EtOAc in hexane) to give 4-tert-butoxycarbonyl-4H-furo[3,2-b]pyrrole-5-carboxylic acid methyl ester as a white solid (987 mg, 62%). $^1$H NMR (400 MHz, CDCl$_3$) δ (ppm) 7.45 (d, J=1.47 Hz, 1H), 6.82 (s, 1H), 6.59 (s, 1H), 3.80 (s, 3H), 1.55 (s, 9H).

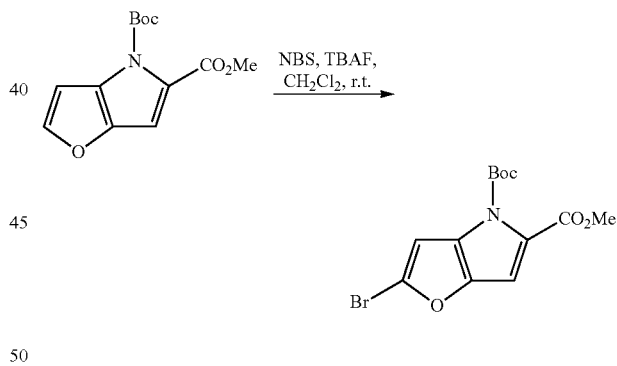

To a solution of 4-tert-butoxycarbonyl-4H-furo[3,2-b]pyrrole-5-carboxylic acid methyl ester (100 mg, 0.38 mmol) in DCM (1 mL) was added a solution of TBAF in THF (1.0 M, 0.57 ml, 0.57 mmol) followed by the addition of NBS (87 mg, 0.49 mmol). The resulting mixture was stirred at rt overnight. The reaction mixture was diluted with DCM (10 mL), washed with 10 mL of water and then with 10 mL of brine and dried with Na$_2$SO$_4$. The solid was removed by filtration. The filtrate was concentrated by evaporation. The crude product was purified by chromatography (0-20% EtOAc in hexane) to give 85 mg of 4-tert-butoxycarbonyl-2-bromo-4H-furo[3,2-b]pyrrole-5-carboxylic acid methyl ester (85 mg, 65%). $^1$H NMR (400 MHz, CDCl$_3$) δ (ppm) 6.81 (s, 1H), 6.61 (s, 1H), 3.83 (s, 3H), 1.59 (s, 9H).

2.9. Synthesis of methyl 6-iodo-4H-furo[3,2-b]pyrrole-5-carboxylate

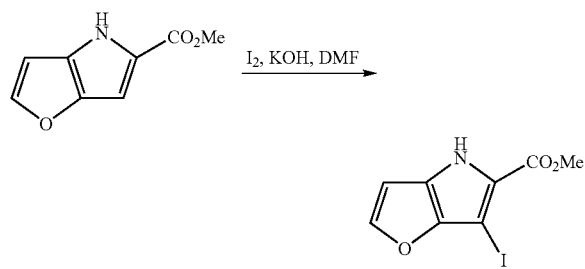

A mixture of methyl 4H-furo[3,2-b]pyrrole-5-carboxylate (5.00 g, 30.3 mmol) and KOH (3.40 g, 60.6 mmol) in DMF (100 mL) was cooled to −10° C. Iodine (7.31 g, 28.8 mmol) in DMF (40 mL) was charged via an addition funnel over 30 min. The resulting mixture was warmed to rt and stirred for additional 12 h. The reaction mixture was poured into water, adjusted with HCl (2 N) to pH 6-7, and extracted with EtOAc. The crude product was purified by flash chromatography (silica gel, 0 to 30% ethyl acetate in hexanes) to give a light tan solid methyl 6-iodo-4H-furo[3,2-b]pyrrole-5-carboxylate (3.85 g, 44% yield). $^1$H NMR (400 MHz, CDCl$_3$) δ (ppm) 8.98 (br, s, 1H); 7.55 (d, J=2 Hz, 1H); 6.52 (d, J=2 Hz, 1H); 3.91 (s, 3H). MS (m/z 291).

2.10. Synthesis of methyl 6-fluoro-4H-furo[3,2-b]pyrrole-5-carboxylate

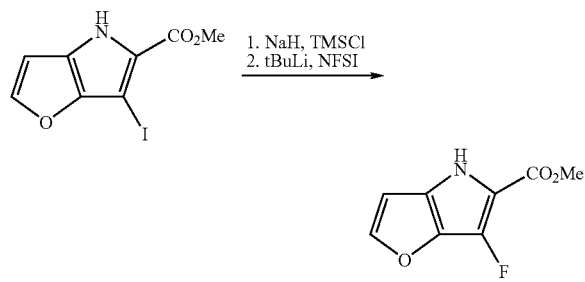

To a suspension of sodium hydride (95%, 0.130 g, 5.16 mmol) in THF (15 mL) cooled to −20° C. was added a solution methyl 6-iodo-4H-furo[3,2-b]pyrrole-5-carboxylate (1.00 g, 3.44 mmol) in THF (15 mL). Chlorotrimethylsilane (0.46 mL, 3.61 mmol) was added after 20 min. The resulting mixture was slowly warmed up to 0° C. over 1 h, and then recooled to −78° C. t-Butyllithium (1.7 M in pentane, 4.45 mL, 7.57 mmol) was added. After 40 minutes, a solution of NFSI (1.09 g, 3.44 mmol) in THF (5 mL) was added. The resulting mixture was stirred at −78° C. for 1 h, then quenched with methanol/water, and warmed to rt. The mixture was diluted with brine and extracted with EtOAc. GCMS of the crude showed 50:50 of methyl 6-fluoro-4H-furo[3,2-b]pyrrole-5-carboxylate: methyl 6-iodo-4H-furo[3,2-b]pyrrole-5-carboxylate, which were separated by column chromatography. $^1$H NMR (400 MHz, (CD$_3$)$_2$CO) δ ppm 3.83 (s, 3H) 6.60 (s, J=2.17, 1H) 7.75 (d, J=2.20 Hz, 1H) 10.32 (br. s., 1H).

2.11. Synthesis of ethyl 3-chloro-4H-furo[3,2-b]pyrrole-5-carboxylate

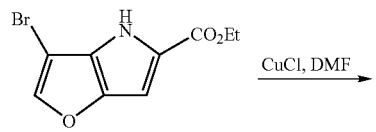

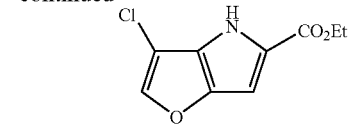

The title compound was synthesized from ethyl 3-bromo-4H-furo[3,2-b]pyrrole-5-carboxylate (200 mg, 0.774 mmol) using the conditions to synthesize ethyl 3-chloro-4H-thieno [3,2-b]pyrrole-5-carboxylate. Chromatography (silica gel, heptane/EtOAc) yielded ethyl 3-chloro-4H-furo[3,2-b]pyrrole-5-carboxylate (70 mg, 42% yield).

2.12 Synthesis of methyl 2,6-diiodo-4H-furo[3,2-b]pyrrole-5-carboxylate

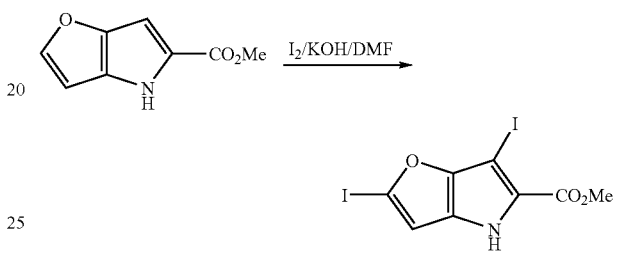

A mixture of methyl 4H-furo[3,2-b]pyrrole-5-carboxylate (1.0 g, 6.1 mmol) and KOH (1.03 g, 18.3 mmol) in DMF (20 mL) was cooled in an ice bath. A solution of iodine (3.1 g, 12.1 mmol) in DMF (115 mL) was charged via an addition funnel over 30 min. The reaction was stirred in an ice bath for 1 h, the more iodine (0.41 g, 1.61 mmol) was added, and the resulting mixture was allowed to warm up to room temperature and stiffed overnight. The reaction mixture was poured into an aqueous solution of sodium thiosulfate and extracted with EtOAc. The crude product was purified by flash chromatography on silica gel (30% EtOAc in hexanes) to give methyl 2,6-diiodo-4H-furo[3,2-b]pyrrole-5-carboxylate (0.903 g). $^1$H NMR (400 MHz, CDCl$_3$) δ (ppm) 8.95 (s, 1H); 6.70 (s, 1H), 3.92 (s, 3H). GCMS: 6.09 min (m/z 417, 385).

2.13 Synthesis of methyl 2,6-difluoro-4H-furo[3,2-b]pyrrole-5-carboxylate

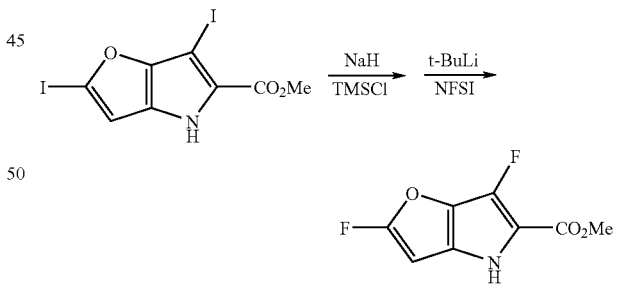

In a suspension of sodium hydride (95%, 0.130 g, 5.16 mmol) in THF (15 mL) cooled at −20° C. was added a solution of a mixture of 6-iodo-4H-furo[3,2-b]pyrrole-5-carboxylate and methyl 2,6-diiodo-4H-furo[3,2-b]pyrrole-5-carboxylate (7:1) (1.00 g, 3.44 mmol) in THF (15 mL). Chlorotrimethylsilane (0.46 mL, 3.61 mmol) was added after 20 min. The resulting mixture was slowly warmed up to 0° C. over 1 h and then recooled to −78° C. t-Butyllithium (1.7 M in pentane, 4.45 mL, 7.57 mmol) was charged in. A solution of NFSI (1.09 g, 3.44 mmol) in THF (5 mL) was charged in after 40 min. The resulting mixture was stirred at −78° C. for 1 h, then quenched with methanol/water, and warmed up to rt. The mixture was diluted with brine and extracted with EtOAc.

GCMS of the crude shows 50:50 of methyl 6-fluoro-4H-furo[3,2-b]pyrrole-5-carboxylate: methyl 6-iodo-4H-furo[3,2-b]pyrrole-5-carboxylate along with 5% of methyl 2,6-difluoro-4H-furo[3,2-b]pyrrole-5-carboxylate. The compounds were separable by silica gel chromatography. Methyl 2,6-difluoro-4H-furo[3,2-b]pyrrole-5-carboxylate: $^1$H NMR (400 MHz, CDCl$_3$) δ (ppm) 5.71-5.69 (dd, J=6.4 Hz, 1.6 Hz, 1H). GCMS showed a peak at 2.99 min (m/z 201, 169).

2.14. Synthesis of Carboxylic Acids from Esters 2.14.a) Synthesis of 4H-furo[3,2-b]pyrrole-5-carboxylic acid (11)

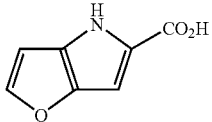

The title compound was synthesized from ethyl 4H-furo[3,2-b]pyrrole-5-carboxylate (0.33 g, 1.84 mmol) according to General Procedure 2 and was purified by silica gel column chromatography (0 to 100% EtOAc in heptane over 30 min) to give 4H-furo[3,2-b]pyrrole-5-carboxylic acid 11 as a light pink solid (0.200 g, 72%). R$_f$=0.07 (1:1 heptane/EtOAc); $^1$H NMR (400 MHz, (CD$_3$)$_2$SO) δ (ppm) 12.34 (s, 1H) 11.48 (s, 1H) 7.75 (s, 1H) 6.68 (s, 1H) 6.57 (s, 1H).

2.14.b) Synthesis of 3-phenethyl-4H-furo[3,2-b]pyrrole-5-carboxylic acid (17)

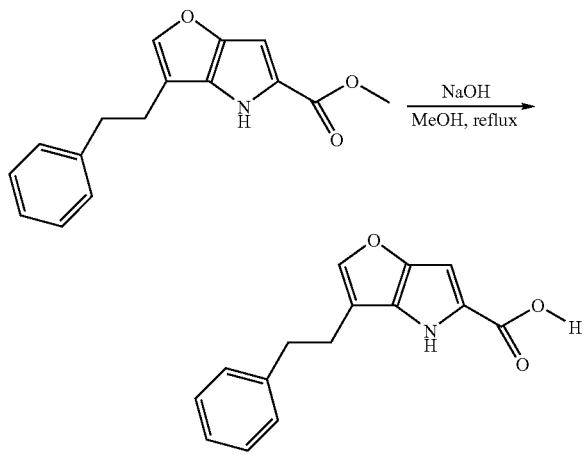

The title compound was prepared from ethyl 3-phenethyl-4H-furo[3,2-b]pyrrole-5-carboxylate (265 mg, 0.935 mmol) according to General Procedure 2 to give 3-phenethyl-4H-furo[3,2-b]pyrrole-5-carboxylic acid 17 as a tan solid (117 mg, 49%). $^1$H NMR (400 MHz, (CD$_3$)$_2$SO) δ ppm 12.34 (br s., 1H) 11.68 (s, 1H) 7.51 (s, 1H) 7.25-7.32 (m, 4H) 7.15-7.22 (m, 1H) 6.63 (d, J=1.7 Hz, 1H) 2.91-2.99 (m, 2H) 2.73-2.81 (m, 2H).

2.14.c) Synthesis of 2-chloro-4H-furo[3,2-b]pyrrole-5-carboxylic acid (23)

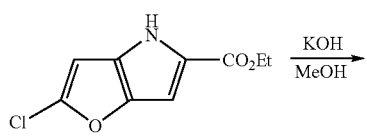

-continued

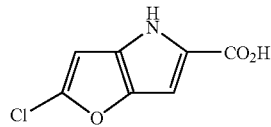

The title compound was prepared from ethyl 2-chloro-4H-furo[3,2-b]pyrrole-5-carboxylate (186 mg, 0.87 mmol) according to General Procedure 2. The crude product was purified by silica gel chromatography to afford 2-chloro-4H-furo[3,2-b]pyrrole-5-carboxylic acid 23 (50 mg, 31%). LCMS m/e 184 (M−H). $^1$H NMR (400 MHz, CD$_3$OD) δ (ppm): 6.70 (d, 1H), 6.45 (d, 1H).

2.14.d) Synthesis of 2-benzyl-4H-furo[3,2-b]pyrrole-5-carboxylic acid (24)

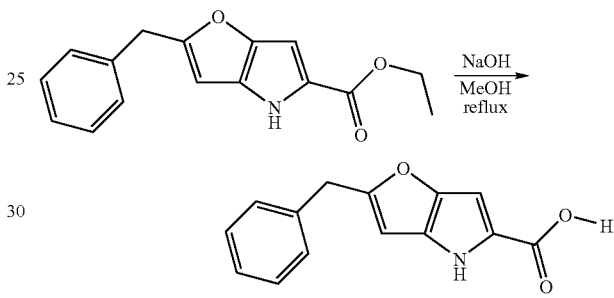

The title compound was prepared from ethyl 2-benzyl-4H-furo[3,2-b]pyrrole-5-carboxylate (17 mg, 63 μmol) according to General Procedure 2 to give 2-benzyl-4H-furo[3,2-b]pyrrole-5-carboxylic acid 24 (13 mg, 87%) as a tan solid. $^1$H NMR (400 MHz, (CD$_3$)$_2$SO) δ ppm 12.17 (br. s., 1H) 11.36 (s, 1H) 7.19-7.36 (m, 5H) 6.59 (dd, J=1.7, 0.9 Hz, 1H) 6.29 (d, J=0.8 Hz, 1H) 4.04 (s, 2H).

2.14.e) Synthesis of 3-benzyl-4H-furo[3,2-b]pyrrole-5-carboxylic acid (26)

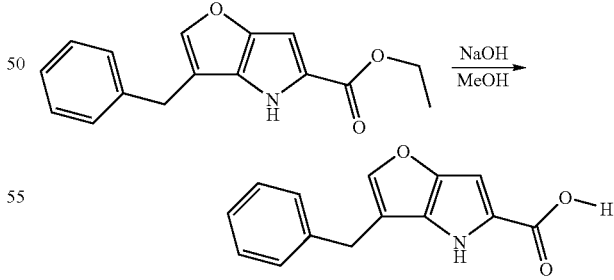

The title compound was prepared from ethyl 3-benzyl-4H-furo[3,2-b]pyrrole-5-carboxylate (52 mg, 0.19 mmol) according to General Procedure 2 to give 3-benzyl-4H-furo[3,2-b]pyrrole-5-carboxylic acid 26 as a tan solid (41 mg, 87%). $^1$H NMR (400 MHz, (CD$_3$)$_2$SO) δ ppm 12.32 (br. s., 1H) 11.60 (s, 1H) 7.57 (s, 1H) 7.33-7.38 (m, 2H) 7.25-7.31 (m, 2H) 7.15-7.21 (m, 1H) 6.63 (d, J=1.5 Hz, 1H) 3.84 (s, 2H). HPLC 99%. LCMS 242 (M+H).

2.14.f) Synthesis of 3-bromo-4H-furo[3,2-b]pyrrole-5-carboxylic acid (30)

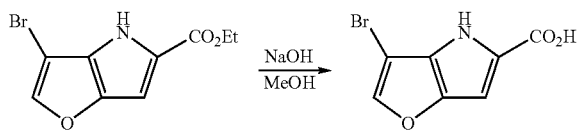

The title compound was synthesized from ethyl 3-bromo-4H-furo[3,2-b]pyrrole-5-carboxylate (100 mg, 0.39 mmol) according to General Procedure 2 and was purified by silica gel column chromatography to give 3-bromo-4H-furo[3,2-b]pyrrole-5-carboxylic acid 30 (46 mg, 52%). LCMS m/e 229 (M–H). $^1$H NMR (400 MHz, CD$_3$OD) δ (ppm): 7.65 (s, 1H), 6.74 (s, 1H).

2.14.g) Synthesis of 3-cyclopropyl-4H-furo[3,2-b]pyrrole-5-carboxylic acid (31)

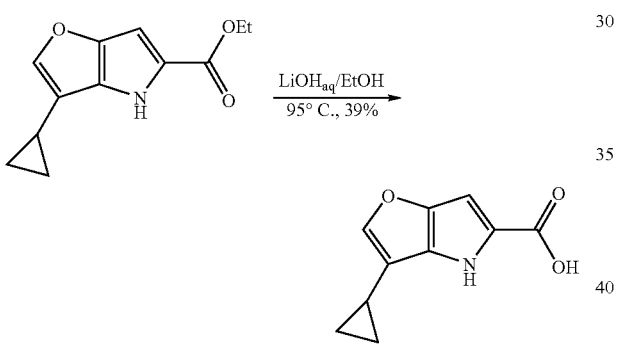

The title compound was synthesized from ethyl 3-cyclopropyl-4H-furo[3,2-b]pyrrole-5-carboxylate (110 mg, 0.50 mmol) according to General Procedure 2 and was purified by flash chromatography (Isco CombiFlash, 0-60% EtOAc/heptane) to afford 3-cyclopropyl-4H-furo[3,2-b]pyrrole-5-carboxylic acid 31 (34 mg, 35%). $^1$H NMR (400 MHz, CD$_3$OD) δ ppm 0.67-0.72 (m, 2H), 0.86-0.92 (m, 2H), 1.75-1.84 (m, 1H), 6.64 (s, 1H), 7.34 (d, J=0.83 Hz, 1H); LCMS-MS (ESI–) 189.8 (M–H); HPLC (UV=95.9%), (ELSD=100%).

2.14.h) Synthesis of 3-vinyl-4H-furo[3,2-b]pyrrole-5-carboxylic acid (32)

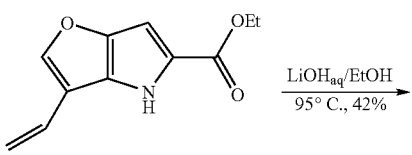

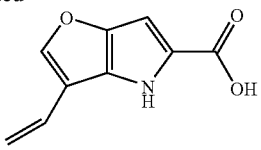

The title compound was synthesized from ethyl 3-vinyl-4H-furo[3,2-b]pyrrole-5-carboxylate (100 mg, 0.49 mmol) according to General Procedure 2 and was purified by flash chromatography (Isco CombiFlash, 0-40% EtOAc/heptane) to give 3-vinyl-4H-furo[3,2-b]pyrrole-5-carboxylic acid 32 (36 mg, 42%). $^1$H NMR (400 MHz, CD$_3$OD) δ ppm 5.29 (dd, J=11.03, 0.73 Hz, 1H), 5.81-5.88 (m, 1H), 6.59-6.68 (m, 1H), 6.72 (s, 1H), 7.63 (s, 1H); LCMS-MS (ESI–) 175.8 (M–H); HPLC (UV=99.2%), (ELSD=100%).

2.14.i) Synthesis of 3-isopropyl-4H-furo[3,2-b]pyrrole-5-carboxylic acid (40)

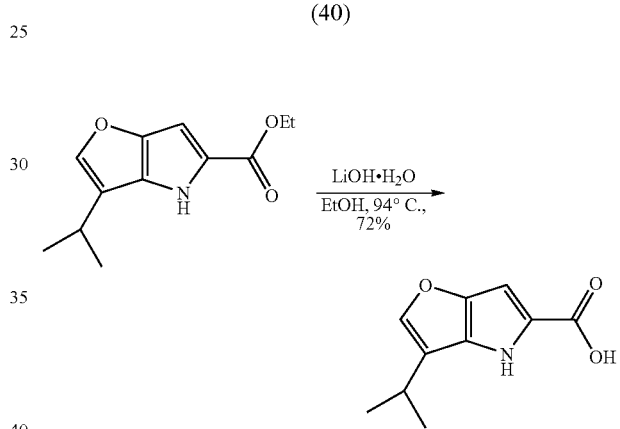

The title compound was synthesized from ethyl 3-isopropyl-4H-furo[3,2-b]pyrrole-5-carboxylate (120 mg, 0.54 mmol) according to General Procedure 2 and was purified through a plug of silica to give 3-vinyl-4H-furo[3,2-b]pyrrole-5-carboxylic acid 40 (76 mg, 72%). $^1$H NMR (400 MHz, CD$_3$OD) δ ppm 1.31 (d, J=6.88 Hz, 6H), 2.91-3.00 (m, 1H), 6.66 (s, 1H), 7.33 (d, J=0.98 Hz, 1H); LCMS-MS (ESI–) 191.8 (M–H); HPLC (UV=100%), (ELSD=100%).

2.14.j) Synthesis of 3-hydroxymethyl-4H-furo[3,2-b]pyrrole-5-carboxylic acid (42)

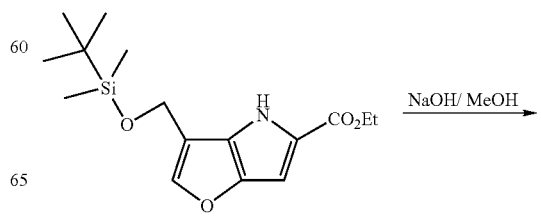

-continued

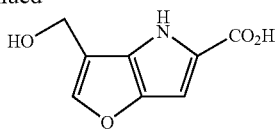

The title compound was synthesized from ethyl 3-(tert-butyl-dimethyl-silanyloxymethyl)-4H-furo[3,2-b]pyrrole-5-carboxylate (0.30 g, 0.93 mmol) according to General Procedure 2 and was purified by silica gel column chromatography (25 to 100% MeOH in CH$_2$Cl$_2$ over 30 min) to give 3-hydroxymethyl-4H-furo[3,2-b]pyrrole-5-carboxylic acid 42 as a white solid (20 mg, 12. $^1$H NMR (400 MHz, (CD$_3$)$_2$SO) δ ppm 4.41 (s, 2H) 6.33 (d, J=0.49 Hz, 1H) 6.43 (s, 1H) 8.46 (s, 1H) 10.95 (br. s., 1H). LCMS m/e 180 (M–H).

2.14.k) Synthesis of 3-formyl-4H-furo[3,2-b]pyrrole-5-carboxylic acid (43)

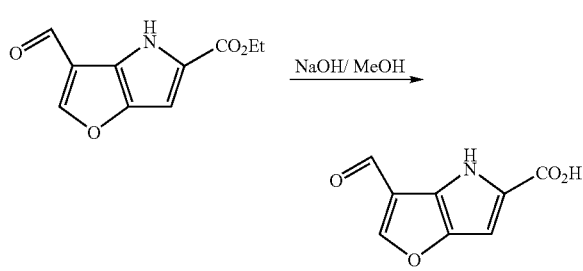

The title compound was synthesized from ethyl 3-formyl-4H-furo[3,2-b]pyrrole-5-carboxylate (0.14 g, 0.67 mmol) according to General Procedure 2 and was purified by silica gel column chromatography (10 to 100% MeOH in CH$_2$Cl$_2$ over 30 min) to give 3-formyl-4H-furo[3,2-b]pyrrole-5-carboxylic acid 43 (30 mg, 25%) as a light green solid. $^1$H NMR (400 MHz, CD$_3$OD) δ ppm 6.62 (s, 1H) 7.42 (s, 1H) 9.45 (s, 1H). LCMS m/e 178 (M–H).

2.14.l) Synthesis of (Z)-3-(Prop-1-enyl)-4H-furo[3,2-b]pyrrole-5-carboxylic acid (46)

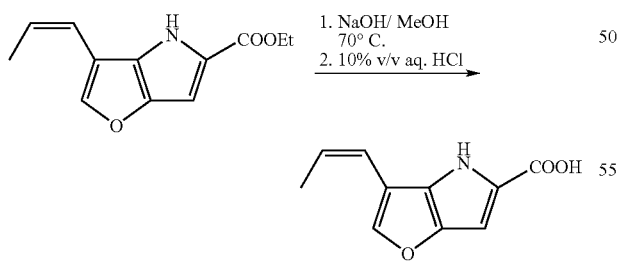

The title compound was synthesized from (Z)-ethyl 3-(prop-1-enyl)-4H-furo[3,2-b]pyrrole-5-carboxylate (0.1445 g, 68 mmol) according to General Procedure 2 and was purified by preparative HPLC using a Chromeleon purification system (50-100% over 7 min methanol/0.1% formic acid-1% acetonitrile in water, 50 mm Dynamax C-18, 28 mL/min) to give (Z)-3-(prop-1-enyl)-4H-furo[3,2-b]pyrrole-5-carboxylic acid 46 (40.4 mg, 32% yield). LC/MS m/e 189.8 (M–H). $^1$H NMR (400 MHz, CD$_3$OD) δ (ppm): 7.64 (s, 1H), 6.72 (s, 1H), 6.32-6.38 (m, 1H), 5.81-5.91 (m, 1H), 1.91 (dd, J=7.03, 1.76 Hz, 3H).

2.14.m) Synthesis of 3-(trifluoromethyl)-4H-furo[3,2-b]pyrrole-5-carboxylic acid (47)

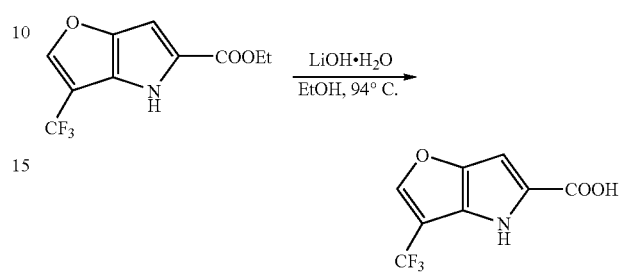

The title compound was synthesized from ethyl 3-(trifluoromethyl)-4H-furo[3,2-b]pyrrole-5-carboxylate (108 mg, 0.44 mmol) according to General Procedure 2 and was purified through a plug of silica to remove baseline impurities to give 3-(trifluoromethyl)-4H-furo[3,2-b]pyrrole-5-carboxylic acid 47 (89 mg, 93%). $^1$H NMR (400 MHz, CD$_3$OD) δ ppm 6.80 (s, 1H), 8.08 (q, J=1.58 Hz, 1H); $^{13}$C NMR (100 MHz, CDCl$_3$) δ 97.53 (dd, J=180.7, 1.3 Hz), 108.78 (qd, J=39.2, 11.7 Hz), 123.79 (q, J=265.4 Hz), 124.73 (m), 127.92 (d, J=5.8 Hz), 148.96 (dq, J=208.7, 5.8 Hz), 150.32 (d, J=8.0 Hz), 164.57 (s); LCMS-MS (ESI–) 217.8 (M–H); HPLC (UV=99.3%), (ELSD=100%).

2.14.n) Synthesis of (E)-3-styryl-4H-furo[3,2-b]pyrrole-5-carboxylic acid (48)

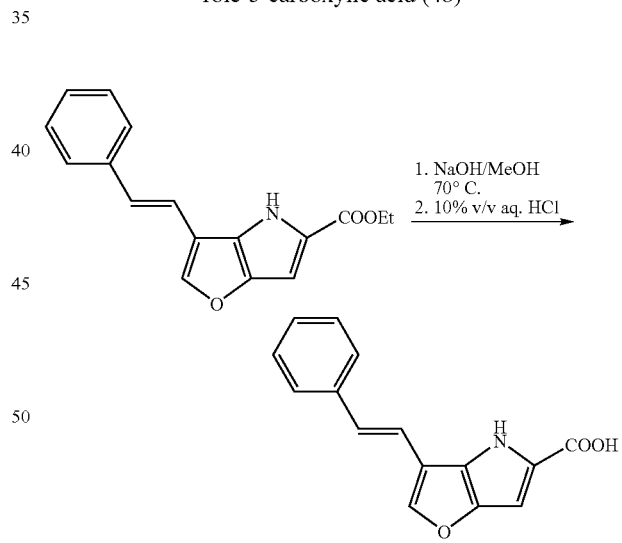

The title compound was synthesized from (E)-ethyl 3-styryl-4H-furo[3,2-b]pyrrole-5-carboxylate (0.0181 g, 0.071 mmol) according to General Procedure 2A and was purified via preparative HPLC (Chromeleon purification system, 40-100% over 7 min, methanol/0.1% formic acid-1% acetonitrile in water, 50 mm Dynamax C-18, 28 mL/min, retention time of product: 3.9-4.0 min) to give (E)-3-styryl-4H-furo[3,2-b]pyrrole-5-carboxylic acid 48 (4.9 mg, 30%). LC/MS m/e 251.9 (M–H). $^1$H NMR (400 MHz, CD$_3$OD) δ (ppm): 8.40 (s, 1H), 7.76 (s, 1H), 7.58-7.62 (m, 2H), 7.34-7.39 (m, 2H), 7.31 (d, J=16.40 Hz, 1H), 7.22-7.27 (m, 1H), 7.12 (d, J=16.40 Hz, 1H), 6.76 (s, 1H).

2.14.o) Synthesis of 3-methyl-4H-furo[3,2-b]pyrrole-5-carboxylic acid (50)

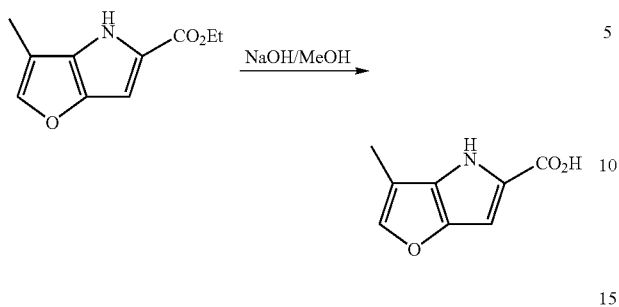

The title compound was synthesized from ethyl 3-methyl-4H-furo[3,2-b]pyrrole-5-carboxylate (0.17 g, 0.88 mmol) according to General Procedure 2 and was purified by silica gel column chromatography (0 to 100% EtOAc in heptane over 30 min) to give 3-methyl-4H-furo[3,2-b]pyrrole-5-carboxylic acid 50 as a solid (90 mg, 62%). $^1$H NMR (400 MHz, CD$_3$OD) δ ppm 2.15 (d, J=1.27 Hz, 3H) 6.65 (s, 1H) 7.34 (d, J=1.27 Hz, 1H). LCMS m/e 164 (M−H). 99.5% pure by HPLC.

2.14.p) Synthesis of 2-methyl-4H-furo[3,2-b]pyrrole-5-carboxylic acid (57)

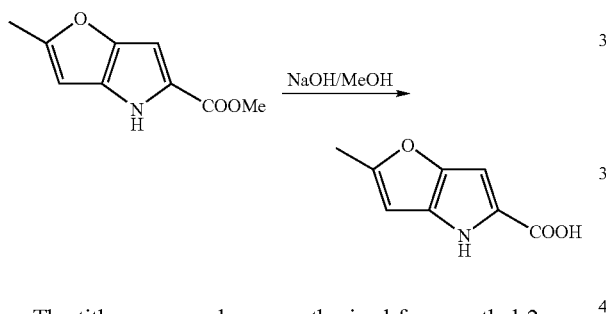

The title compound was synthesized from methyl 2-methyl-4H-furo[3,2-b]pyrrole-5-carboxylate (0.15 g, 0.84 mmol) according to General Procedure 2 and was purified by silica gel column chromatography (0 to 100% EtOAc in heptane over 30 min) to give 2-methyl-4H-furo[3,2-b]pyrrole-5-carboxylic acid 57 as a solid (35 mg, 25%). $^1$H NMR (400 MHz, CD$_3$OD) δ ppm 2.37 (d, J=0.83 Hz, 3H) 6.12 (s, 1H) 6.61 (d, J=0.59 Hz, 1H). LCMS m/e 164 (M−H). 99% pure by HPLC.

2.14.q) Synthesis of 3-ethyl-4H-furo[3,2-b]pyrrole-5-carboxylic acid (58)

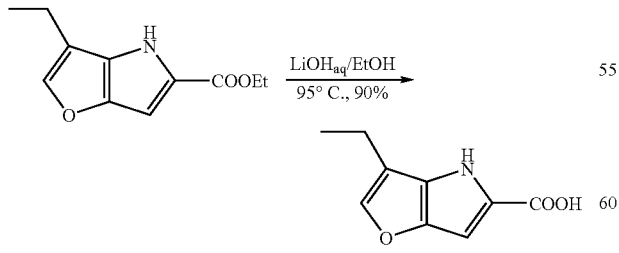

The title compound was synthesized from ethyl 3-ethyl-4H-furo[3,2-b]pyrrole-5-carboxylate (95 mg, 0.46 mmol) according to General Procedure 2 and was purified through a plug of silica to give 3-ethyl-4H-furo[3,2-b]pyrrole-5-carboxylic acid 58 (74 mg, 90%). $^1$H NMR (400 MHz, CD$_3$OD) δ ppm 1.28 (t, J=7.52 Hz, 3H), 2.55-2.63 (m, 2H), 6.66 (s, 1H), 7.35 (t, J=1.15 Hz, 1H); LCMS-MS (ESI−) 177.8 (M−H); HPLC (UV=100%), (ELSD=100%).

2.14.r) Synthesis of 6-bromo-4H-furo[3,2-b]pyrrole-5-carboxylic acid (72)

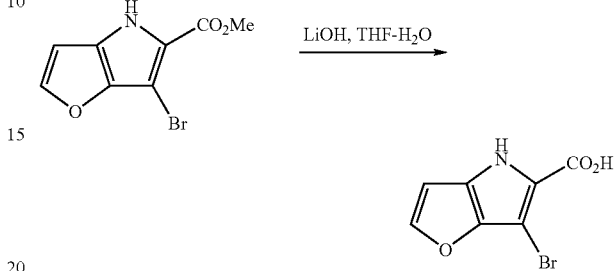

The title compound was synthesized from methyl 6-bromo-4H-furo[3,2-b]pyrrole-5-carboxylate (40 mg, 0.16 mmol) according to General Procedure 2 and was purified by reverse phase HPLC to give 6-bromo-4H-furo[3,2-b]pyrrole-5-carboxylic acid 72 (15 mg, 40%). $^1$H NMR (400 MHz, CD$_3$OD) δ (ppm) 7.64 (d, J=2.2 Hz, 1H), 6.55 (d, J=2.2 Hz, 1H).

2.14.s) Synthesis of 2-bromo-4H-furo[3,2-b]pyrrole-5-carboxylic acid (73)

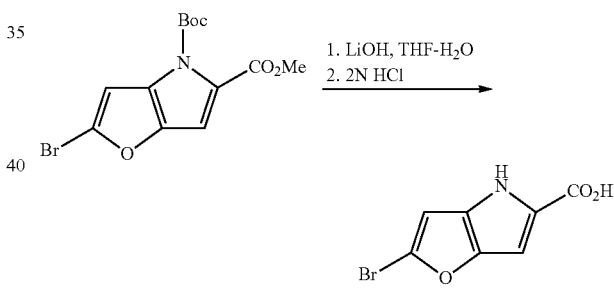

The title compound was synthesized from 4-tert-butoxycarbonyl-2-bromo-4H-furo[3,2-b]pyrrole-5-carboxylic acid methyl ester (78 mg, 0.226 mmol) according to General Procedure 2 and was purified by reverse phase HPLC to give 2-bromo-4H-furo[3,2-b]pyrrole-5-carboxylic acid 73 (14 mg, 27%). $^1$H NMR (400 MHz, CD$_3$OD) δ (ppm) 6.69 (s, 1H), 6.55 (s, 1H).

2.14.t) Synthesis of 3-fluoro-4H-furo[3,2-b]pyrrole-5-carboxylic acid (74)

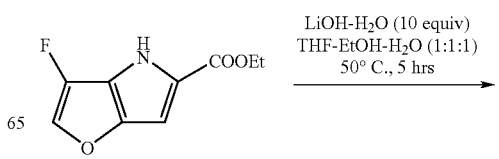

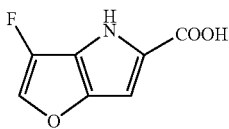

The title compound was synthesized from ethyl 3-fluoro-4H-furo[3,2-b]pyrrole-5-carboxylate (40 mg, 0.203 mmol) according to General Procedure 2 and was purified by silica gel chromatography (0-50% EtOAc in hexane) to yield 3-fluoro-4H-furo[3,2-b]pyrrole-5-carboxylic acid 74 (23 mg, 68%) as a white solid. $^1$H NMR (400 MHz, CD$_3$OD) δ ppm 6.68 (t, J=2.25, 1H), 7.67 (d, J=4.30 Hz, 1H); $^{19}$F NMR (376.19 MHz, CD$_3$OD) δ −182.87 (dd, J=4.29, 2.30 Hz, 1F); LCMS-MS (ESI+) 170.1 (M+H); HPLC (UV=100%).

2.14.u) Synthesis of 6-fluoro-4H-furo[3,2-b]pyrrole-5-carboxylic acid (75)

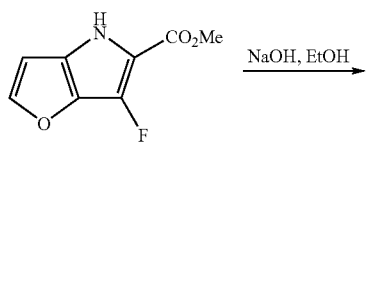

The title compound was synthesized from methyl 6-fluoro-4H-furo[3,2-b]pyrrole-5-carboxylate (5 mg, 0.0295 mmol) according to General Procedure 2. Purification was not required, and 4.2 mg (84% yield) of 6-fluoro-4H-furo[3,2-b]pyrrole-5-carboxylic acid 75 was obtained. $^{19}$F NMR (376 MHz, CD$_3$OD) δ ppm −168.28 (d, J=1.53 Hz, 1F). $^1$H NMR (400 MHz, CD$_3$OD) δ ppm 6.50 (t, J=2.16 Hz, 1H) 7.62 (d, J=2.20 Hz, 1H).

2.14.v) Synthesis of 3-chloro-4H-furo[3,2-b]pyrrole-5-carboxylic acid (76)

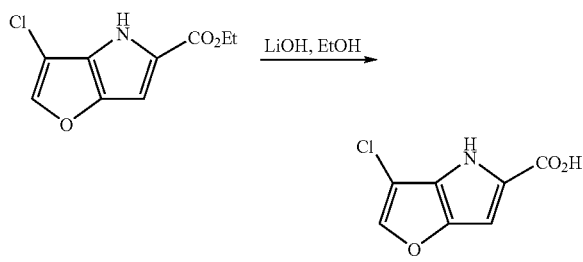

The title compound was synthesized from ethyl 3-chloro-4H-furo[3,2-b]pyrrole-5-carboxylate (30 mg, 0.1404 mmol) according to General Procedure 2. Purification was not required, and 13 mg (50% yield) of 3-chloro-4H-furo[3,2-b]pyrrole-5-carboxylic acid 76 was obtained. $^1$H NMR (400 MHz, CD$_3$OD) δ ppm 6.72 (s, 1H) 7.66 (s, 1H).

2.14.w) Synthesis of 2-trifluoromethyl-4H-furo[3,2-b]pyrrole-5-carboxylic acid (77)

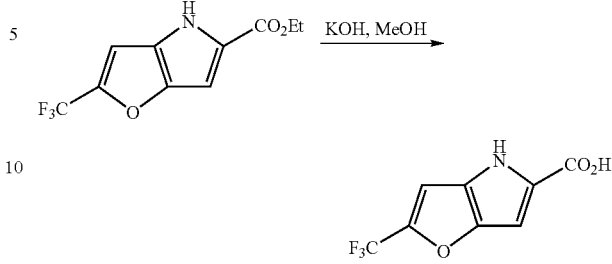

The title compound was synthesized from ethyl 2-trifluoromethyl-4H-furo[3,2-b]pyrrole-5-carboxylate (0.05 g, 0.20 mmol) according to General Procedure 2, and was purified by chromatography over silica gel (reverse phase gradient 20 to 100% MeOH in H$_2$O w/0.1% formic acid over 7 min) to give 2-trifluoromethyl-4H-furo[3,2-b]pyrrole-5-carboxylic acid 77 as an off-white solid (0.07 g, 16%). R$_f$=0.08 (50:50 heptane/EtOAc); $^{19}$F NMR (376 MHz, CDCl$_3$) δ (ppm) −66.13 (s, 3F) $^1$H NMR (400 MHz, CD$_3$OD) δ (ppm) 7.05 (m, J=0.8 Hz, 1H) 6.75 (s, 1H). LCMS m/e 218 (M−H).

2.14.x) Synthesis of 2-fluoro-4H-furo[3,2-b]pyrrole-5-carboxylic acid (78)

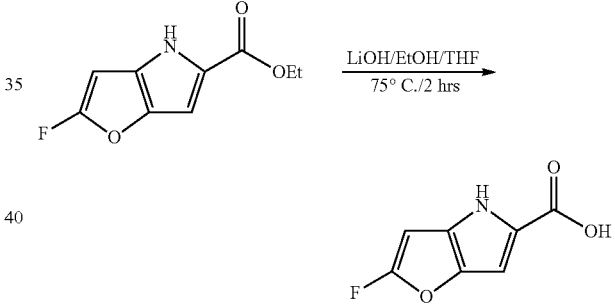

The title compound was synthesized from ethyl 2-fluoro-4H-furo[3,2-b]pyrrole-5-carboxylic acid ethyl ester (0.040 g, 0.203 mmol) according to General Procedure 2, and was purified by chromatography over silica gel (0 to 100% EtOAc in heptane over 20 min) to give a pure 2-fluoro-4H-furo[3,2-b]pyrrole-5-carboxylic acid 78 as an off white solid (0.020 g, 59%). $^1$H NMR (400 MHz, CD$_3$OD) δ ppm 5.85 (dd, J=6.30, 0.63 Hz, 1H) 6.71 (s, 1H), $^{19}$F NMR (376 MHz, CD$_3$OD) δ ppm −108.82 (d, J=5.94 Hz). LCMS m/e 168 (M−H). 100.0% pure by HPLC.

2.14.y) Synthesis of 2,6-difluoro-4H-furo[3,2-b]pyrrole-5-carboxylic acid (83)

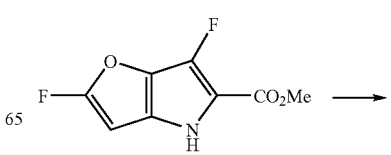

-continued

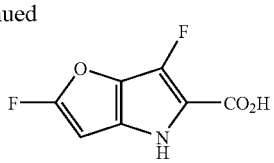

The title compound was synthesized from methyl 2,6-difluoro-4H-furo[3,2-b]pyrrole-5-carboxylate according to General Procedure 2.

2.15. Synthesis of 3-cyano-4H-furo[3,2-b]pyrrole-5-carboxylic acid (51)

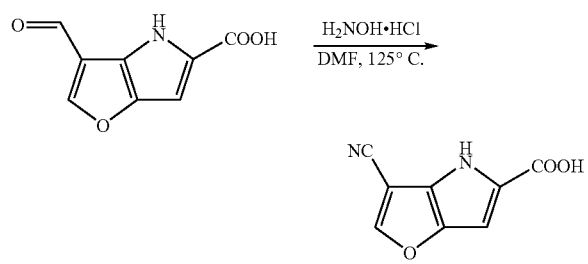

To a solution of 3-formyl-4H-furo[3,2-b]pyrrole-5-carboxylic acid (0.20 g, 0.2 M, 1.12 mmol) in DMF (6.0 mL) was added hydroxylamine hydrochloride (0.16 g, 2.24 mmol). The reaction mixture was heated at 125° C. overnight, then cooled to rt. The mixture was partitioned between EtOAc (20 mL) and H$_2$O (20 mL). The aqueous phase was extracted with EtOAc (3×20 mL). The combined organic phases were washed with H$_2$O and saturated aq NaCl, filtered and concentrated in vacuo. The crude product was chromatographed over silica gel (0 to 40% MeOH in CH$_2$Cl$_2$ over 30 min) to give 3-cyano-4H-furo[3,2-b]pyrrole-5-carboxylic acid 51 (4 mg, 2.1%) as a brown solid. $^1$H NMR (400 MHz, CD$_3$OD) δ ppm 6.65 (d, J=0.68 Hz, 1H) 7.33 (d, J=0.68 Hz, 1H). LCMS m/e 175 (M−H).

2.16. Synthesis of 6-chloro-4H-furo[3,2-b]pyrrole-5-carboxylic acid (79)

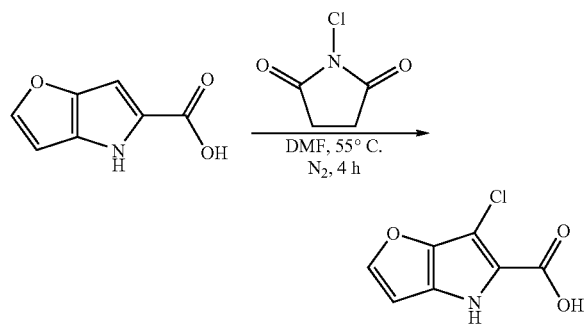

A stirred solution of 4H-furo[3,2-b]pyrrole-5-carboxylic acid (5.00 g, 33.09 mmol) in anhydrous DMF (40.0 mL) was cooled to 0° C. under nitrogen. Solid N-chlorosuccinimide (4.86 g, 36.39 mmol, 1.10 equiv) was added in several portions over 10 min while monitoring the internal reaction temperature. The reaction was stirred at 0° C. for 30 min, and then allowed to warm to rt, followed by heating at 55° C. for a period of 4 h. The progress of the reaction was followed by TLC (8:2 heptane/EtOAc, R$_f$=0.6) and LCMS m/e 184 (M−1). After 4 h, the reaction would progress no further and the black reaction mixture was poured into water (600 mL) and extracted with EtOAc (4×500 mL). The combined organic extracts were passed through a large Celite®/Silica-gel pad to remove the solid material, flushing with more EtOAc to afford a dark brown, clear solution which was a very complex mixture by TLC. Celite 521 (50 g) was added to the solution and the solvent was removed in vacuo. The dried material was loaded into a cartridge and flushed onto a silica-gel column (120 g, ISCO preloaded flash SG) with 5% EtOAc/heptane, then chromatographed using a 5%-20% EtOAc/heptane gradient to obtain 5.20 g of a three-component co-eluting mixture, consisting solely of the 4H-furo[3,2-b]pyrrole-5-carboxylic acid starting material, the desired 6-chloro-4H-furo[3,2-b]pyrrole-5-carboxylic acid in approximately 8-10% of the total material isolated, and a considerable quantity of the 2-chloro-4H-furo[3,2-b]pyrrole-5-carboxylic acid as the major component. The material was reverse-phase purified, using a 95/5 MeCN/H$_2$O 0.05% TFA: 5/95% MeCN/H$_2$O 0.05% TFA elution system, to isolate 49.7 mg of the desired 6-chloro derivative with an 88% purity after extraction with EtOAc (2 L total volume) and washing with a copious amount of water (3 L total volume) to facilitate the removal of any trace amount of TFA. After drying in vacuo at rt, the reddish-brown material obtained was further purified by normal phase, silica-gel chromatography using 10% MeOH/DCM to achieve 92% purity by HPLC. This material was dissolved in 0.5 mL MeOH, 1.0 mL of EtOAc was added, then the solution triturated with heptane to precipitate a brown, clumpy impurity that was filtered away to yield a clear, light yellow filtrate. The solvent was again removed in vacuo at rt to afford 10.3 mg (0.056 mmol, 1.68% yield) of a pale reddish-orange solid which was of 98.3% purity by HPLC. $^1$H NMR (400 MHz, CD$_3$OD) δ 6.53 (d, J=2.15 Hz, 1H) 7.64 (d, J=2.34 Hz, 1H). LCMS m/e 184 (M−1).

Example 3

Synthesis of Fused Pyrrole Analogs 3.1. Synthesis of Intermediate Aldehydes 3.1.a) Synthesis of 1-benzyl-1H-pyrrole-2-carboxaldehyde

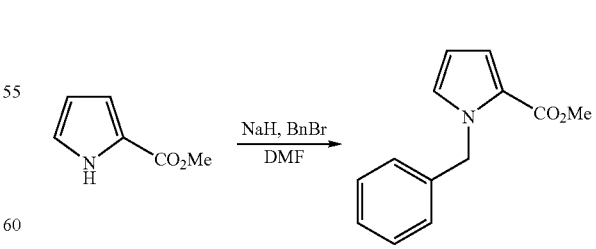

To a cooled (0° C.) solution of methyl-2-pyrrole carboxylate (8.00 g, 63.9 mmol) in DMF (320 mL) was added NaH (60% by weight 5.10 g, 128 mmol). After 20 min, benzylbromide (11.4 mL, 95.9 mmol) was added and the reaction was warmed to rt. Stirring was continued for 2 h before quenching with saturated aq NH₄Cl (0.5 L). The mixture was extracted 3× with EtOAc and the combined organic layers were washed with H₂O (3×) and brine, dried over MgSO₄, filtered and concentrated in vacuo to give a yellow oil. The crude product was chromatographed over silica gel (0 to 10% EtOAc in heptane over 25 min) to give methyl 1-benzyl-1H-pyrrole-2-carboxylate as a colorless oil (7.75 g, 56%). $R_f$=0.48 (25:75 heptane/EtOAc); ¹H NMR (400 MHz, CDCl₃) δ (ppm) 7.28-7.34 (m, 2H) 7.23-7.27 (m, 1H) 7.09-7.13 (m, 2H) 7.01 (dd, J=4.0, 1.8 Hz, 1H) 6.88-6.91 (m, 1H) 6.19 (dd, J=4.0, 2.6 Hz, 1H) 5.57 (s, 2H).

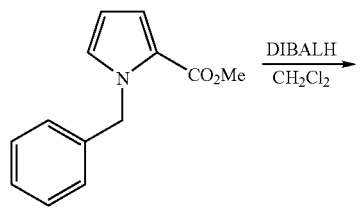

To a solution of methyl 1-benzyl-1H-pyrrole-2-carboxylate (3.00 g, 13.9 mmol) in DCM (70 mL) at −78° C. was added a 1M solution of diisobutylaluminum hydride (DIBAL-H) in heptane (35.0 mL, 34.8 mmol). After 45 min the reaction was quenched with saturated aqueous solution of NH₄Cl (20 mL) and Rochell's salt (100 g). The mixture was allowed to warm to rt and was stirred for 2.5 h. The reaction mixture was extracted with EtOAc (3×). The combined organic layers were washed with H₂O, saturated aq NaCl, dried over MgSO₄, filtered and concentrated in vacuo to give a pale yellow oil. The crude product was chromatographed over silica gel (0 to 20% EtOAc in heptane over 20 min) to give (1-benzyl-1H-pyrrol-2-yl)-methanol as a colorless oil (2.30 g, 88%). $R_f$=0.47 (1:1 heptane/EtOAc); ¹H NMR (400 MHz, CDCl₃) δ (ppm) 7.27-7.35 (m, 4H) 7.08-7.10 (m, 1H) 7.06-7.08 (m, 1H) 6.73 (dd, J=2.7, 1.8 Hz, 1H) 6.19 (dd, J=3.5, 1.8 Hz, 1H) 6.12-6.16 (m, 1H) 5.21-5.23 (s, 2H) 4.53 (d, J=5.1 Hz, 2H).

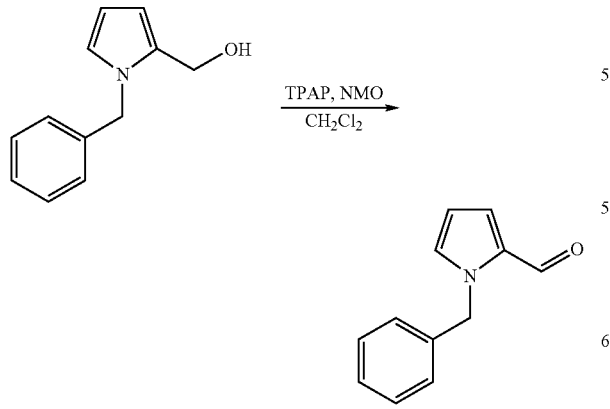

To a mixture of (1-benzyl-1H-pyrrol-2-yl)-methanol (3.08 g, 16.4 mmol) and powdered 4 Å molecular sieves (3.0 g) in DCM (33 mL) was added NMO (2.89 g, 24.7 mmol) along with tetrapropylammonium perruthenate (TPAP) (289 mg, 0.822 mmol). The mixture turned black and exothermed. After 20 min, the crude mixture was filtered through a plug of silica gel (EtOAc) to give a red solution. The solution was concentrated in vacuo and the resulting oil was chromatographed over silica gel (0 to 35% EtOAc in heptane over 35 min) to give 1-benzyl-1H-pyrrole-2-carboxaldehyde as a colorless oil (2.09 g, 69%). ¹H NMR (400 MHz, CDCl₃) δ (ppm) 9.58 (s, 1H) 7.24-7.35 (m, 3H) 7.16 (dd, J=7.7, 1.1 Hz, 2H) 6.98 (d, J=3.5 Hz, 2H) 6.26-6.31 (m, 1H) 5.58 (s, 2H).

3.2. Synthesis of Esters

Unless otherwise indicated, the following ethyl esters were synthesized from the indicated aldehyde according to General Procedure 1A (to yield an intermediate acrylate) followed by General Procedure 1B.

3.2.a) Synthesis of ethyl 4-methyl-1,4-dihydropyrrolo[3,2-b]pyrrole-2-carboxylate

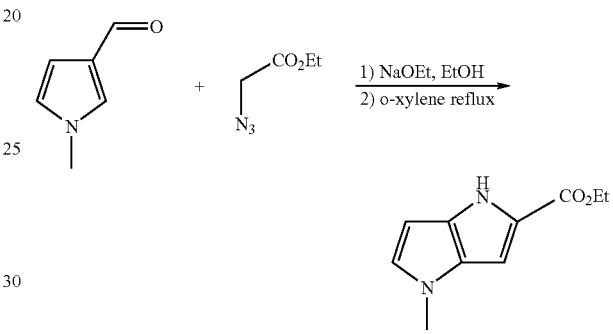

The title compound was synthesized from N-methyl-2-pyrrolecarboxaldehyde (3.00 g, 27.4 mmol) in two steps. The crude product was chromatographed over silica gel (0 to 20% EtOAc in heptane over 45 min) to give ethyl 4-methyl-1,4-dihydropyrrolo[3,2-b]pyrrole-2-carboxylate as a white solid (0.870 g, 16%). $R_f$=0.34 (25:75 heptane/EtOAc); ¹H NMR (400 MHz, CDCl₃) δ (ppm) 8.46 (s, 1H) 6.80 (d, J=2.9 Hz, 1H) 6.75 (s, 1H) 5.94 (dd, J=2.9, 0.8 Hz, 1H) 4.35 (q, J=7.1 Hz, 2H) 3.69 (s, 3H) 1.38 (t, J=7.1 Hz, 3H).

3.2.b) Synthesis of ethyl 4-benzyl-1,4-dihydropyrrolo[3,2-b]pyrrole-2-carboxylate

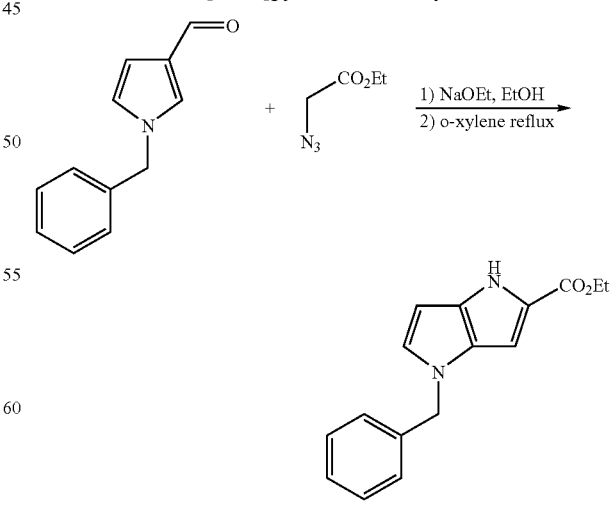

The title compound was synthesized from 1-benzyl-1H-pyrrole-2-carbaldehyde (2.09 g, 11.2 mmol) in two steps. The crude product was purified by silica gel column chromatography (0 to 20% EtOAc in heptane over 55 min) to give a brown solid (0.393 g, 13%). $^1$H NMR (400 MHz, CDCl$_3$) δ (ppm) 8.46 (s, 1H) 7.28-7.36 (m, 3H) 7.16-7.21 (m, 2H) 6.91 (d, J=3.0 Hz, 1H) 6.58 (dd, J=1.5, 0.7 Hz, 1H) 6.00 (dd, J=3.0, 0.7 Hz, 1H) 5.13 (s, 2H) 4.31 (q, J=7.1 Hz, 2H) 1.35 (t, J=7.1 Hz, 3H).

3.3. Synthesis of Carboxylic Acids from Esters

3.3.a) Synthesis of 4-methyl-1,4-dihydropyrrolo[3,2-b]pyrrole-2-carboxylic acid (12)

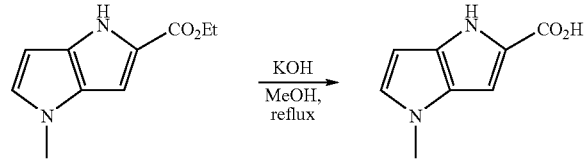

The title compound was synthesized from ethyl 4-methyl-1,4-dihydro-pyrrolo[3,2-b]pyrrole-2-carboxylate (0.35 g, 1.8 mmol) according to General Procedure 2 and was purified by silica gel column chromatography (0 to 50% EtOAc in heptane over 11 min) to give 4-methyl-1,4-dihydropyrrolo[3,2-b]pyrrole-2-carboxylic acid 12 (0.26 g, 88%) as an off white solid. R$_f$=0.08 (50:50 heptane/EtOAc); $^1$H NMR (400 MHz, (CD$_3$)$_2$SO) δ (ppm) 11.92 (s, 1H) 10.82 (s, 1H) 6.91 (d, J=2.9 Hz, 1H) 6.59 (dd, J=1.7, 0.8 Hz, 1H) 5.78 (dd, J=2.9, 0.8 Hz, 1H) 3.62 (s, 3H). LCMS m/e 165 (M+H).

3.3.b) Synthesis of 4-methyl-1,4-dihydropyrrolo[3,2-b]pyrrole-2-carboxylate potassium salt (12a)

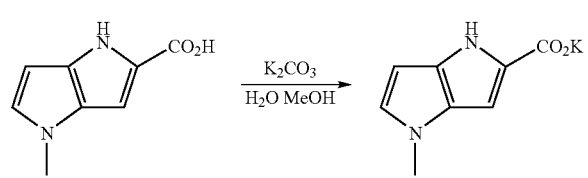

To a suspension of K$_2$CO$_3$ (0.110 g, 0.798 mmol) in H$_2$O (0.4 mL) and MeOH (2 mL) was added a solution of 4-methyl-1,4-dihydropyrrolo[3,2-b]pyrrole-2-carboxylic acid 12 (262 mg, 1.60 mmol) in MeOH (2 mL). The solution was stirred for 20 min and was then concentrated in vacuo to give potassium-4-methyl-1,4-dihydro-pyrrolo[3,2-b]pyrrole-2-carboxylate 12a as a grey solid (294 mg, 91%). $^1$H NMR (400 MHz, (CD$_3$)$_2$SO) δ (ppm) 9.80 (s, 1H) 6.58 (d, J=2.8 Hz, 1H) 6.10 (s, 1H) 5.70 (dd, J=2.8, 0.8 Hz, 1H) 3.55-3.57 (m, 3H).

3.3.c) Synthesis of 4-benzyl-1,4-dihydro-pyrrolo[3,2-b]pyrrole-2-carboxylic acid (13)

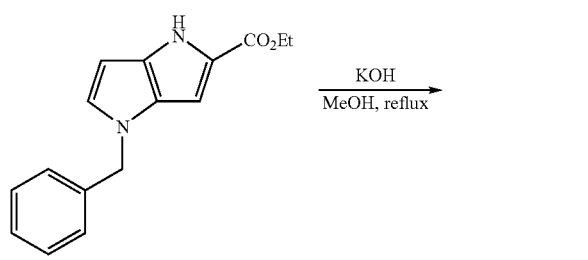

The title compound was synthesized from ethyl 4-benzyl-1,4-dihydropyrrolo[3,2-b]pyrrole-2-carboxylate (158 mg, 0.589 mmol) according to General Procedure 2 and was purified by silica gel column chromatography (0 to 50% EtOAc in heptane over 12 min) to give 4-benzyl-1,4-dihydro-pyrrolo[3,2-b]pyrrole-2-carboxylic acid 13 as an off white solid (82 mg, 58%). R$_f$=0.06 (1:1 heptane/EtOAc); $^1$H NMR (400 MHz, (CD$_3$)$_2$SO) δ (ppm) 11.91 (s, 1H) 10.86 (s, 1H) 7.29-7.36 (m, 2H) 7.22-7.28 (m, 3H) 7.11 (d, J=2.9 Hz, 1H) 6.44 (dd, J=1.7, 0.8 Hz, 1H) 5.84 (dd, J=3.0, 0.7 Hz, 1H) 5.13 (s, 2H).

3.3.d) Synthesis of 4-benzyl-1,4-dihydro-pyrrolo[3,2-b]pyrrole-2-carboxylate potassium salt (13a)

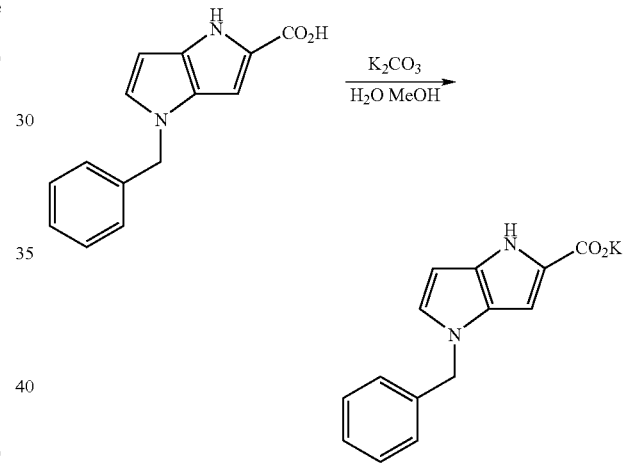

To a suspension of K$_2$CO$_3$ (24 mg, 0.17 mmol) in H$_2$O (0.2 mL) and MeOH (1 mL) was added a solution of 4-benzyl-1,4-dihydropyrrolo[3,2-b]pyrrole-2-carboxylic acid 13 (82 mg, 0.34 mmol) in MeOH (2 mL). The solution was stirred for 35 min and then concentrated in vacuo to give potassium 4-benzyl-1,4-dihydro-pyrrolo[3,2-b]pyrrole-2-carboxylate 13a as a grey solid (93 mg, 98%). $^1$H NMR (400 MHz, (CD$_3$)$_2$SO) δ (ppm) 9.61 (s, 1H) 7.27-7.33 (m, 2H) 7.19-7.26 (m, 3H) 6.74 (d, J=2.9 Hz, 1H) 5.90 (s, 1H) 5.73 (dd, J=2.9, 0.8 Hz, 1H) 5.04 (s, 2H).

Example 4

Synthesis of Fused Pyrrole Analogs

4.1. Synthesis of Intermediate Aldehydes

4.1.a) Synthesis of 1-Benzyl-1H-pyrazole-4-carbaldehyde

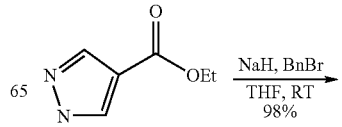

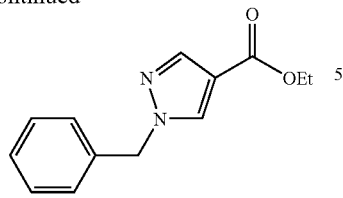

To a stirred suspension of NaH (53 mg, 1.33 mmol, 60% dispersion in mineral oil) in THF (5 mL), was added dropwise over 3 min a solution of ethyl 1H-pyrazole-4-carboxylate (155 mg, 1.11 mmol). The mixture was stirred at rt for 45 min and then treated with benzyl bromide (neat). After 2 h, the reaction was quenched with saturated solution of NH$_4$Cl and extracted with EtOAc (3×50 mL). The combined organic layers were washed with water, brine, dried (Na$_2$SO$_4$), filtered and concentrated. Purification by flash chromatography (Isco CombiFlash) 0-60% EtOAc/heptane provided ethyl 1-benzyl-1H-pyrazole-4-carboxylate (256 mg, 98%). $^1$H NMR (400 MHz, CDCl$_3$) δ ppm 1.33 (t, J=7.09 Hz, 3H), 4.28 (q, J=7.08 Hz, 2H), 5.31 (s, 2H), 7.24-7.28 (m, 2H), 7.31-7.42 (m, 3H), 7.86 (s, 1H), 7.95 (s, 1H); LCMS-MS (ESI+) 230.80 (M+H).

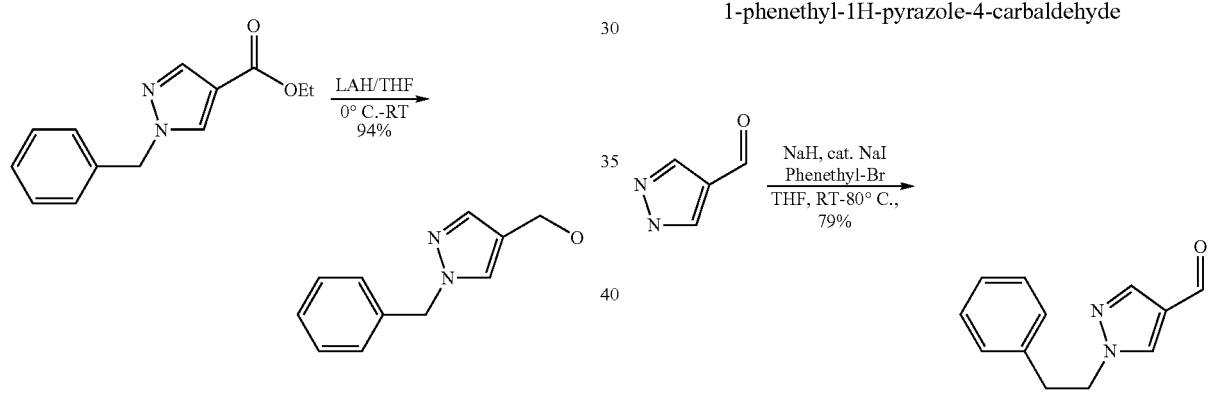

To a stirred suspension of lithium aluminum hydride (LAH) (68 mg, 1.79 mmol) in THF (8 mL) at 0° C. was added dropwise over 5 min a solution of ethyl 1-benzyl-1H-pyrazole-4-carboxylate (250 mg, 1.1 mmol) in THF (5 mL). After stirring for 1 h at 0° C., it was warmed to rt for 30 min and then quenched with 1N HCl until a clear solution was obtained. Extraction with EtOAc (3×50 mL) and washing of the combined organic layers with water, and then brine, provided the crude (1-benzyl-1H-pyrazol-4-yl)methanol after drying and evaporation of the solvent. Crude $^1$H NMR was clean enough to be used as is without further purification: crude yield 192 mg (94%). $^1$H NMR (400 MHz, CDCl$_3$) δ ppm 4.58 (s, 2H), 5.29 (s, 2H), 7.21-7.26 (m, 2H), 7.29-7.38 (m, 3H), 7.39 (s, 1H), 7.55 (s, 1H); LCMS-MS (ESI+) 188.90 (M+H).

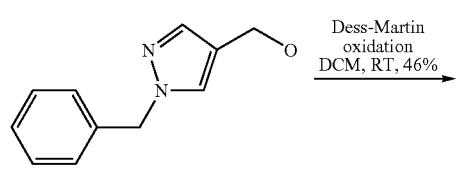

(1-Benzyl-1H-pyrazol-4-yl)methanol (190 mg, 1.0 mmol) in DCM (8 mL) at rt was treated with Dess-Martin periodinane (670 mg, 1.58 mmol). After 1.5 h, the reaction was quenched with a mixture of saturated solution of sodium thiosulfate and 10% NaHCO$_3$ (1:1) at rt, stirred for 30 min before extraction with DCM (3×30 mL). The combined extracts were washed with a saturated aqueous solution of NaHCO$_3$, brine, dried (Na$_2$SO$_4$), filtered and concentrated. Purification by flash chromatography (Isco CombiFlash) 0-40% EtOAc/heptane provided 1-benzyl-1H-pyrazole-4-carbaldehyde (86 mg, 46%). $^1$H NMR (400 MHz, CDCl$_3$) δ ppm 5.35 (s, 2H), 7.27-7.30 (m, 2H), 7.36-7.43 (m, 3H), 7.88 (s, 1H), 8.01 (s, 1H), 9.85 (s, 1H); LCMS-MS (ESI+) 186.90 (M+H).

4.1.b) Synthesis of 1-phenethyl-1H-pyrazole-4-carbaldehyde

To a stirred suspension of NaH (125 mg, 3.12 mmol, 60% dispersion in mineral oil) in THF (10 mL), was added dropwise over 5 min, a solution of 1H-pyrazole-4-carbaldehyde (250 mg, 2.60 mmol) in THF (5 mL). The mixture was stirred at rt for 45 min; sodium iodide (10 mg) was added before the addition of phenethyl bromide (0.42 mL, 3.12 mmol). After 15 min, the reaction was heated at 80° C. for 4 h, then cooled to rt, quenched with saturated solution of NH$_4$Cl and extracted with EtOAc (3×50 mL). The combined organic layers were washed with water, brine, dried (Na$_2$SO$_4$), filtered and concentrated. Purification by flash chromatography (Isco CombiFlash) 0-40% EtOAc/heptane provided 1-phenethyl-1H-pyrazole-4-carbaldehyde: Yield 410 mg (79%). $^1$H NMR (400 MHz, CDCl$_3$) δ ppm 3.20 (t, J=7.03 Hz, 2H), 4.39 (t, J=7.05 Hz, 2H), 7.06 (dd, J=7.91, 1.46 Hz, 2H), 7.22-7.32 (m, 3H), 7.63 (s, 1H), 8.00 (s, 1H), 9.79 (s, 1H); LCMS-MS (ESI+) 200.87 (M+H).

Cottineau, B. et al., *J. Bioorg. Med. Lett.* 2002, 12, 2105.

4.1.c) Synthesis of 2-phenethyl-2H-pyrazole-3-carbaldehyde

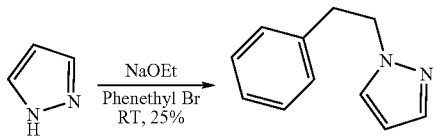

To a solution prepared by dissolving sodium (1.01 g, 44.07 mmol) in absolute EtOH (25 mL), was added 1H-pyrazole (2.5 g, 36.72 mmol). The solution was heated to gentle reflux, then allowed to cool to about 50° C. and treated with a catalytic amount of NaI (25 mg) followed by a slow addition of phenethyl bromide (6.0 mL, 44.07 mmol). The reaction was returned to reflux and after a few min, a white solid precipitated out of solution. After refluxing for 16 h, the solvent was removed by evaporation and the residue dissolved in water (30 mL) and extracted with EtOAc (4×50 mL). The combined organic extracts were washed with water and brine, dried ($Na_2SO_4$), filtered and concentrated. The crude product was purified by flash chromatography (Isco CombiFlash) 0-20% EtOAc/heptane to afford 1-phenethyl-1H-pyrazole (1.56 g, 25%). $^1$H NMR (400 MHz, $CDCl_3$) δ ppm 3.18 (t, J=7.28 Hz, 2H), 4.34-4.39 (m, 2H), 6.18 (t, J=2.06 Hz, 1H), 7.07-7.11 (m, 2H), 7.17 (d, J=2.20 Hz, 1H), 7.20-7.31 (m, 3H), 7.55 (d, J=1.74 Hz, 1H); LCMS-MS (ESI+) 172.86 (M+H).

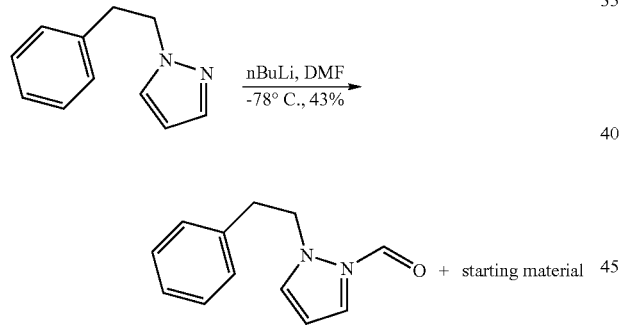

To a stirred, pre-cooled solution of 1-phenethyl-1H-pyrazole (1.10 g, 6.39 mmol) in THF (30 mL) at −78° C., was added dropwise n-BuLi (4.8 mL, 7.66 mmol; 1.6 M in hexane) at such a rate that the internal temperature stayed below −70° C. The mixture was stirred at −78° C. for 1.5 h, during which time the anion precipitated out as a yellow solid. Then DMF (1.25 mL, 15.97 mmol) was added neat and dropwise, and the reaction stirred at −78° C. for 90 min when TLC indicated the reaction was not progressing any further. It was quenched with $NH_4Cl$ solution (10 mL), allowed to warm to rt and extracted with EtOAc (4×50 mL). The combined organic extracts were washed with water, brine, dried ($Na_2SO_4$), filtered and concentrated. Purification by flash chromatography (Isco CombiFlash) 0-10% EtOAc/heptane provided 2-phenethyl-2H-pyrazole-3-carbaldehyde (540 mg, 43%). $^1$H NMR (400 MHz, $CDCl_3$) δ ppm 3.09-3.15 (m, 2H), 4.74-4.80 (m, 2H), 6.88 (d, J=2.10 Hz, 1H), 7.16-7.20 (m, 2H), 7.20-7.32 (m, 3H), 7.58 (d, J=2.01 Hz, 1H), 9.77 (s, 1H); LCMS-MS (ESI+) 200.88 (M+H).

4.2. Synthesis of Esters

Unless otherwise indicated, the following ethyl esters were synthesized from the indicated aldehyde according to General Procedure 1A (to yield an intermediate acrylate) followed by General Procedure 1B.

4.2.a) Synthesis of ethyl 1-benzyl-1,6-dihydropyrrolo[2,3-c]pyrazole-5-carboxylate

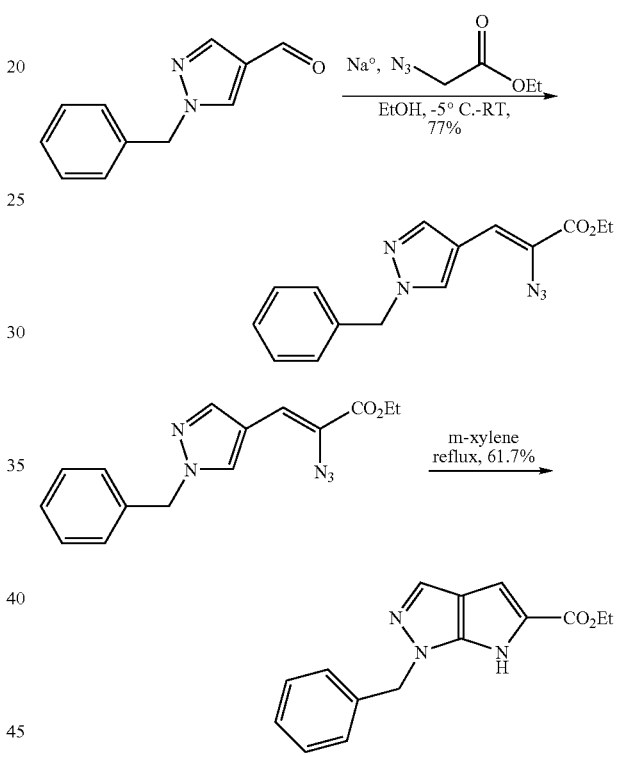

A) Ethyl 2-azido-3-(1-benzyl-1H-pyrazol-4-yl)acrylate (248 mg, 78%) was synthesized from 1-benzyl-1H-pyrazole-4-carbaldehyde (200 mg, 1.07 mmol) and was purified by flash chromatography (Isco CombiFlash, 0-40% EtOAc/heptane); $^1$H NMR (400 MHz, $CDCl_3$) δ ppm 1.37 (t, J=7.14 Hz, 3H), 4.33 (q, J=7.14 Hz, 2H), 5.33 (s, 2H), 6.83 (s, 1H), 7.25 (dd, J=7.87, 1.65 Hz, 2H), 7.31-7.40 (m, 3H), 7.82 (s, 1H), 7.94 (s, 1H); LCMS-MS (ESI+) 269.86 (M-$N_2$).

B) The title compound was prepared from ethyl 2-azido-3-(1-benzyl-1H-pyrazol-4-yl)acrylate and was purified by flash chromatography (Isco CombiFlash, 0-30% EtOAc/heptane) to afford ethyl 1-benzyl-1,6-dihydropyrrolo[2,3-c]pyrazole-5-carboxylate (137 mg, 62%) as a straw-colored solid. $^1$H NMR (400 MHz, $CDCl_3$) δ ppm 1.34 (t, J=7.14 Hz, 3H), 4.29 (q, J=7.14 Hz, 2H), 5.40 (s, 2H), 6.85 (d, J=1.65 Hz, 1H), 7.31-7.35 (m, 2H), 7.39-7.44 (m, 3H), 7.60 (d, J=0.64 Hz, 1H), 7.72 (s, 1H); LCMS-MS (ESI+) 269.84 (M+H).

4.2.b) Ethyl 1-phenethyl-1,6-dihydropyrrolo[2,3-c]pyrazole-5-carboxylate

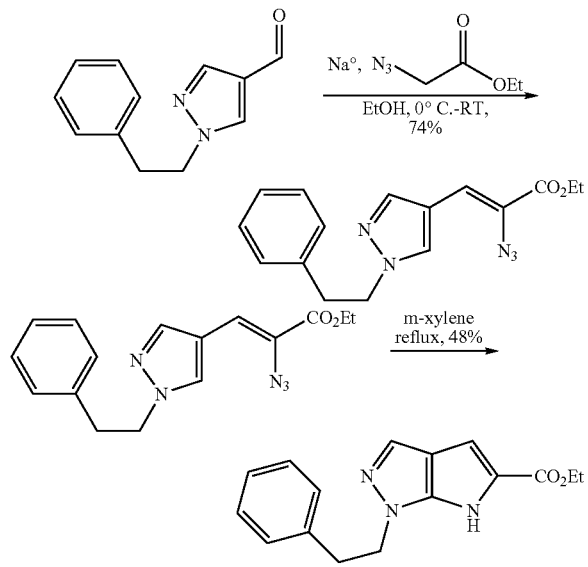

A) Ethyl 2-azido-3-(1-phenethyl-1H-pyrazol-4-yl)acrylate (462 mg, 74%) was prepared from 1-phenethyl-1H-pyrazole-4-carbaldehyde (400 mg, 2.0 mmol) and was purified by flash chromatography (Isco CombiFlash 0-40% EtOAc/heptane). $^1$H NMR (400 MHz, CDCl$_3$) δ ppm 1.38 (t, J=7.15 Hz, 3H), 3.19 (t, J=7.27 Hz, 2H), 4.30-4.39 (m, 4H), 6.80 (s, 1H), 7.09-7.12 (m, 2H), 7.22-7.32 (m, 3H), 7.72 (s, 1H), 7.80 (s, 1H); LCMS-MS (ESI+) 283.88 (M-N$_2$).

B) The title compound was prepared from ethyl 2-azido-3-(1-phenethyl-1H-pyrazol-4-yl)acrylate and was purified by flash chromatography (Isco CombiFlash 0-30% EtOAc/heptane) to afford ethyl 1-phenethyl-1,6-dihydropyrrolo[2,3-c]pyrazole-5-carboxylate (198 mg, 48%) as a white solid. $^1$H NMR (400 MHz, CDCl$_3$) δ ppm 1.35 (t, J=7.13 Hz, 3H), 3.17 (t, J=6.78 Hz, 2H), 4.28 (q, J=7.13 Hz, 2H), 4.45 (t, J=6.78 Hz, 2H), 6.80 (d, J=1.56 Hz, 1H), 7.08-7.13 (m, 2H), 7.22-7.31 (m, 3H), 7.53 (s, 1H), 7.71 (s, 1H); LCMS-MS (ESI+) 283.84 (M+H).

4.2.c) Synthesis of ethyl 1-phenethyl-1,4-dihydropyrrolo[3,2-c]pyrazole-5-carboxylate

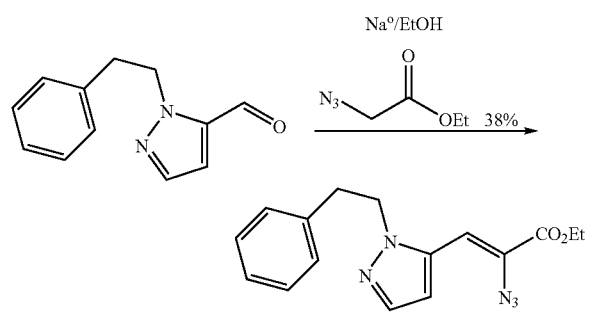

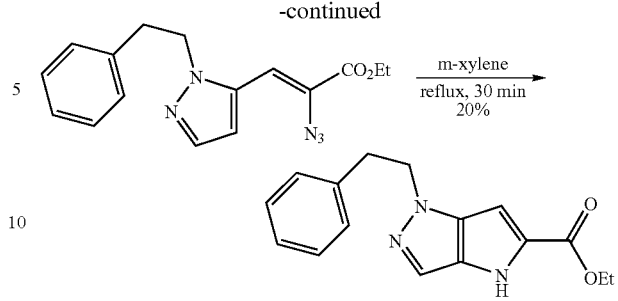

A) Ethyl 2-azido-3-(1-phenethyl-1H-pyrazol-5-yl)acrylate (306 mg, 38%) was prepared from 2-phenethyl-2H-pyrazole-3-carbaldehyde (530 mg, 2.65 mmol) and was purified by flash chromatography (Isco CombiFlash 0-20% EtOAc/heptane). $^1$H NMR (400 MHz, CDCl$_3$) δ ppm 1.41 (t, J=7.15 Hz, 2H), 3.11 (t, J=7.17 Hz, 2H), 4.35 (q, J=7.13 Hz, 2H), 4.41 (t, J=7.15 Hz, 2H), 6.46 (s, 1H), 6.93 (d, J=2.05 Hz, 1H), 7.01-7.06 (m, 2H), 7.18-7.29 (m, 3H), 7.58 (dd, J=2.07, 0.71 Hz, 1H); LCMS-MS (ESI+) 283.86 (M-N$_2$).

B) The title compound was synthesized from ethyl 2-azido-3-(1-phenethyl-1H-pyrazol-5-yl)acrylate and was purified by flash chromatography (Isco CombiFlash 0-30% EtOAc/heptane) to afford ethyl 1-phenethyl-1,4-dihydropyrrolo[3,2-c]pyrazole-5-carboxylate (50.6 mg, 19%) as a white solid. $^1$H NMR (400 MHz, CDCl$_3$) δ ppm 1.40 (t, J=7.13 Hz, 3H), 3.18-3.25 (m, 2H), 4.37 (q, J=7.13 Hz, 2H), 4.45 (dd, J=8.15, 7.03 Hz, 2H), 6.53-6.57 (m, 1H), 7.13-7.18 (m, 2H), 7.19-7.31 (m, 3H), 7.39 (s, 1H), 8.49 (s, 1H); LCMS-MS (ESI+) 283.86 (M+H).

4.3. Synthesis of Carboxylic Acids from Esters

4.3.a) Synthesis of 1-benzyl-1,6-dihydropyrrolo[2,3-c]pyrazole-5-carboxylic acid (21)

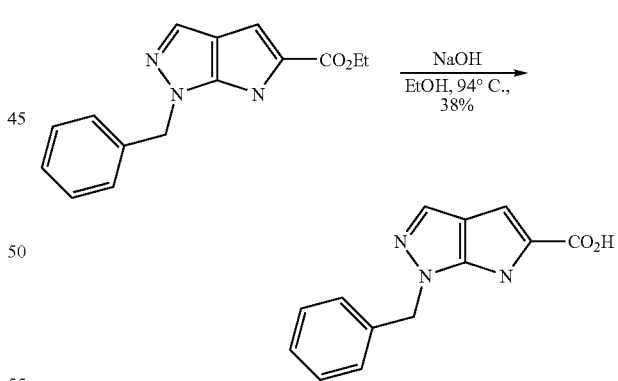

The title compound was prepared from ethyl 1-benzyl-1,6-dihydro-pyrrolo[2,3-c]pyrazole-5-carboxylate (118 mg, 0.44 mmol) according to General Procedure 2. The crude product was purified by flash chromatography (Isco CombiFlash, 0-60% MeOH/DCM) and preparative TLC on silica with 10% MeOH/DCM to afford 1-benzyl-1,6-dihydropyrrolo[2,3-c]pyrazole-5-carboxylic acid 21 (40 mg, 38%) as an off-white solid. $^1$H NMR (400 MHz, CD$_3$OD) δ ppm 5.40 (s, 2H), 6.78 (s, 1H), 7.18-7.22 (m, 2H), 7.22-7.33 (m, 3H), 7.49 (s, 1H); LCMS-MS (ESI+) 241.79 (M+H); HPLC (UV=97%), (ELSD=100%).

4.3.b) Synthesis of 1-phenethyl-1,6-dihydropyrrolo[2,3-c]pyrazole-5-carboxylic acid (22)

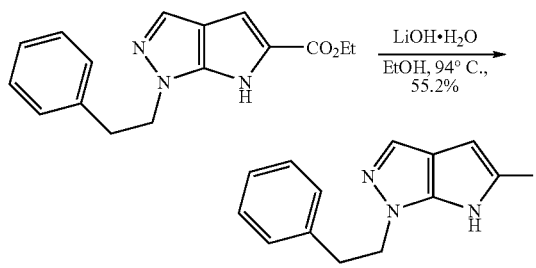

The title compound was synthesized from ethyl 1-phenethyl-1,6-dihydropyrrolo[2,3-c]pyrazole-5-carboxylate (190 mg, 0.67 mmol) according to General Procedure 2. The crude product was purified through a silica plug (10% MeOH/EtOAc) to give 1-phenethyl-1,6-dihydropyrrolo[2,3-c]pyrazole-5-carboxylic acid 22 (94.4 mg, 55%). $^1$H NMR (400 MHz, CD$_3$OD) δ ppm 3.12 (t, J=7.27 Hz, 2H), 4.41 (t, J=7.27 Hz, 2H), 6.79 (s, 1H), 7.09-7.12 (m, 2H), 7.13-7.22 (m, 3H), 7.47 (s, 1H); LCMS-MS (ESI+) 255.82 (M+H); HPLC (UV=97.8%), (ELSD=100%).

4.3.c) Synthesis of 1-Phenethyl-1,4-dihydro-pyrrolo[3,2-c]pyrazole-5-carboxylic acid (28)

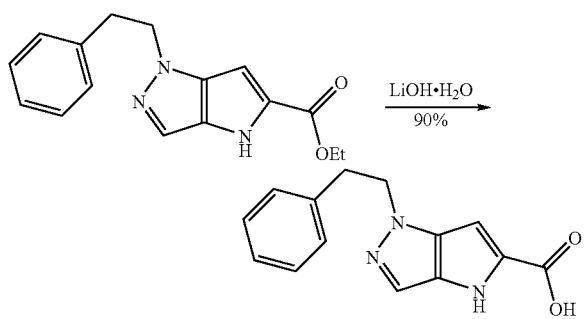

The title compound was prepared from ethyl 1-phenethyl-1,4-dihydropyrrolo[3,2-c]pyrazole-5-carboxylate (50 mg, 0.18 mmol) according to General Procedure 2. The crude product was purified through a plug of silica (EtOAc) to give 1-phenethyl-1,4-dihydropyrrolo[3,2-c]pyrazole-5-carboxylic 28 (40.6 mg, 90%). $^1$H NMR (400 MHz, CD$_3$OD) δ ppm 3.15 (t, J=7.05 Hz, 2H), 4.43 (t, J=7.08 Hz, 2H), 6.48 (d, J=0.54 Hz, 1H), 7.07-7.11 (m, 2H), 7.12-7.23 (m, 3H), 7.34 (s, 1H); LCMS-MS (ESI+) 255.82 (M+H); HPLC (UV=100%), (ELSD=100%).

Example 5

Synthesis of Fused Thiazole Pyrrole Analogs

5.1. Synthesis of Esters

5.1.a) Synthesis of ethyl 4H-Pyrrolo[3,2-d]thiazole-5-carboxylate

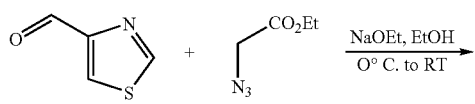

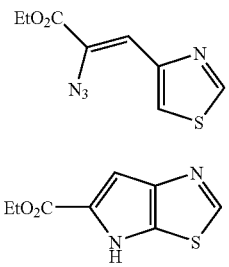

A) Ethyl 2-Azido-3-thiazol-4-yl-acrylate (400 mg, 67%) was synthesized from thiazole-4-carbaldehyde (300 mg, 2.6 mmol) according to General Procedure 1A and was purified by flash chromatography (Isco CombiFlash 0-40% EtOAc/heptane). $^1$H NMR (400 MHz, CDCl$_3$) δ ppm 1.40 (t, J=7.13 Hz, 3H), 4.38 (q, J=7.14 Hz, 2H), 7.27 (s, 1H), 8.23 (d, J=1.95 Hz, 1H), 8.81 (d, J=2.00 Hz, 1H); LCMS-MS (ESI+) 196.84 (M-N$_2$).

B) The title compound was prepared from ethyl 2-azido-3-thiazol-4-yl-acrylate (400 mg, 1.78 mmol) according to General Procedure 1B and was purified by flash chromatography (Isco CombiFlash 0-30% EtOAc/heptane) to afford ethyl 4H-pyrrolo[3,2-d]thiazole-5-carboxylate as a white solid (350 mg, 53%). $^1$H NMR (400 MHz, CDCl$_3$) δ ppm 1.41 (t, J=7.13 Hz, 3H), 4.40 (q, J=7.13 Hz, 2H), 7.33 (d, J=1.95, 1H), 8.56 (s, 1H), 9.39 (s, 1H); LCMS-MS (ESI+) 196.85 (M+H).

5.1.b) Synthesis of ethyl 4H-pyrrolo[2,3-d]thiazole-5-carboxylate

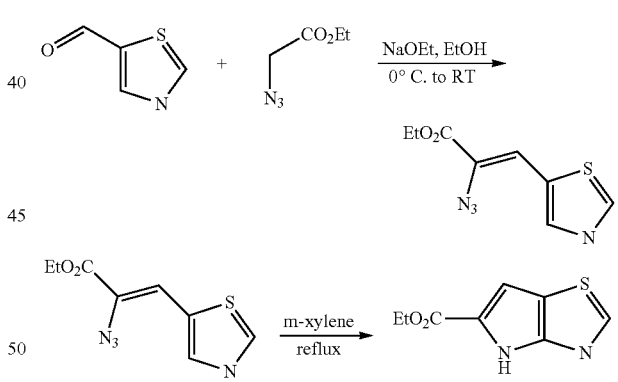

A) Ethyl 2-azido-3-thiazol-5-yl-acrylate (246 mg, 41%) was synthesized from thiazole-5-carbaldehyde (300 mg, 2.6 mmol) according to General Procedure 1A and was purified by flash chromatography (Isco CombiFlash 0-40% EtOAc/heptane). $^1$H NMR (400 MHz, CDCl$_3$) δ ppm 1.41 (t, J=7.13 Hz, 3H), 4.39 (q, J=7.13 Hz, 2H), 7.19 (s, 1H), 8.08 (s, 1H), 8.88 (s, 1H); LCMS-MS (ESI+) 196.81 (M-N$_2$).

B) The title compound was prepared from ethyl 2-azido-3-thiazol-5-yl-acrylate (240 mg, 1.1 mmol) according to General Procedure 1B and was purified by flash chromatography (Isco CombiFlash 0-30% EtOAc/heptane) to afford ethyl 4H-pyrrolo[2,3-d]thiazole-5-carboxylate as a white solid (191 mg, 91%). $^1$H NMR (400 MHz, CDCl$_3$) δ ppm 1.42

(t, J=7.15 Hz, 3H), 4.41 (q, J=7.14 Hz, 2H), 7.16 (d, J=1.95, 1H), 8.76 (s, 1H), 9.86 (s, 1H); LCMS-MS (ESI+) 196.82 (M+H).

5.2. Synthesis of Carboxylic Acids from Esters

5.2.a) Synthesis of 4H-pyrrolo[3,2-d]thiazole-5-carboxylic acid (41)

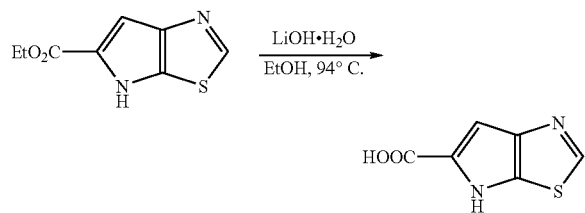

The title compound was synthesized from ethyl 4H-pyrrolo[3,2-d]thiazole-5-carboxylate (180 mg, 0.95 mmol) according to General Procedure 2 to give 4H-pyrrolo[3,2-d]thiazole-5-carboxylic acid 41 (83 mg, 54%) as a beige solid. $^1$H NMR (400 MHz, CD$_3$OD) δ ppm 7.14 (s, 1H), 8.68 (s, 1H); LCMS-MS (ESI−) 166.7 (M−H); HPLC (UV=99.5%), (ELSD=100%).

5.2.b) Synthesis of 4H-pyrrolo[2,3-d]thiazole-5-carboxylic acid (44)

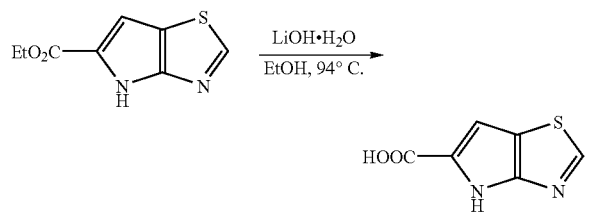

The title compound was synthesized from ethyl 4H-pyrrolo[2,3-d]thiazole-5-carboxylate (190 mg, 0.97 mmol) according to General Procedure 2 to give 4H-pyrrolo[2,3-d]thiazole-5-carboxylic acid 44 (170 mg, 86%) (HCl salt) as a beige solid. $^1$H NMR (400 MHz, CD$_3$OD) δ ppm 7.14 (s, 1H), 8.87 (s, 1H); LCMS-MS (ESI−) 166.8 (M−H); HPLC (UV=100%), (ELSD=100%).

Example 6

Synthesis of Fused Thiophene Analogs

6.1. Synthesis of Carboxylic Acids

6.1.a) Synthesis of 6-(4-chlorobenzyl)-thieno[3,2-b]thiophene-2-carboxylic acid (25)

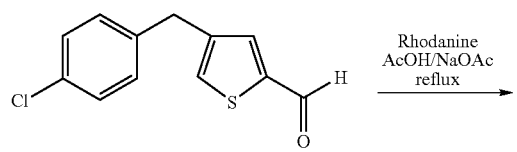

-continued

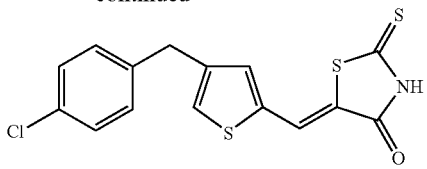

A) To a 20-mL scintillation vial fitted with a magnetic stir bar was added 3 mL of glacial acetic acid (AcOH). The vial was capped tightly and heated to 80° C. To the hot AcOH was added 4-(4-chlorobenzyl)thiophene-2-carbaldehyde (example 1.1.a); 0.37 g, 1.56 mmol, 1 equiv) and rhodanine (0.23 g, 1.7 mmol, 1.1 equiv) with stirring until a solution was formed. To the mixture was then added anhydrous sodium acetate (0.45 g, 5.5 mmol, 3.5 equiv), and the vial was capped tightly and heated to 110° C. for approx. 1 h. The reaction vial was cooled to rt and the contents were poured into water. The resulting precipitate was filtered, washed with water and a cold mixture of 1:1 water/ethanol. The solid was dried thoroughly in vacuo at 40° C. to give 5-((4-(4-chlorobenzyl)thiophen-2-yl)methylene)-2-thioxothiazolidin-4-one (451 mg, 81%). $^1$H NMR (400 MHz, (CD$_3$)$_2$SO) δ (ppm): 7.70 (s, 1H), 7.67 (s, 1H), 7.46 (s, 1H), 7.34-7.38 (m, 2H), 7.25-7.29 (m, 2H), 3.96 (s, 2H).

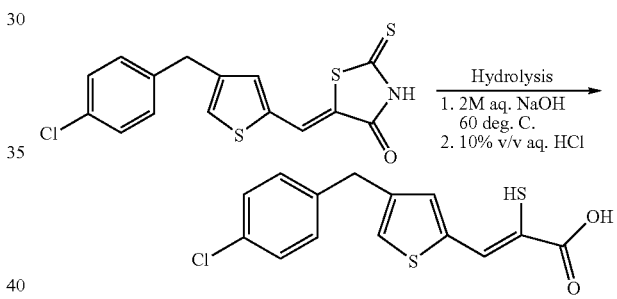

B) To a 20-mL scintillation vial fitted with a magnetic stir bar under a N$_2$ atmosphere was added 3.5 mL of NaOH (2.0 M), and heated to 45° C. 5-((4-(4-chlorobenzyl)thiophen-2-yl)methylene)-2-thioxothiazolidin-4-one was added to the 2 M NaOH solution. After complete dissolution, the temperature of the reaction vial was increased to 60° C. over a 30 min period. The vial was subsequently cooled to 5° C. and cold 10% (v/v) aq. HCl solution was added until a precipitate formed (approx. pH 2-3). The resulting precipitate was collected by filtration, washed several times with water, and dried thoroughly under vacuum at 40° C. to give 3-(4-(4-chlorobenzyl)thiophen-2-yl)-2-mercaptoacrylic acid (379 mg, 95% yield). Note: $^1$H NMR showed a number of peaks in the aromatic region. The presence of the signal for the vinyl proton and the loss of the rhodanine moiety (i.e.; absence of the proton attached to the nitrogen in the rhodanine moiety) was used as an indicator of the desired compound. The material was used in the next step without further purification.

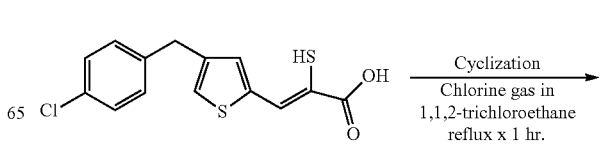

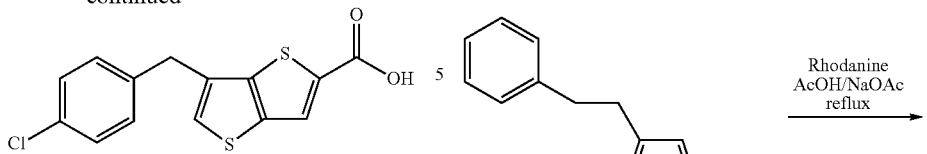

C) To a 100-mL three-necked round bottom flask fitted with a reflux condenser, an addition funnel, and a magnetic stir bar was added 3-(4-(4-chlorobenzyl)thiophen-2-yl)-2-mercaptoacrylic acid (0.38 g, 1.3 mmol, 1 equiv) and 8 mL of 1,1,2-trichloroethane. In a separate vessel, a solution of chlorine (using approx. 0.1 g of $Cl_2$ gas) was formed using 20 mL of 1,1,2-trichloroethane in a 40 mL scintillation vial. The $Cl_2$ solution was added to the main reaction vessel dropwise over 45 min at 25° C. Stirring was continued for 1 h at 25° C. before heating the reaction vessel to reflux (approx. 110-115° C.) for 1 h. The reaction was cooled to rt, the contents filtered, and the collected solid was washed with a small volume of 1,1,2-trichloroethane. The crude product was purified by preparative HPLC using a Chromeleon purification system (60% to 100% over 7 min methanol/0.1% formic acid-1% acetonitrile in water, 50 mm Dynamax C-18, 28 mL/min) to give 6-(4-chlorobenzyl)-thieno[3,2-b]thiophene-2-carboxylic acid 25 (16 mg, 5%). LC/MS m/e 341 (M+Na). $^1$H NMR (400 MHz, $CD_3OD$) δ (ppm): 7.96 (s, 1H), 7.48 (s, 1H), 7.27-7.36 (m, 4H), 4.10 (s, 2H).

6.1.b) Synthesis of 5-chloro-4-(4-chlorobenzyl)-thieno[2,3-b]thiophene-2-carboxylic acid (27)

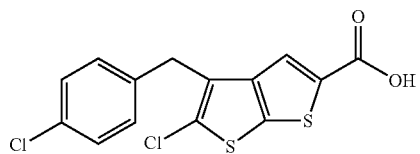

The title compound was prepared from 4-(4-chlorobenzyl)thiophene-3-carbaldehyde according to procedures A-C outlined above in Example 6.1.a) to afford 5-chloro-4-(4-chlorobenzyl)-thieno[2,3-b]thiophene-2-carboxylic acid 27 (12 mg, 10% for the final step). Under these conditions, a chlorine substituent was added to the 5-position. LC/MS m/e 343 (M+H). $^1$H NMR (400 MHz, $CD_3OD$) δ (ppm): 7.65 (s, 1H), 7.29-7.33 (m, 2H), 7.23-7.28 (m, 2H), 4.17 (s, 2H). *J. Med. Chem.* 1985, 28(12): 1896-1903.

6.2.c) Synthesis of 6-phenethylthieno[3,2-b]thiophene-2-carboxylic acid (60)

The title compound was synthesized from 4-phenethylthiophene-2-carbaldehyde (Example 1.1.b)) in three steps according to the procedures outlined above in Example 6.1.a).

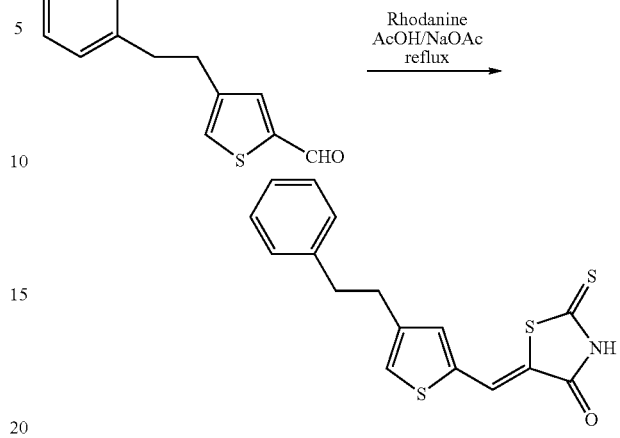

A) (Z)-5-((4-phenethylthiophen-2-yl)methylene)-2-thioxothiazolidin-4-one (343 mg, 82%). $^1$H NMR (400 MHz, $(CD_3)_2SO$) δ (ppm): 7.80 (s, 1H), 7.70 (s, 1H), 7.56 (s, 1H), 7.15-7.31 (m, 5H), 2.91 (s, 4H).

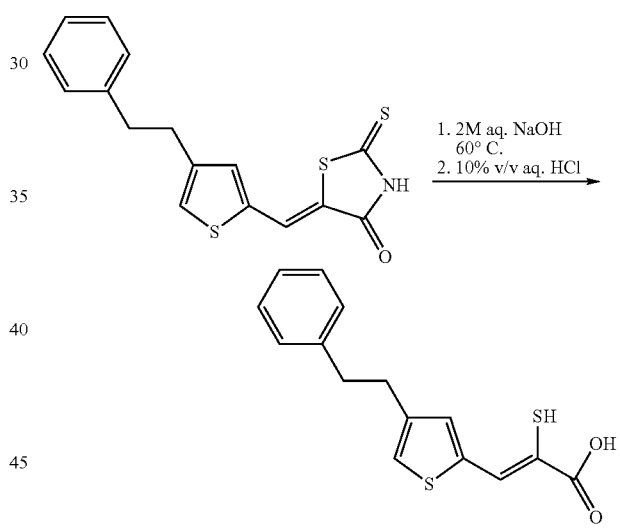

B) (Z)-2-mercapto-3-(4-phenethylthiophen-2-yl)acrylic acid (0.2675 g (89% yield). The $^1$H NMR showed a number of peaks in the aromatic region, presence of the vinyl proton and loss of the rhodanine moiety. The material was used in the next step without further purification.

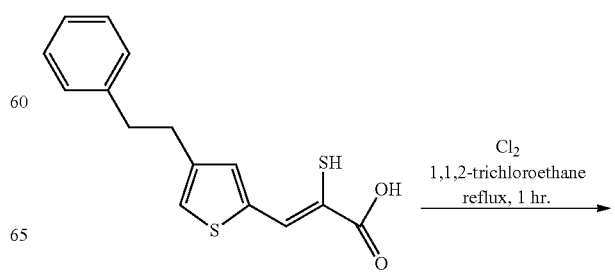

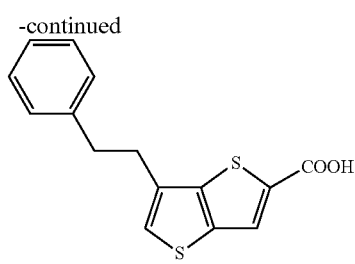

C) The title compound was synthesized from (Z)-2-mercapto-3-(4-phenethylthiophen-2-yl)acrylic acid (0.2675 g, 0.93 mmol) and was purified by preparative HPLC as described above to give 6-phenethylthieno[3,2-b]thiophene-2-carboxylic acid 60 (52 mg, 20%). LC/MS m/e 289 (M+H). $^1$H NMR (400 MHz, CD$_3$OD) δ (ppm): 8.09 (s, 1H), 7.30 (d, J=6.39 Hz, 2H), 7.25 (d, J=7.17 Hz, 2H), 7.16-7.20 (m, 3H), 2.91 (s, 4H).

Example 7

Synthesis of Fused Pyrrole Thiophene Analogs 7.1. Synthesis of 4H-thieno[3,2-b]pyrrole-2-carboxylic acid (53)

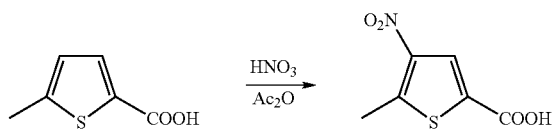

Under N$_2$, fuming nitric acid (4.7 mL, 112.0 mmol) was added slowly over 10 min to acetic anhydride (16.6 mL, 175.6 mmol) cooled in a dry ice/acetone bath to −78° C. 5-methyl-2-thiophene carboxylic acid (5.0 g, 35.2 mmol) was added in 1 g portions over 10 min to the solution. The reaction was kept at −20° C. for 1 h before quenching over ice. The yellow solid was filtered off and washed with water (200 mL). The crude product was recrystallized from 95% EtOH to give 5-methyl-4-nitro-2-thiophene carboxylic acid as a pale yellow solid (4.6 g, 70%). $^1$H NMR (400 MHz, CD$_3$OD) δ (ppm) 8.13 (s, 1H) 2.82 (s, 3H).

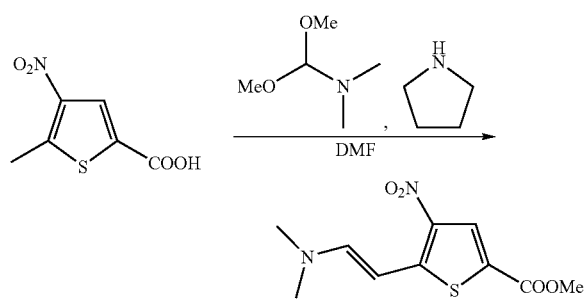

To a solution of 5-methyl-4-nitro-2-thiophene carboxylic acid (4.6 g, 24.6 mmol) in DMF (14.5 mmol) was added N,N-dimethylformamide dimethyl acetal (3.8 mL, 28.5 mmol) and pyrrolidine (2 drops). The mixture was refluxed for 3 h, concentrated in vacuo and the residue taken up in EtOAc (0.2 L). The organic phase was washed with water, saturated aq NaCl, dried over Na$_2$SO$_4$, filtered and concentrated in vacuo. The crude product was chromatographed over silica gel (0 to 40% EtOAc/heptane over 60 min) to give methyl 5-(2-dimethylaminovinyl)-4-nitrothiophene-2-carboxylate as a dark red solid (1.0 g, 16%). $^1$H NMR (400 MHz, CDCl$_3$) δ (ppm) 8.10 (s, 1H) 7.31 (d, J=13.1 Hz, 1H) 6.56 (d, J=13.1 Hz, 1H) 3.87 (s, 3H) 3.07 (s, 6H). LCMS m/e 279 (M+Na).

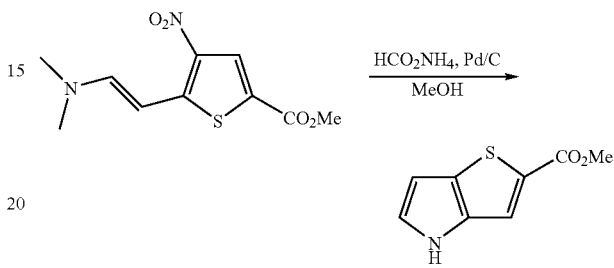

To a solution of methyl 5-(2-dimethylaminovinyl)-4-nitrothiophene-2-carboxylate (0.698 g, 2.73 mmol) in MeOH (15.0 mL) were added ammonium formate (0.332 g, 5.26 mmol) and Pd/C (33.2 mg, 10% by weight). The mixture was refluxed for 6 h. Additional ammonium formate (0.664 g, 10.53 mmol) was added to the reaction and the mixture was refluxed for 20 h. Additional ammonium formate (0.664 g, 10.53 mmol) and Pd/C (0.1 g, 30% by weight) were added and the reaction mixture was refluxed for another 8 h. Additional Pd/C (0.1 g, 30% by weight) was added and the mixture was refluxed for another 16 h. The reaction was cooled and filtered through a Celite® plug. The filtrate was concentrated in vacuo, taken up in EtOAc (0.2 L) and washed with water, saturated aq NaCl, dried over Na$_2$SO$_4$, filtered and concentrated in vacuo. The crude product was purified by HPLC to obtain methyl 4H-thieno[3,2-b]pyrrole-2-carboxylate as a yellow solid (0.078 g, 16%). $^1$H NMR (400 MHz, CDCl$_3$) δ (ppm) 8.40 (s, 1H) 7.71 (s, 1H) 7.20 (t, J=2.7 Hz, 1H) 6.50 (m, 1H), 3.90 (s, 3H).

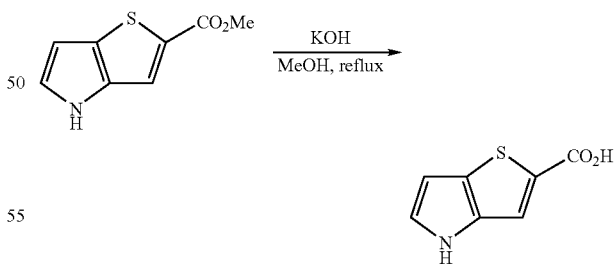

The title compound was synthesized from methyl 4H-thieno[3,2-b]pyrrole-2-carboxylate (0.078 g, 0.43 mmol) according to General Procedure 2 and was purified by silica gel column chromatography (gradient 25 to 100% EtOAc/heptane over 30 min) to give 4H-thieno[3,2-b]pyrrole-2-carboxylic acid 53 as an off-white (0.030 g, 42%). $^1$H NMR (400 MHz, CD$_3$OD) δ (ppm) 7.66 (d, J=0.6 Hz, 1H) 7.22 (d, J=2.9 Hz, 1H) 6.39 (dd, J=2.9, 0.6 Hz, 1H). LCMS m/e 166 (M−H).

Example 8

D-Amino Acid Oxidase Inhibition

8.1. D-Amino Acid Oxidase Enzyme Assay

DAAO enzyme activity was measured using the substrate D-serine at its Michaelis-Menton $K_m$ of 5 mM. The rate of oxidation is measured as a rate of production of hydrogen peroxide, which was detected using the enzyme horseradish peroxidase (Sigma cat. No. P-8375). This coupled reaction uses the enzyme substrate Amplex Red (Molecular Probes), which is converted to the fluorescent reaction product, resorufin (excitation 530-560 nm; emission ~590 nm). All reagents were prepared in 50 mM sodium phosphate buffer at pH 7.4 and inhibition curves were generated at this pH.

The final concentrations of components in 200 µl total volume per well (black clear-bottom 96-well plate, Costar) were:

(a) Horseradish peroxidase: 4 Units per ml
(b) D-serine: 5 mM
(c) Test Compound: 100-0.0064 uM for IC50s
(d) Amplex Red reagent: 50 uM
(e) DMSO: 1.6%

The reactions were initiated by addition of DAAO enzyme while the fluorescence was monitored. $H_2O_2$ was added at 16 uM final concentration to a control well on each plate to test for compound interference with a coupled enzyme. Inhibition curves were generated in the presence of varying concentrations of the inhibitor and $IC_{50}$ values were calculated for each inhibitor.

8.2. Results of DAAO Inhibition Assay $IC_{50}$ values were determined for compounds 78, 23, 73, 55, 4, 5, 66, 80, 65, 74, 76, 30, 56, 67, 49, 68, 81, 8, 75, 79, 72, 54, 70, 71, 82, 69, 64, 84, and 6 and are summarized in Table 2 of Example 9, below.

Example 9

In Vivo Elevation of D-Serine Levels in the Cerebellum (Fluor-Substituted Analogs Versus Other Halo-Substituted Analogs)

9.1 Methods

Mice (C57BL/6, 8-9 weeks of age) were dosed intraperitoneally at 10 mL/kg with 50 mg/kg or 10 mg/kg of compound suspended in 45% (w/v) hydroxy-β-cyclodextrin vehicle. Animals were sacrificed at either 2 or 6 hours post compound administration with an N=3 per time point. At sacrifice, trunk blood was collected into tubes containing potassium EDTA, which were then centrifuged to permit isolation of plasma. The cerebellum from each animal was dissected. Plasma and cerebellum samples were stored at −80° C. until samples were analyzed (LC/MS/MS).

9.2 Results

The results for compounds 55, 4, 5, 66, 74, 76, 30, 56, 67, 49, 68, 8, 75, 72, 54, 70, 71, and 64 are summarized in Table 2. In summary, a number of compounds, dosed at 10 mg/kg or 50 mg/kg i.p., were effective at increasing cerebellar D-serine levels at the two-hour time point, when compared to vehicle. In this experiment, most fluoro-substituted analogs were significantly more active than at least one of the respective Cl- or Br-substituted analog. In addition, most of the fluoro-substituted compounds were also effective at maintaining elevated D-serine levels through the 6-hour time point. This activity was not observed for any of the Cl- or Br-substituted analogs.

TABLE 2

Human DAAO Inhibition ($IC_{50}$, µM) and In vivo Elevation of D-Serine Levels in the cerebellum (fold increase over vehicle, i.p., mice)

| No. | Compound Name | Human DAAO (µM) | 50 mg/kg i.p. Fold increase in D-serine | | 10 mg/kg i.p. Fold increase in D-serine | |
|---|---|---|---|---|---|---|
| | | | 2 h | 6 h | 2 h | 6 h |
| 78 | 2-Fluoro-4H-furo[3,2-b]pyrrole-5-carboxylate acid | (++++) | | | | |
| 23 | 2-Chloro-4H-furo[3,2-b]pyrrole-5-carboxylic acid | (+) | | | | |
| 73 | 2-Bromo-4H-furo[3,2-b]pyrrole-5-carboxylic acid | (+) | | | | |
| 55 | 2-Fluoro-4H-thieno[3,2-b]pyrrole-5-carboxylic acid | (++++) | (++) | (+) | (−) | (−) |
| 4 | 2-Chloro-4H-thieno[3,2-b]pyrrole-5-carboxylic acid | (+) | (−) | (−) | | |
| 5 | 2-Bromo-4H-thieno[3,2-b]pyrrole-5-carboxylic acid | (++) | (+) | (−) | (−) | (−) |
| 66 | 2-Fluoro-6H-thieno[2,3-b]pyrrole-5-carboxylic acid | (++++) | (++) | (+) | (+) | (−) |
| 80 | 2-Chloro-6H-thieno[2,3-b]pyrrole-5-carboxylic acid | (+) | | | | |
| 65 | 2-Bromo-6H-thieno[2,3-b]pyrrole-5-carboxylic acid | (+) | | | | |
| 74 | 3-Fluoro-4H-furo[3,2-b]pyrrole-5-carboxylic | (++++) | (++) | (++) | (++) | (+) |
| 76 | 3-Chloro-4H-furo[3,2-b]pyrrole-5-carboxylic | (+++) | | | (−) | (−) |
| 30 | 3-Bromo-4H-furo[3,2-b]pyrrole-5-carboxylic acid | (+++) | (+) | (−) | (−) | (−) |
| 56 | 3-Fluoro-4H-thieno[3,2-b]pyrrole-5-carboxylic acid | (++++) | | | (+) | (−) |
| 67 | 3-Chloro-4H-thieno[3,2-b]pyrrole-5-carboxylic acid | (++++) | (−) | (−) | (−) | (−) |
| 49 | 3-Bromo-4H-thieno[3,2-b]pyrrole-5-carboxylic acid | (+++) | (−) | (−) | | |
| 68 | 3-Fluoro-6H-thieno[2,3-b]pyrrole-5-carboxylic acid | (++++) | (+) | (+) | (−) | (−) |
| 81 | 3-Chloro-6H-thieno[2,3-b]pyrrole-5-carboxylic acid | (+++) | | | | |
| 8 | 3-Bromo-6H-thieno[2,3-b]pyrrole-5-carboxylic acid | (++) | (+) | (+) | (−) | (−) |
| 75 | 6-Fluoro-4H-furo[3,2-b]pyrrole-5-carboxylic | (++++) | (++) | (++) | (++) | (+) |
| 79 | 6-Chloro-4H-furo[3,2-b]pyrrole-5-carboxylic acid | (+++) | | | | |
| 72 | 6-Bromo-4H-furo[3,2-b]pyrrole-5-carboxylic acid | (++) | (−) | (−) | (−) | (−) |
| 54 | 6-Fluoro-4H-thieno[3,2-b]pyrrole-5-carboxylic acid | (++++) | | | (++) | (++) |

TABLE 2-continued

Human DAAO Inhibition ($IC_{50}$, μM) and In vivo Elevation of D-Serine
Levels in the cerebellum (fold increase over vehicle, i.p., mice)

| No. | Compound Name | Human DAAO (μM) | 50 mg/kg i.p. 2 h | 50 mg/kg i.p. 6 h | 10 mg/kg i.p. 2 h | 10 mg/kg i.p. 6 h |
|---|---|---|---|---|---|---|
| 70 | 6-Chloro-4H-thieno[3,2-b]pyrrole-5-carboxylic acid | (+++) | | | (−) | (−) |
| 71 | 6-Bromo-4H-thieno[3,2-b]pyrrole-5-carboxylic acid | (++) | | | (−) | (−) |
| 82 | 4-Fluoro-6H-thieno[2,3-b]pyrrole-5-carboxylate | (+++) | | | | |
| 69 | 4-Chloro-6H-thieno[2,3-b]pyrrole-5-carboxylate | (+++) | | | | |
| 64 | 4-Bromo-6H-thieno[2,3-b]pyrrole-5-carboxylic acid | (++) | (−) | (−) | (−) | (−) |
| 84 | 2,4-dibromo-6H-thieno[2,3-b]pyrrole-5-carboxylic acid | 33% inhibition at 100 uM | | | | |
| 6 | 2,3-dibromo-4H-thieno[3,2-b)]pyrrole-5-carboxylic acid | (+) | | | | |

$IC_{50}$: (++++) < 25 nM; (+++) < 100 nM; (++) < 1 μM (+) < 100 μM;
Fold increase in D-serine over vehicle: (++) > 2.0×; (+) 1.5 to 2.0×; (−) < 1.5×

Example 10

Chung Model Data for Compounds 1 and 11

10.1. Methods

Adult male Sprague-Dawley rats, weighing 200-230 g at the time of surgery, were used. They were housed in groups of 4 in an air-conditioned room on a 12 h light/dark cycle. Food and water were available ad libitum. The animals were allowed to acclimatize to the experimental environment for three days by leaving them on a lifted metal mesh for at least 40 min. The baseline paw withdrawal threshold (PWT) was examined using a series of graduated von Frey hairs for 3 consecutive days before surgery and re-assessed on the 7th day after surgery and on the $11^{th}$ to $14^{th}$ day before drug dosing. The rat Chung model was prepared as described by Kim and Chung (1992). The rat was anaesthetized with 5% isoflurane mixed with oxygen (2 L per min) followed by an i.p. injection of sodium pentobarbitone at 50 mg/kg. The back was shaved and sterilized with 75% ethanol. The animal was placed in a prone position and a para-medial incision was made on the skin covering L4-6 level. The L5 spinal nerve was carefully isolated and tightly ligated with 6/0 silk suture. The wound was then closed in layers after a complete hemostasis. A single dose of antibiotics (Amoxipen 15 mg/rat, ip) was routinely given for prevention of infection after surgery. The animals were placed in a temperature controlled recovery chamber until fully awake before being returned to the home cage. The animals were placed in individual Perspex boxes on a raised metal mesh for at least 40 min before the test. Starting with the filament of lowest force, each filament was applied perpendicularly to the centre of the ventral surface of the paw until slightly bent for 6 seconds. If the animal withdrew or lifted the paw upon stimulation, then a hair with force immediately lower than that tested was used. If no response was observed, then a hair with force immediately higher was tested. The lowest amount of force required to induce reliable responses (positive in 3 out of 5 trials) was recorded as the value of PWT. Only those animals with significant allodynia (PWT≦3.5 g) were selected for drug dosing experiments. The rats in a neuropathic pain state were randomly divided into experimental groups: Vehicle group and 1 group had 8 rats and the gabapentin group had 9 rats. The drug test was carried out 12 to 14 days after surgery. Isotonic 50 mM phosphate buffer (PB), dosed orally at 3 mL/kg, served as the vehicle control. Gabapentin was dissolved in normal saline and given orally at 100 mg/kg. 1 was dissolved in PB to 10 mg/mL and given orally at 30 mg/kg. The PWT was assessed at 1, 3, 6 and 24 h following drug or vehicle administration. The animals were returned to their home cage for a break (about 30 min) between two neighboring testing time points. One-way analysis of variance (ANOVA) (SPSS software) was used for statistical analysis to compare different groups on the same time points. Paired Student-t test was used to compare different time points in the same group. The significance level was set at P<0.05.

10.2. Results for
4H-thieno[3,2-b]pyrrole-5-carboxylic acid (1)

In naive rats before surgery, the PWT ranged from 8.6 to 20 g, with an average value around 10-13 g (12.53±1.53 g and 12.63±1.49 for the left and right limbs, respectively, in the vehicle group on the day before surgery, 11.71±1.05 g and 11.62±1.07 g for both the left and right sides, respectively in the gabapentin group and 11.4±1.06 g and 11.30±1.09 g for both the left and right sides, respectively, in the 1 group). There was no statistical difference between the groups (one-way ANOVA). On day 7 after surgery, the PWT on the side ipsilateral to the ligated nerve was significantly lower that of pre-surgical levels (2.26±0.64 g for the vehicle control group, 1.62±0.23 g for the gabapentin group and 1.76±0.21 g for the 1 group, P<0.001 for all groups compared to pre-surgery values, paired Student-t test). On day 12 to 14, before dosing, the PWT on the ipsilateral side were further decreased. The animals also showed some degree of disuse of the affected limb or limping. However, the general behavior of animals was not remarkably different from their naive counterparts. After surgery, the PWT on the operated side was significantly lower compared to the contralateral side. Prior to vehicle administration on the day of experiment, the PWT was 1.34±0.30 g on the ipsilateral side versus 8.15±0.19 g on the contralateral side (n=8). After vehicle treatment, the PWT were not significantly changed in either hind limb over a period of 24 hours (P>0.05, compared to the pre-dosing level). On the ipsilateral side, the PWT was 1.09±0.10 g, 1.18±0.27 g, 1.30±0.34 g and 1.19±0.20 g at the 1, 3, 6 and 24 hour time points, respectively. On the contralateral side, the PWT was 8.95±0.97 g, 9.05±0.97 g, 9.15±0.97 g and 8.86±1.09 g at the 1, 3, 6 and 24 hour time points, respectively. Gabapentin, after oral dosing, significantly increased the PWT on the ipsilateral side. The effect became significant 1 hour after dosing (from 1.48±0.22 g before dosing to 3.77±0.42 g 1 hour after dosing, P<0.001, n=9). Three hours after dosing, the effect reached a peak (6.27±0.76 g, P<0.001 compared to pre-dosing level). At 6 and 24 hours after gabapentin, the PWT was 2.38±0.29 g and 2.69±0.60 g, respectively (P<0.01 and P>0.05, respectively, paired Student's t-test, compared to the pre-drug level). The PWT at 1, 3 and 24 hour time points were significantly higher than those observed in the vehicle group at the same time points (P<0.001 in general and from P<0.05 to P<0.001 at different time points, one way ANOVA). In contrast, the PWT on the side contralateral to the nerve ligation were not significantly changed over the whole observation period in general. The PWTs were 9.67±0.68 g before drug dosing and 10.11±0.93 g, 10.11±0.93 g, 8.29±0.42 g and 9.40±0.71 g at 1, 3, 6 and 24 hours after drug dosing, respectively (P>0.05 for all time points, compared to the pre-dosing level, paired Student's t-test). Compound 1, at 30 mg/kg, induced a significant increase in PWT in the ipsilateral side of Chung model rats. The effect was observed 1 hour after dosing and reached a peak 6 hours after dosing. The PWT were 1.25±0.18 g before drug dosing and 2.50±0.33 g an hour after dosing (P<0.01, compared to pre-dosing control level, paired Student's t-test). From 3 hours onward, the PWT gradually increased to reach a maximum level at 6 hours after drug administration (4.44±0.27 g and 5.71±0.66 g at 3 and 6 hours, respectively, P<0.001 for both time points, compared to the pre-dosing level, paired Student's t-test). At 24 hours after dosing, the PWT declined to near the pre-dosing control level (1.90±0.38 g, P>0.05). At all of the time points observed from 1 to 24 hours, the PWT were significantly (P<0.001 and 0.01) higher than those recorded at the same time points in the vehicle control group. The PWT on the contralateral side were not significantly changed over the whole observation period. The PWT observed at 1, 3, 6 and 24 hours after dosing were 8.15±0.45 g, 8.90±0.15 g, 9.70±0.77 g and 8.35±0.50 g, respectively (P>0.05, compared to pre-drug level of 8.80±0.13 g).

10.3. Results for 4H-furo[3,2-b]pyrrole-5-carboxylic acid (11)

In rats that were dosed orally with vehicle, there were no significant changes in PWT from the baseline value over the 24-hour observation period. Gabapentin, as a positive control, orally dosed at 100 mg/kg, significantly increased the PWT, with effects commencing the first hour after oral dosing and reaching a peak 3 hours after dosing. The effect of gabapentin gradually declined from 6 hours onwards. 11, at an oral dose of 10 mg/kg, also significantly elevated the PWT. Similar to gabapentin, the increase in PWT was first observed 1 hour after dosing. The effect reached a peak at 6 hours after dosing.

Example 11

Contextual Fear Conditioning Data for 4H-furo[3,2-b]pyrrole-5-carboxylic acid (11) and 4H-thieno[3,2-b]pyrrole-5-carboxylic acid (1)

11.1. Methods

Young-adult C57BL/6 male mice were used. Mice were received at 6-7 weeks of age. Upon arrival, mice were assigned unique identification numbers (tail marked) and were group housed in polycarbonate cages with filter tops. All mice were acclimated to the colony room for at least four weeks prior to testing and were subsequently tested at an average age of 10-12 weeks of age. During the period of acclimation, mice were examined on a regular basis, handled, and weighed to assure adequate health and suitability. Mice were maintained on a 12/12 light/dark cycle with the light on at 6:00 a.m. The experiments were always conducted during the light phase of the cycle. The day before the initiation of the experiment, mice were housed single in individual cages and maintained so till the end of the experiment. Animals were randomly assigned across treatment groups. With the exception of testing times, the mice had ad lib access to food and water. Rolipram (0.1 mg/kg) was dissolved in 1% DMSO i.p. 20 min prior to training at a dose volume of 8 ml/kg. To assess contextual conditioning, we use a standardized contextual fear conditioning task originally developed for evaluation of memory in CREB mutant mice (Bourtchouladze, R. et al.; *Cell* 1994, 79, 59-68). Specifically, on the training day, the mouse is placed into the conditioning chamber for 2 minutes before the onset of the unconditioned stimulus (US), a 0.75 mA foot shock of 2 seconds duration. The US is repeated two times with a 1 min inter-trial interval between shocks. Training is performed using an automated software package. After the last training trial, a mouse is left in the conditioning chamber for another 30 sec and then placed back in its home cage. Contextual memory is tested 24 hours after training. The mouse is placed into the same training chamber and conditioning is assessed by scoring freezing behavior. Freezing is defined as the complete lack of movement in intervals of 5 seconds (Kim et al., 1993; Phillips & LeDoux, 1992; Bourtchouladze et al., 1994; 1998; Abel et al., 1997; Kogan et al., 1997). Total testing time lasted 3 minutes. After each experimental subject, the experimental apparatus is thoroughly cleaned with 75% ethanol, water, dried, and ventilated for a few minutes. To evaluate the effects of compounds on contextual memory, we injected mice with a compound or vehicle 2 hours before training and trained them with 2 training trials. In parallel, a separate group of mice was injected with a reference compound, Rolipram or vehicle alone, 20 minutes before training. Mice were tested in the same context 24 hours after training.

11.2. Results

Compound 11 was dissolved in vehicle A and administered p.o. 2 hrs prior to training at a dose volume of 10 ml/kg. 10 mg/kg of 11-injected mice froze significantly more than vehicle injected mice (69.7%+/−3.0% and 33.3%+/−5.1% for a compound- and vehicle-injected, respectively; p<0.001; n=10 per dose). Similarly, Rolipram injected mice froze significantly more than their corresponding vehicle-injected mice (44.4%+/−4.4% vs. 27.2%+/−3.6% for Rolipram and vehicle, respectively; p<0.05). Importantly, there was no effect of drug-compound injections on immediate freezing responses measured 30 sec after training.

4H-thieno[3,2-b]pyrrole-5-carboxylic acid (1) was active at 10 mg/kg P.O.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A method for treating neuropathic pain, said method comprising administering to a subject in need thereof a therapeutically effective amount of a compound of Formula (I) or a pharmaceutically acceptable salt thereof:

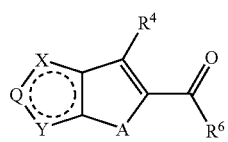

wherein
- A is NH or S;
- Q is a member selected from $CR^1$ and N;
- X and Y are members independently selected from O, S, $CR^2$, N and NH;
- $R^1$, $R^2$ and $R^4$ are members independently selected from H and F, with the proviso that at least one member selected from $R^1$, $R^2$ and $R^4$ is F; and
- $R^6$ is a member selected from $O^-X^+$ and OH, wherein $X^+$ is a positive ion, which is a member selected from inorganic positive ions and organic positive ions.

2. The method according to claim 1, wherein said compound has a structure according to Formula (II):

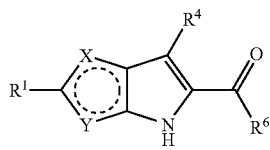

wherein one member selected from X and Y is O or S and the other member is $CR^2$.

3. The method according to claim 2, wherein said compound has a structure according to Formula (III):

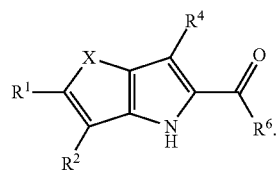

4. The method according to claim 2, wherein said compound has a structure according to Formula (IV):

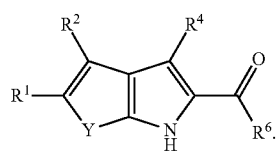

5. The method according to claim 2, wherein $R^1$ is F.
6. The method according to claim 2, wherein $R^2$ is F.
7. The method according to claim 2, wherein $R^4$ is F.

8. The method according to claim 1, wherein said neuropathic pain is selected from neuropathic cancer pain, HIV/AIDS induced pain, phantom limb pain, complex regional pain syndrome, chronic migraine, fibromyalgia, lower back pain, causalgia, sensory loss, allodynia, hyperalgesia, hyperpathia, mechanical spinal pain, radiculopathy, myelopathy, and neck pain.

9. The method according to claim 1, wherein said neuropathic pain is selected from central neuropathic pain and peripheral neuropathic pain.

10. The method according to claim 9, wherein said neuropathic pain is central neuropathic pain.

11. The method according to claim 10, wherein said central neuropathic pain is associated with damage to the brain, damage to the spinal cord or a combination thereof.

12. The method according to claim 11, wherein said central neuropathic pain follows stroke.

13. The method according to claim 11, wherein said central neuropathic pain follows spinal cord injury.

14. The method according to claim 11, wherein said central neuropathic pain results from multiple sclerosis.

15. The method according to claim 9, wherein the neuropathic pain is peripheral neuropathic pain.

16. The method according to claim 15, wherein said peripheral neuropathic pain is selected from diabetic peripheral neuropathic pain, post-herpetic neuralgia and trigeminal neuralgia.

17. The method according to claim 16, wherein said peripheral neuropathic pain is diabetic peripheral neuropathic pain.

18. The method according to claim 16, wherein said peripheral neuropathic pain is post-herpetic neuralgia.

19. The method according to claim 16, wherein said peripheral neuropathic pain is trigeminal neuralgia.

20. The method according to claim 1, wherein said compound is administered as a pharmaceutical composition comprising a pharmaceutically acceptable carrier and a dosage of from about 1 mg to about 7000 mg of said compound.

21. A method for treating a condition which is a member selected from loss of memory, loss of cognition and a combination thereof, said method comprising administering to a subject in need thereof a therapeutically effective amount of a compound of Formula (I) or a pharmaceutically acceptable salt thereof:

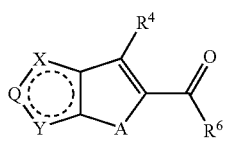

wherein
- A is NH or S;
- Q is a member selected from $CR^1$ and N;
- X and Y are members independently selected from 0, S, $CR^2$, N and NH;
- $R^1$, $R^2$ and $R^4$ are members independently selected from H and F, with the proviso that at least one member selected from $R^1$, $R^2$ and $R^4$ is F; and
- $R^6$ is a member selected from $O^-X^+$ and OH, wherein $X^+$ is a positive ion, which is a member selected from inorganic positive ions and organic positive ions.

22. The method according to claim 21, wherein said compound has a structure according to Formula (II):

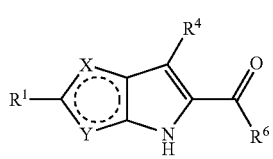
(II)

wherein one member selected from X and Y is O or S and the other member is $CR^2$.

23. The method according to claim 22, wherein said compound has a structure according to Formula (III):

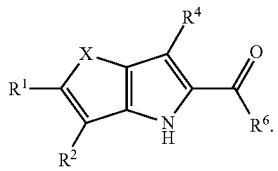
(III)

24. The method according to claim 22, wherein said compound has a structure according to Formula (IV):

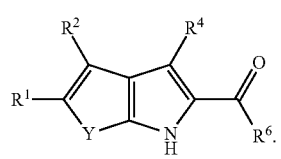
(IV)

25. The method according to claim 22, wherein $R^1$ is F.

26. The method according to claim 22, wherein $R^2$ is F.

27. The method according to claim 22, wherein $R^4$ is F.

28. The method according to claim 21, wherein said condition is associated with Alzheimer's disease.

29. The method according to claim 21, wherein said condition is associated with schizophrenia.

30. The method according to claim 21, wherein said compound is administered as a pharmaceutical composition comprising a pharmaceutically acceptable carrier and a dosage of from about 1 mg to about 7000 mg of said compound.

* * * * *